(12) United States Patent
Bellinger et al.

(10) Patent No.: US 11,992,552 B2
(45) Date of Patent: May 28, 2024

(54) GEOMETRIC CONFIGURATIONS FOR GASTRIC RESIDENCE SYSTEMS

(71) Applicant: Lyndra Therapeutics, Inc., Watertown, MA (US)

(72) Inventors: Andrew Bellinger, Wellesley, MA (US); Rosemary Kanasty, Somerville, MA (US); Tyler Grant, Watertown, MA (US); Colin Gardner, Watertown, MA (US)

(73) Assignee: LYNDRA THERAPEUTICS, INC., Watertown, MA (US)

( * ) Notice: Subject to any disclaimer, the term of this patent is extended or adjusted under 35 U.S.C. 154(b) by 329 days.

(21) Appl. No.: 15/782,021

(22) PCT Filed: Dec. 7, 2016

(86) PCT No.: PCT/US2016/065453
§ 371 (c)(1),
(2) Date: Jun. 6, 2018

(87) PCT Pub. No.: WO2017/100367
PCT Pub. Date: Jun. 15, 2017

(65) Prior Publication Data
US 2019/0262265 A1    Aug. 29, 2019

Related U.S. Application Data

(60) Provisional application No. 62/264,811, filed on Dec. 8, 2015.

(51) Int. Cl.
*A61M 9/00* (2006.01)
*A61K 9/00* (2006.01)
(Continued)

(52) U.S. Cl.
CPC ............ *A61K 9/0065* (2013.01); *A61K 9/146* (2013.01); *A61K 9/20* (2013.01); *A61K 47/34* (2013.01);
(Continued)

(58) Field of Classification Search
CPC ...... A61K 9/0065; A61K 9/20; A61K 9/0053; A61K 31/357; A61K 31/65;
(Continued)

(56) References Cited

U.S. PATENT DOCUMENTS 1,957,564 A * 5/1934 West ..................... A61M 31/00
604/288
3,154,461 A    10/1964 Johnson
(Continued)

FOREIGN PATENT DOCUMENTS

AU    643219 B2    1/1991
AU    6199090 A    3/1991
(Continued)

OTHER PUBLICATIONS

Agrawal, A. et al. (Jul. 2006). "Clinical Relevance of the Nutcracker Esophagus: Suggested Revision of Criteria for Diagnosis," J Clin Gastroenterol. 40(6):504-509.
(Continued)

*Primary Examiner* — Emily L Schmidt
*Assistant Examiner* — Antarius S Daniel
(74) *Attorney, Agent, or Firm* — MORRISON & FOERSTER LLP

(57) ABSTRACT

The invention provides gastric residence systems with configurations and geometrical dimensions that allow for improved shelf life during prolonged storage, and optimal residence properties when the systems are deployed in the stomach of a patient.

20 Claims, 42 Drawing Sheets

(51) Int. Cl.
  *A61K 9/14* (2006.01)
  *A61K 9/20* (2006.01)
  *A61K 47/34* (2017.01)
  *A61K 47/46* (2006.01)
  *A61M 31/00* (2006.01)
  *C08G 18/12* (2006.01)
  *C08G 18/42* (2006.01)
  *C08G 18/73* (2006.01)

(52) U.S. Cl.
  CPC ........... *A61K 47/46* (2013.01); *A61M 31/002* (2013.01); *C08G 18/12* (2013.01); *C08G 18/4202* (2013.01); *C08G 18/4277* (2013.01); *C08G 18/73* (2013.01)

(58) Field of Classification Search
  CPC .... A61K 31/7048; A61K 47/10; A61K 47/32; A61K 47/34; A61K 47/40; A61K 47/42; A61K 47/58; A61K 47/69; A61K 9/48; A61M 31/002; A61M 31/00; A61M 2210/1042; A61M 2210/1053; A61M 2210/1057; A61M 2210/106; A61M 2210/1064; C08G 18/4277; C08G 18/73; C08G 2230/00; C08G 63/08; C08G 83/006; C08G 33/02; C08G 33/08; C08G 33/14; C08L 2203/02
  See application file for complete search history.

(56) References Cited

U.S. PATENT DOCUMENTS

| | | | |
|---|---|---|---|
| 3,531,368 A | 9/1970 | Okamoto | |
| 3,716,614 A | 2/1973 | Watanabe | |
| 3,844,285 A * | 10/1974 | Laby | A61D 7/00 604/890.1 |
| 3,976,764 A | 8/1976 | Watanabe | |
| 4,304,767 A | 12/1981 | Heller | |
| 4,451,260 A | 5/1984 | Mitra | |
| 4,525,358 A | 6/1985 | Baltes | |
| 4,676,507 A | 6/1987 | Patterson | |
| 4,735,804 A | 4/1988 | Caldwell | |
| 4,758,436 A | 7/1988 | Caldwell | |
| 4,767,627 A * | 8/1988 | Caldwell | A61K 9/0065 424/400 |
| 4,812,012 A | 3/1989 | Terada | |
| 4,996,058 A | 2/1991 | Sinnreich | |
| 5,002,772 A | 3/1991 | Curatolo | |
| 5,007,790 A | 4/1991 | Shell | |
| 5,047,464 A | 9/1991 | Pogany | |
| 5,121,329 A | 6/1992 | Crump | |
| 5,340,433 A | 8/1994 | Crump | |
| 5,369,142 A | 11/1994 | Culbertson | |
| 5,443,843 A | 8/1995 | Curatolo | |
| 5,491,586 A | 2/1996 | Phillips | |
| 5,762,637 A * | 6/1998 | Berg | A61M 25/001 604/523 |
| 5,840,332 A | 11/1998 | Lerner | |
| 5,939,467 A | 8/1999 | Wnuk et al. | |
| 6,120,802 A | 9/2000 | Breitenbach et al. | |
| 6,120,803 A | 9/2000 | Wong | |
| RE37,314 E | 8/2001 | Hirai | |
| 6,306,420 B1 | 10/2001 | Cheikh | |
| 6,306,439 B1 | 10/2001 | Penners | |
| 6,316,460 B1 | 11/2001 | Creekmore | |
| 6,375,649 B1 | 4/2002 | Jellie | |
| 6,436,069 B1 | 8/2002 | Jellie | |
| 6,488,962 B1 | 12/2002 | Berner | |
| 6,500,168 B1 | 12/2002 | Jellie | |
| 6,548,083 B1 | 4/2003 | Wong | |
| 6,685,962 B2 | 2/2004 | Friedman | |
| 6,776,999 B1 | 8/2004 | Krumme | |
| 6,780,168 B2 | 8/2004 | Jellie | |
| 6,825,308 B1 | 11/2004 | Kulkarni | |
| 6,962,579 B2 | 11/2005 | Jellie | |
| 7,276,252 B2 | 10/2007 | Payumo | |
| 7,691,151 B2 | 4/2010 | Kutsko | |
| 7,964,196 B2 | 6/2011 | De Los Rios | |
| 8,021,384 B2 | 9/2011 | Weiss | |
| 8,038,659 B2 | 10/2011 | Boyden | |
| 8,158,143 B2 | 4/2012 | Lendlein | |
| 8,267,888 B2 * | 9/2012 | Marco | A61F 2/02 604/104 |
| 8,277,843 B2 | 10/2012 | Singh | |
| 8,298,574 B2 | 10/2012 | Tsabari | |
| 8,377,453 B2 | 2/2013 | Han | |
| 8,414,559 B2 | 4/2013 | Gross | |
| 8,586,083 B2 | 11/2013 | Mohammad | |
| 8,609,136 B2 | 12/2013 | Tsabari | |
| 8,753,678 B2 | 6/2014 | Tsabari | |
| 8,771,730 B2 | 7/2014 | Navon | |
| 9,072,663 B2 | 7/2015 | Navon | |
| 9,107,816 B2 | 8/2015 | Lee | |
| 9,220,688 B2 | 12/2015 | Alon | |
| 9,259,387 B2 | 2/2016 | Navon | |
| 10,182,985 B2 | 1/2019 | Bellinger | |
| 10,195,143 B2 | 2/2019 | Zalit et al. | |
| 10,485,758 B2 * | 11/2019 | Menachem | A61K 9/2013 |
| 10,517,819 B2 | 12/2019 | Bellinger et al. | |
| 10,517,820 B2 | 12/2019 | Bellinger | |
| 10,532,027 B2 | 1/2020 | Bellinger | |
| 10,596,110 B2 | 3/2020 | Bellinger | |
| 10,610,482 B2 | 4/2020 | Bellinger | |
| 10,716,751 B2 | 7/2020 | Bellinger et al. | |
| 10,716,752 B2 | 7/2020 | Bellinger et al. | |
| 11,077,056 B2 | 8/2021 | Bellinger et al. | |
| 11,246,829 B2 | 2/2022 | Bellinger et al. | |
| 11,357,723 B2 | 6/2022 | Bellinger et al. | |
| 11,389,399 B2 | 7/2022 | Bellinger et al. | |
| 2002/0022048 A1 * | 2/2002 | Bromberg | A61K 6/20 424/439 |
| 2002/0132008 A1 | 9/2002 | Mumper | |
| 2003/0021822 A1 | 1/2003 | Lloyd | |
| 2003/0232895 A1 | 12/2003 | Omidian | |
| 2004/0180086 A1 | 9/2004 | Ramtoola | |
| 2004/0219186 A1 | 11/2004 | Ayres | |
| 2005/0033331 A1 | 2/2005 | Burnett | |
| 2005/0165136 A1 | 7/2005 | Mays | |
| 2005/0175702 A1 | 8/2005 | Muller-schulte | |
| 2005/0249807 A1 | 11/2005 | Brown et al. | |
| 2006/0069214 A1 | 3/2006 | Deiss | |
| 2006/0142794 A1 | 6/2006 | Lendlein | |
| 2006/0182788 A1 | 8/2006 | Singh | |
| 2007/0048383 A1 | 3/2007 | Helmus | |
| 2007/0104754 A1 | 5/2007 | Sterling | |
| 2007/0123809 A1 | 5/2007 | Weiss | |
| 2007/0129784 A1 | 6/2007 | Lendlein | |
| 2007/0131144 A1 | 6/2007 | Winter et al. | |
| 2007/0264307 A1 | 11/2007 | Chen | |
| 2008/0075766 A1 | 3/2008 | Li | |
| 2008/0153779 A1 | 6/2008 | Liao | |
| 2008/0241238 A1 | 10/2008 | Dharmadhikari | |
| 2008/0249156 A1 | 10/2008 | Palepu | |
| 2008/0260824 A1 | 10/2008 | Nangia | |
| 2008/0292691 A1 | 11/2008 | Lloyd | |
| 2009/0092415 A1 | 4/2009 | Murakami | |
| 2009/0105531 A1 | 4/2009 | Boyden | |
| 2009/0155326 A1 | 6/2009 | Mack | |
| 2009/0182424 A1 | 7/2009 | Marco | |
| 2009/0246142 A1 | 10/2009 | Bhatia | |
| 2009/0324694 A1 | 12/2009 | Mohammad | |
| 2010/0152410 A1 | 6/2010 | East | |
| 2010/0168439 A1 | 7/2010 | Olson | |
| 2010/0256342 A1 | 10/2010 | Salemme | |
| 2010/0266655 A1 | 10/2010 | Dadey | |
| 2010/0297009 A1 | 11/2010 | Olson | |
| 2010/0316712 A1 | 12/2010 | Nangia | |
| 2011/0038912 A1 | 2/2011 | Darby et al. | |
| 2011/0040318 A1 | 2/2011 | Marco | |
| 2011/0052700 A1 | 3/2011 | Han | |
| 2011/0097395 A1 | 4/2011 | Babul et al. | |
| 2011/0125091 A1 * | 5/2011 | Abbate | A61K 9/0043 606/199 |

(56) References Cited

U.S. PATENT DOCUMENTS

| | | |
|---|---|---|
| 2011/0245909 A1 | 10/2011 | Schmid |
| 2011/0268666 A1 | 11/2011 | Friedman |
| 2011/0305685 A1 | 12/2011 | Tseng |
| 2012/0009261 A1 | 1/2012 | Sesha |
| 2012/0116285 A1 | 5/2012 | Duggirala |
| 2012/0165793 A1 | 6/2012 | Ortiz |
| 2012/0165794 A1 | 6/2012 | Ortiz |
| 2012/0301547 A1 | 11/2012 | Gan |
| 2012/0321706 A1 | 12/2012 | Masri |
| 2013/0045530 A1 | 2/2013 | Gracias |
| 2013/0131637 A1* | 5/2013 | DiCesare ............ A61M 31/002 604/517 |
| 2013/0226104 A1 | 8/2013 | Hyde |
| 2013/0273135 A1 | 10/2013 | Brooks |
| 2014/0050784 A1 | 2/2014 | Kagan |
| 2014/0052171 A1 | 2/2014 | Tegels |
| 2014/0249499 A1 | 9/2014 | Selaru |
| 2015/0265536 A1 | 9/2015 | Muley |
| 2015/0335592 A1 | 11/2015 | Barnscheid |
| 2015/0342877 A1 | 12/2015 | Menachem |
| 2016/0317796 A1 | 11/2016 | Zhang |
| 2017/0051099 A1 | 2/2017 | Diciccio |
| 2017/0106099 A1 | 4/2017 | Bellinger |
| 2017/0128576 A1 | 5/2017 | Zhang |
| 2017/0135954 A1 | 5/2017 | Bellinger |
| 2017/0266112 A1 | 9/2017 | Bellinger |
| 2018/0250226 A1 | 9/2018 | Betser et al. |
| 2018/0311154 A1 | 11/2018 | Kanasty |
| 2018/0369138 A1 | 12/2018 | Zalit et al. |
| 2019/0070107 A1 | 3/2019 | Bellinger |
| 2019/0070108 A1 | 3/2019 | Bellinger |
| 2019/0125667 A1 | 5/2019 | Bellinger |
| 2019/0133936 A1 | 5/2019 | Bellinger |
| 2019/0175500 A1 | 6/2019 | Bellinger |
| 2019/0231697 A1 | 8/2019 | Bellinger |
| 2019/0254966 A1 | 8/2019 | Bellinger |
| 2019/0290799 A1 | 9/2019 | Arshi et al. |
| 2019/0298652 A1 | 10/2019 | Bellinger et al. |
| 2019/0365645 A1 | 12/2019 | Traverso et al. |
| 2019/0365646 A1 | 12/2019 | Menachem et al. |
| 2019/0366064 A1 | 12/2019 | Traverso et al. |
| 2020/0030589 A1 | 1/2020 | Ben Menachem et al. |
| 2020/0085736 A1 | 3/2020 | Bellinger et al. |
| 2020/0085737 A1 | 3/2020 | Bellinger et al. |
| 2020/0146979 A1 | 5/2020 | Kanasty |
| 2020/0230244 A1 | 7/2020 | Traverso et al. |
| 2020/0376242 A1 | 12/2020 | Ben Menachem et al. |
| 2020/0405635 A1 | 12/2020 | Menachem et al. |
| 2021/0093564 A1 | 4/2021 | Bellinger et al. |
| 2021/0113460 A1 | 4/2021 | Bellinger et al. |
| 2021/0128460 A1 | 5/2021 | Bellinger et al. |
| 2021/0177750 A1 | 6/2021 | Bellinger et al. |
| 2023/0039421 A1 | 2/2023 | Bellinger et al. |

FOREIGN PATENT DOCUMENTS

| | | | |
|---|---|---|---|
| AU | 6199090 | * 7/1991 | |
| CA | 2951884 A1 | 12/2015 | |
| CN | 1049787 A | 3/1991 | |
| CN | 1754898 A | 4/2006 | |
| CN | 102245127 A | 11/2011 | |
| CN | 103654903 A | 3/2014 | |
| EP | 0202159 A2 | 11/1986 | |
| EP | 0253554 A2 | 1/1988 | |
| EP | 0253554 A3 | 7/1988 | |
| EP | 0344939 A2 | 12/1989 | |
| EP | 0388234 A1 | 9/1990 | |
| EP | 0406015 A1 | 1/1991 | |
| EP | 0415671 A2 | 3/1991 | |
| EP | 0415671 A2 * | 3/1991 | ........... A61K 9/0065 |
| EP | 0202159 B1 | 7/1991 | |
| EP | 0344939 B1 | 1/1993 | |
| EP | 0820258 B1 | 10/2002 | |
| EP | 1124534 B1 | 1/2004 | |
| EP | 1687379 | 8/2006 | |
| EP | 1911518 A1 | 4/2008 | |
| EP | 2324822 A2 | 5/2011 | |
| EP | 2329810 A1 | 6/2011 | |
| EP | 1528916 B1 | 12/2012 | |
| EP | 3386488 | 10/2018 | |
| JP | S58174312 A | 10/1983 | |
| JP | S6226215 A | 2/1987 | |
| JP | S6323815 A | 8/1987 | |
| JP | H0229268 A | 11/1989 | |
| JP | H03044318 A | 2/1991 | |
| JP | H03128934 A | 5/1991 | |
| JP | H03163011 A | 7/1991 | |
| JP | 2006518392 A | 8/2006 | |
| JP | 2013500293 A | 1/2013 | |
| JP | 2013530193 A | 7/2013 | |
| JP | 2004325508 A | 11/2018 | |
| RU | 2070029 C1 | 12/1996 | |
| RU | 2242219 C2 | 12/2004 | |
| WO | WO199738969 A1 | 10/1997 | |
| WO | WO200025742 A1 | 5/2000 | |
| WO | WO200137812 A2 | 5/2001 | |
| WO | WO200137812 A3 | 2/2002 | |
| WO | WO2003015745 A1 | 2/2003 | |
| WO | WO2004010978 A1 | 2/2004 | |
| WO | WO2004073690 A1 | 9/2004 | |
| WO | WO2004112755 A1 | 12/2004 | |
| WO | WO2005065660 A2 | 7/2005 | |
| WO | WO2006072948 A2 | 7/2006 | |
| WO | WO2006084164 A2 | 8/2006 | |
| WO | WO2006072948 A3 | 11/2006 | |
| WO | WO2006084164 A3 | 11/2006 | |
| WO | WO2007027812 A2 | 3/2007 | |
| WO | WO2007048223 A2 | 5/2007 | |
| WO | WO2005065660 A3 | 6/2007 | |
| WO | WO2007048223 A3 | 6/2007 | |
| WO | WO2007083309 A2 | 7/2007 | |
| WO | WO2007093999 A1 | 8/2007 | |
| WO | WO2007083309 A3 | 9/2007 | |
| WO | WO2008015162 A1 | 2/2008 | |
| WO | WO2008039698 A1 | 4/2008 | |
| WO | WO2008140651 A2 | 11/2008 | |
| WO | WO2008140651 A3 | 1/2009 | |
| WO | WO2007027812 A3 | 4/2009 | |
| WO | WO2009132461 A1 | 11/2009 | |
| WO | WO2009144558 A1 | 12/2009 | |
| WO | 2010042879 A2 | 4/2010 | |
| WO | WO2010035273 A2 | 4/2010 | |
| WO | 2010042879 A3 | 6/2010 | |
| WO | WO2010064100 A1 | 6/2010 | |
| WO | WO2010064139 A2 | 6/2010 | |
| WO | WO2010035273 A3 | 7/2010 | |
| WO | WO2010064139 A3 | 9/2010 | |
| WO | WO2010099466 A2 | 9/2010 | |
| WO | WO2010099466 A3 | 1/2011 | |
| WO | WO2011012369 A2 | 2/2011 | |
| WO | WO2011032087 A2 | 3/2011 | |
| WO | WO2011032087 A3 | 6/2011 | |
| WO | WO2011012369 A3 | 9/2011 | |
| WO | WO2011139796 A2 | 11/2011 | |
| WO | 2012003968 A1 | 1/2012 | |
| WO | WO2011139796 A3 | 3/2012 | |
| WO | WO2012087658 A1 | 6/2012 | |
| WO | 2013011438 A1 | 1/2013 | |
| WO | WO2013049188 A2 | 4/2013 | |
| WO | WO2014014348 A1 | 1/2014 | |
| WO | WO2015083171 A1 | 6/2015 | |
| WO | 2015187746 A1 | 12/2015 | |
| WO | WO2015191920 A1 | 12/2015 | |
| WO | WO2015191922 A1 | 12/2015 | |
| WO | WO2015191925 A1 | 12/2015 | |
| WO | WO2017070612 A1 | 4/2017 | |
| WO | 2017100367 A1 | 6/2017 | |
| WO | WO2017205844 A2 | 11/2017 | |
| WO | WO2017205844 A3 | 1/2018 | |
| WO | WO2018064630 A1 | 4/2018 | |
| WO | WO2018227147 A1 | 12/2018 | |
| WO | WO2019060458 A1 | 3/2019 | |

(56) References Cited

FOREIGN PATENT DOCUMENTS

| WO | 2019111132 A1 | 6/2019 |
|---|---|---|
| WO | 2020102650 A2 | 5/2020 |
| WO | 2020102650 A3 | 8/2020 |

OTHER PUBLICATIONS

Ajili, S.H. et al. (Jun. 2009, e-pub. Jan. 3, 2009). "Polyurethane/Polycaprolactane Blend With Shape Memory Effect as a Proposed Material for Cardiovascular Implants," Acta Biomaterialia 5(5):1519-1530.
Alhnan, M.A. et al. (Aug. 2016; e-published on May 18, 2016). "Emergence of 3D Printed Dosage Forms: Opportunities and Challenges," Pharm. Res. 33(8):1817-1832, 38 pages.
Barbucci, R. et al. (1989). "Vinyl Polymers Containing Amido and Carboxyl Groups as Side Substituents, 2 a). Thermodynamic and Fourier-Transform Infrared Spectroscopic Studies for the Protonation of poly(N-Acryloylglycine) and the poly(N-N-acryoyl-6-aminocaproic acid)," Makromol. Chem. 190:2627-2638.
Belknap, R. et al. (Jan. 7, 2013). "Feasibility of an Ingestible Sensor-Based System for Monitoring Adherence to Tuberculosis Therapy," Plos One 8(1):e53373, pp. 1-5.
Bellinger, A.M. et al. (Nov. 16, 2016). "Oral, Ultra-Long-Lasting Drug Delivery: Application Toward Malaria Elimination Goals," Sci. Transl. Med. 8(365ra157):1-12., (with Supplementary Material), 21 pages.
Byrne, C. et al. (Mar. 2007; e-pub. Dec. 18, 2006). "The Ingestible Telemetric Body Core Temperature Sensor. A Review of Validity and Exercise Applications," Brit J Sport Med. 41(3):126-133.
Cargill, R. et al. (Aug. 1988). "Controlled Gastric Emptying. 1. Effects of Physical Properties on Gastric Residence Times of Nondisintegrating Geometric Shapes in Beagle Dogs," Pharm Res. 5(8):533-536.
Cargill, R. et al. (Jun. 1989). "Controlled Gastric Emptying. II. In Vitro Erosion and Gastric Residence Times of an Erodible Device in Beagle Dogs," Pharm Res. 6(6):506-509.
Choudhry, N.K. et al. (Dec. 1, 2011; e-pub. Nov. 14, 2011). "Full Coverage for Preventive Medications After Myocardial Infarction," N Engl J Med. 365:2088-2097.
Cirillo, G. et al. (Jan. 21, 2014). "Carbon Nanotubes Hybrid Hydrogels in Drug Delivery: A Perspective Review," BioMed Res Intl. 2014(Article ID 825017), 17 pages.
Cong, H.-P. et al. (2013, e-pub. Jul. 23, 2013). "Stretchable and Self-Healing Graphene Oxide-Polymer Composite Hydrogels: A Dual-Network Design," Chem Mater. 25:3357-3362.
Dash, S. et al. (May-Jun. 2010). "Kinetic Modeling on Drug Release From Controlled Drug Delivery Systems," Acta Poloniae Pharmaceutica 67(3):217-223.
Davies, G.C. et al. (Mar. 1993). "Release Characteristics, Ovarian Activity and Menstrual Bleeding Pattern with a Single Contraceptive Implant Releasing 3-Ketodesogestrel," Contraception 47(3):251-261.
Dumortier, G. et al. (Dec. 2006, e-pub. Nov. 11, 2006). "A Review of Poloxamer 407 Pharmaceutical and Pharmacological Characteristics," Pharmaceutical Research 23(12):2709-2728.
Dunn, D.L. et al. (2005). Wound Closure Manual Ethicon, Inc. A Johnson and Johnson company, 127 pages.
Edwards, D.A.W. (Nov. 1961). "Physiological Concepts of the Pylorus," Proceedings of the Royal Society of Medicine 54:930-933.
Ereqat, S. et al. (Sep. 2011). "MDR Tuberculosis and Non-Compliance With Therapy," Lancet Infect Dis. 11(9):662.
European Extended Search Report dated Jul. 5, 2019, for Application No. EP 16873798.9, filed on Apr. 26, 2018, 9 pages.
European Search Report dated May 27, 2019 for Application No. EP 16858392.0, filed on Apr. 26, 2018, 10 pages.
Evonik Industries AG, (Dec. 2012). Eudragit Technical Information Sheet, EUDRAGIT L 100 and EUDRAGIT S 100, Specification and Test Methods, 7 pages.
Extended European Search Report dated Feb. 23, 2018 for Application No. EP 15806483.2, filed Jun. 11, 2015, 3 pages.
Extended European Search Report dated Dec. 20, 2017 for Application No. EP 15806017.8, filed on Apr. 26. 2018, 10 pages.
Extended European Search Report dated Nov. 20, 2019 for Application No. EP 17803732.1, 9 pages.
Fallon, S.C. et al. (Apr. 2013). "The Surgical Management of Rapunzel Syndrome: A Case Series and Literature Review," J Pediatr Surg. 48(4):830-834.
Farra, R. et al. (Feb. 22, 2012; e-pub Feb. 16, 2012.). "First-In-Human Testing of a Wirelessly Controlled Drug Delivery Microchip," Sci Transl Med. 4(122):122ra21, 12 pages.
Fix, J.A. et al. (1993). "Controlled Gastric Emptying. III. Gastric Residence Time of a Nondisintegrating Geometric Shape in Human Volunteers," Pharm. Res. 10(7):1087-1089.
Fuhrmann, G. et al. (Jul. 2013). "Sustained Gastrointestinal Activity of Dendronized Polymer-Enzyme Conjugates," Nat Chem. 5:582-589.
Genco, A. et al. (2005). "Bioenterics Intragastric Balloon: The Italian Experience With 2,515 Patients," Obes Surg. 15:1161-1164.
Gordi, T. et al. (May 2008). "Pharmacokinetics of Gabapentin After a Single Day and at Steady State Following the Administration of Gastric-Retentive-Extended-Release and Immediate-Release Tablets: A Randomized, Open-Label, Multiple-Dose, Three-Way Crossover, Exploratory Study in Healthy Subjects," Clin Ther. 30(5):909-916.
Harrison, S.K. et al. (2006). "Comparison of Shear Modulus Test Methods," Virginia Tech. 8 pages.
Haslauer, C.M. et al. (Jul. 2015; e-published on Sep. 17, 2014). "Translating Textiles to Tissue Engineering: Creation and Evaluation of Microporous, Biocompatible, Degradable Scaffolds Using Industry Relevant Manufacturing Approaches and Human Adipose Derived Stem Cells," J. Biomed. Mater. Res. B Appl. Biomater. 103(5):1050-1058, 22 pages.
Hiemke, C. et al. (Sep. 2011; e-published on Sep. 27, 2011). "AGNP Consensus Guidelines for Therapeutic Drug Monitoring in Psychiatry: Update 2011," Pharmacopsychiatry 44(6):195-235.
Huang, W.M. et al. (Jul.-Aug. 2010). "Shape Memory Materials," Materials Today 13(7-8):54-61.
Hwang, S.-J. et al. (1998). "Gastric Retentive Drug-Delivery Systems," Crit Rev Ther Drug Carrier Syst. 15(3):243-284.
International Preliminary Report on Patentability for PCT/US2015/035425 dated Dec. 15, 2016, filed Jun. 11, 2015, 6 pages.
International Preliminary Report on Patentability for PCT/US2015/035429 dated Dec. 15, 2016, filed Jun. 11, 2015, 8 pages.
International Preliminary Report on Patentability dated Dec. 10, 2019 for PCT Application No. PCT/US2018/036743 filed on Jun. 8, 2018, 16 pages.
International Preliminary Report on Patentability dated Apr. 11, 2019 for PCT Application No. PCT/US2017/054608 filed on Sep. 29, 2017, 16 pages.
International Preliminary Report on Patentability dated Dec. 6, 2018 for PCT Application No. PCT/US2017/034856, filed on May 26, 2017, 11 pages.
International Preliminary Report on Patentability dated Dec. 22, 2016 for PCT Application No. PCT/US2015/035423 filed on Jun. 11, 2015, 11 pages.
International Preliminary Report on Patentability dated Jun. 21, 2018 for PCT Application No. PCT/US2016/065453 filed on Dec. 7, 2016, 11 pages.
International Preliminary Report on Patentability dated May 3, 2018 for PCT Application No. PCT/US2016/058309 filed on Oct. 21, 2016, 6 pages.
International Preliminary Report on Patentability dated Nov. 16, 2017 for PCT Application No. PCT/US2016/030020 filed on Apr. 29, 2016, 8 pages.
International Search Report and Written Opinion for PCT/US2015/035425 dated Sep. 15, 2015, filed Jun. 11, 2015, 8 pages.
International Search Report and Written Opinion for PCT/US2015/035429 dated Sep. 15, 2015, filed Jun. 11, 2015, 9 pages.
International Search Report and Written Opinion dated Dec. 14, 2017 for PCT Application No. PCT/US2017/054608 filed on Sep. 29, 2017, 18 pages.

(56) References Cited

OTHER PUBLICATIONS

International Search Report and Written Opinion dated Dec. 29, 2016 for PCT Application No. PCT/US2016/058309 filed on Oct. 21, 2016, 8 pages.

International Search Report and Written Opinion dated Feb. 28, 2017 for PCT Application No. PCT/US2016/065453 filed on Dec. 7, 2016, 14 pages.

International Search Report and Written Opinion dated Jul. 21, 2016 for PCT Application No. PCT/US2016/030020 filed on Apr. 29, 2016, 10 pages.

International Search Report and Written Opinion dated Nov. 13, 2017 for PCT Application No. PCT/US2017/034856, filed on May 26, 2017, 15 pages.

International Search Report and Written Opinion dated Sep. 10, 2018 for PCT Application No. PCT/US2018/036743 filed on Jun. 8, 2018, 26 pages.

International Search Report and Written Opinion dated Sep. 15, 2015 for PCT Application No. PCT/US2015/035423 filed on Jun. 11, 2015, 13 pages.

Invitation to Pay Additional Fees and, Where Applicable, Protest Fee, dated Sep. 5, 2017, for PCT Application No. PCT/US2017/034856, filed on May 26, 2017, 3 pages.

Jantratid, E. et al. (Jul. 2008; e-pub. Apr. 11, 2008). "Dissolution Media Simulating Conditions in the Proximal Human Gastrointestinal Tract: An Update," Pharm. Res. 25(7):1663-1676.

Javed, I. et al. (2014). "Drug Release Optimization From Microparticles of Poly(c-caprolactone) and Hydroxypropyl Methylcellulose Polymeric Blends: Formulation and Characterization," J. Drug Del. Sci. Tech. 24(6);607-612.

Kanis, L.A. et al. (2014). "Cellulose Acetate Butyrate/Poly(caprolactonetriol) Blends: Miscibility, Mechanical Properties, and in vivo Inflammatory Response," J. of Biomaterials Applications 29(5):654-661.

Kao, E.C. et al. (Jan. 1996). "Preparation of Glass Ionomer Cement Using N-acryloyl Substituted Amino Acid Monomers-Evaluationof Physical Properties," Dent Mater. 12:44-51.

Karim, Q.A. et al. (Sep. 3, 2010, e-pub. Jul. 19, 2010). "Effectiveness and Safety of Tenofovir Gel, an Antiretroviral Microbicide, for the Prevention of HIV Infection in Women," Science 329(5996):1168-1174, 19 pages.

Kethu, S.R. et al. (2012). "Endoluminal Bariatric Techniques," Gastrointestinal Endoscopy 76(1):1-7.

Khaled, S.A. et al. (Jan. 30, 2014). "Desktop 3D Printing of Controlled Release Pharmaceutical Bilayer Tablets," International Journal of Pharmaceutics 461(1-2):105-111, 17 pages.

Khanna, S.C. et al. (Sep. 1969). "Epoxy Resin Beads as a Pharmaceutical Dosage Form. I.: Method of Preparation," Journal of Pharmaceutical Sciences 58(9):1114-1117.

Kim, B.K. et al. (1996). "Polyurethanes Having Shape Memory Effects," Polymer 37(26):5781-5793.

Kim, Y.J. et al. (Dec. 24, 2013). "Biologically Derived Melanin Electrodes in Aqueous Sodium-Ion Energy Storage Devices," P Natl Acad Sci USA. 110(52): 20912-20917.

Lam, P.L. et al. (2014). "Advanced Progress of Microencapsulation Technologies: In Vivo and In Vitro Models for Studying Oral and Transdermal Drug Deliveries," J. Control Release 178:25-45.

Laulicht, B. et al. (Feb. 8, 2011). "Localization of Magnetic Pills," Proc Natl Acad Sci. 108(6):2252-2257.

Li, L.C. et al. (Oct. 16, 2002). "Polyanhydride Implant for Antibiotic Delivery—From the Bench to the Clinic," Adv Drug Deliv Rev. 54(7):963-986.

Lipton, S.A. (Jan. 2004). "Failures and Successes of NMDA Receptor Antagonists: Molecular Basis for the Use of Open-Channel Blockers Like Memantine in the Treatment of Acute and Chronic Neurologic Insults," NeuroRx: The Journal of the American Society for experimental Neuro Therapeutics 1(1):101-110.

Liu, Y. et al. (2009; e-pub. Aug. 29, 2008). "Review of Electro-Active Shape-Memory Polymer Composite," Compos Sci and Technol. 69(13):2064-2068.

López-Pousa, S. et al. (Sep. 2012). "Consumption of Pharmaceuticals in Primary Non-Alzheimer's Degenerative Dementias: A Cross-Sectional Study By the Registry of Dementias of Girona (ReDeGi)," Drugs Aging 29(9):733-740, 22 pages.

Marrazzo, J.M. et al. (Feb. 5, 2015). "Tenofovir-Based Preexposure Prophylaxis for HIV Infection Among African Women," N Engl J Med. 372(6):509-518.

Meng, Q. et al. (2009). "A Review of Shape Memory Polymer Composites and Blends," Composites Part A: Applied Science and Manufacturing 40(11):1661-1672.

Miao, L. et al. (2015). "Exploring the Tumor Microenvironment With Nanoparticles," Cancer Treat Res. 166:193-226, 36 pages.

Mintchev, M.P. et al. (Feb. 2010; e-pub Dec. 11, 2009). "Pilot Study of Temporary Controllable Gastric Pseudobezoars for Dynamic Non-Invasive Gastric Volume Reduction," Physiol Meas. 31(2):131-144.

Moes, A.J. (Jan. 1993). "Gastroretentive Dosage Forms," Crit Rev Ther Drug Carrier Syst. 10(2):143-195.

Mohr, R. et al. (Mar. 7, 2006; e-pub Feb. 28, 2006.). "Initiation of Shape-Memory Effect by Inductive Heating of Magnetic Nanoparticles in Thermoplastic Polymers," Proc Natl Acad Sci USA. 103(10):3540-3545.

Muthu, M.S. et al. (2008). "Studies on Biodegradable Polymeric Nanoparticles of Risperidone: in vitro and in vivo Evaluation," Nanomedicine 3(3):305-319.

Neto-Ferreira, R. et al. (2013). "Pleiotropic Effects of Rosuvastatin on the Glucose Metabolism and the Subcutaneous and Visceral Adipose Tissue Behavior in C57Bl/6 Mice," Diabetology Metabol Synd. 5:32, 10 pages.

Olson, A.J. et al. (Dec. 26, 2007; e-pub Dec. 18, 2007). "Chemical Mimicry of Viral Capsid Self-Assembly," Proc Natl Acad Sci USA 104(52):20731-20736.

Osterberg, L. et al. (Aug. 4, 2005). "Adherence to Medication," N Engl J Med. 353(5):487-497.

Phadke, A. et al. (Mar. 20, 2012; e-pub Mar. 5, 2012). "Rapid Self-Healing Hydrogels," Proc Natl Acad Sci USA 109(12):4383-4388.

Phillips, M.R. et al. (Jul. 1998). "Gastric Trichobezoar: Case Report and Literature Review," Mayo Clin Proc. 73(7):653-656.

Pittenger, C. (Jun. 2015, e-published on Jun. 11, 2015). "Glutamate Modulators in the Treatment of Obsessive-Compulsive Disorder," Psychiatr. Ann. 45(6):308-315, 13 pages.

Puso, M. A. et al. (Jan. 1, 2006). "A Stabilized Nodally Integrated Tetrahedral," International Journal for Numerical Methods in Engineering 67(6):841-867.

Rammes, G. et al. (Mar. 2008). "Pharmacodynamics of Memantine: An Update," Curr. Neuropharmacol. 6(1):55-78.

Ren, S. et al. (2009). "Noncovalently Connected Micelles Based on a β-cyclodextrin-Contaiing Polymer and Adamantane End-Capped Poly(e-ecaprolactone) via Host-Guest Interactions," J Polym Sci. 47:4267-4278.

Richter, J.E. et al. (Jun. 1987). "Esophageal Manometry in 95 Healthy Adult Volunteers. Variability of Pressures With Age and Frequency of "Abnormal" Contractions," Dig Dis Sci. 32(6):583-592.

Salessiotis, N. (Sep. 1972). "Measurement of the Diameter of the Pylorus in Man: Part I. Experimental Project for Clinical Application," The Amer J of Surgery. 124:331-333.

Salunke, D.M. et al. (Sep. 12, 1986). "Self-Assembly of Purified Polyomavirus Capsid Protein VP1," Cell 46(6):895-904, 10 pages.

Singer, S.J. et al. (Feb. 18, 1972). "The Fluid Mosaic Model of the Structure of Cell Membranes," Science 175(4023):720-731.

Singh, B.N. et al. (Feb. 3, 2000). "Floating Drug Delivery Systems: An Approach to Oral Controlled Drug Delivery via Gastric Retention," J Control Release 63(3):235-259.

Singh, P. et al. (2015, e-pub, Dec. 18, 2014). "Synthesis and Characterization of Nano Micelles of poly(N-acrylamidohexanoic acid)-b-poly(N-vinylcaprolactam) via RAFT Process: Solubilizing and Releasing of Hydrophobic Molecules," Polymer. 57:51-61.

Six-Pentagons (Dec. 23, 2017). "Six-Pentagons Polylink," retreived from http:/makingmathvisible.com/polylinks/polylinks-3.html, lasted visited Dec. 23, 2017, 4 pages.

(56) References Cited

OTHER PUBLICATIONS

Szakács, R. et al. (2012). "The "Blue" Side of Glutamatergic Neurotransmission: NMDA Receptor Antagonists as Possible Novel Therapeutics for Major Depression," Neuropsychopharmacol. Hung. 14(1):29-40.
Tao, H. et al. (Feb. 21, 2012). "Silk-Based Conformal, Adhesive, Edible Food Sensors," Adv Mater. 24(8):1067-1072.
Timmer, C.J. et al. (Sep. 2000). "Pharmacokinetics of Etonogestrel and Ethinylestradiol Released From a Combined Contraceptive Vaginal Ring," Clin Pharmacokinet. 39(3):233-242.
Traverso, G. et al. (Mar. 26, 2015). "Special Delivery for the Gut," Nature. 519:S19.
Uhrich, K.E. et al. (1999, e-pub. Oct. 26, 1999). "Polyermic Systems for Controlled Drug Relase," Chem. Rev. 99:3181-3198.
Ursan, I.D. et al. (Mar.-Apr. 2013). "Three-Dimensional Drug Printing: A Structured Review," J. Am. Pharm. Assoc. 53(2):136-144.
US Dept Health "Q3C—Tables and List Guidance for Industy," (2017). Retrieved from www.fda.gov/downloads/drugs/guidances/ucm073395.pdf, last visited Jun. 2017, 10 pages.
US Dept. Health "Guidance for Industry: Size, Shape, and Other Physical Attributes of Generic Tables and Capsules," (2013). Retrieved from www:v.regulations.gov/#ldocumentDetail;D=FDA-2013-N-1434-0002, last visited Dec. 2013, 11 pages.
Whitesides, G.M. et al. (Mar. 29, 2002). "Self-Assembly at all Scales," Science 295(5564):2418-2421.
Wilber, A.W. et al. (Nov. 7, 2009). "Self-Assembly of Monodisperse Clusters: Dependence on Target Geometry," J Chem Phys. 131(17):175101, 14 pages.
Wilber, A.W. et al. (Nov. 7, 2009; e-pub. Nov. 2, 2009). "Monodisperse Self-Assembly in a Model With Protein-Like Interactions," J Chem Phys. 131(17):175102, 11 pages.
Won, Y.W. et al. (Dec. 2014). "Oligopeptide Complex for Targeted Non-Viral Gene Delivery to Adipocytes," Nat Mater. 13:1157-1164.
Yerragunta, B. et al. (January-Mar. 2015). "Development of a Novel 3-Month Drug Releasing Risperidone Microspheres," J. Pharm Bioall Sci. 7(1):37-44.
Yu, D.G. et al. (Sep. 2008). "Three-Dimensional Printing in Pharmaceutics: Promises and Problems," J. Pharm. Sci. 97(9):3666-3690.
Zhang, S. et al. (Oct. 2015; e-pub. Jul. 27, 2015). "A Ph-Responsive Supramolecular Polymer Gel as an Enteric Elastomer for Use in Gastric Devices," Nature Materials 14(10):1065-1071, 19 pages.
Zhang, X. et al. (2013; e-pub Oct. 15, 2012). "Biodegradable Shape Memory Nanocomposites With Thermal and Magnetic Field Responsiveness," J Biomater Sci Polym Ed. 24(9):1057-1070.
Zu, Y. et al. (2008, e-pub. Sep. 26, 2008). "Effect of Neutralization of poly(methacrylic acid-co-ethyl acrylate) on Drug Release from Enteric-Coated Pellets Upon Accelerated Storage," Drug Dev. Ind. Pharm. 33(4):457-473.
Murphy, CS, et al. (Oct. 2009). "Gastro-Retentive Drug Delivery Systems: Current Developments in Novel System Design and Evaluation"; Curr. Drug Deliv. 6(5):451-460.
Welding Techniques for Thermoplastics (2021). retrieved from the Internet: URL:https://www.twi-global.com/technical-knowledge/job-knowledge/welding-techniques-forthermoplastics-055 (http:/web.archive.org/web/20150416235739/ http://www.twiglobal.com/technical-knowledge/job-knowledge/welding-techniques-for-thermoplastics-055/, last visited Mar. 17, 2021, 8 pages.
Yang X, et al. (May 14, 2014), e-pub. May 5, 2014). "Triple Shape Memory Effect of Star-Shaped Polyurethane"; ACS Appl Mater Interfaces 6(9):6545-6554.
Extended European Search Report dated Jun. 4, 2021 for Application No. EP 18813515.6, 8 pages.
Nakamichi, K. (2004). "The Preparation of Enteric Solid Dispersions With Hydroxypropylmethylcellulose Acetate Succinate Using a Twin-Screw Extruder," J. Drug Del. Sci. Tech. 3(14):193-198.
Abraham, N. (May 15, 2015). "Dow Corning QP1-2 Liquid Silicone Rubber Supports Cost-Effective Medical Device Designs," Medical Design & Outsourcing, retrieved from the Internet https://www.medicaldesignandoutscourcing.com/dow-coming-qp1-2-liquid-silicone-rubber-supports-cost-effective-medical-device-designs/, last visited Nov. 16, 2021, 8 pages.
Chourasia, M.K. et al. (2003). "Pharmaceutical Approaches to Colon Targeted Drug Delivery Systems," J. Pharm. Pharmaceut Sci. 6(1):33-66.
Woodruff, M.A. et al. (Apr. 2010, e-pub. Apr. 7, 2010). "The Return of a Forgotten Polymer—Polycaprolactone in the 21st Century," Progress in Polymer Science 35:1217-1256.
Non-Final Office Action, dated Aug. 24, 2023, for U.S. Appl. No. 17/836,972, filed Jun. 9, 2022, 26 pages.
U.S. Appl. No. 18/272,786, filed Jan. 19, 2022 by Kanasty, et al. (Copy not submitted herewith pursuant to the waiver of 37 C.F.R. § 1.98(a)(2)(iii) issued by the Office on Sep. 21, 2004).

* cited by examiner

FIG. 6B1

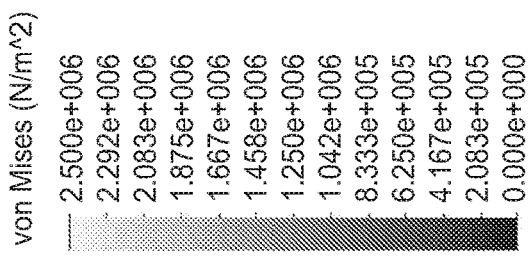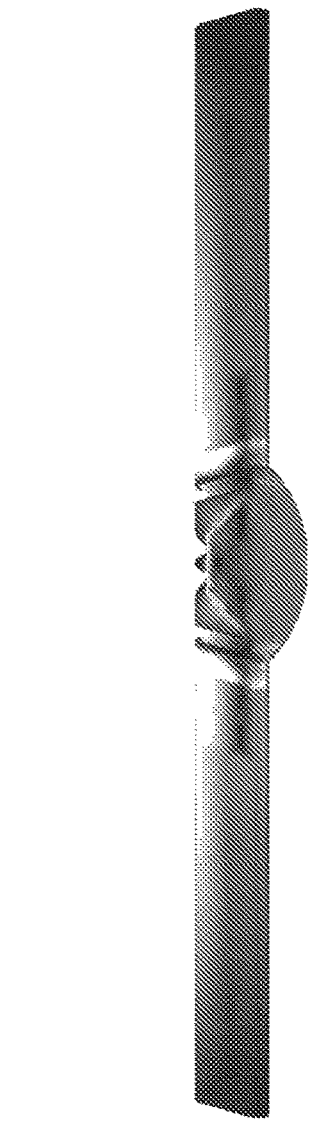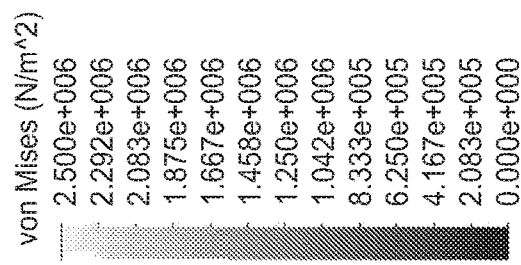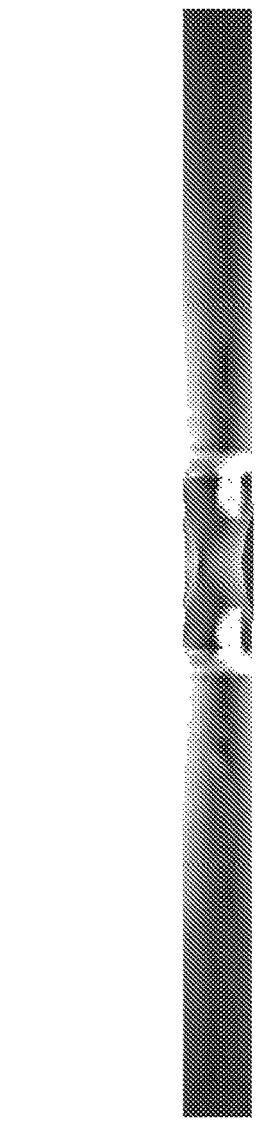
FIG. 19C
FIG. 19D

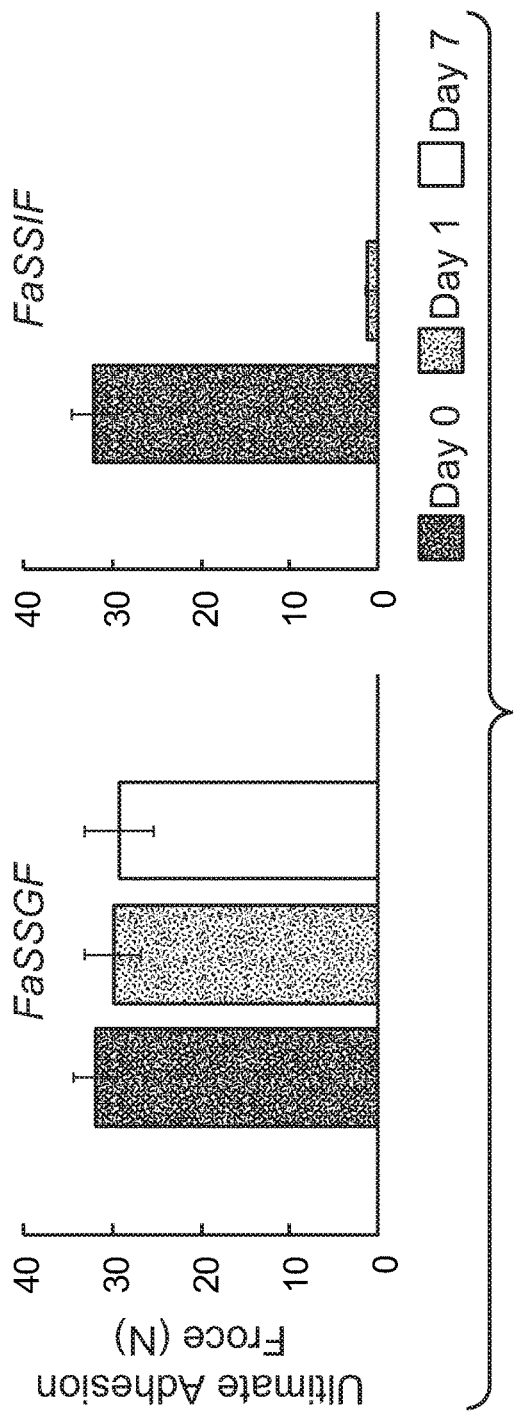
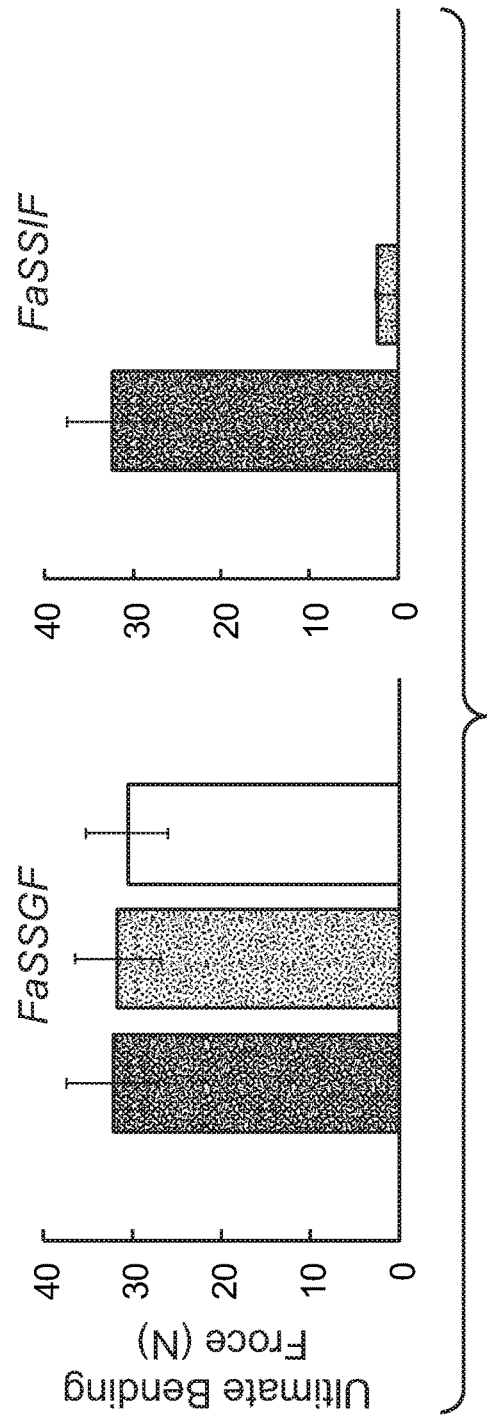
FIG. 25A
FIG. 25B

GEOMETRIC CONFIGURATIONS FOR GASTRIC RESIDENCE SYSTEMS

CROSS-REFERENCE TO RELATED APPLICATIONS

This application is a National Phase filing under 35 U.S.C. § 371 of International Application No. PCT/US2016/065453 having an International Filing Date of Dec. 7, 2016, which claims priority benefit of U.S. Provisional Patent Application No. 62/264,811, filed Dec. 8, 2015. The entire contents of those applications are hereby incorporated by reference herein.

FIELD OF THE INVENTION

The invention relates to systems which remain in the stomach for extended periods for sustained release of pharmaceuticals, and methods of use thereof.

BACKGROUND OF THE INVENTION

Gastric residence systems are delivery systems for therapeutic agents which remain in the stomach for days to weeks, or even over longer periods, during which time drugs or other agents can elute from the systems for absorption in the gastrointestinal tract. Examples of such systems are described in International Patent Application No. PCT/US2015/035423 (WO 2015/191920); Zhang et al., Nature Materials 14:1065-1071 (2015); and Bellinger et al., Science Translational Medicine 8(365): 365ra157 (2016). Gastric residence systems are most conveniently administered to a patient via a capsule in a compacted form. Upon dissolution of the capsule in the stomach, the systems expand to a size which resists passage through the pyloric sphincter over the desired residence period. These characteristics require careful selection of both the materials from which the system is constructed, and the dimensions and arrangement of the system.

The current invention describes advancements in design and manufacture of gastric residence systems which extend shelf life by, for example, minimizing system stress during storage. The manufacturing methods described herein both lower the cost of manufacture and improve the performance of the systems when administered to a patient.

SUMMARY OF THE INVENTION

The invention provides gastric residence systems, which are administered to the stomach of a patient, for sustained release of a therapeutic agent, and methods of making and using such gastric residence systems.

In one embodiment, the invention provides gastric residence systems for administration to the stomach of a patient, comprising an elastomer component, wherein the elastomer can be mono-concave, bi-concave, concavo-convex, or toroidal; a plurality of at least three carrier polymer-agent components comprising a carrier polymer and a therapeutic agent or a salt thereof, wherein each of the plurality of carrier polymer-agent components comprises an elongate member comprising a proximal end, a distal end, and an outer surface therebetween; wherein the proximal end of each elongate member can be attached to the elastomer component and projects radially from the elastomer component, each elongate member having its distal end not attached to the elastomer component and located at a larger radial distance from the elastomer component than the proximal end; wherein the elastomer can be attached directly or indirectly to each elongate member by an intercomponent anchor; wherein the gastric residence system can be configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach.

In some embodiments, the gastric residence systems have a first portion of each intercomponent anchor located within the elastomer, and a second portion of each intercomponent anchor located within either a) a corresponding first segment of interfacing polymer, wherein each corresponding first segment of interfacing polymer is also attached directly or indirectly to a corresponding one of the elongate members; or b) a corresponding segment of linker, wherein each corresponding segment of linker is also attached directly or indirectly to a corresponding one of the elongate members; or c) a corresponding one of the elongate members. In some embodiments, the gastric residence systems can have a first portion of each intercomponent anchor located within the elastomer, and a second portion of each intercomponent anchor is located within a corresponding first segment of interfacing polymer, wherein each corresponding first segment of interfacing polymer is also attached to a corresponding linker, such as an enteric linker or time-dependent linker, and each corresponding linker (such as an enteric linker or time-dependent linker) is attached to a corresponding one of the elongate members.

In some embodiments of the gastric residence systems, a first portion of each intercomponent anchor is located within the elastomer, and a second portion of each intercomponent anchor is located within a corresponding first segment of interfacing polymer, wherein each corresponding first segment of interfacing polymer is also attached to a corresponding linker, such as an enteric linker or time-dependent linker, wherein each corresponding linker (such as an enteric linker or time-dependent linker) is attached to a corresponding second segment of interfacing polymer; and each corresponding second segment of interfacing polymer is attached to a corresponding one of the elongate members.

In any of the embodiments of the gastric residence systems described herein, the linkers can comprise hydroxypropyl methyl cellulose acetate succinate (HPMCAS) and polycaprolactone (PCL); that is, the linkers can be enteric linkers. The ratio of HPMCAS to polycaprolactone can be between about 80% HPMCAS:20% PCL to about 20% HPMCAS:80% PCL. The linker can further comprise a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

In any of the embodiments of the gastric residence systems described herein which use intercomponent anchors, the elastomer can be overmolded over the first portions of the intercomponent anchors. In any of the embodiments of the gastric residence systems described herein which use intercomponent anchors, the first segment of each interfacing polymer, linker, or elongate member can be overmolded over the corresponding second portion of the intercomponent anchors.

In any of the embodiments of the gastric residence systems described herein, the elastomer can comprise a material selected from the group comprising silicone rubber, a polysiloxane, polydimethylsiloxane, silicone rubber mixed with silica, a polysiloxane mixed with silica, and polydimethylsiloxane mixed with silica. The elastomer can comprise silicone rubber. The elastomer can comprise a polysiloxane. The elastomer can comprise polydimethylsiloxane. The elastomer can comprise silicone rubber mixed with silica. The elastomer can comprise a polysiloxane mixed with silica. The elastomer can comprise polydimethylsiloxane mixed with silica.

In any of the embodiments of the gastric residence systems described herein which use intercomponent anchors, the intercomponent anchors can comprise a material selected from the group consisting of polycarbonate, polyphenylsulfone, a polyphenylene ether-polystyrene blend, polyphenylene ether, polystyrene, and polyether ether ketone.

In any of the embodiments of the gastric residence systems described herein, the elastomer can be mono-concave, bi-concave, concavo-convex, or toroidal. The elastomer can be mono-concave. The elastomer can be bi-concave. The elastomer can be concavo-convex. The elastomer can be toroidal. In any of the embodiments of the gastric residence systems described herein, the elastomer can be bi-concave or concavo-convex. The elastomer can be bi-concave. The elastomer can be concavo-convex.

In any of the embodiments of the gastric residence systems described herein, the elastomer can be asterisk-shaped. The center of the asterisk comprises the mono-concave, bi-concave, or concavo-convex portion of the corresponding mono-concave, bi-concave, or concavo-convex elastomer.

In any of the embodiments of the gastric residence systems described herein, the elastomer can comprise a material which has a compression set of less than about 15%. In any of the embodiments of the gastric residence systems described herein, the elastomer can comprise a material which has a tear strength greater than about 20 kN/m. In any of the embodiments of the gastric residence systems described herein, the elastomer can comprise a material which has a compression set of less than about 15% and a tear strength greater than about 20 kN/m.

In any of the embodiments of the gastric residence systems described herein, the gastric residence system can have a folding force of at least about 0.2 newtons. In any of the embodiments of the gastric residence systems described herein, the gastric residence system can have a folding force of at least about 0.2 newtons when the elongate members are at an angle between about 0 degrees and about 70 degrees from the fully unfolded plane of the system. In any of the embodiments of the gastric residence systems described herein, the maximum folding force of the gastric residence system can occur when the elongate members are at an angle between about 0 degrees and about 70 degrees from the fully unfolded plane of the system.

In any of the embodiments of the gastric residence systems described herein, the gastric residence system has an x-y bending force of at least about 0.2 newtons. In any of the embodiments of the gastric residence systems described herein, the gastric residence system has an x-y bending force of at least about 0.2 newtons when the arms are bent more than about 5 degrees from the position occupied when not subjected to an x-y bending force. In any of the embodiments of the gastric residence systems described herein, the gastric residence system has an x-y bending force of at least about 0.2 newtons when the arms are bent more than about 10 degrees from the position occupied when not subjected to an x-y bending force.

In any of the embodiments of the gastric residence systems described herein, the elastomer can be formed by injection molding.

In any of the embodiments of the gastric residence systems described herein, the plurality of carrier polymer-agent components can have a triangular cross-section. Triangular cross-sections include triangular cross-sections with rounded or filleted edges and corners.

In any of the embodiments of the gastric residence systems described herein, the elastomer can be asterisk-shaped and the branches of the asterisk can have a triangular cross-section. Triangular cross-sections include triangular cross-sections with rounded or filleted edges and corners.

In any of the embodiments of the gastric residence systems described herein, the plurality of carrier polymer-agent components can comprise between four and eight carrier polymer-agent components inclusive, between five and seven carrier polymer-agent components inclusive, or six carrier polymer-agent components.

In some embodiments, the invention provides gastric residence systems for administration to the stomach of a patient, comprising an elastomer component, wherein the elastomer is mono-concave, bi-concave, concavo-convex, or toroidal; a plurality of at least three carrier polymer-agent components comprising a carrier polymer and a therapeutic agent or a salt thereof, wherein each of the plurality of carrier polymer-agent components can comprise an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach. In some embodiments, the proximal end of each elongate member can be directly attached to the elastomer component. In some embodiments, the proximal end of each elongate member can be indirectly attached to the elastomer component. In some embodiments, the elastomer can be bi-concave. In some embodiments, the elastomer can be mono-concave. In some embodiments, the elastomer can be concavo-convex. In some embodiments, the elastomer can be toroidal.

In any of the embodiments of the gastric residence systems described herein, the elastomer can comprise a material which has a compression set of less than about 15%. In any of the embodiments of the gastric residence systems described herein, the elastomer can comprise a material which has a tear strength greater than about 20 kN/m. In any of the embodiments of the gastric residence systems described herein, the elastomer can comprise a material which has a compression set of less than about 15% and a tear strength greater than about 20 kN/m.

In some embodiments, the gastric residence system can have a folding force of at least about 0.2 newtons when the elongate members are at an angle between about 0 degrees and about 70 degrees from the fully unfolded plane of the system. In some embodiments, wherein the maximum folding force of the gastric residence system occurs when the elongate members are at an angle between about 0 degrees and about 70 degrees from the fully unfolded plane of the system.

In any of the embodiments of the gastric residence systems described herein, the gastric residence system has an x-y bending force of at least about 0.2 newtons. In any of the embodiments of the gastric residence systems described herein, the gastric residence system has an x-y bending force of at least about 0.2 newtons when the arms are bent more than about 5 degrees from the position occupied when not subjected to an x-y bending force. In any of the embodiments of the gastric residence systems described herein, the gastric residence system has an x-y bending force of at least about 0.2 newtons when the arms are bent more than about 10 degrees from the position occupied when not subjected to an x-y bending force.

In any of the embodiments of the gastric residence systems described herein, the gastric residence system has a folding force of at least about 0.2 newtons, and an x-y bending force of at least about 0.2 newtons. In any of the embodiments of the gastric residence systems, the x-y bending force required to bend the structure is at least about 0.2 Newtons (N), at least about 0.3 N, at least about 0.4 N, at least about 0.5 N, at least about 0.75 N, at least about 1 N, at least about 1.5 N, at least about 2 N, at least about 2.5 N, at least about 3 N, at least about 4 N, or at least about 5 N; and the folding force required to fold the structure is at least about 0.2 Newtons (N), at least about 0.3 N, at least about 0.4 N, at least about 0.5 N, at least about 0.75 N, at least about 1 N, at least about 1.5 N, at least about 2 N, at least about 2.5 N, at least about 3 N, at least about 4 N, or at least about 5 N. In any of the embodiments of the gastric residence systems, the x-y bending force required to bend the structure is at least about 0.2 N; and the folding force required to fold the structure is at least about 0.2 N. In any of the embodiments of the gastric residence systems, the x-y bending force required to bend the structure is at least about 0.2 N; and the folding force required to fold the structure is at least about 0.3 N. In any of the embodiments of the gastric residence systems, the x-y bending force required to bend the structure is at least about 0.3 N; and the folding force required to fold the structure is at least about 0.2 N. In any of the embodiments of the gastric residence systems, the x-y bending force required to bend the structure is at least about 0.2 N; and the folding force required to fold the structure is at least about 0.4 N. In any of the embodiments of the gastric residence systems, the x-y bending force required to bend the structure is at least about 0.4 N; and the folding force required to fold the structure is at least about 0.2 N. In any of the embodiments of the gastric residence systems, the x-y bending force required to bend the structure is at least about 0.4 N; and the folding force required to fold the structure is at least about 0.4 N. In any of the embodiments, the x-y bending force required to bend the structure is between about 0.2 N to about 5 N, between about 0.3 N to about 5 N, between about 0.4 N to about 5 N, between about 0.5 N to about 5 N, between about 0.75 N to about 5 N, between about 1 N to about 5 N, between about 1.5 N to about 5 N, between about 2 N to about 5 N, between about 2.5 N to about 5 N, between about 3 N to about 5 N, or between about 4 N to about 5 N; and the folding force required to fold the structure is between about 0.2 N to about 5 N, between about 0.3 N to about 5 N, between about 0.4 N to about 5 N, between about 0.5 N to about 5 N, between about 0.75 N to about 5 N, between about 1 N to about 5 N, between about 1.5 N to about 5 N, between about 2 N to about 5 N, between about 2.5 N to about 5 N, between about 3 N to about 5 N, or between about 4 N to about 5 N. In any of the embodiments, the x-y bending force required to bend the structure is between about 0.2 N to about 4 N, between about 0.3 N to about 4 N, between about 0.4 N to about 4 N, between about 0.5 N to about 4 N, between about 0.75 N to about 4 N, between about 1 N to about 4 N, between about 1.5 N to about 4 N, between about 2 N to about 4 N, between about 2.5 N to about 4 N, between about 3 N to about 4 N, or between about 3.5 N to about 4 N; and the folding force required to fold the structure is between about 0.2 N to about 4 N, between about 0.3 N to about 4 N, between about 0.4 N to about 4 N, between about 0.5 N to about 4 N, between about 0.75 N to about 4 N, between about 1 N to about 4 N, between about 1.5 N to about 4 N, between about 2 N to about 4 N, between about 2.5 N to about 4 N, between about 3 N to about 4 N, or between about 3.5 N to about 4 N. In any of the embodiments, the x-y bending force required to bend the structure is between about 0.2 N to about 4 N, between about 0.2 N to about 3.5 N, between about 0.2 N to about 3 N, between about 0.2 N to about 2.5 N, between about 0.2 N to about 2 N, between about 0.2 N to about 1.5 N, between about 0.2 N to about 1 N, between about 0.2 N to about 0.75 N, between about 0.2 N to about 0.5 N, between about 0.2 N to about 0.4 N, or between about 0.2 N to about 0.3 N; and the folding force required to fold the structure is between about 0.2 N to about 4 N, between about 0.2 N to about 3.5 N, between about 0.2 N to about 3 N, between about 0.2 N to about 2.5 N, between about 0.2 N to about 2 N, between about 0.2 N to about 1.5 N, between about 0.2 N to about 1 N, between about 0.2 N to about 0.75 N, between about 0.2 N to about 0.5 N, between about 0.2 N to about 0.4 N, or between about 0.2 N to about 0.3 N.

In any of the embodiments of the gastric residence systems described herein, the elastomer can comprise a material selected from the group comprising silicone rubber, a polysiloxane, polydimethylsiloxane, silicone rubber mixed with silica, a polysiloxane mixed with silica, and polydimethylsiloxane mixed with silica. The elastomer can be formed by injection molding.

In any of the embodiments of the gastric residence systems described herein, the plurality of carrier polymer-agent components can have a triangular cross-section. Triangular cross-sections include triangular cross-sections with rounded or filleted edges and corners.

In any of the embodiments of the gastric residence systems described herein, the elastomer can be asterisk-shaped and the branches of the asterisk can have a triangular cross-section. Triangular cross-sections include triangular cross-sections with rounded or filleted edges and corners.

In any of the embodiments of the gastric residence systems described herein, the plurality of carrier polymer-agent components can comprise between four and eight carrier polymer-agent components inclusive, between five and seven carrier polymer-agent components inclusive, or six carrier polymer-agent components.

In some embodiments, the invention provides a method of making an elastomer-intercomponent anchor assembly, comprising overmolding an elastomer component over a first portion of a plurality of at least three intercomponent anchors. In some embodiments, the method further comprises overmolding each one of a plurality of interfacing polymer components over a second portion of a corresponding one of the at least three intercomponent anchors of the elastomer-intercomponent anchor assembly. That is, each second portion of each intercomponent anchor is overmolded with a separate interfacing polymer component, such that the number of interfacing polymer components is equal to the number of intercomponent anchors.

In some embodiments, the invention provides an elastomer-intercomponent anchor assembly, comprising a plurality of intercomponent anchors comprising a first portion and a second portion; and an elastomer, wherein the elastomer covers the first portion of the plurality of intercomponent anchors. In some embodiments, the invention provides an elastomer-intercomponent anchor-interfacing polymer assembly comprising a plurality of interfacing polymer components covering the second portion of a corresponding one of the at least three intercomponent anchors of the elastomer-intercomponent anchor assembly. That is, each second portion of each intercomponent anchor is covered by a separate interfacing polymer component, such that the number of interfacing polymer components is equal to the number of intercomponent anchors.

In some embodiments, the invention provides a method of making a gastric residence system assembly, comprising overmolding an elastomer component over a first portion of a plurality of at least three intercomponent anchors; and overmolding a plurality of interfacing polymer components over a second portion of each intercomponent anchor, wherein each interfacing polymer component is overmolded over a corresponding one of the at least three intercomponent anchors. That is, each second portion of each intercomponent anchor is overmolded with a separate interfacing polymer component, such that the number of interfacing polymer components is equal to the number of intercomponent anchors.

In any of the embodiments described herein, the overmolding of the elastomer component and the overmolding of the interfacing polymer components can be performed by injection molding. In any of the embodiments described herein, the intercomponent anchors can comprise a material selected from the group consisting of polycarbonate, polyphenylsulfone, a polyphenylene ether-polystyrene blend, polyphenylene ether, polystyrene, and polyether ether ketone. In any of the embodiments described herein, the elastomer component can comprise a material selected from the group comprising silicone rubber, a polysiloxane, polydimethylsiloxane, silicone rubber mixed with silica, a polysiloxane mixed with silica, and polydimethylsiloxane mixed with silica.

In some embodiments of the method, the plurality of intercomponent anchors can be connected by a first scaffold, where the first scaffold maintains the anchors in a desired position prior to overmolding the elastomer component. In some embodiments of the method, the method further comprises removing the first scaffold after overmolding the elastomer component.

In some embodiments of the method, the overmolded plurality of interfacing polymer components can be connected by a second scaffold formed during the overmolding of the interfacing polymer components, where the second scaffold maintains the interfacing polymer components in a desired position. In some embodiments of the method, the method further comprises removing the second scaffold after overmolding the interfacing polymer components.

In some embodiments of the method, the method further comprises trimming the interfacing polymer components to a radial length of about 1 mm to 5 mm. That is, the length of the interfacing polymer components, when measured from the point most proximal to the elastomer to the point most distal from the elastomer, can be trimmed to about 1 mm to about 5 mm.

In some embodiments of the method, the method further comprises attaching a plurality of linkers to the plurality of interfacing polymer components, wherein each one of the linkers can be attached to a corresponding one of the interfacing polymer components. In any of the embodiments described herein, the linkers can be enteric linkers or time-dependent linkers.

In some embodiments of the method, the method further comprises attaching a plurality of carrier polymer-agent components to the plurality of linkers, wherein each one of the carrier polymer-agent components can be attached to a corresponding one of the linkers, to form the gastric residence system.

In some embodiments, the invention provides a method of forming a gastric residence system, comprising comprising attaching a plurality of interfacing polymer-(carrier polymer-agent) components to the plurality of linkers, wherein each one of the interfacing polymer-(carrier polymer-agent) components can be attached to a corresponding one of the linkers, to form the gastric residence system.

In any embodiment of the method described herein, the attaching of a first component to a second component can be performed by heat welding. The heat welding can be performed by contacting a first component with a heated object (such as a heated platen) at a first temperature to form a heated surface on the first component, contacting a second component with a heated object (such as a heated platen) at a second temperature to form a heated surface on the second component, and contacting the heated surface of the first component with the heated surface of the second component to form a heat weld between the first component and the second component. The method can further comprise applying pressure during the contacting step.

In some embodiments of the method described herein, the attaching of a linker to a carrier polymer-agent component (or to an interfacing polymer-(carrier polymer-agent) component) can be performed by heat welding. The heat welding can be performed by contacting each linker with a heated object (such as a heated platen) at a first temperature to form a heated surface on the linker, contacting each carrier polymer-agent component (or each interfacing polymer-(carrier polymer-agent) component) with a heated object (such as a heated platen) at a second temperature to form a heated surface on the carrier polymer-agent component, and contacting the heated surface of the linker with the heated surface of the carrier polymer-agent component (or the heated surface of the interfacing polymer-(carrier polymer-agent) component) to form a heat weld between each linker and each corresponding carrier polymer-agent component (or each interfacing polymer-(carrier polymer-agent) component).

In any embodiment of the method where a first component is attached to a second component by heat welding, the method can further comprise annealing the heat weld. The annealing can be performed by heating the gastric residence system in an oven at a third temperature. The annealing can be performed by irradiating the heat weld with infrared radiation.

In any embodiment of the method described herein, the attaching of a first component to a second component can be performed by infrared welding. In any embodiment of the method where a first component is attached to a second component by infrared welding, the method can further comprise annealing the infrared weld. The annealing can be performed by heating the gastric residence system in an oven. The annealing can be performed by irradiating the infrared weld with infrared radiation.

In any of the embodiments of the gastric residence systems described herein, the elastomer component can comprise a plurality of branches equal in number to the plurality of at least three carrier polymer-agent components attached to the elastomer, and the elastomer further can comprise webbing between the plurality of branches.

In any of the embodiments of the elastomer-intercomponent anchor assembly or the elastomer-intercomponent anchor-interfacing polymer assembly, the elastomer component can comprise a plurality of branches (where the plurality of branches is equal in number to the plurality of at least three carrier polymer-agent components to be attached directly or indirectly to the elastomer), and the elastomer further can comprise webbing between the plurality of branches.

In one embodiment, the invention provides a gastric residence system for administration to the stomach of a patient, said gastric residence system comprising an elastomer component, a plurality of at least three carrier polymer-agent components comprising a carrier polymer and a therapeutic agent or a salt thereof, wherein each of the plurality of carrier polymer-agent components is an elongate member comprising a proximal end, a distal end, and a curved outer surface therebetween; wherein the proximal end of each elongate member is attached to the elastomer and projects radially from the elastomer, each elongate member having its distal end not attached to the elastomer and located at a larger radial distance from the elastomer than the proximal end; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach.

In some embodiments, a separation angle between one elongate member of the plurality of at least three carrier polymer-agent components to a nearest adjacent other elongate member is approximately equal for each elongate member.

In some embodiments, each elongate member is comprised of at least two segments, each segment comprising a proximal end, a distal end, and a curved outer surface therebetween, where the segments are linked together by an enteric polymer, and the enteric polymer is adherent to a distal end of a first segment and an adjacent proximal end of a second segment, thereby joining the first and second segments.

In some embodiments, each elongate member is comprised of at least two segments, each segment comprising a proximal end, a distal end, and a curved outer surface therebetween, where the segments are linked together by an enteric polymer, and the enteric polymer is a film wrapped around a distal portion of the curved outer surface of a first segment and an adjacent proximal portion of the curved outer surface of a second segment, thereby forming a collar joint between the first and second segments.

In some embodiments wherein each elongate member is comprised of at least two segments, the distal end of the first segment is concave and the adjacent proximal end of the second segment is convex, or the distal end of the first segment is convex and the adjacent proximal end of the second segment is concave.

In some embodiments where the enteric polymer is adherent to a distal end of a first segment and an adjacent proximal end of a second segment, the enteric polymer adherent to the ends of the segments extends beyond the area between the ends of the segments.

In some embodiments, the enteric polymer is selected from the group consisting of poly(methacrylic acid-co-ethyl acrylate), cellulose acetate phthalate, cellulose acetate succinate, and hydroxypropyl methylcellulose phthalate.

In any of the embodiments of the gastric residence system, the carrier polymer can comprise polycaprolactone.

In any of the embodiments of the gastric residence system, the elastomer can comprise cross-linked polycaprolactone.

In any of the embodiments of the gastric residence system, the gastric residence system can measure at least about 2 cm in length over at least two perpendicular directions.

In any of the embodiments of the gastric residence system, the carrier polymer-agent components can be produced by hot melt extrusion.

In any of the embodiments of the gastric residence system, the therapeutic agent or a salt thereof can comprise particles, wherein at least about 80% of the mass of particles have sizes between about 2 microns and about 50 microns in diameter. The particles can be crystalline or amorphous.

In any of the embodiments of the gastric residence system, the elastomer component can have the approximate shape of an oblate ellipsoid, that is, a disk.

In any of the embodiments of the gastric residence system, the elastomer component can have an approximately asterisk shape, wherein the asterisk shape has at least three branches, and the proximal end of each elongate member is attached to a different branch of the elastomer.

In further embodiments, the invention provides a gastric residence system according to any embodiment described herein, wherein the gastric residence system is in its compacted form in a container or capsule.

In further embodiments, the invention provides a method of making a gastric residence system, comprising forming an elastomer component; forming a plurality of at least three carrier polymer-agent components, which are elongate members comprising a proximal end and a distal end; and attaching the elongate members to the elastomer component. The method can further comprise compacting the gastric residence system and inserting the system into a container suitable for oral administration or administration through a gastric tube or feeding tube.

In the method of making the systems, forming a plurality of at least three carrier polymer-agent components which are elongate members can comprise forming the elongate members from at least two segments. Forming the elongate members from at least two segments can comprise forming a collar joint between the segments.

In the method of making the systems, the elastomer component can be asterisk-shaped with a plurality of at least three branches.

In the method of making the systems, attaching the elongate members to the elastomer component can comprise adhering the elongate members to the elastomer component.

In the method of making the systems, attaching the elongate members to the elastomer component can comprise forming a collar joint between the elongate members and the branches of the asterisk-shaped elastomer component.

In further embodiments, the invention provides methods of administering a therapeutic agent to a patient, comprising administering a gastric residence system according to any of the embodiments disclosed herein. In some embodiments, the gastric residence system has a gastric retention period of about D days, and a new gastric residence system is administered to the patient every D days over a total desired treatment period. The gastric retention period can be about three days, about five days, about seven days, about fourteen days, or about thirty days.

This disclosure provides several embodiments. It is contemplated that any features from any embodiment can be combined with any features from any other embodiment where possible. In this fashion, hybrid configurations of the disclosed features are within the scope of the present invention.

BRIEF DESCRIPTION OF THE DRAWINGS

FIG. 19C shows stress distribution in a concavo-convex design (deep convex).

FIG. 19D shows stress distribution in a biconcave disk design.

FIG. 25A shows the change in the adhesion force of an arm with a linker after immersion in FaSSGF and FaSSIF.

FIG. 25B shows the change in the bending force of an arm with a linker after immersion in FaSSGF and FaSSIF.

DETAILED DESCRIPTION OF THE INVENTION

Definitions

Figure 1:
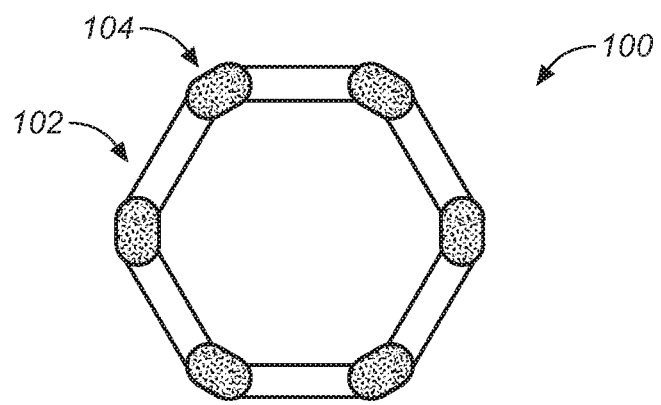
FIG. 1 shows one embodiment of a gastric residence system of the invention.

A "carrier polymer" is a polymer suitable for blending with a therapeutic agent, such as a drug, for use in the invention.

A "dispersant" is defined as a substance which aids in the minimization of particle size of therapeutic agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of therapeutic agent that is not the therapeutic agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component.

"Substantially constant plasma level" refers to a plasma level that remains within plus-or-minus 25% of the average plasma level measured over the period that the gastric residence system is resident in the stomach.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

As used herein, the singular forms "a", "an", and "the" include plural references unless indicated otherwise or the context clearly dictates otherwise.

A "patient," "individual," or "subject" refers to a mammal, preferably a human or a domestic animal such as a dog or cat. In a preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional therapeutic agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional therapeutic agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of a therapeutic agent is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

General Principles of Operation of Gastric Residence Systems

Gastric residence systems are designed to be administered to the stomach of a patient, either by swallowing or other method of administration (for example, feeding tube or gastric tube). Once a gastric residence system is in place in the stomach, the system remains in the stomach for the desired residence time (such as three days, seven days, two weeks, etc.), which thus entails resistance to passage through the pyloric valve separating the stomach and the small intestine. It releases therapeutic agent over the period of residence, with minimal burst release. While resident in the stomach, the system does not interfere with the normal passage of food or other gastric contents. The system passes out of the stomach at the end of the desired residence time, and is readily eliminated from the patient. If the system prematurely passes from the stomach into the small intestine, it does not cause intestinal obstruction, and again is readily eliminated from the patient.

Administration

The gastric residence system is contained in a capsule or other container which can be swallowed by the patient, or which is otherwise able to be administered to the stomach for patients unable to swallow (e.g., via gastrostomy tube, feeding tube, gastric tube, or other route of administration to the stomach). Accordingly, the gastric residence system is capable of being compacted or compressed into a form small enough to be swallowed or otherwise administered, and is preferably placed inside a container such as a capsule. Thus, the system is configured to have a compacted form in a container (by folding, compression, or other method of reducing the size of the system).

Figure 2:
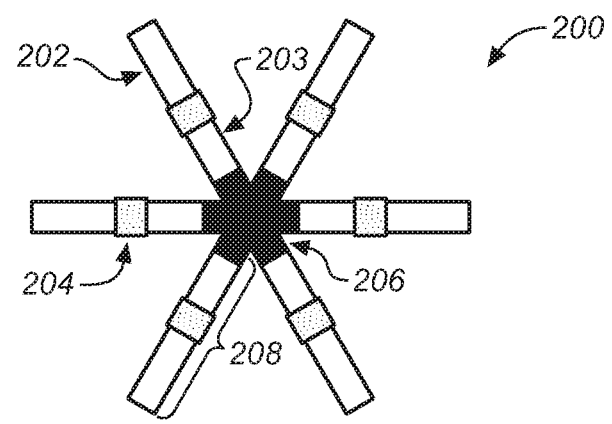
FIG. 2 shows another embodiment of a gastric residence system of the invention.
Figure 2A:
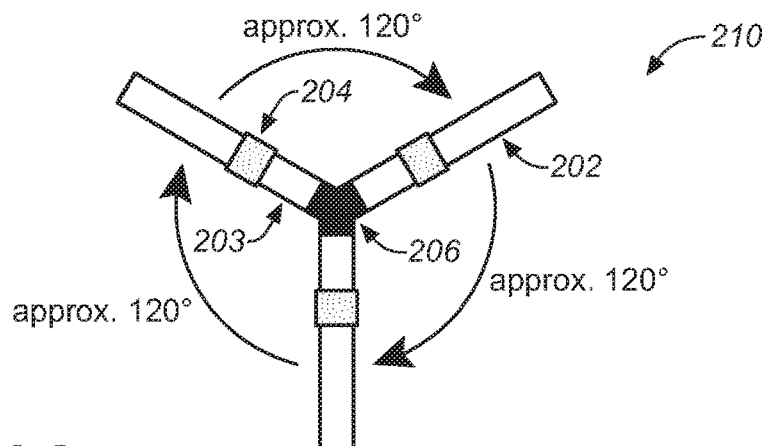
FIG. 2A shows another embodiment of a gastric residence system of the invention.

Such compressible or compactable systems are shown in FIG. 1, FIG. 2, and FIG. 2A. The ring-shaped design for a gastric residence system shown in FIG. 1 can be twisted into a double helix, which compresses the structure to a roughly cylindrical shape which can be placed in a capsule. The star-shaped (stellate) design for a gastric residence system shown in FIG. 2 and FIG. 2A can be folded at its central portion, which can then be placed into a capsule. The system is administered to a patient by swallowing the capsule or by gastric tube.

Deployment of the System in the Stomach

Once the capsule or other container arrives in the stomach of the patient, the capsule dissolves and releases the compacted gastric residence system. Upon release, the system returns to its original shape, such as a ring shape or a star shape. The dimensions of the uncompressed/uncompacted system are suitable to prevent passage of the system through the pyloric sphincter for the period of time during which the system is to reside in the stomach.

While in the stomach, the gastric residence system is compatible with digestion and other normal functioning of the stomach or gastrointestinal tract. The gastric residence system does not interfere with or impede the passage of chyme (partially digested food) or other gastric contents which exit the stomach through the pyloric sphincter into the duodenum.

Elution of Therapeutic Agent from the System while Resident in the Stomach

The gastric residence system comprises a plurality of polymer-agent components. In one embodiment, the polymer-therapeutic agent components comprise a carrier polymer, a dispersant, and a therapeutic agent (or a salt thereof). In another embodiment, the polymer-therapeutic agent components comprise a carrier polymer and a therapeutic agent (or a salt thereof). The plurality of polymer-agent components are linked together by one or more elastomer components and/or one or more coupling polymer components. Therapeutic agent is eluted from the carrier polymer-agent components into the gastric fluid of the patient over the desired residence time of the system. Release of the therapeutic agent is controlled by appropriate formulation of the carrier polymer-agent components, including by the use of the dispersant in formulation of the carrier polymer-agent components.

Retention in Stomach; Passage of the System from the Stomach

The gastric residence system passes out of the stomach at an appropriate time point, that is, once the useful therapeutic agent delivery lifetime of the system has been reached, or at a reasonable fraction of the useful therapeutic agent delivery lifetime of the system. This is accomplished by suitable choice of the coupling polymer components and the dimensions of the system. In its intact, uncompressed form, the gastric residence system is designed to resist passage through the pyloric sphincter. That is, in its intact form, the gastric residence system is too large to pass through the pyloric sphincter. The coupling polymer components are chosen such that they gradually weaken and/or degrade over the residence period in the stomach. When the coupling polymer components are sufficiently weakened or degraded, the gastric residence system breaks apart into smaller pieces, which are able to pass through the pyloric sphincter. The system then passes through the intestines and is eliminated from the patient.

The gastric residence system should also be resistant to being transiently re-folded by the compressive forces in the stomach, which may cause premature passage of the system. In order to prevent transient re-folding in the stomach, the gastric residence system should maintain its uncompressed form, or approximately its uncompressed form when subject to forces typically present in the stomach. Therefore, in any of the embodiments of the gastric residence systems, the folding force required to fold the structure is at least about 0.2 Newtons (N), at least about 0.3 N, at least about 0.4 N, at least about 0.5 N, at least about 0.75 N, at least about 1 N, at least about 1.5 N, at least about 2 N, at least about 2.5 N, at least about 3 N, at least about 4 N, or at least about 5 N. In any of the embodiments, the folding force required to fold the structure is between about 0.2 N to about 5 N, between about 0.3 N to about 5 N, between about 0.4 N to about 5 N, between about 0.5 N to about 5 N, between about 0.75 N to about 5 N, between about 1 N to about 5 N, between about 1.5 N to about 5 N, between about 2 N to about 5 N, between about 2.5 N to about 5 N, between about 3 N to about 5 N, or between about 4 N to about 5 N. In any of the embodiments, the folding force required to fold the structure is between about 0.2 N to about 4 N, between about 0.3 N to about 4 N, between about 0.4 N to about 4 N, between about 0.5 N to about 4 N, between about 0.75 N to about 4 N, between about 1 N to about 4 N, between about 1.5 N to about 4 N, between about 2 N to about 4 N, between about 2.5 N to about 4 N, between about 3 N to about 4 N, or between about 3.5 N to about 4 N. In any of the embodiments, the folding force required to fold the structure is between about 0.2 N to about 4 N, between about 0.2 N to about 3.5 N, between about 0.2 N to about 3 N, between about 0.2 N to about 2.5 N, between about 0.2 N to about 2 N, between about 0.2 N to about 1.5 N, between about 0.2 N to about 1 N, between about 0.2 N to about 0.75 N, between about 0.2 N to about 0.5 N, between about 0.2 N to about 0.4 N, or between about 0.2 N to about 0.3 N.

Safety Elements

In its desired mode of operation, the gastric residence systems have their intact uncompressed form while resident in the stomach, and do not pass through the pylorus until they break apart after the desired residence time. If a gastric residence system passes intact into the intestine, it has the potential to result in intestinal blockage. Thus, the gastric residence systems are designed to uncouple rapidly in the intestinal environment by dissolution of the coupling polymer, within 48 hours, preferably within 24 hours, more preferably within 12 hours, yet more preferably within 1-2 hours, so as to avoid potential intestinal blockage. This is readily accomplished by using enteric polymers as the coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient.

System Geometry

"Star" configurations have been proposed for gastric residence systems (see PCT/US2015/035423), and the invention discloses, inter alia, several improvements in such star or stellate embodiments. The "star" configuration uses a central elastomer with carrier polymer-agent components in the form of elongate members—that is, "arms" loaded with therapeutic agent—that project radially from the central elastomer. The improvements disclosed herein include new designs for the central elastomer, new designs and shapes for the elongate members, and new coupling configurations for segments of which the elongate members are comprised. The shape and dimensions of the system will affect the stress placed on the central elastomer, the "arm" elongate members, and the couplings (connections) between each component, both when the system is constrained within a capsule or other container in its compacted configuration, and when the system is in the gastric environment in its uncompacted configuration. The shape and dimensions will also determine the forces experienced by the capsule or other container which constrain the system in its compacted configuration.

Figure 2B:
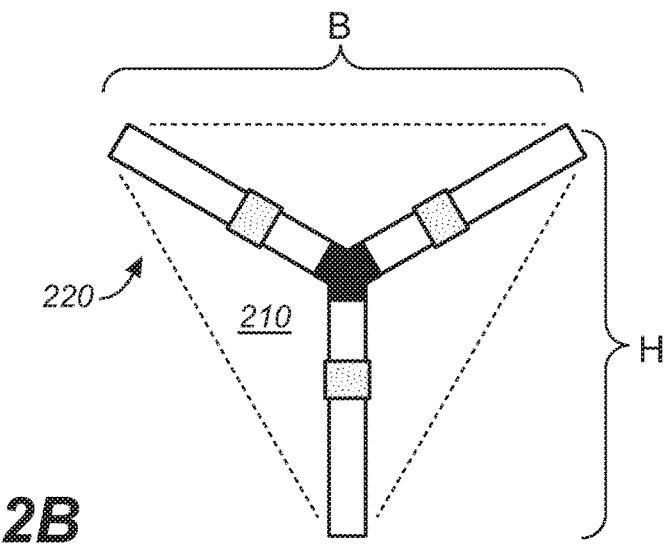
FIG. 2B shows certain dimensions of the gastric residence system of FIG. 2B.
Figure 2C:
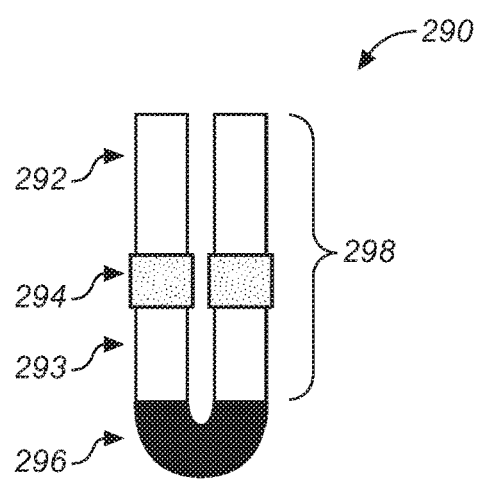
FIG. 2C shows the embodiment of a gastric residence system of FIG. 2 in a folded configuration. The capsule holding the system in the folded configuration is not shown.
Figure 3A:
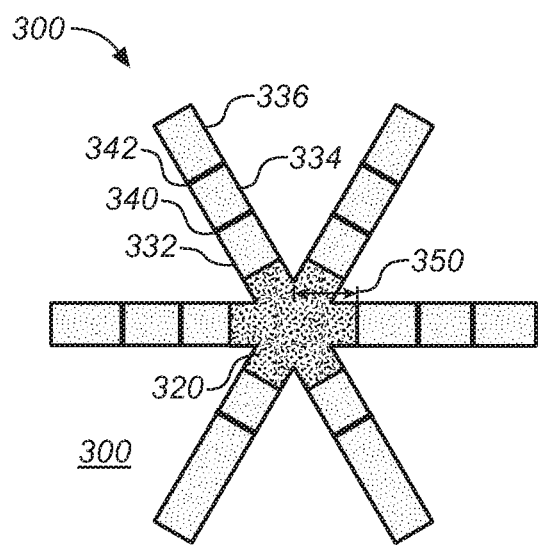
FIG. 3, panels 3A, 3B, 3C, and 3D show additional embodiments of gastric residence systems of the invention, with varying radial dimensions.
Figure 3B:
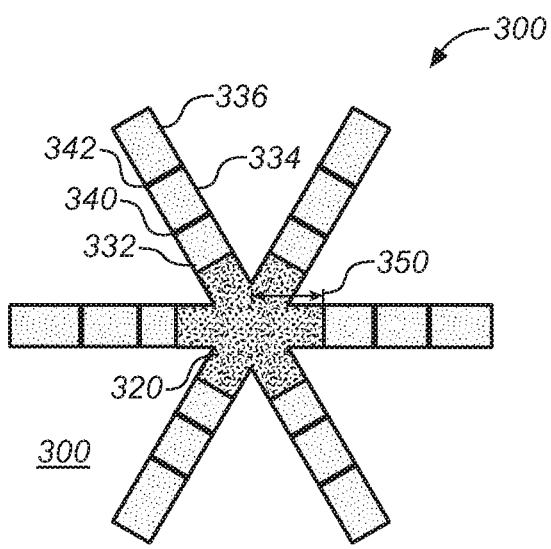
Figure 3C:
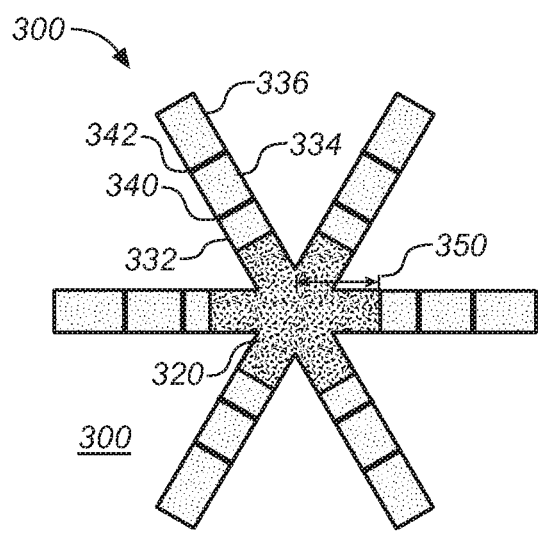
Figure 3D:
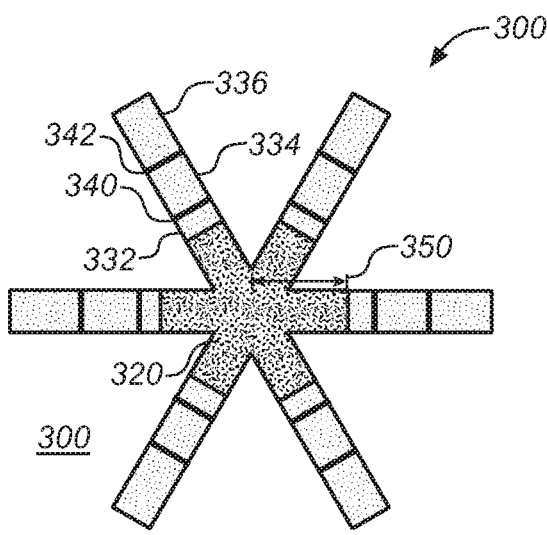

An example of a stellate system 200 is shown schematically in FIG. 2. Multiple "arms" (only one such arm, 208, is labeled for clarity) are affixed to asterisk-shaped (disk-shaped) central elastomer 206. The arms depicted in FIG. 2 are comprised of segments 202 and 203, joined by a coupling polymer 204. This configuration permits the system to be folded or compacted in the manner shown for the system 290 in FIG. 2C. Only two arms are shown in FIG. 2C for clarity, and only one arm (298) is labeled for clarity. The central elastomer 296 is folded, such that the overall length of the system is reduced by approximately a factor of two, and the system can be conveniently placed in a container such as a capsule or other container suitable for oral administration.

FIG. 2A shows another embodiment of the system, with three arms. For the star-shaped configurations of FIG. 2 or FIG. 2A, it will be appreciated that the arms can be spaced substantially evenly around the circumference of the connecting elastomer 206. Thus, for a star-shaped device having N arms, the arms will be spaced apart by (360/N) degrees. For example, the three arms in the device of FIG. 2A are spaced apart by about 120 degrees. As for FIG. 1 and FIG. 2, the components are not necessarily drawn to scale.

FIG. 2C shows the folded state of the system of FIG. 2 or of FIG. 2A, as it would be folded for packaging into a capsule (not shown in the figure), with arms 298 comprising outer carrier polymer-agent components 292, inner carrier polymer-agent components 293, couplings 294 comprising coupling polymer, and elastomer 296, where the elastomer has been deformed from its configuration in FIG. 2 or FIG. 2A. For the sake of clarity, only two "arms" formed by outer carrier polymer-agent components 292, couplings 294, and inner carrier polymer-agent components 293 are shown in FIG. 2C; additional arms may be present such as shown in the systems in FIG. 2 and FIG. 2A. Upon dissolution of the retaining capsule in the stomach, system 290 unfolds to the star-shaped configuration depicted in FIG. 2 or FIG. 2A, preventing passage through the pyloric sphincter over the residence time of the system. The carrier polymer-agent components, couplings, and elastomer are not necessarily drawn to scale; the dimensions (such as length or diameter) of the carrier polymer-agent components, couplings, and elastomer can vary from those shown in the figure.

FIG. 3 shows a different arrangement of the "star" configuration. View 3A is labelled to show the various elements of this configuration. The system 300 comprises a central elastomeric core 320 which is in the shape of an "asterisk" having six short branches or arms. That is, the asterisk shape has a round central portion with six short branches or arms protruding from the central portion, where the central portion and branches or arms lie in the same plane. Segment 332 of the elongate member arm is attached to one short asterisk branch. Another segment 334 is attached to segment 332 via coupling polymer 340, and a further segment 336 is attached to segment 334 via coupling polymer 342.

The length of the asterisk branch is measured from the center of the elastomeric polymer to the end of the branch where the carrier polymer-agent arms are attached. The location of the interface between the elastomer and carrier polymer-agent arms can be varied radially, as indicated in View 3A by the double-headed arrow labelled 350 and in accompanying Views 3B, 3C, and 3D. This location, with its associated length of the asterisk branches, will affect the internal stress of the elastomer 320 and stresses applied to the couplings 340 and 342 when compacting or folding the system for packaging into a capsule or other container, during storage of the system, and when the system is in its unfolded/uncompacted (deployed) configuration in the stomach. Finite element analysis can be used in structural analysis of the system. This enables determination of the optimal radial distance from the center of the system, which is chosen to provide enough elastic recoil to deploy the system, while preventing a large build-up of stress within the system.

FIG. 10 shows the effect of varying the length of the asterisk branches of the central elastomer. Branches which are too short (FIG. 10, Panel A) hinder the folding of the elastomer into its compacted form (FIG. 10, Panel AA), which in turn hinders packing of the gastric residence system into a capsule or other container. This also generates large loads on the elastomer, which can cause polymer creep. Branches which are too long (FIG. 10, Panel C) may bulge when compacted (FIG. 10, Panel CC) and again hinder placement into a capsule. The elastomer may also not provide enough force to prevent travel through the pylorus, as it may fold too easily in response to forces generated in the stomach. FIG. 10, Panel B and FIG. 10, Panel BB show an intermediate branch length, which minimizes stress concentrations and bulging, while still providing sufficient force for gastric retention.

Figure 11:
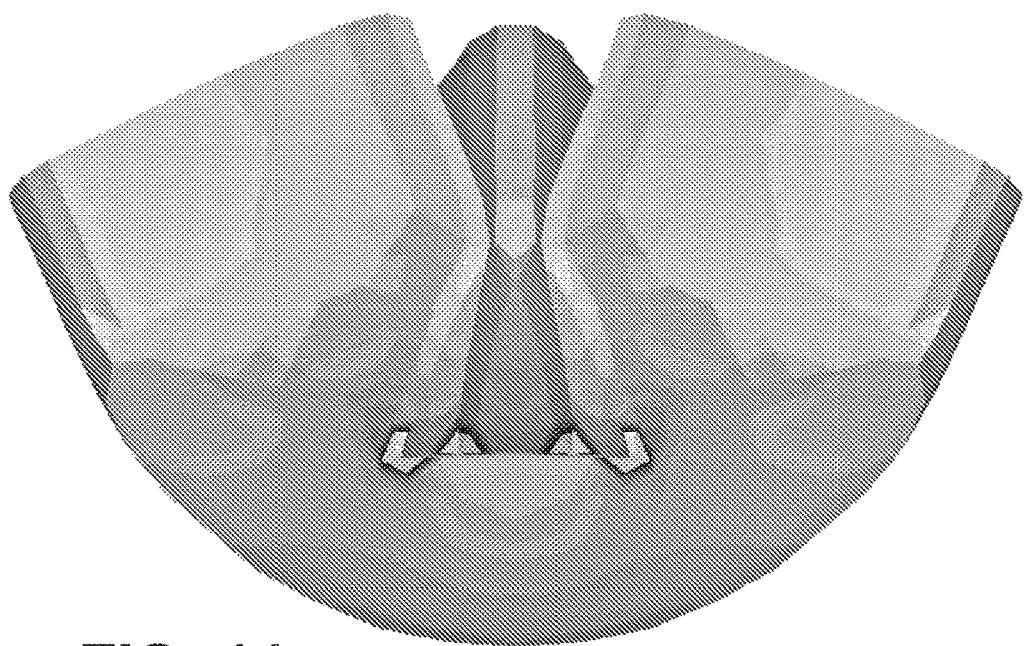
FIG. 11 shows a stress map of a central elastomer with relatively short asterisk branches.
Figure 12:
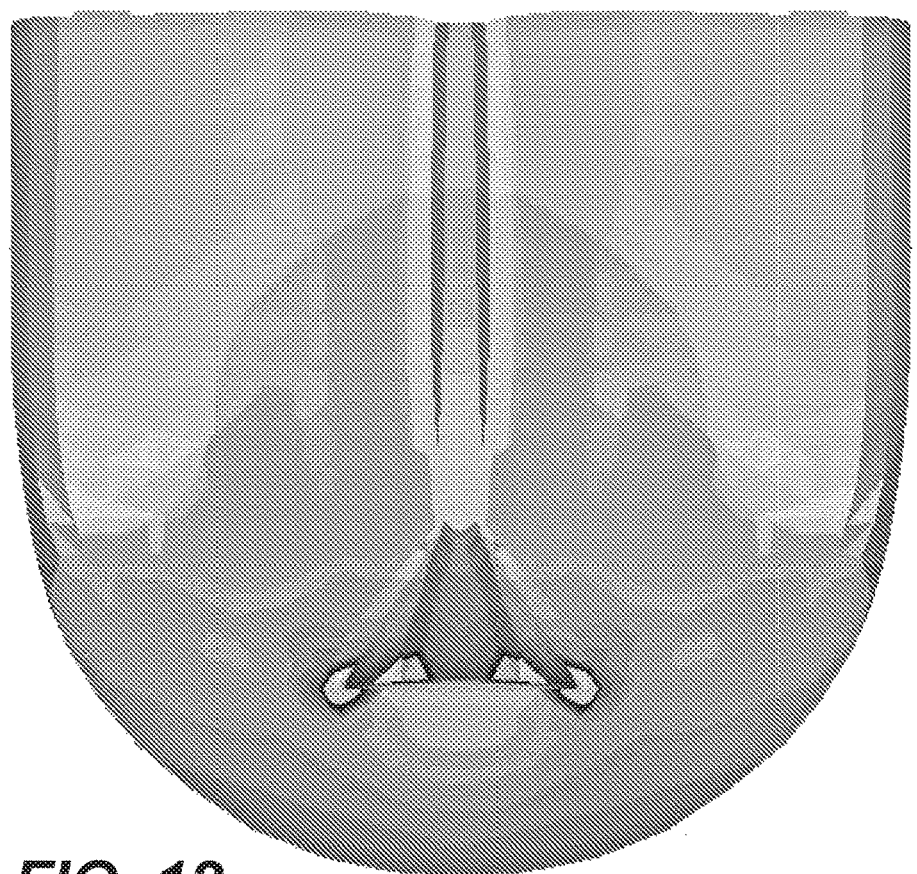
FIG. 12 shows a stress map of a central elastomer with asterisk branches of intermediate length.
Figure 13:
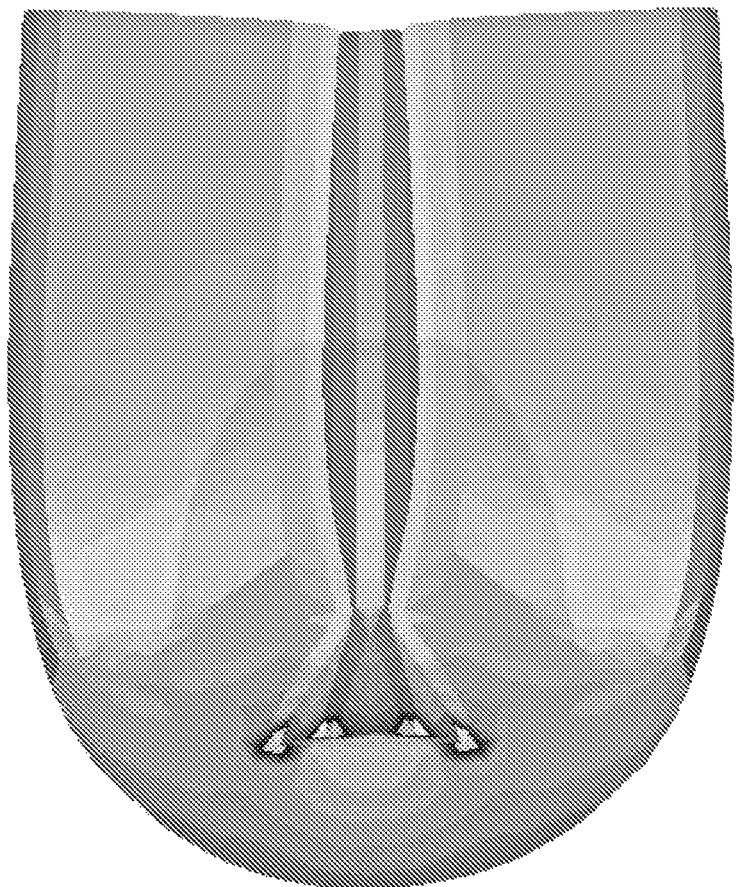
FIG. 13 shows a stress map of a central elastomer with relatively long asterisk branches.

FIG. 11, FIG. 12, and FIG. 13 show stress maps from simulations of central elastomers with asterisk branches of varying length. The stress maps were generated using finite element analysis using the ABAQUS program. The elastomer of FIG. 11 is 10 mm in width, that is, it has relatively short branches. When folded, it shows very high stress concentrations (darker regions of the map), to the point where the material can fail. The elastomer of FIG. 12 is 15 mm in width, and when folded, shows no bulging and minimal stress concentrations. The elastomer of FIG. 13 is 20 mm in width, and while stress concentrations are reasonable, the elastomer shows significant bulging. Thus, proper design of the central elastomer requires minimizing both stress and bulging, as in the elastomer of FIG. 12.

Figure 4A:
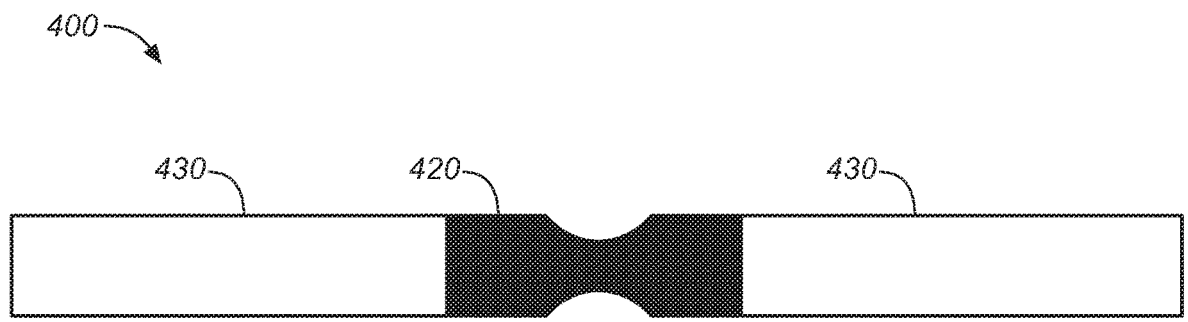
FIG. 4A shows one embodiment of the system using a bi-concave disk for the central elastomer.
Figure 4B:
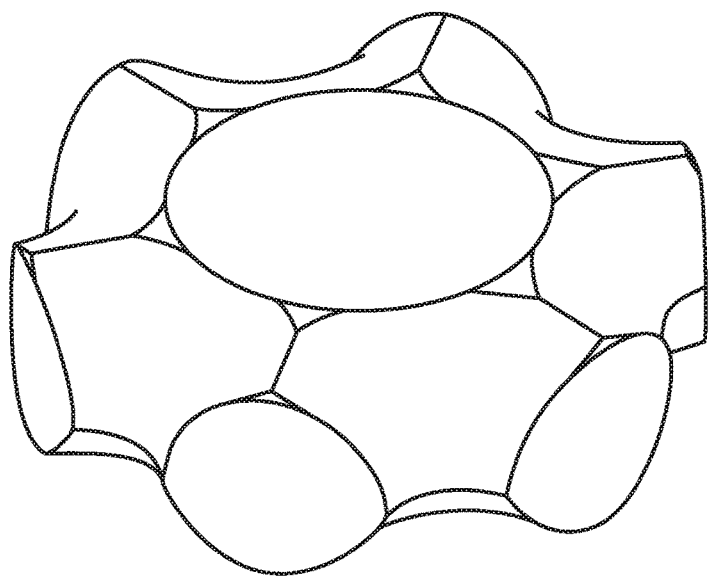
FIG. 4B is a solid depiction of the two-dimensional depiction of FIG. 4A.
Figure 4C:
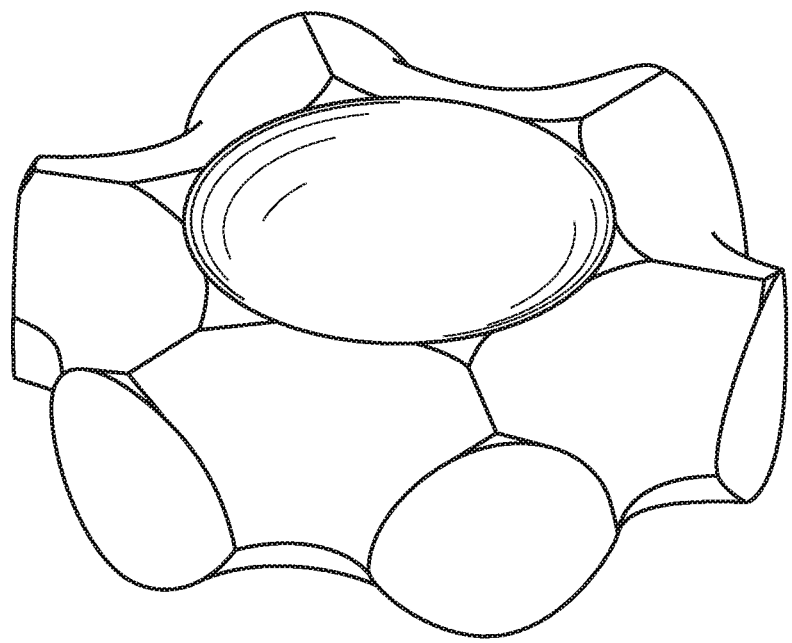
FIG. 4C is a further solid depiction of the two-dimensional depiction of FIG. 4A.
Figure 4D:
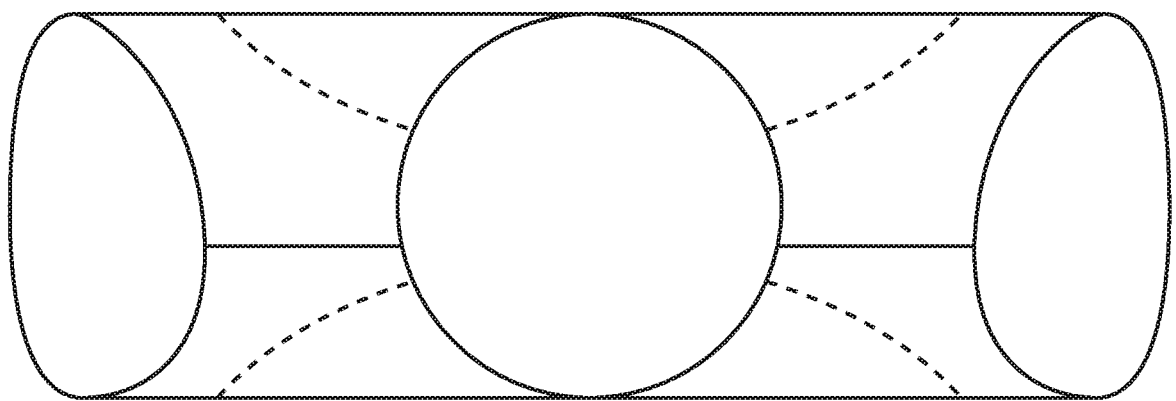
FIG. 4D is a side view of the depiction of FIG. 4C.
Figure 5A:
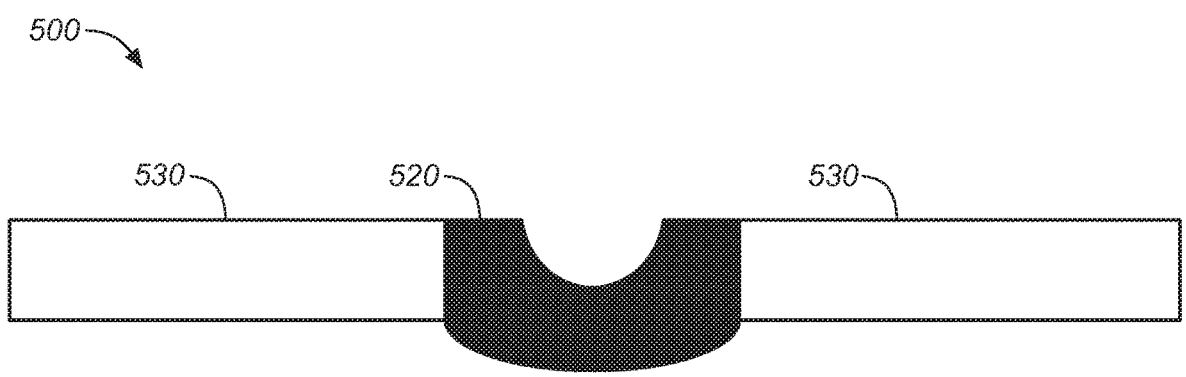
FIG. 5A shows another embodiment of the system using a concavo-convex disk for the central elastomer.
Figure 5B:
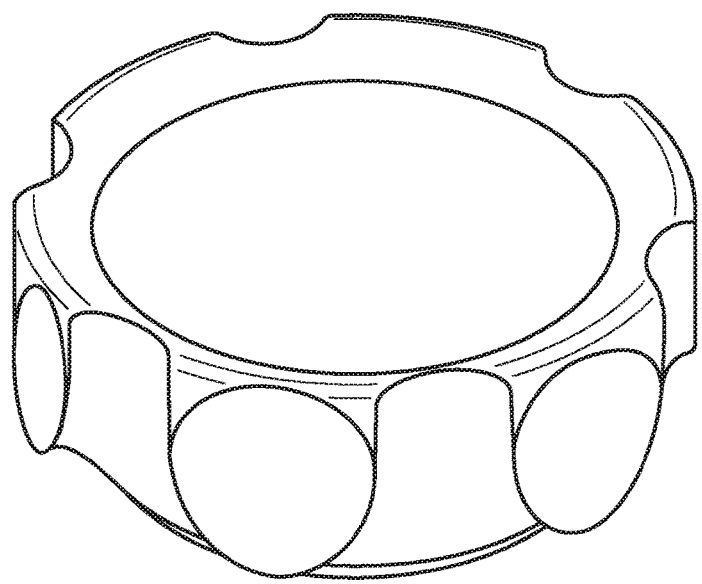
FIG. 5B is a solid depiction of the two-dimensional depiction of FIG. 5A.
Figure 5C:
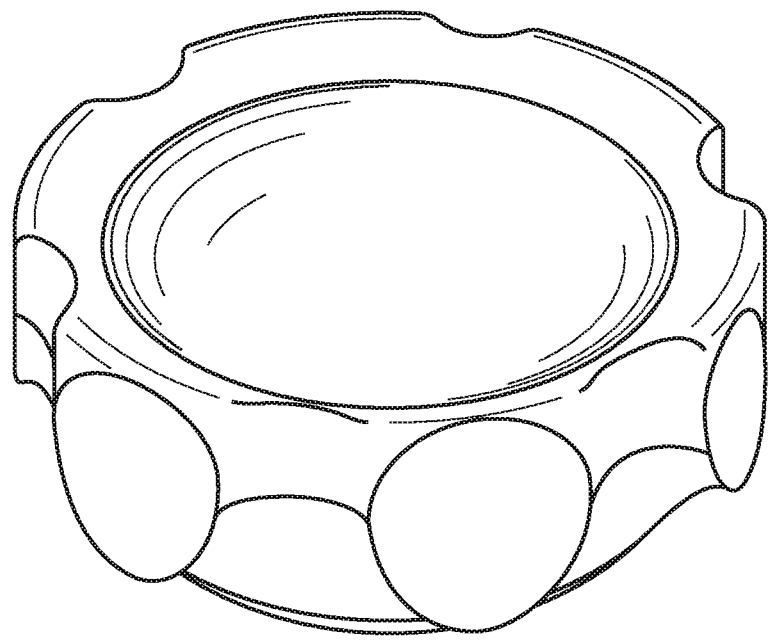
FIG. 5C is a further solid depiction of the two-dimensional depiction of FIG. 5A.
Figure 5D:
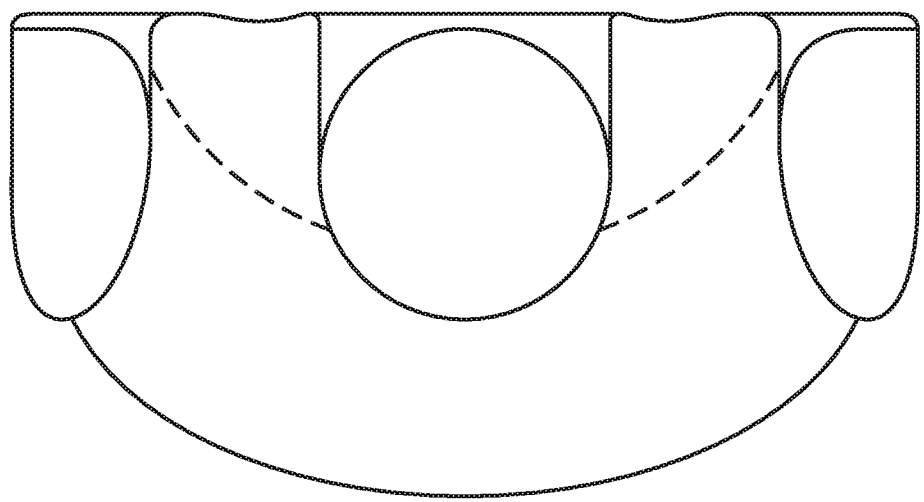
FIG. 5D is a side view of the depiction of FIG. 5C.
Figure 6A:
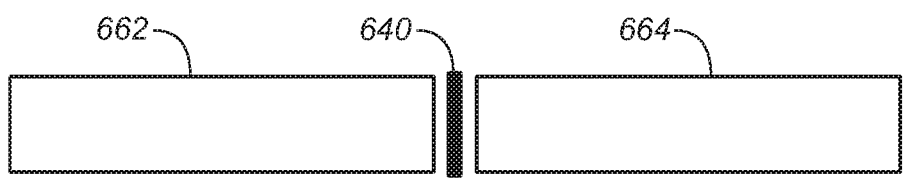
FIG. 6, with views 6A, 6B, 6B1, 6C, and 6D, shows different embodiments for coupling of segments of carrier polymer-agent component in the arms of the system.
Figure 6B:
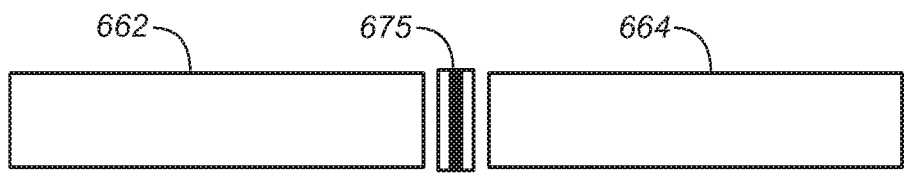
Figure 6C:
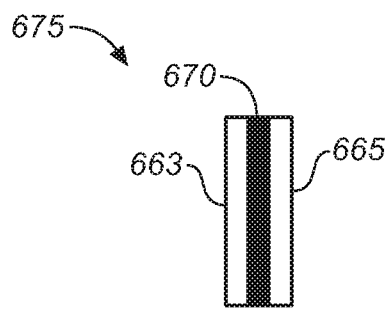
Figure 6C:
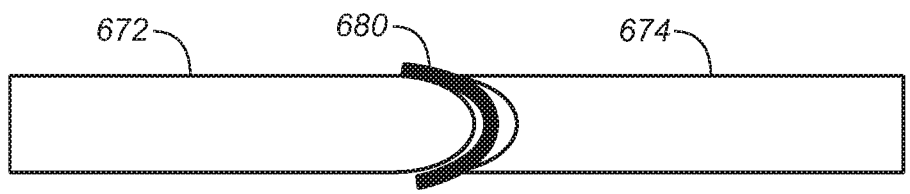
Figure 6D:
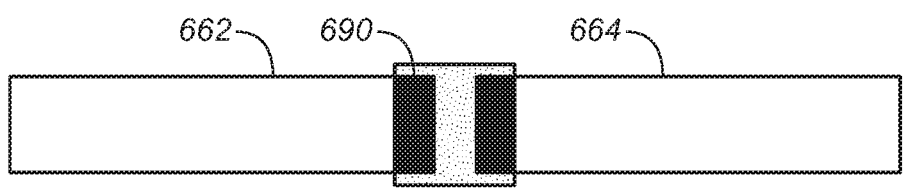

FIG. 4A depicts a configuration 400 which can be used to adjust stress distribution within the system during storage in a capsule and in the stomach during gastric retention. In this configuration, carrier polymer-agent component arms 430 are attached to central elastomer 420 (only two arms are shown for clarity). Elastomer 420 is a bi-concave disk, which permits flexing of the arms in either direction; the mechanical response to a folding force should be equivalent in both directions. This geometry will conform to a circular geometry upon folding, which minimizes stress concentrations. FIG. 4B and FIG. 4C depict solid perspective views of this bi-concave asterisk-shaped disk, while FIG. 4D depicts a side view (with the dashed lines indicating hidden lines). FIG. 5A depicts another configuration 500 which can be used to adjust stress distribution within the system. Carrier polymer-agent component arms 530 are attached to central elastomer 520 (again, only two arms are shown for clarity). Elastomer 520 is a concavo-convex disk (that is, concave on one side, and convex on the other side), and folds more readily in one direction. FIG. 5B and FIG. 5C depict solid perspective views of this concavo-convex asterisk-shaped disk, while FIG. 5D depicts a side view (with the dashed lines indicating hidden lines).

Minimizing stress during storage of the system, in a capsule or other container, is important for preventing creep of the elastomers and permanent deformation over time, which would interfere with proper deployment in the stomach. Minimizing stress is also important for preventing premature weakening of the couplings, which might alter the retention time of the system when it is eventually deployed in the stomach.

Central Elastomer

Various designs and dimensions can be used for the central elastomer to provide appropriate folding force for the gastric residence system, while minimizing stress on the system during storage. The folding force is the force required to fold the gastric residence system to a size where it can pass through the pyloric valve, and is measured by determining the force required to push the gastric residence system through a round hold 2 cm in diameter (such as a funnel which has as its smallest diameter a circular opening of 2 cm). As noted above, the system must resist passage through the pyloric valve in its intact state, and thus the force needed to fold the system to a size where it can pass through the pyloric valve must be greater than the forces exerted on the system when the system resides in the stomach. Typical forces experienced in the stomach are approximately 0.2 newtons; as noted in the section above, "Retention in stomach; passage of the system from the stomach," various folding forces can be used in different embodiments of the invention.

Figure 17A:
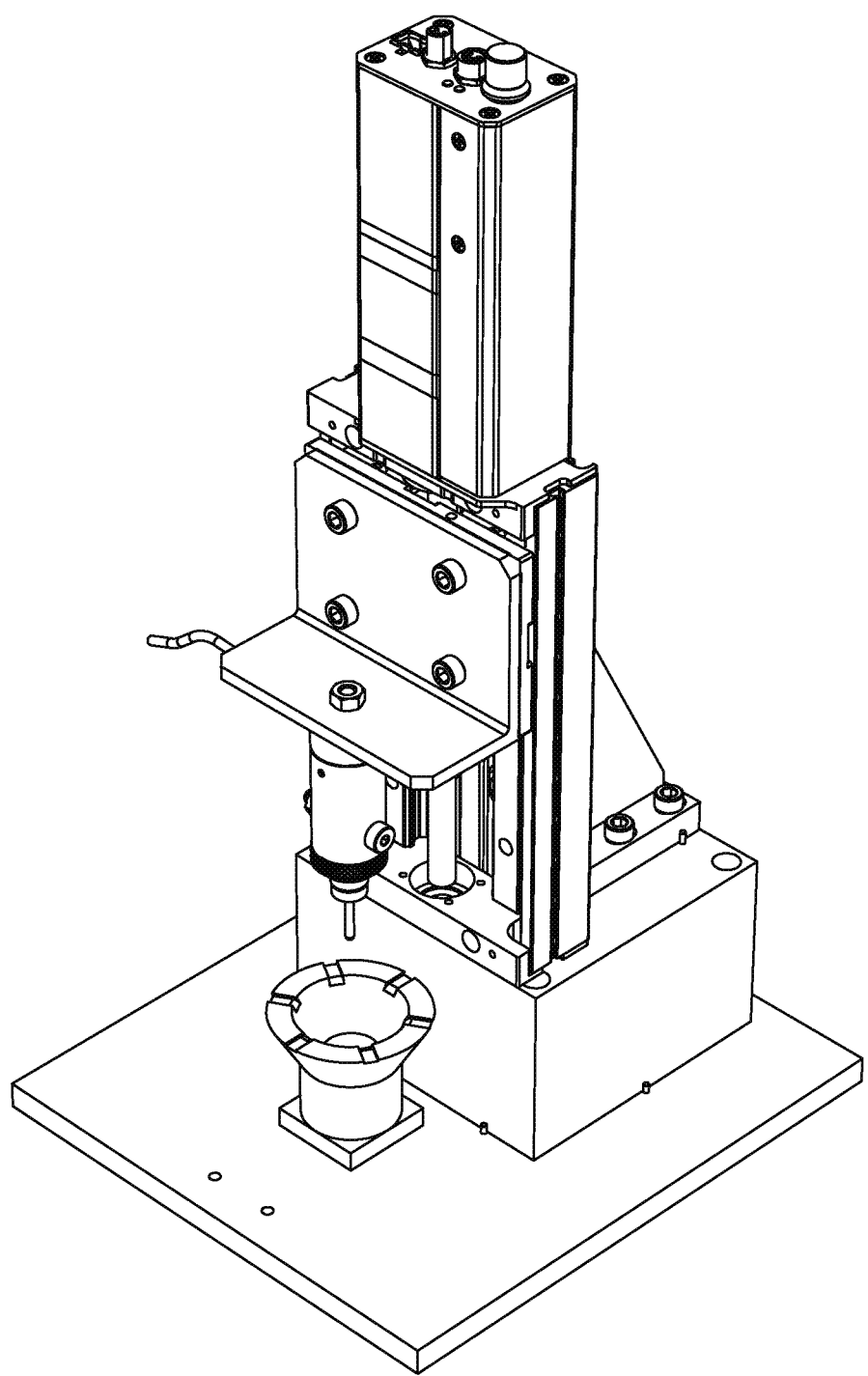
FIG. 17A shows an apparatus used to measure folding force.
Figure 17B:
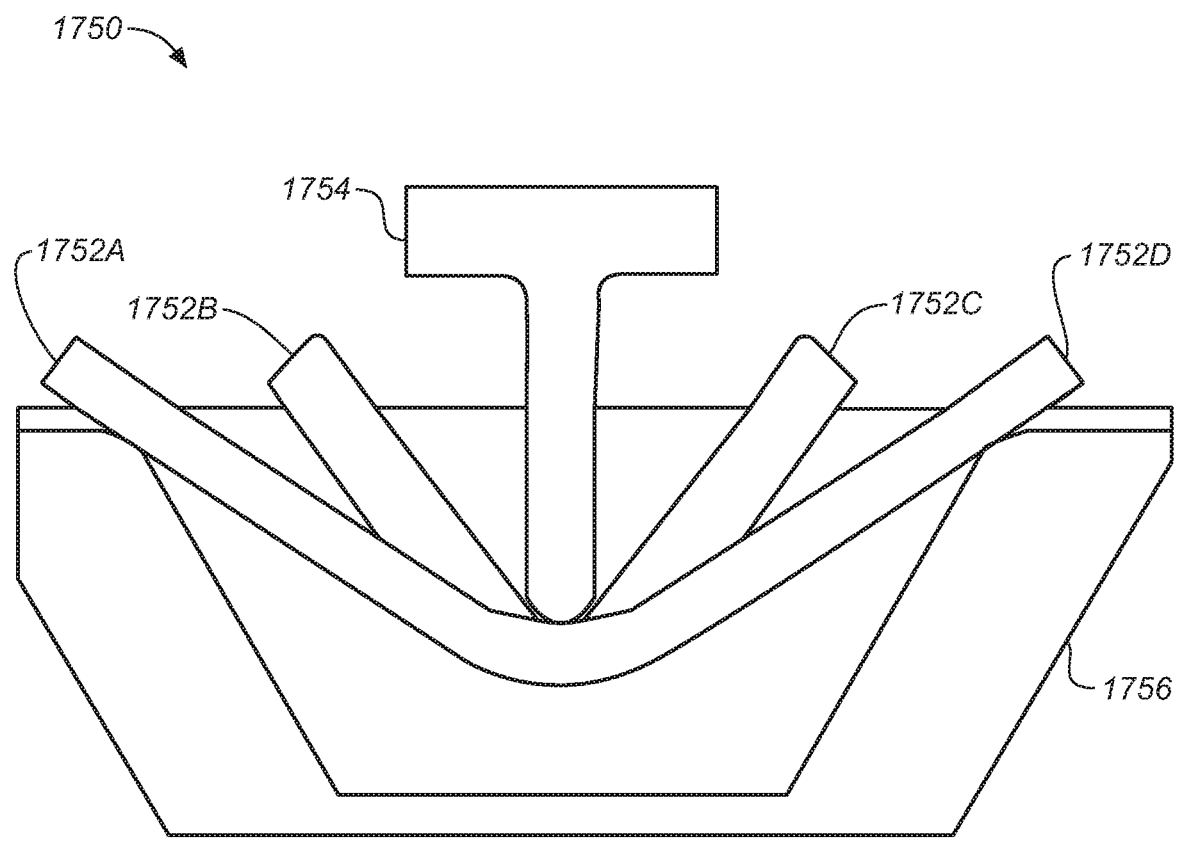
FIG. 17B shows a close-up schematic of a portion of the apparatus of FIG. 17A used to measure folding force.

Measurement of the folding force can be performed using an apparatus such as that depicted in FIG. 17A and FIG. 17B, as described in Example 7. An expanded schematic view of a portion of the apparatus in FIG. 17A is shown in FIG. 17B. In the plunger-gastric residence system-funnel setup 1750, a plunger 1754 is used to push the gastric residence system through a funnel 1756 which has as its smallest diameter a circular opening of 2 cm. A four-armed gastric residence system is depicted, with arms 1752A, 1752B, 1752C, and 1752D; however, the apparatus can be used with a gastric residence system having any number of arms (such as 3, 4, 5, 6, 7, or 8 arms). The force measured on the plunger 1754 required to push the system through the funnel is the folding force of the gastric residence system. (See also FIG. 13A, page 56, and Example 9 of WO 2015/191920, hereby incorporated by reference herein.)

Figure 18A:
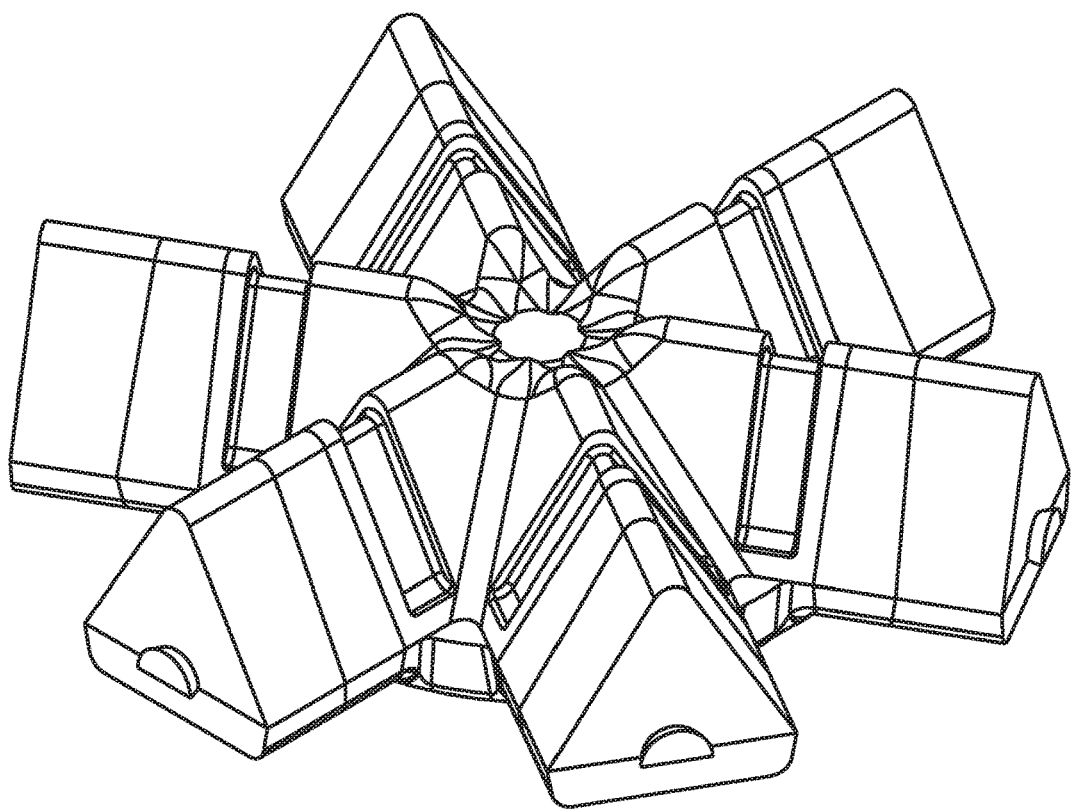
FIG. 18A shows a view of a concavo-convex design of the central elastomer in an intermediate polymeric assembly/elastomer hub.
Figure 18B:
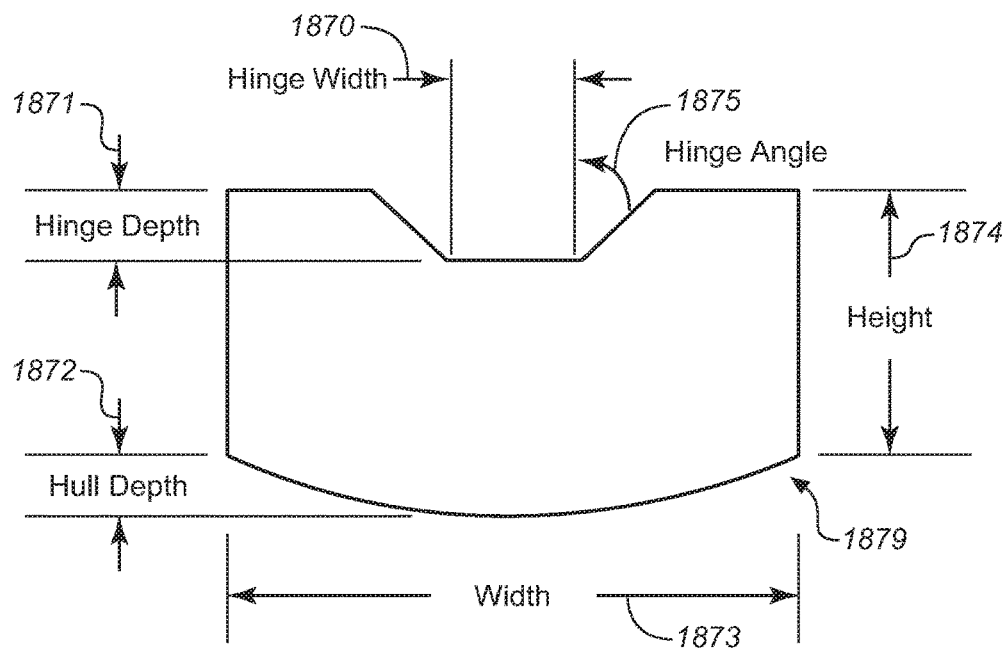
FIG. 18B shows several dimensions that can be varied to adjust folding forces in a concavo-convex design of the central elastomer in an intermediate polymeric assembly/elastomer hub.
Figure 18C:
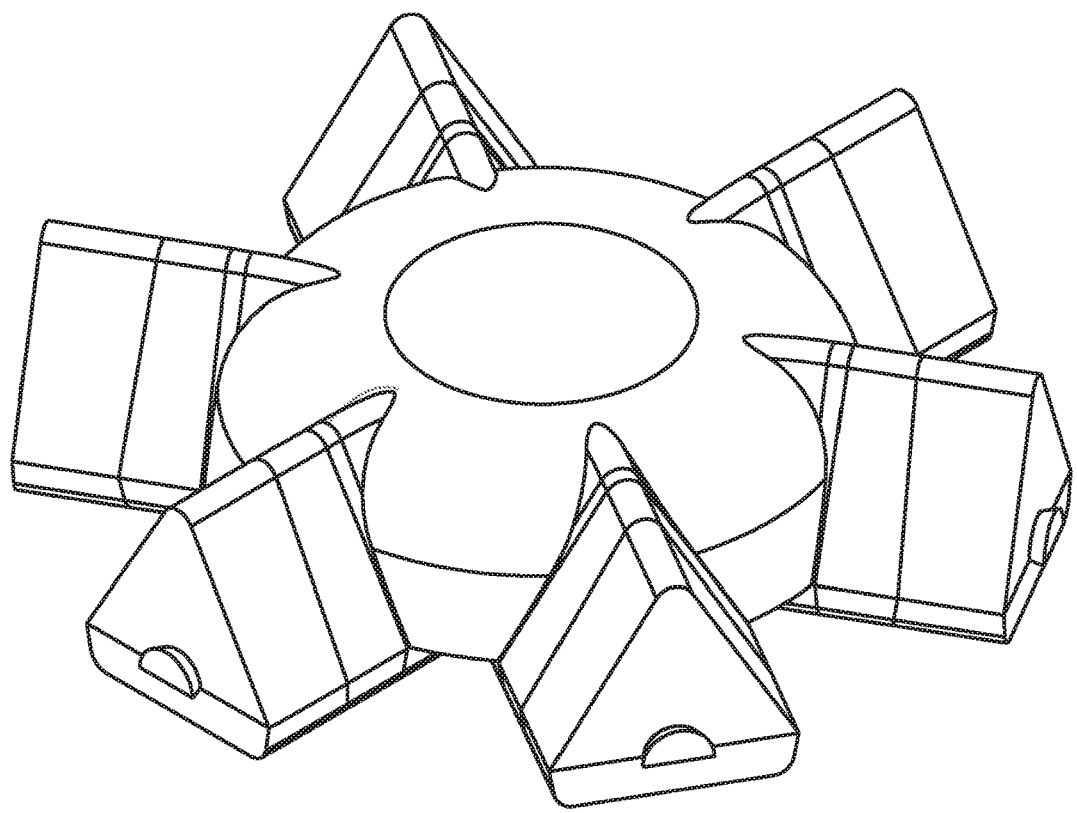
FIG. 18C shows a view of a bi-concave design of the central elastomer in an intermediate polymeric assembly/elastomer hub.
Figure 18D:
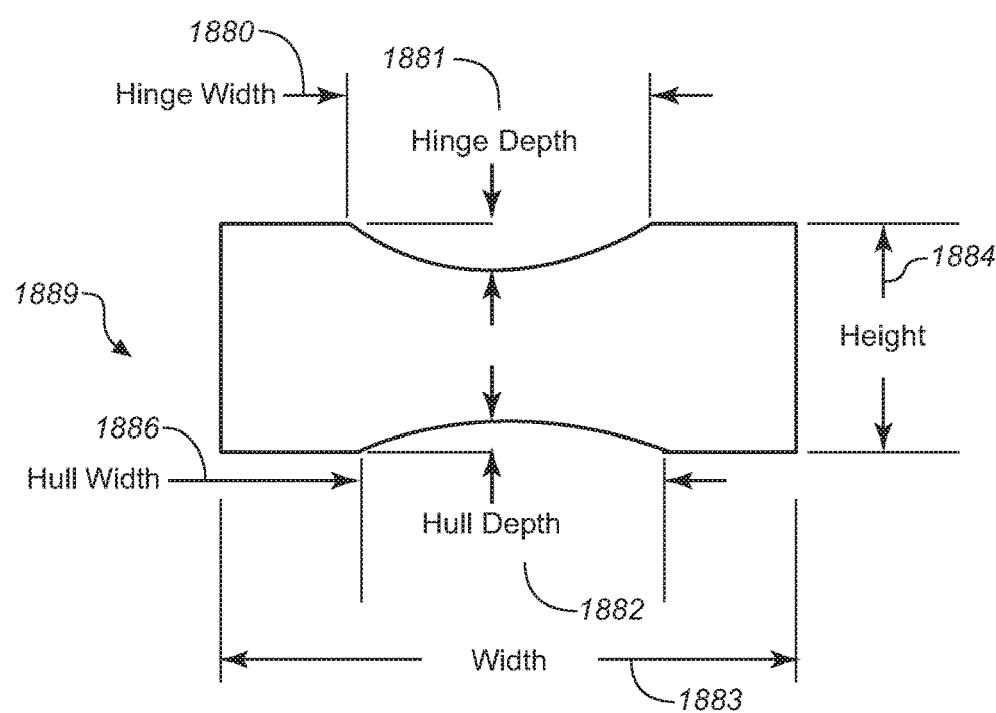
FIG. 18D shows several dimensions that can be varied to adjust folding forces in a bi-concave design of the central elastomer in an intermediate polymeric assembly/elastomer hub.
Figure 18E:
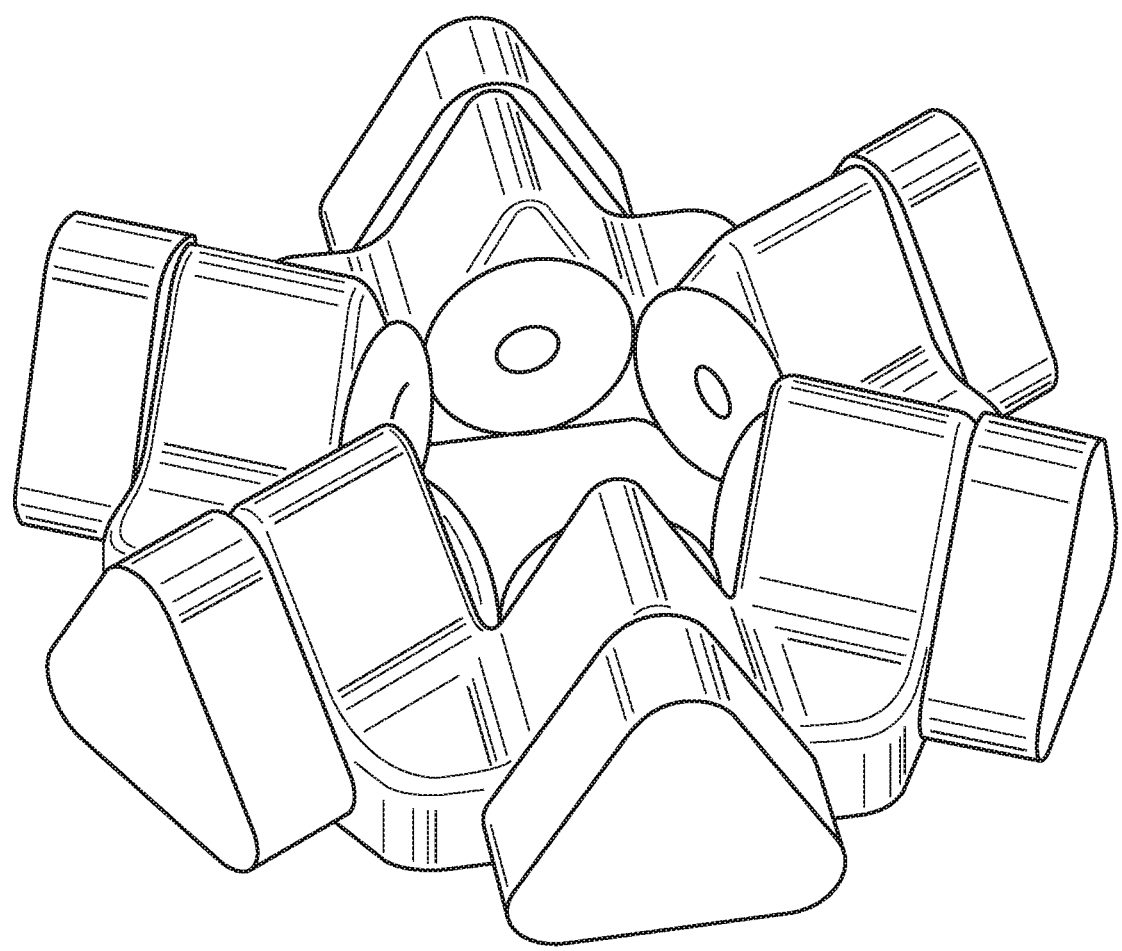
FIG. 18E shows a view of a toroidal design of the central elastomer in an intermediate polymeric assembly/elastomer hub.
Figure 19A:
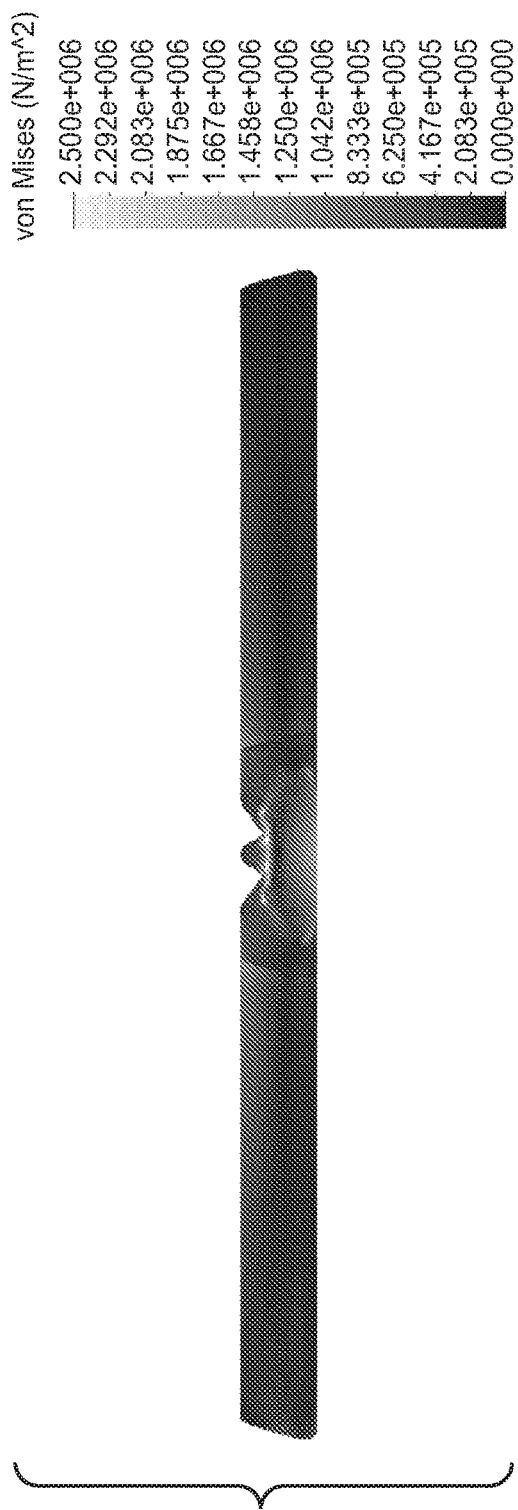
FIG. 19A shows stress distribution in a mono-concave design.
Figure 19B:
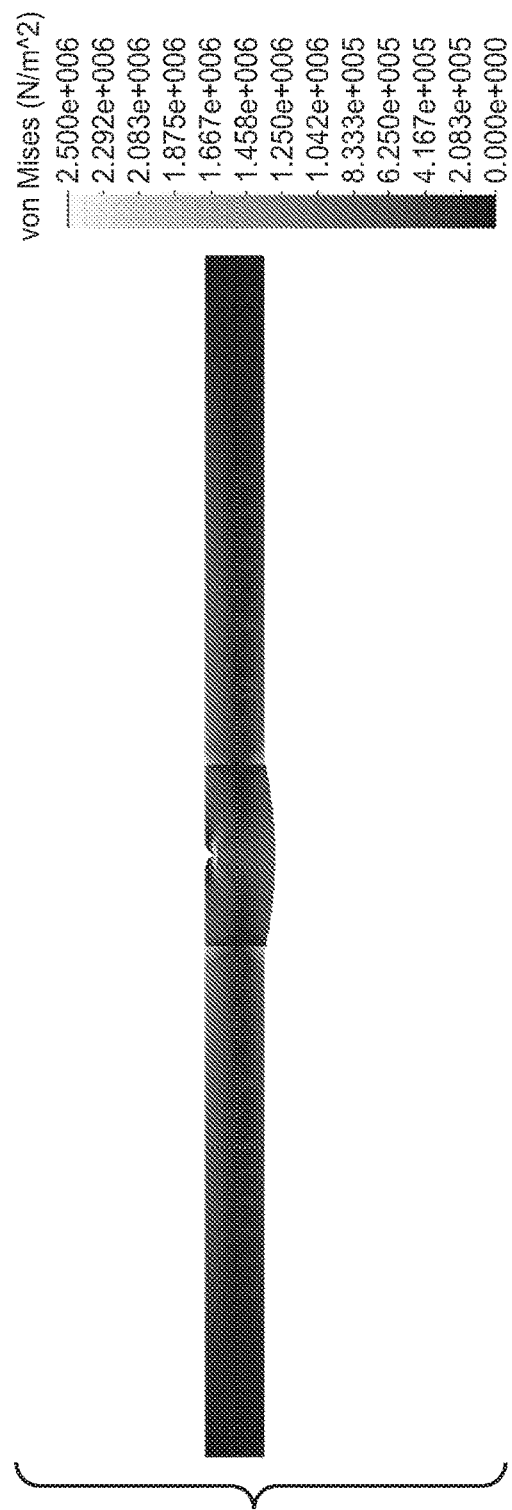
FIG. 19B shows stress distribution in a concavo-convex design (shallow convex).

A range of designs were analyzed and three major families emerged that met the desired design requirements: a concavo-convex design (FIG. 18A, FIG. 18B), biconcave disk design (FIG. 18C, FIG. 18D), and torus design (FIG. 18E). The stress and strain distributions were analyzed and features were added to minimize stress concentrations (FIG. 19A, FIG. 19B, FIG. 19C, FIG. 19D). Designs were also modified to ensure they incorporated parting lines that would enable them to be formed with injection molding techniques.

The concavo-convex design (FIG. 18A, FIG. 18B) had four major features that affected the folding force of the gastric residence system: 1) increasing the depth of the design increased the folding force; 2) decreasing the width of the gastric residence system increased the folding force; 3) decreasing the depth of the hinge increased the folding force; and 4) decreasing the width of the hinge increased the folding force. These four parameters were adjusted to modify the folding force of the gastric residence system.

The biconcave disk design (FIG. 18C, FIG. 18D) had two major features that affected the folding force of the gastric residence system: 1) increasing the height of the design increased the folding force; and 2) decreasing the width of the gastric residence system increased the folding force.

Figure 20:
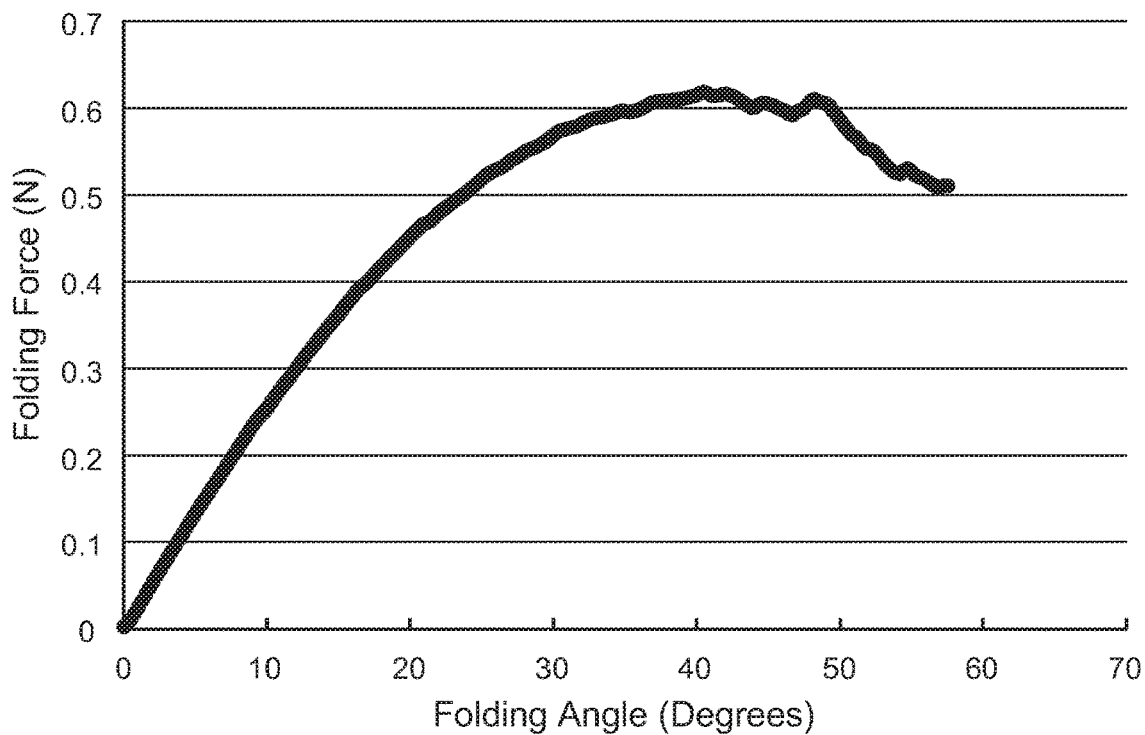
FIG. 20 shows the folding force—angle relationship of a concavo-convex design.

Incorporating a concave recess in both the concavo-convex and biconcave disk designs led to an optimal force-displacement curve (FIG. 20). Optimally, the folding force of a gastric residence system would reach a maximum prior to passing through a 2 cm hole (approximate size of the human pylorus). A drop in the force following this displacement would decrease the stress applied to the elastomer while stored in a capsule increasing the mechanical stability. Both designs incorporated this feature.

The geometries of the central elastomer depicted in FIG. 18A, FIG. 18C, and FIG. 18E enable adjustment of the folding force of the corresponding gastric residence system by varying the physical dimensions of the central elastomer. FIG. 18B shows the relevant dimensions for the concavo-convex elastomer of FIG. 18A, while FIG. 18D shows the relevant dimensions for the bi-concave elastomer of FIG. 18C. In FIG. 18B, the hinge width 1870, the hinge depth 1871, the hull depth 1872, the width 1873, the height 1874, and the hinge angle 1875 influence the folding force of the concavo-convex elastomer 1879 of FIG. 18A. The hinge side of the elastomer is the side towards which the arms will be folded when the system is stored in a capsule, while the hull is the opposite side of the elastomer. Ranges of values for these parameters, preferred ranges, and optimal values are shown in Table 1 below. (Each range or value below can be considered to be "about" the range or value indicated, or exactly the range or value indicated.)

TABLE 1

| Parameter | Range | Preferred Range | Optimal Value |
| --- | --- | --- | --- |
| Hinge Width | 0.5-6 mm | 1-3 mm | 2 mm |
| Hinge Depth | 0.1-2 mm | 0.1-0.4 mm | 0.25 mm |
| Hull Depth | 0-2 mm | 0.5-1.5 mm | 1 mm |
| Width | 6-12 mm | 6-10 mm | 8 mm |
| Height | 1-4 mm | 2-3 mm | 2.5 mm |
| Hinge Angle | 0-80 degrees | 30-60 degrees | 45 degrees |

In FIG. 18D, the hinge width 1880, the hinge depth 1881, the hull depth 1882, the width 1883, the height 1884, and the hull width 1886 influence the folding force of the bi-concave elastomer 1889 of FIG. 18C. Again, the hinge side of the elastomer is the side towards which the arms will be folded when the system is stored in a capsule, while the hull is the opposite side of the elastomer. Ranges of values for these parameters, preferred ranges, and optimal values are shown in Table 2 below. (Each range or value below can be considered to be "about" the range or value indicated, or exactly the range or value indicated.)

TABLE 2

| Parameter | Range | Preferred Range | Optimal Value |
|---|---|---|---|
| Hinge Width | 1-6 mm | 2-4 mm | 3 mm |
| Hinge Depth | 0.1-2 mm | 0.25-0.75 mm | 0.5 mm |
| Hull Depth | 0.1-2 mm | 0.25-0.75 mm | 0.5 mm |
| Width | 6-12 mm | 6-10 mm | 8 mm |
| Height | 1-4 mm | 2-4 mm | 3 mm |
| Hull Width | 1-6 mm | 3-5 mm | 4 mm |

Folding Force

An advantageous property of the central elastomer of the stellate gastric residence systems of the invention is that its folding force reaches a maximum point before the system is fully folded, and then the folding force decreases as folding increases. In its fully unfolded form, the components of the gastric residence system lie in a plane (see, for example, FIG. 2); that is, the system is flattened out as much as possible. This plane is referred to as the "fully unfolded plane" of the gastric residence system, where the cross-sectional area of the system is at a maximum. Alternatively, the fully unfolded plane can be referred to as the x-y plane of the system. The folding of the gastric residence system can be measured by the angle that the arms of the stellate system make with the fully unfolded plane. When the gastric residence system lies in the fully unfolded plane, the angle that the arms make with the fully unfolded plane is 0 degrees; this angle is called the "folding angle." In its fully folded form (see, for example, FIG. 2C), the folding angle that the arms make with the fully unfolded plane is 90 degrees.

Figure 22:
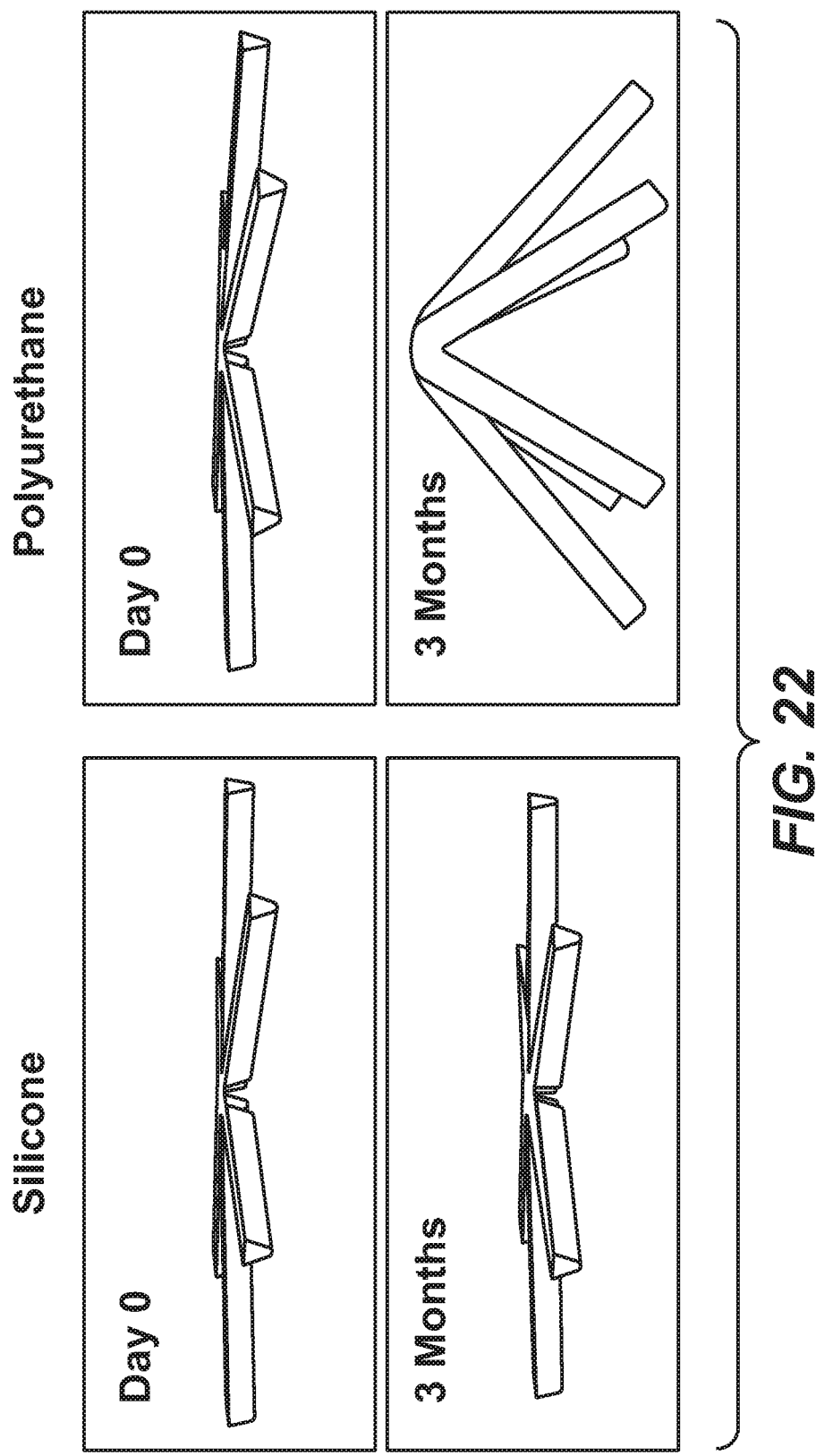
FIG. 22 shows the creep in-capsule of a silicone elastomer assembly (left panels; top panel, day 0, bottom panel, after 3 months) and of a polyurethane elastomer assembly (right panels; top panel, day 0, bottom panel, after 3 months).

As can be seen in FIG. 20, the folding force increases as the folding angle increases from zero degrees to about 40-42 degrees. The folding force then begins to decrease. This decrease in folding force as the folding angle approaches 90 degrees is advantageous for long-term storage of the gastric residence systems. The lower force at high angles of folding (at or above about 70 degrees) results in lowered stress on the gastric residence system when fully folded and contained in a capsule or other container, which in turn reduces the creep of the elastomer over long-term storage. A high creep during storage will result in incomplete unfolding of the gastric residence system when liberated from a capsule in the stomach. An example of the undesirability of high creep is shown in FIG. 22. A system using a polyurethane elastomer shown in the right-side panels lies relatively flat at day 0 of storage (top right panel), but shows incomplete unfolding after 3 months of storage (bottom right panel). In contrast, a system using a silicone elastomer lies flat at day 0 of storage (top left panel), and also completely unfolds after 3 months of storage (bottom left panel).

Accordingly, in one embodiment, the maximum folding force of the gastric residence system occurs at a folding angle between about 0 degrees and about 70 degrees. In another embodiment, the maximum folding force of the gastric residence system occurs at a folding angle between about 10 degrees and about 70 degrees. In another embodiment, the maximum folding force of the gastric residence system occurs at a folding angle between about 20 degrees and about 70 degrees. In another embodiment, the maximum folding force of the gastric residence system occurs at a folding angle between about 30 degrees and about 70 degrees. In another embodiment, the maximum folding force of the gastric residence system occurs at a folding angle between about 10 degrees and about 60 degrees. In another embodiment, the maximum folding force of the gastric residence system occurs at a folding angle between about 10 degrees and about 50 degrees.

In a further embodiment, the folding force of the gastric residence system is lower at a folding angle of about 70 degrees or more than the maximum folding force occurring at a folding angle between about 0 degrees and 70 degrees, such as at least about 10% lower, at least about 20% lower, at least about 30% lower, or between about 1% to about 10% lower, about 1% to about 20% lower, or about 1% to about 30% lower. In another embodiment, the folding force of the gastric residence system is lower at a folding angle of about 80 degrees or more than the maximum folding force occurring at a folding angle between about 0 degrees and 70 degrees, such as at least about 10% lower, at least about 20% lower, at least about 30% lower, or between about 1% to about 10% lower, about 1% to about 20% lower, or about 1% to about 30% lower. In another embodiment, the folding force of the gastric residence system is lower at a folding angle of about 85 degrees or more than the maximum folding force occurring at a folding angle between about 0 degrees and 70 degrees, such as at least about 10% lower, at least about 20% lower, at least about 30% lower, or between about 1% to about 10% lower, about 1% to about 20% lower, or about 1% to about 30% lower. In another embodiment, the folding force of the gastric residence system is lower at a folding angle of about 90 degrees than the maximum folding force occurring at a folding angle between about 0 degrees and 70 degrees, such as at least about 10% lower, at least about 20% lower, at least about 30% lower, or between about 1% to about 10% lower, about 1% to about 20% lower, or about 1% to about 30% lower.

X-Y Bending Force

To maintain gastric residence, gastric residence systems must have sufficient mechanical strength to resist deformation in three dimensions. A fully extended gastric residence system can be envisioned as lying in an x-y plane; when it is fully folded into its compact form, it has been folded so that the arms are parallel to an axis perpendicular to the x-y plane, termed the z-axis. Gastric forces may cause the gastric residence systems to fold in the z-direction, as simulated in the funnel test described immediately above and in Example 5, or they may cause bending in the x-y plane, moving arms of the gastric residence systems together laterally. See FIG. 34A and FIG. 34B for an example of such gastric residence system x-y bending (referred to herein as transverse bending or x-y bending); in FIG. 34B, arms 3406A and 3406F have been moved closer to arm 3406C, while arms 3406B and 3406F have been moved closer to arm 3406D. Measurement of x-y bending is described in Example 22. Such x-y bending mode can also lead to undesired premature passage of the gastric residence systems, and the force required to bend the gastric residence systems in the x-y plane, referred to as the x-y bending force, should be sufficiently large to resist forces typically present in the stomach. The resistance of the gastric residence system to bending in the x-y direction is referred to as the x-y bending force, while the resistance of the gastric residence system to being refolded along its z-axis, referred to as the folding force.

Figure 35A:
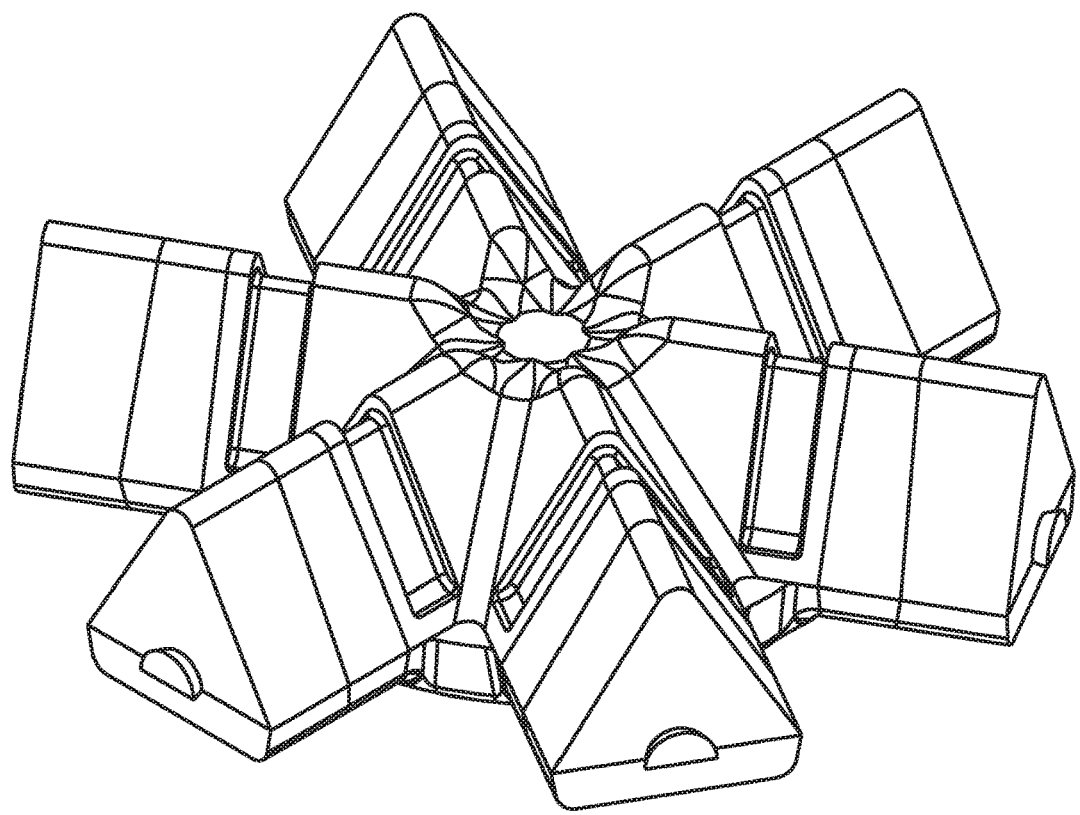
FIG. 35A shows an unwebbed elastomer design.
Figure 35B:
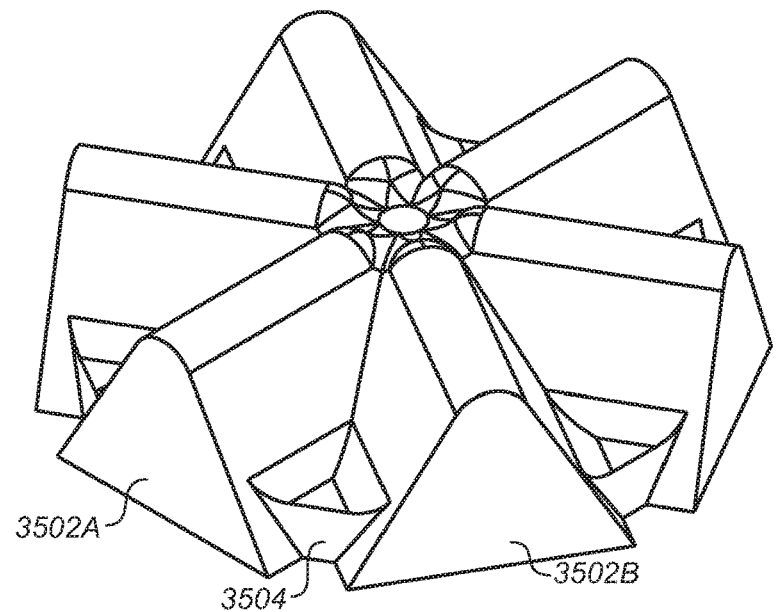
FIG. 35B shows an elastomer design with moderate webbing.
Figure 35C:
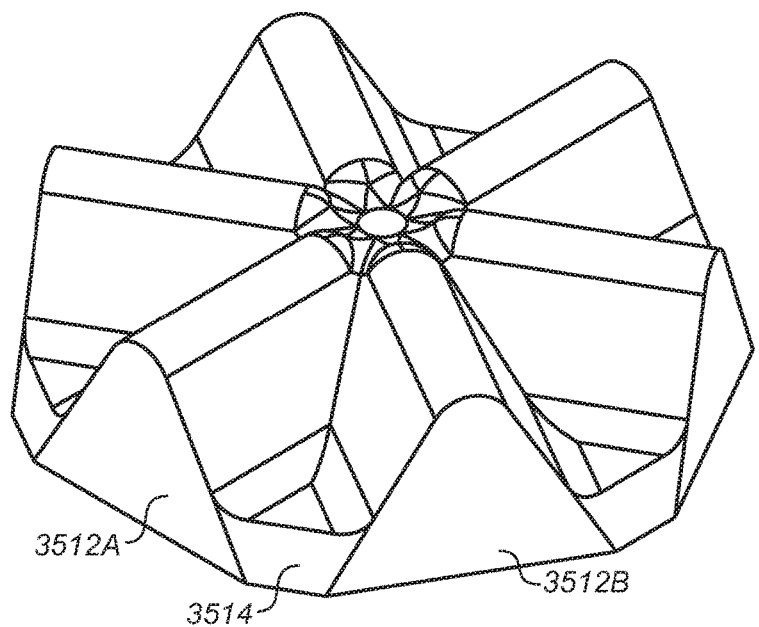
FIG. 35C shows an elastomer design with major webbing.
Figure 35D:
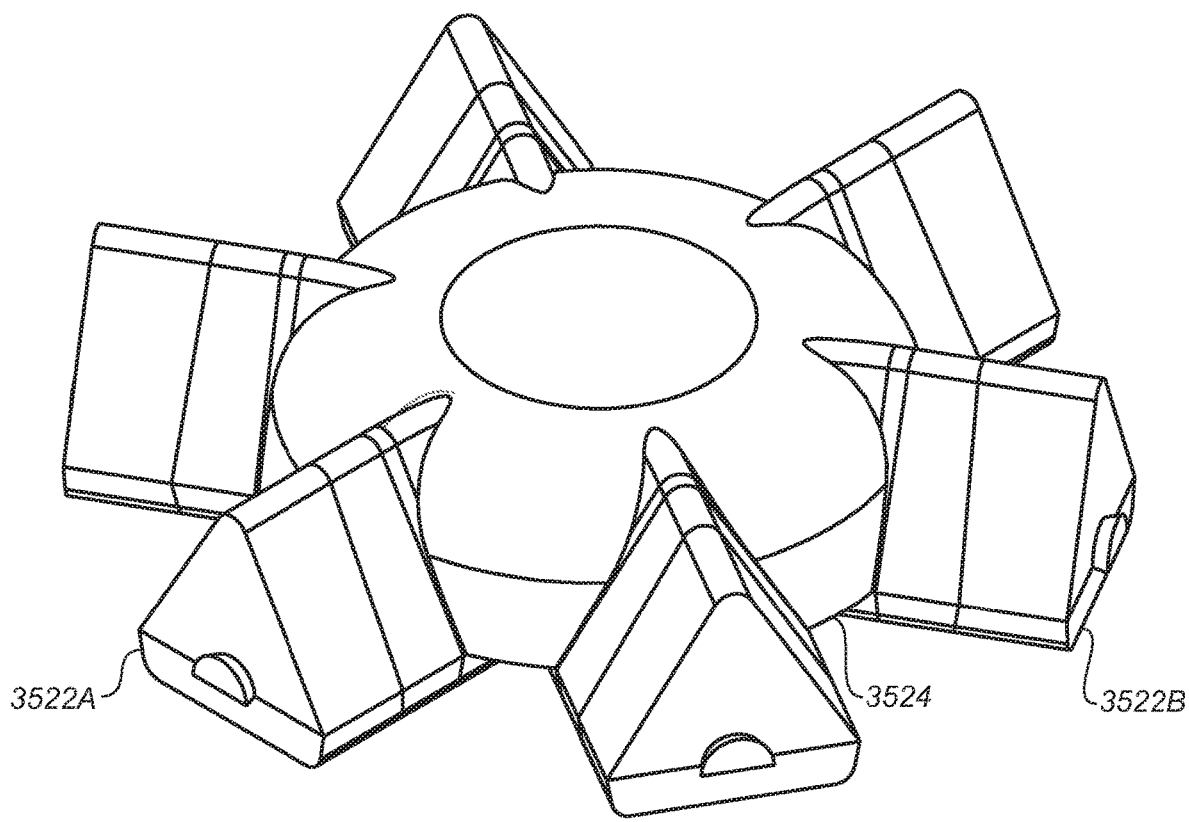
FIG. 35D shows a maximally webbed elastomer design.

The elastomer geometry can be designed to provide sufficient x-y bending force, providing resistance to x-y bending. For example, webbed designs that include additional elastomer material connecting the elastomer branches attached to the arms can provide added resistance to x-y bending. FIG. 35A shows an unwebbed elastomer design, FIG. 35B shows an elastomer design with moderate webbing 3504 between elastomer branches 3502A and 3502B (and similar webbing between the other branches). FIG. 35C shows an elastomer design with major webbing 3514 between elastomer branches 3512A and 3512B (and similar webbing between the other branches). FIG. 35D shows a maximally webbed elastomer design, with webbing 3524 between elastomer branches 3522A and 3522B (and similar webbing between the other branches). The webbed designs have more resistance to x-y bending than the unwebbed designs; as the amount of webbing is increased, the x-y bending force increases.

Resistance to x-y bending is also dependent on the durometer of the material and amount of webbing between elastomer arms. As durometer is increased, the x-y bending force increases.

As noted above, forces in the stomach tend to be about 0.2 Newtons. Therefore, in any of the embodiments of the gastric residence systems, the x-y bending force required to bend the structure is at least about 0.2 Newtons (N), at least about 0.3 N, at least about 0.4 N, at least about 0.5 N, at least about 0.75 N, at least about 1 N, at least about 1.5 N, at least about 2 N, at least about 2.5 N, at least about 3 N, at least about 4 N, or at least about 5 N. In any of the embodiments, the x-y bending force required to bend the structure is between about 0.2 N to about 5 N, between about 0.3 N to about 5 N, between about 0.4 N to about 5 N, between about 0.5 N to about 5 N, between about 0.75 N to about 5 N, between about 1 N to about 5 N, between about 1.5 N to about 5 N, between about 2 N to about 5 N, between about 2.5 N to about 5 N, between about 3 N to about 5 N, or between about 4 N to about 5 N. In any of the embodiments, the x-y bending force required to bend the structure is between about 0.2 N to about 4 N, between about 0.3 N to about 4 N, between about 0.4 N to about 4 N, between about 0.5 N to about 4 N, between about 0.75 N to about 4 N, between about 1 N to about 4 N, between about 1.5 N to about 4 N, between about 2 N to about 4 N, between about 2.5 N to about 4 N, between about 3 N to about 4 N, or between about 3.5 N to about 4 N. In any of the embodiments, the x-y bending force required to bend the structure is between about 0.2 N to about 4 N, between about 0.2 N to about 3.5 N, between about 0.2 N to about 3 N, between about 0.2 N to about 2.5 N, between about 0.2 N to about 2 N, between about 0.2 N to about 1.5 N, between about 0.2 N to about 1 N, between about 0.2 N to about 0.75 N, between about 0.2 N to about 0.5 N, between about 0.2 N to about 0.4 N, or between about 0.2 N to about 0.3 N.

The x-y bending forces described above can occur when an arm or arms are moved by about 5 degrees from the position they would occupy when not subjected to an x-y bending force. The x-y bending forces described above can occur when an arm or arms are moved by about 10 degrees from the position they would occupy when not subjected to an x-y bending force. The x-y bending forces described above can occur when an arm or arms are moved by about 15 degrees from the position they would occupy when not subjected to an x-y bending force.

Segment Couplings

The star design of the system utilizes a central elastomer with multiple carrier polymer-agent components in the form of elongate members ("arms") extending radially from the central elastomer. Forming the carrier polymer-agent component arms from multiple segments is advantageous, whether the central elastomer is in the shape of a disk, an asterisk, or in another shape. Segmented arms permit use of an enteric polymer as a coupling polymer between the segments, which provides for gradual degradation of the connections between segments during gastric residence (and eventual passage of the device after the desired residence period). Segmented arms also provide for rapid degradation of the connections between segments if the system passes intact into the small intestine; such rapid degradation in the intestine is desirable in order to prevent intestinal obstruction.

FIG. 6 shows different embodiments for coupling of the segments in the arms. View 6A shows segments 662 and 664 held together by coupling polymer 640; coupling polymer 640 is an enteric polymer. Coupling polymer 640 can be applied to the end of either segment (662 or 664) by wetting with solvent and placing on the end of the segment. The other segment can then be pressed against coupling polymer 640. Once the solvent dries, the coupling polymer joins segments 662 and 664.

An alternative method of coupling the segments is shown in View 6B and View 6B1. A central piece 675 composed of a "sandwich" of coupling polymer 670 between two small segments 663 and 665 of carrier polymer is prepared, such as by wetting a small piece of coupling polymer 670 with solvent, compressing between small segments 663 and 665, and drying. Segments 662 is then pressed against small segment 663, segment 664 is then pressed against small segment 665, and the materials are heated to fuse together segment 662 with segment 663 and segment 665 with segment 664. Prefabrication of the piece 675 permits a stronger bond to be formed between coupling polymer 670 and the carrier polymer of small segments 663 and 665, although the manufacturing procedure is more complex.

Yet another embodiment of a segment coupling configuration is shown in View 6C of FIG. 6. In this embodiment, one end of a first segment 672 is convex, while the end of the segment 674 that attaches to the convex end of the first segment 672 is concave, with the same or similar curvature, so that the ends of segments 672 and 674 fit together. Coupling polymer 680 is placed between the convex end of segment 672 and the concave end of segment 674.

It should be noted that in any of the embodiments shown in View 6A, View 6B, or View 6C of FIG. 6, the coupling polymer can extend beyond the region formed by the ends of the segments. For example, if segments 662 and 664 in View 6A are cylindrical pieces, with a diameter of 3 mm, coupling polymer 640 can have a diameter of 4 mm, and extend by half a millimeter beyond the junction or joint formed between segments 662 and 664 in all directions. When, as in preferred embodiments, coupling polymer 640 (or 670 or 680) is an enteric polymer, extension of the coupling polymer beyond the region where the segments join serves to expose the polymer to the environment more extensively; the region of the polymer extending beyond the junction wicks liquid from the environment into the region of the polymer contained between the junction of the two segments. This is advantageous in the event that the system moves intact into the small intestine. The region of the polymer extending beyond the inter-segment junction acts as a wick, and the enteric polymer will be more quickly wetted by the more alkaline intestinal fluid. The enteric polymer will begin to degrade more rapidly than it would if the polymer were confined only to the exact region of the joint.

Yet another embodiment of a segment coupling configuration is shown in View 6D of FIG. 6. In this configuration, instead of placing the coupling polymer in the junction between the two segments 662 and 664, the coupling polymer 690 is in the form of a thin film wrapped around the ends of the two segments, forming a collar around the junction, and which thus forms a collar joint or collar junction. This external wrapping provides for simpler manufacture of the elongate members or "arms" of the gastric residence system. This manufacturing advantage is realized whether the cross-section of segments 662 and 664 is rectangular (that is, the segments are solid rectangular prisms), triangular (that is, the segments are in the form of solid triangular prisms), or circular (that is, the segments are solid cylinders), and is particularly easy to manufacture when the segments are in the form of cylindrical pieces. The external wrapping also provides for very fast response of an enteric coupling polymer to the external environment. If the system passes through the pyloric valve, about half of the surface of the coupling polymer is immediately exposed to the more alkaline environment of the small intestine, and intestinal fluid has a much shorter distance to penetrate before the entire coupling polymer is saturated. Thus, an enteric coupling polymer used in this film embodiment will begin to degrade very rapidly. The collar design also increases the strength of the interface through greater surface area for bonding and fixation of multiple degrees of freedom.

The coupling polymer 690 for the collar joint can be readily produced by casting thin films of enteric polymers which are cut into ribbons. Alternatively, the coupling polymer can be extruded as a ribbon. Alternatively, the coupling polymer 690 can be extruded in a hollow tube shape (pipe-like shape), fitted over the segments 662 and 664, and heated in order to heat-shrink the polymer onto the segments.

Example 2 below describes the preparation of an enteric polymer well-suited for use in any of the segment coupling configurations described in FIG. 6, such as the collar joint coupling.

Shape of Arms

Figure 8A:
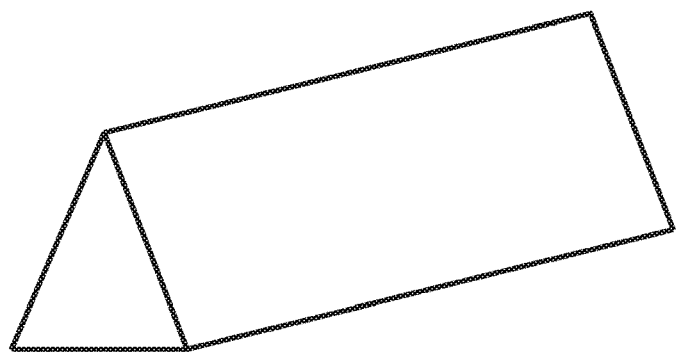
FIG. 8 shows different shapes for the carrier polymer-agent component arms of some embodiments of the system.
Figure 8B:
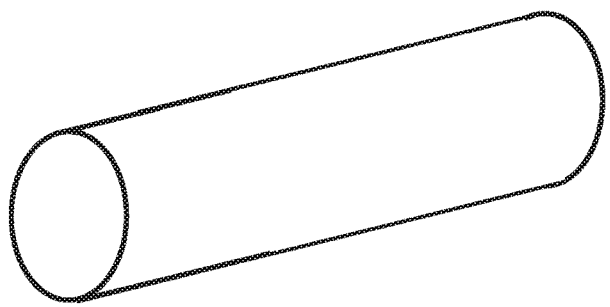
Figure 8C:
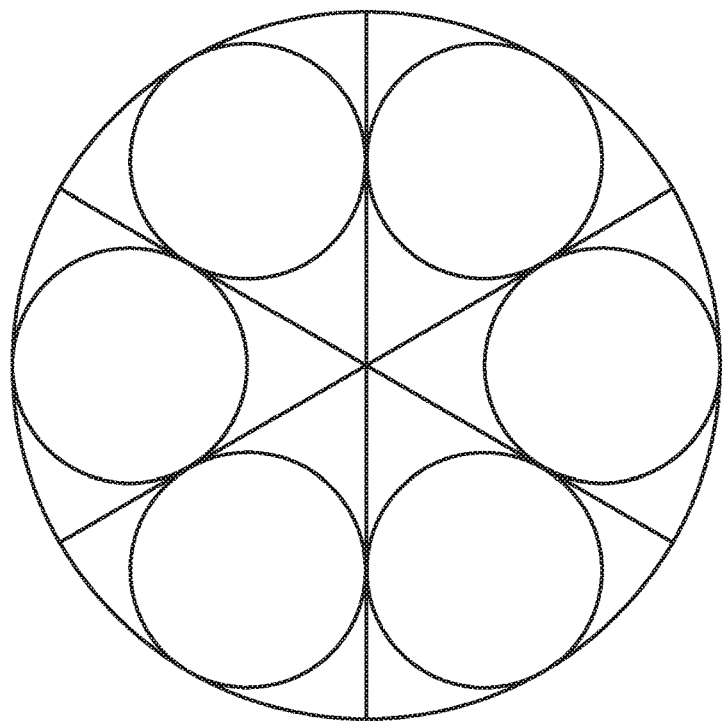

FIG. 8 shows different geometries for the carrier polymer-agent component "arms." Arms with a circular cross-section (that is, cylindrically-shaped arms) as shown in panel B have many benefits over arms with a triangular cross-section (that is, arms shaped as triangular prisms) as shown in panel A, including reduced stress concentrations and improved manufacturability. Active pharmaceutical ingredients (APIs) are blended into polymers using a micro-compounder. The standard dies for hot melt extrusion are circular, which makes a circular arm more easily manufactured. A circular geometry also has fewer stress concentrations than a triangle, which improves the durability of the arms. However, the use of cylindrical arms results in a loss of volume of carrier polymer-agent. Arms with triangular cross-section can be folded to pack against each other in a capsule with minimal loss of space, while arms with circular cross-sections will have gaps between the arms, as illustrated in panel C of FIG. 8.

Arms which have cross-sections in the shape of a polygon (such as arms with a triangular cross-section, rectangular cross-section, or square cross-section) can have rounded corners and edges, for enhanced safety in vivo. That is, instead of having a sharp transition between intersecting edges or planes, an arc is used to transition from one edge or plane to another edge or plane. Thus, "triangular cross-section" includes cross-sections with an approximately triangular shape, such as a triangle with rounded corners. An arm with a triangular cross-section includes an arm where the edges are rounded, and the corners at the end of the arm are rounded. Rounded corners and edges are also referred to as fillet corners, filleted corners, fillet edges, or filleted edges. An arm with a rectangular cross-section includes an arm where the edges are rounded, and the corners at the end of the arm are rounded; the shape of a rectangle with rounded corners is sometimes referred to as a rectellipse. An arm with a square cross-section includes an arm where the edges are rounded, and the corners at the end of the arm are rounded; the shape of a square with rounded corners is sometimes referred to as a squircle.

System Dimensions

The system must be able to adopt a compacted state with dimensions that enable the patient to swallow the system (or for the system to be introduced into the stomach by alternate means, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in Table 3 (see "Draft Guidance for Industry on Size, Shape, and Other Physical Attributes of Generic Tablets and Capsules" at URL www-.regulations.gov/#!documentDetail;D=FDA-2013-N-1434-0002; and Tablets & Capsules November 2015 Annual Buyer's Guide Volume 13, Number 8, available from www.tabletscapsules.com). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in Table 3.

TABLE 3

| Capsule Size | Outer Diameter (mm) | Length (mm) | Capsule Volume (mL) |
| --- | --- | --- | --- |
| 000 | 9.91 | 26.10 | 1.37 |
| 00el | 8.53 | 25.30 | 1.02 |
| 00 | 8.53 | 23.30 | 0.91 |
| 0el | 7.65 | 23.50 | 0.78 |
| 0 | 7.64 | 21.70 | 0.68 |
| 1el | 6.91 | 20.42 | 0.54 |
| 1 | 6.91 | 19.40 | 0.50 |
| 2el | 6.36 | 19.30 | 0.41 |
| 2 | 6.35 | 18.00 | 0.37 |
| 3 | 5.82 | 15.90 | 0.30 |
| 4el | 5.32 | 14.30 | 0.21 |
| 4 | 5.32 | 14.30 | 0.21 |
| 5 | 4.91 | 11.10 | 0.13 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule, for example, in a manner such as that shown in FIG. 2C. Once the capsule dissolves in the stomach, the system will adopt a configuration suitable for gastric retention, for example, in a manner such as that shown in FIG. 2 or FIG. 2A. Preferred capsule sizes are 00 and 00el (a 00el-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In another embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter.

For star-shaped polymers with N arms (where N is greater than or equal to three), the arms can have dimensions such that the system has at least two perpendicular dimensions, each of length as noted above. For example, the system of FIG. 2A can be circumscribed by a triangle, as shown in FIG. 2B, where the triangle is described by the length of its base B and height H, where B and H are perpendicular, and which comprise the two perpendicular dimensions of length as noted above. These two perpendicular dimensions are chosen as noted above in order to promote retention of the gastric residence system.

The system is designed to eventually break apart in the stomach at the end of the desired residence time. Once the coupling polymers break, the remaining components of the system are of dimensions that permit passage of the system through the pyloric sphincter, small intestine, and large intestine. Finally, the system is eliminated from the body by defecation, or by eventual complete dissolution of the system in the small and large intestines.

System Polymeric Composition

The choice of the individual polymers for the carrier polymer, coupling polymer, and elastomer influence many properties of the system, such as therapeutic agent elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of therapeutic agent from the carrier polymer-agent component is affected by numerous factors, including the composition and properties of the carrier polymer, which may itself be a mixture of several polymeric and non-polymeric components; the properties of the therapeutic agent such as hydrophilicity/hydrophobicity, charge state, pKa, and hydrogen bonding capacity; and the properties of the gastric environment. In the aqueous environment of the stomach, avoiding burst release of a therapeutic agent (where burst release refers to a high initial delivery of active pharmaceutical ingredient upon initial deployment of the system in the stomach), particularly a hydrophilic therapeutic agent, and maintaining sustained release of the therapeutic agent over a period of time of days to weeks is challenging.

The residence time of the systems in the stomach is adjusted by the choice of coupling polymers. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

Carrier Polymers for Carrier Polymer-Agent Component

The carrier polymer-agent component contains the therapeutic agent substance to be eluted from the gastric residence system in the gastric environment. Therapeutic agent is blended into the carrier polymer to form a carrier polymer-agent mixture. This mixture can be formed into the desired shape or shapes for use as carrier polymer-agent components in the systems, such as rods for the systems depicted in FIG. 2 and FIG. 2A. Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), poly(methacrylic acid), polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly (2-ethyl-2-oxazoline), poly(ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer, particularly PCL with a number-average molecular weight ($M_n$) of 80,000.

Other excipients can be added to the carrier polymers to modulate the release of therapeutic agent. Such excipients can be added in amounts from about 1% to 15%, preferably from about 5% to 10%, more preferably about 5% or about 10%. Examples of such excipients include Poloxamer 407 (available as Kolliphor P407, Sigma Cat #62035); Pluronic P407; Eudragit EPO (available from Evonik); hypromellose (available from Sigma, Cat #H3785), Kolliphor RH40 (available from Sigma, Cat #07076), polyvinyl caprolactam, polyvinyl acetate, polyethylene glycol, and Soluplus (available from BASF; a copolymer of polyvinyl caprolactam, polyvinyl acetate, and polyethylene glycol).

Methods of Manufacture of Carrier Polymer Agent Components

Blending temperatures for incorporation of the therapeutic agent into polymeric matrices typically range from about 80° C. to about 120° C., although higher or lower temperatures can be used for polymers which are best blended at temperatures outside that range. When using free crystals of the agent, and when maintaining the crystalline particles is desired, blending temperatures are preferably from about 80° C. to about 100° C., so as not to melt the particles or crystals of the agent.

Hot melt extrusion can be used to prepare the carrier polymer-agent components. Single-screw or, preferably, twin-screw systems can be used. As noted, carrier polymers can be used which can be melted at temperatures which do not melt the particles of the agent blended into the polymer, since melting the agent particles may dramatically change the size distribution characteristics of the particles. In some embodiments, however, using the agent in amorphous form is advantageous, or impossible to avoid, in which case the particles of agent can be melted.

Melting and casting can also be used to prepare the carrier polymer-agent components. The carrier polymer and therapeutic agent, and any other desired components, are mixed together. The carrier polymer is melted (again, at temperatures which do not melt the therapeutic agent particles), and the melt is mixed so that the therapeutic agent particles are evenly distributed in the melt, poured into a mold, and allowed to cool. Injection molding of carrier polymer-agent components can also be used.

Solvent casting can also be used to prepare the carrier polymer-agent components. The polymer is dissolved in a solvent, and therapeutic agent particles are added. A solvent should be used which does not dissolve the agent particles, so as to avoid altering the size characteristics of the particles. The solvent-carrier polymer-agent particle mixture is then mixed to evenly distribute the particles, poured into a mold, and the solvent is evaporated.

Therapeutic Agent Particle Size and Milling

Control of particle size used in the gastric residence systems is important for both optimal therapeutic agent release and mechanical stability of the systems. The particle size of the therapeutic agents affects the surface area of the agents available for dissolution when gastric fluid permeates the carrier polymer-agent components of the system. Also, as the "arms" (elongate members) of the systems are relatively thin in diameter (for example, 1 millimeter to 5 millimeters), the presence of an agent particle of a size in excess of a few percent of the diameter of the arms will result in a weaker arm, both before the agent elutes from the device, and after elution when a void is left in the space formerly occupied by the agent particle. Such weakening of the arms is disadvantageous, as it may lead to premature breakage and passage of the system before the end of the desired residence period.

In one embodiment, the therapeutic agent particles used for blending into the carrier polymer-agent components are smaller than about 100 microns in diameter. In another embodiment, the therapeutic agent particles are smaller than about 75 microns in diameter. In another embodiment, the therapeutic agent particles are smaller than about 50 microns in diameter. In another embodiment, the therapeutic agent particles are smaller than about 40 microns in diameter. In another embodiment, the therapeutic agent particles are smaller than about 30 microns in diameter. In another embodiment, the therapeutic agent particles are smaller than about 25 microns in diameter. In another embodiment, the therapeutic agent particles are smaller than about 20 microns in diameter. In another embodiment, the therapeutic agent particles are smaller than about 10 microns in diameter. In another embodiment, the therapeutic agent particles are smaller than about 5 microns in diameter.

In one embodiment, at least about 80% of the therapeutic agent particles used for blending into the carrier polymer-agent components are smaller than about 100 microns in diameter. In another embodiment, at least about 80% of the therapeutic agent particles are smaller than about 75 microns in diameter. In another embodiment, at least about 80% of the therapeutic agent particles are smaller than about 50 microns in diameter. In another embodiment, at least about 80% of the therapeutic agent particles are smaller than about 40 microns in diameter. In another embodiment, at least about 80% of the therapeutic agent particles are smaller than about 30 microns in diameter. In another embodiment, at least about 80% of the therapeutic agent particles are smaller than about 25 microns in diameter. In another embodiment, at least about 80% of the therapeutic agent particles are smaller than about 20 microns in diameter. In another embodiment, at least about 80% of the therapeutic agent particles are smaller than about 10 microns in diameter. In another embodiment, at least about 80% of the therapeutic agent particles are smaller than about 5 microns in diameter.

In one embodiment, at least about 80% of the mass of therapeutic agent particles used for blending into the carrier polymer-agent components have sizes between about 1 micron and about 100 microns in diameter. In another embodiment, at least about 80% of the mass of therapeutic agent particles have sizes between about 1 micron and about 75 microns in diameter. In another embodiment, at least about 80% of the mass of therapeutic agent particles have sizes between about 1 micron and about 50 microns in diameter. In another embodiment, at least about 80% of the mass of therapeutic agent particles have sizes between about 1 micron and about 40 microns in diameter. In another embodiment, at least about 80% of the mass of therapeutic agent particles have sizes between about 1 micron and about 30 microns in diameter. In another embodiment, at least about 80% of the mass of therapeutic agent particles have sizes between about 1 micron and about 25 microns in diameter. In another embodiment, at least about 80% of the mass of therapeutic agent particles have sizes between about 1 micron and about 20 microns in diameter. In another embodiment, at least about 80% of the mass of therapeutic agent particles have sizes between about 1 micron and about 10 microns in diameter. In another embodiment, at least about 80% of the mass of therapeutic agent particles have sizes between about 1 micron and about 5 microns in diameter.

In one embodiment, at least about 80% of the mass of therapeutic agent particles used for blending into the carrier polymer-agent components have sizes between about 2 microns and about 100 microns in diameter. In another embodiment, at least about 80% of the mass of therapeutic agent particles have sizes between about 2 microns and about 75 microns in diameter. In another embodiment, at least about 80% of the mass of therapeutic agent particles have sizes between about 2 microns and about 50 microns in diameter. In another embodiment, at least about 80% of the mass of therapeutic agent particles have sizes between about 2 microns and about 40 microns in diameter. In another embodiment, at least about 80% of the mass of therapeutic agent particles have sizes between about 2 microns and about 30 microns in diameter. In another embodiment, at least about 80% of the mass of therapeutic agent particles have sizes between about 2 microns and about 25 microns in diameter. In another embodiment, at least about 80% of the mass of therapeutic agent particles have sizes between about 2 microns and about 20 microns in diameter. In another embodiment, at least about 80% of the mass of therapeutic agent particles have sizes between about 2 microns and about 10 microns in diameter. In another embodiment, at least about 80% of the mass of therapeutic agent particles have sizes between about 2 microns and about 5 microns in diameter.

In one embodiment, at least about 80% of the mass of therapeutic agent particles used for blending into the carrier polymer-agent components have sizes between about 5 microns and about 100 microns in diameter. In another embodiment, at least about 80% of the mass of therapeutic agent particles have sizes between about 5 microns and about 75 microns in diameter. In another embodiment, at least about 80% of the mass of therapeutic agent particles have sizes between about 5 microns and about 50 microns in diameter. In another embodiment, at least about 80% of the mass of therapeutic agent particles have sizes between about 5 microns and about 40 microns in diameter. In another embodiment, at least about 80% of the mass of therapeutic agent particles have sizes between about 5 microns and about 30 microns in diameter. In another embodiment, at least about 80% of the mass of therapeutic agent particles have sizes between about 5 microns and about 25 microns in diameter. In another embodiment, at least about 80% of the mass of therapeutic agent particles have sizes between about 5 microns and about 20 microns in diameter. In another embodiment, at least about 80% of the mass of therapeutic agent particles have sizes between about 5 microns and about 10 microns in diameter.

The particle size of the therapeutic agents can be readily adjusted by milling. Several milling techniques are available to reduce larger particles to smaller particles of desired size. Fluid energy milling is a dry milling technique which uses inter-particle collisions to reduce the size of particles. A type of fluid energy mill called an air jet mill shoots air into a cylindrical chamber in a manner so as to maximize collision between therapeutic agent particles. Ball milling utilizes a rolling cylindrical chamber which rotates around its principal axis. The therapeutic agent and grinding material (such as steel balls, made from chrome steel or CR-NI steel; ceramic balls, such as zirconia; or plastic polyamides) collide, causing reduction in particle size of the agent. Ball milling can be performed in either the dry state, or with liquid added to the cylinder where the therapeutic agent and the grinding material are insoluble in the liquid. Further information regarding milling is described in the chapter by R. W. Lee et al. entitled "Particle Size Reduction" in *Water-Insoluble Drug Formulation*, Second Edition (Ron Liu, editor), Boca Raton, Florida: CRC Press, 2008; and in the chapter by A. W. Brzeczko et al. entitled "Granulation of Poorly Water-Soluble Drugs" in *Handbook of Pharmaceutical Granulation Technology*, Third Edition (Dilip M. Parikh, editor), Boca Raton, Florida: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Milling Additives

Substances can be added to the therapeutic agent material during milling to assist in obtaining particles of the desired size, and minimize aggregation during handling. Silica (silicon dioxide, $SiO_2$) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 5% of milling additive, such as silica, can be used for fluid milling or ball milling, or about 0.1% to about 4%, about 0.1% to about 3%, about 0.1% to about 2%, about 0.1% to about 1%, about 1% to about 5%, about 1% to about 4%, about 1% to about 3%, about 1% to about 2%, or about 0.1%, about 0.5%, about 1%, about 2%, about 3%, about 4% or about 5%.

Particle Sizing

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

Dispersants for Modulation of Therapeutic Agent Release and Stability of Polymer Blend The use of a dispersant in the carrier polymer-agent component provides numerous advantages. The rate of elution of therapeutic agent from the carrier polymer-agent component is affected by numerous factors as previously noted, including the composition and properties of the carrier polymer (which may itself comprise multiple polymeric and non-polymeric components); the physical and chemical properties of the therapeutic agent; and the gastric environment. Avoiding burst release of therapeutic agent, especially hydrophilic agents, and maintaining sustained release of the therapeutic agent over the residence period is an important characteristic of the systems. The use of a dispersant according to the invention enables better control of release rate and suppression of burst release. Burst release and release rate can be tuned by using varied concentrations of dispersant.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant.

Therapeutic agents, such as drugs, to be incorporated into the carrier polymers can be granulated by wet granulation or dry granulation. Granulation of drugs can be useful for enhancing solubility, particularly for hydrophobic drugs which are poorly soluble in water. Drugs can be granulated with solutions of solubilizers such as polyalkylene oxides (for example, polyethylene glycol (PEG), polypropylene glycol (PPG), PEG-PPG co-polymers, PEG-PPG block co-polymers), polyethoxylated castor oil, and detergents. In some embodiments, where the carrier polymer-agent components comprise a therapeutic agent having a solubility lower than about 1 mg/ml, 0.5 mg/ml, 0.1 mg/ml, or 0.05 mg/ml in 0.1N HCl, the therapeutic agent is granulated with one or more solubilizers, such as one of the foregoing solubilizers (polyalkylene oxides (for example, polyethylene glycol (PEG), polypropylene glycol (PPG), PEG-PPG co-polymers, PEG-PPG block co-polymers), polyethoxylated castor oil, and detergents) prior to blending with the carrier polymer.

Granulation for hydrophobic drugs is preferably used in combination with relatively small drug particle sizes, such as embodiments where the therapeutic agent particles are smaller than about 20 microns in diameter, embodiments where the therapeutic agent particles are smaller than about 10 microns in diameter, embodiments where the therapeutic agent particles are smaller than about 5 microns in diameter, embodiments where at least about 80% of the therapeutic agent particles are smaller than about 20 microns in diameter, embodiments where at least about 80% of the therapeutic agent particles are smaller than about 10 microns in diameter, embodiments where at least about 80% of the therapeutic agent particles are smaller than about 5 microns in diameter, embodiments where at least about 80% of the mass of the therapeutic agent particles have sizes between about 1 micron and about 20 microns in diameter, embodiments where at least about 80% of the mass of the therapeutic agent particles have sizes between about 1 micron and about 10 microns in diameter, embodiments where at least about 80% of the mass of the therapeutic agent particles have sizes between about 1 micron and about 5 microns in diameter, embodiments where at least about 80% of the mass of the therapeutic agent particles have sizes between about 2 microns and about 20 microns in diameter, embodiments where at least about 80% of the mass of the therapeutic agent particles have sizes between about 2 microns and about 10 microns in diameter, embodiments where at least about 80% of the mass of the therapeutic agent particles have sizes between about 2 microns and about 5 microns in diameter, embodiments where at least about 80% of the mass of the therapeutic agent particles have sizes between about 5 microns and about 20 microns in diameter, or embodiments where at least about 80% of the mass of the therapeutic agent particles have sizes between about 5 microns and about 10 microns in diameter.

In addition to anti-aggregation/anti-flocculation activity, the dispersant can help prevent phase separation during fabrication and/or storage of the systems. This is particularly useful for manufacture of the systems by hot melt extrusion.

The weight/weight ratio of dispersant to therapeutic agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Linkers/Coupling Polymers

The coupling polymer is used to link one or more carrier polymer-agent components to one or more carrier polymer-agent components, to link one or more carrier polymer-agent components to one or more elastomer components, or to link one or more elastomer components to one or more elastomer components, to link one or more interfacing polymers to one or more elastomer components, or to link one or more carrier polymer-agent components to one or more interfacing polymers. The coupling polymer component of the gastric residence systems that is used to link carrier polymer-agent components, elastomer components, or interfacing polymers to other polymer-agent components, elastomer components, or interfacing polymers can be referred to simply as a linker. The linkers used in the gastric residence systems are designed to eventually disintegrate, whether due to the influence of a change in pH, due to the passage of time, such as time spent in an aqueous environment, due to other factors such as an external stimulus, or due to any combination of the foregoing causes. In some embodiments, enteric polymers are used as coupling polymers, and can be referred to as enteric linkers. In some embodiments, time-dependent polymers which are pH-resistant, that is, less sensitive to changes in pH than enteric polymers, are used as coupling polymers, and can be referred to as time-dependent linkers. In some embodiments, both enteric polymers and time-dependent polymers which are less sensitive to changes in pH than enteric polymers are used as coupling polymers. Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. If, during treatment, the gastric residence system must be removed quickly for any reason, the patient can drink a mildly basic aqueous solution (such as a bicarbonate solution) in order to induce immediate de-coupling of the gastric residence system.

It should be noted that a "time-dependent linker" is made of a material which degrades over time, but does not exclude some weakening under conditions where an enteric polymer would no longer function to link components. By "time-dependent polymer which are pH-resistant" (or equivalently, "pH-resistant time-dependent polymers") is meant that, under conditions where an enteric polymer would degrade to the point that it would no longer link the components together, the time-dependent polymer will still have sufficient mechanical strength to link the components together. In some embodiments, the time-dependent polymer retains about the same linking capacity, that is, about 100% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer retains at least about 90% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer retains at least about 75% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer retains at least about 60% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer retains at least about 50% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer retains at least about 25% of its linkage strength, after exposure to a solution between about pH 7 to about pH 8 as it has after exposure to a solution between about pH 2 to about pH 3, where the exposure is for about an hour, about a day, about three days, or about a week; a preferable exposure period for the measurement is about a day. In some embodiments, the time-dependent polymer resists breaking under a flexural force of up to about 0.2 Newtons (N), about 0.3 N, about 0.4 N, about 0.5 N, about 0.75 N, about 1 N, about 1.5 N, about 2 N, about 2.5 N, about 3 N, about 4 N, about 5 N, about 10 N, about 20 N, about 25 N, about 30 N, about 40 N, or about 50 N, after exposure to a solution between about pH 7 to about pH 8, where the exposure is for about an hour, about a day, about three days, or about a week; a preferable exposure period for the measurement is about a day. In some embodiments, the time-dependent polymer resists breaking under a flexural force of about 0.2 N to about 5 N, about 0.3 N to about 5 N, about 0.4 N to about 5 N, about 0.5 N to about 5 N, about 0.75 N to about 5 N, about 1 N to about 5 N, about 1.5 N to about 5 N, about 2 N to about 5 N, about 2.5 N to about 5 N, about 3 N to about 5 N, or about 4 N to about 5 N, after exposure to a solution between about pH 7 to about pH 8, where the exposure is for about an hour, about a day, about three days, or about a week; a preferable exposure period for the measurement is about a day. In some embodiments, the time-dependent polymer resists breaking under a flexural force of about 0.2 N to about 50 N, about 0.2 N to about 40 N, about 0.2 N to about 30 N, about 0.2 N to about 25 N, about 0.2 N to about 20 N, or about 0.2 N to about 10 N, after exposure to a solution between about pH 7 to about pH 8, where the exposure is for about an hour, about a day, about three days, or about a week; a preferable exposure period for the measurement is about a day. Linkage strength can be measured by any relevant test that serves to test coupling ability, such as the four-point bending flexural test (ASTM D790) described in Example 3.

Polymers that degrade or otherwise weaken in a time-dependent manner in the gastric environment can be prepared from a variety of materials, or blends of materials. For example, the liquid plasticizer triacetin releases from a polymer formulation in a time-dependent manner over seven days in simulated gastric fluid, while Plastoid B retains its strength over a seven-day period in simulated gastric fluid. Thus, a polymer that degrades or weakens in a time-dependent manner can be readily prepared by mixing Plastoid B and triacetin; the degradation time of the Plastoid B-triacetin mixture can be extended by increasing the amount of Plastoid B used in the mixture (that is, by using less triacetin in the mixture), while the degradation time can be decreased by decreasing the amount of Plastoid B used in the mixture (that is, by using more triacetin in the mixture). As the triacetin releases over time, the Plastoid B-triacetin mixture weakens over time.

Exemplary coupling polymers include, but are not limited to, hydroxypropyl methylcellulose acetate succinate (hypromellose acetate succinate, HPMC-AS), cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, poly(methacrylic acid-co-ethyl acrylate), methacrylic acid methylmethacrylate copolymer, methyl acrylate-methacrylic acid copolymer, methacrylate-methacrylic acid-octyl acrylate copolymer, poly(ethylene-co-vinyl acetate), poly (butyl methacrylate), poly(lactic-co-glycolic acid) (PLGA), and copolymers, mixtures, blends and combinations thereof. Some of the enteric polymers that can be used in the invention are listed in Table 4, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Hydroxypropyl methylcellulose acetate succinate (hypromellose acetate succinate, HPMC-AS) is a preferred enteric polymer. HPMC-AS is available from several suppliers, such as Ashland, Covington, Kentucky, United States, under the trademark AQUASOLVE. Poly(methacrylic acid-co-ethyl acrylate) (sold under the trade name EUDRAGIT L 100-55; EUDRAGIT is a registered trademark of Evonik Rohm GmbH, Darmstadt, Germany) is another preferred enteric polymer. Cellulose acetate phthalate, cellulose acetate succinate, and hydroxypropyl methylcellulose phthalate are also suitable enteric polymers.

Since enteric linkers are chosen to weaken at higher pH, the enteric linkers used in the gastric residence system weaken to a greater extent when incubated in simulated intestinal fluid (SIF, preferably fasted-state SIF) than in simulated gastric fluid (SGF; preferably fasted-state SGF).

The relative percentage of weakening after incubation in SIF versus SGF is calculated by dividing the force at which the linker breaks or yields after incubation in SIF by the force at which the linker breaks or yields after incubation in SGF; subtracting that quotient from 1; and then multiplying by 100 to obtain a relative percentage weakening in SIF versus SGF. Thus, if a linker breaks under a force of 50 Newtons after incubation in SGF, and breaks under a force of 10 Newtons after incubation in SIF, the relative weakening is $\{[1-(5/50)]\times100\}=90\%$, or 90% relative weakening in SIF versus SGF. The force at which a linker breaks can be measured by the test as described in Example 13 below. In one embodiment, the relative weakening of the enteric linkers after incubation in SIF versus incubation in SGF is at least about 10%. In one embodiment, the relative weakening of the enteric linkers after incubation in SIF versus incubation in SGF is at least about 20%. In one embodiment, the relative weakening of the enteric linkers after incubation in SIF versus incubation in SGF is at least about 25%. In one embodiment, the relative weakening of the enteric linkers after incubation in SIF versus incubation in SGF is at least about 30%. In one embodiment, the relative weakening of the enteric linkers after incubation in SIF versus incubation in SGF is at least about 40%. In one embodiment, the relative weakening of the enteric linkers after incubation in SIF versus incubation in SGF is at least about 50%. In one embodiment, the relative weakening of the enteric linkers after incubation in SIF versus incubation in SGF is at least about 60%. In one embodiment, the relative weakening of the enteric linkers after incubation in SIF versus incubation in SGF is at least about 70%. In one embodiment, the relative weakening of the enteric linkers after incubation in SIF versus incubation in SGF is at least about 75%. In one embodiment, the relative weakening of the enteric linkers after incubation in SIF versus incubation in SGF is at least about 80%. In one embodiment, the relative weakening of the enteric linkers after incubation in SIF versus incubation in SGF is at least about 90%. The relative weakening can be measured for about an hour, about a day, about two days, or about three days; a preferable period for measuring relative weakening is about a day.

In another embodiment, the relative weakening of the enteric linkers after incubation in SIF versus incubation in SGF is between about 10% to about 90%. In one embodiment, the relative weakening of the enteric linkers after incubation in SIF versus incubation in SGF is between about 20% to about 90%. In one embodiment, the relative weakening of the enteric linkers after incubation in SIF versus incubation in SGF is between about 25% to about 90%. In one embodiment, the relative weakening of the enteric linkers after incubation in SIF versus incubation in SGF is between about 30% to about 90%. In one embodiment, the relative weakening of the enteric linkers after incubation in SIF versus incubation in SGF is between about 40% to about 90%. In one embodiment, the relative weakening of the enteric linkers after incubation in SIF versus incubation in SGF is between about 50% to about 90%. In one embodiment, the relative weakening of the enteric linkers after incubation in SIF versus incubation in SGF is between about 60% to about 90%. In one embodiment, the relative weakening of the enteric linkers after incubation in SIF versus incubation in SGF is between about 70% to about 90%. In one embodiment, the relative weakening of the enteric linkers after incubation in SIF versus incubation in SGF is between about 75% to about 90%. In one embodiment, the relative weakening of the enteric linkers after incubation in SIF versus incubation in SGF is between about 80% to about 90%. In one embodiment, the relative weakening of the enteric linkers after incubation in SIF versus incubation in SGF is between about 90% to about 99%. The relative weakening can be measured for about an hour, about a day, about two days, or about three days; a preferable period for measuring relative weakening is about a day.

Enteric linkers can also be characterized by the pH at which they no longer function to link components together ("linkage failure"), in addition to characterization by relative weakening in SIF versus SGF. Enteric linkers are intended to weaken at the pH values found in the small intestine, and thus it is desirable for linkage failure to occur at high pH. In one embodiment, the enteric linkers used in the gastric residence system no longer link components at a pH above about 4. In another embodiment, the enteric linkers used in the gastric residence system no longer link components at a pH above about 5. In another embodiment, the enteric linkers used in the gastric residence system no longer link components at a pH above about 6. In another embodiment, the enteric linkers used in the gastric residence system no longer link components at a pH above about 7. In another embodiment, the enteric linkers used in the gastric residence system no longer link components at a pH above about 7.5. In another embodiment, the enteric linkers used in the gastric residence system no longer link components at a pH between about 4 and about 5. In another embodiment, the enteric linkers used in the gastric residence system no longer link components at a pH between about 4 and about 6. In another embodiment, the enteric linkers used in the gastric residence system no longer link components at a pH between about 4 and about 7. In another embodiment, the enteric linkers used in the gastric residence system no longer link components at a pH between about 4 and about 7.5. In another embodiment, the enteric linkers used in the gastric residence system no longer link components at a pH between about 5 and about 6. In another embodiment, the enteric linkers used in the gastric residence system no longer link components at a pH between about 5 and about 7. In another embodiment, the enteric linkers used in the gastric residence system no longer link components at a pH between about 5 and about 7.5. In another embodiment, the enteric linkers used in the gastric residence system no longer link components at a pH between about 6 and about 7. In another embodiment, the enteric linkers used in the gastric residence system no longer link components at a pH between about 6 and about 7.5. The linkage failure can occur after exposure to the pH values as indicated for about an hour, about a day, about two days, or about three days; a preferable period for measuring linkage failure is about a day.

Enteric linkers can also be characterized by the pH at which they dissolve. In one embodiment, the enteric linkers used in the gastric residence system dissolve at a pH above about 4. In another embodiment, the enteric linkers used in the gastric residence system dissolve at a pH above about 5. In another embodiment, the enteric linkers used in the gastric residence system dissolve at a pH above about 6. In another embodiment, the enteric linkers used in the gastric residence system dissolve at a pH above about 7. In another embodiment, the enteric linkers used in the gastric residence system dissolve at a pH above about 7.5. In another embodiment, the enteric linkers used in the gastric residence system dissolve at a pH between about 4 and about 5. In another embodiment, the enteric linkers used in the gastric residence system dissolve at a pH between about 4 and about 6. In another embodiment, the enteric linkers used in the gastric residence system dissolve at a pH between about 4 and about 7. In another embodiment, the enteric linkers used in the gastric residence system dissolve at a pH between about 4 and about 7.5. In another embodiment, the enteric linkers used in the gastric residence system dissolve at a pH between about 5 and about 6. In another embodiment, the enteric linkers used in the gastric residence system dissolve at a pH between about 5 and about 7. In another embodiment, the enteric linkers used in the gastric residence system dissolve at a pH between about 5 and about 7.5. In another embodiment, the enteric linkers used in the gastric residence system dissolve at a pH between about 6 and about 7. In another embodiment, the enteric linkers used in the gastric residence system dissolve at a pH between about 6 and about 7.5. The dissolution can occur after exposure to the pH values as indicated for about an hour, about a day, about two days, or about three days; a preferable period for measuring dissolution is about a day.

The enteric polymers used for enteric linkers can also be characterized by their weakening, linkage failure, or dissolution properties. This characterization is carried out on the enteric polymer itself. In one embodiment, the relative weakening of the enteric polymers after incubation in SIF versus incubation in SGF is at least about 10%. In one embodiment, the relative weakening of the enteric polymers after incubation in SIF versus incubation in SGF is at least about 20%. In one embodiment, the relative weakening of the enteric polymers after incubation in SIF versus incubation in SGF is at least about 25%. In one embodiment, the relative weakening of the enteric polymers after incubation in SIF versus incubation in SGF is at least about 30%. In one embodiment, the relative weakening of the enteric polymers after incubation in SIF versus incubation in SGF is at least about 40%. In one embodiment, the relative weakening of the enteric polymers after incubation in SIF versus incubation in SGF is at least about 50%. In one embodiment, the relative weakening of the enteric polymers after incubation in SIF versus incubation in SGF is at least about 60%. In one embodiment, the relative weakening of the enteric polymers after incubation in SIF versus incubation in SGF is at least about 70%. In one embodiment, the relative weakening of the enteric polymers after incubation in SIF versus incubation in SGF is at least about 75%. In one embodiment, the relative weakening of the enteric polymers after incubation in SIF versus incubation in SGF is at least about 80%. In one embodiment, the relative weakening of the enteric polymers after incubation in SIF versus incubation in SGF is at least about 90%. The relative weakening can be measured for about an hour, about a day, about two days, or about three days; a preferable period for measuring relative weakening is about a day.

In another embodiment, the relative weakening of the enteric polymers after incubation in SIF versus incubation in SGF is between about 10% to about 90%. In one embodiment, the relative weakening of the enteric polymers after incubation in SIF versus incubation in SGF is between about 20% to about 90%. In one embodiment, the relative weakening of the enteric polymers after incubation in SIF versus incubation in SGF is between about 25% to about 90%. In one embodiment, the relative weakening of the enteric polymers after incubation in SIF versus incubation in SGF is between about 30% to about 90%. In one embodiment, the relative weakening of the enteric polymers after incubation in SIF versus incubation in SGF is between about 40% to about 90%. In one embodiment, the relative weakening of the enteric polymers after incubation in SIF versus incubation in SGF is between about 50% to about 90%. In one embodiment, the relative weakening of the enteric polymers after incubation in SIF versus incubation in SGF is between about 60% to about 90%. In one embodiment, the relative weakening of the enteric polymers after incubation in SIF versus incubation in SGF is between about 70% to about 90%. In one embodiment, the relative weakening of the enteric polymers after incubation in SIF versus incubation in SGF is between about 75% to about 90%. In one embodiment, the relative weakening of the enteric polymers after incubation in SIF versus incubation in SGF is between about 80% to about 90%. In one embodiment, the relative weakening of the enteric polymers after incubation in SIF versus incubation in SGF is between about 90% to about 99%. The relative weakening can be measured for about an hour, about a day, about two days, or about three days; a preferable period for measuring relative weakening is about a day.

In terms of linkage failure, in one embodiment, the enteric polymers used in the gastric residence system no longer link components at a pH above about 4. In another embodiment, the enteric polymers used in the gastric residence system no longer link components at a pH above about 5. In another embodiment, the enteric polymers used in the gastric residence system no longer link components at a pH above about 6. In another embodiment, the enteric polymers used in the gastric residence system no longer link components at a pH above about 7. In another embodiment, the enteric polymers used in the gastric residence system no longer link components at a pH above about 7.5. In another embodiment, the enteric polymers used in the gastric residence system no longer link components at a pH between about 4 and about 5. In another embodiment, the enteric polymers used in the gastric residence system no longer link components at a pH between about 4 and about 6. In another embodiment, the enteric polymers used in the gastric residence system no longer link components at a pH between about 4 and about 7. In another embodiment, the enteric polymers used in the gastric residence system no longer link components at a pH between about 4 and about 7.5. In another embodiment, the enteric polymers used in the gastric residence system no longer link components at a pH between about 5 and about 6. In another embodiment, the enteric polymers used in the gastric residence system no longer link components at a pH between about 5 and about 7. In another embodiment, the enteric polymers used in the gastric residence system no longer link components at a pH between about 5 and about 7.5. In another embodiment, the enteric polymers used in the gastric residence system no longer link components at a pH between about 6 and about 7. In another embodiment, the enteric polymers used in the gastric residence system no longer link components at a pH between about 6 and about 7.5. The linkage failure can occur after exposure to the pH values as indicated for about an hour, about a day, about two days, or about three days; a preferable period for measuring linkage failure is about a day.

In terms of dissolution, in one embodiment, the enteric polymers used in the gastric residence system dissolve at a pH above about 4. In another embodiment, the enteric polymers used in the gastric residence system dissolve at a pH above about 5. In another embodiment, the enteric polymers used in the gastric residence system dissolve at a pH above about 6. In another embodiment, the enteric polymers used in the gastric residence system dissolve at a pH above about 7. In another embodiment, the enteric polymers used in the gastric residence system dissolve at a pH above about 7.5. In another embodiment, the enteric polymers used in the gastric residence system dissolve at a pH between about 4 and about 5. In another embodiment, the enteric polymers used in the gastric residence system dissolve at a pH between about 4 and about 6. In another embodiment, the enteric polymers used in the gastric residence system dissolve at a pH between about 4 and about 7. In another embodiment, the enteric polymers used in the gastric residence system dissolve at a pH between about 4 and about 7.5. In another embodiment, the enteric polymers used in the gastric residence system dissolve at a pH between about 5 and about 6. In another embodiment, the enteric polymers used in the gastric residence system dissolve at a pH between about 5 and about 7. In another embodiment, the enteric polymers used in the gastric residence system dissolve at a pH between about 5 and about 7.5. In another embodiment, the enteric polymers used in the gastric residence system dissolve at a pH between about 6 and about 7. In another embodiment, the enteric polymers used in the gastric residence system dissolve at a pH between about 6 and about 7.5. The dissolution can occur after exposure to the pH values as indicated for about an hour, about a day, about two days, or about three days; a preferable period for measuring dissolution is about a day.

It should be noted that an "enteric linker" is made of a material which degrades at pH values higher than the average stomach pH, but does not exclude weakening over time in addition to degradation at higher pH. That is, an enteric linker will degrade at the desired pH, and in addition, may or may not degrade over time as well.

TABLE 4

| Polymer | Dissolution pH |
|---|---|
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate (HPMCAS) | 7.0 |
| HPMCAS-L (AQUASOLVE) | ~5.8-6.0 |
| HPMCAS-M (AQUASOLVE) | ~6.0-6.2 |
| HPMCAS-H (AQUASOLVE) | ~6.8-7.0 |
| Poly (methyl vinyl ether/maleic acid) monoethyl ester | 4.5-5.0 |
| Poly (methyl vinyl ether/maleic acid) n-butyl ester | 5.4 |

In some embodiments, the carrier polymer-agent components are elongate members comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

In the stellate gastric residence system, linkers, whether time-dependent linkers, enteric linkers, or other types of linkers, can be characterized by a "radial length." Radial length refers to the length of the linker, measured from the part of the linker most proximal to the central elastomer to the part of the linker most distal from the central elastomer. Linkers can have a radial length of about 0.25 mm, about 0.5 mm, about 0.75 mm, about 1 mm, about 1.5. mm, about 2 mm, about 3 mm, about 4 mm, or about 5 mm. Linkers can have a radial length varying from about 0.25 mm to about 5 mm, about 0.25 mm to about 4 mm, about 0.25 mm to about 3 mm, about 0.25 mm to about 2 mm, about 0.25 mm to about 1.5 mm, about 0.25 mm to about 1 mm, about 0.25 mm to about 0.75 mm, about 0.25 mm to about 0.5 mm, about 0.5 mm to about 5 mm, about 0.5 mm to about 4 mm, about 0.5 mm to about 3 mm, about 0.5 mm to about 2 mm, about 0.5 mm to about 1.5 mm, about 0.5 mm to about 1 mm, about 0.5 mm to about 0.75 mm, about 0.75 mm to about 5 mm, about 0.75 mm to about 4 mm, about 0.75 mm to about 3 mm, about 0.75 mm to about 2 mm, about 0.75 mm to about 1.5 mm, about 0.75 mm to about 1 mm, about 1 mm to about 5 mm, about 1 mm to about 4 mm, about 1 mm to about 3 mm, about 1 mm to about 2 mm, about 1 mm to about 1.5 mm, about 1.5 mm to about 5 mm, about 2 mm to about 5 mm, about 3 mm to about 5 mm, or about 4 mm to about 5 mm.

Plasticizers can also be added to either enteric (pH-dependent) linkers or time-dependent linkers to adjust their properties as desired. Examples of plasticizers that can be added to the linkers are triacetin, triethyl citrate, tributyl citrate, poloxamers. Additional plasticizers that can be added to the linkers include polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, or diacetylated monoglycerides.

Elastomers

Elastomers (also referred to as elastic polymers or tensile polymers) enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In a one embodiment, the elastomer is an enteric polymer, such as those listed in Table 4. In another embodiment, the coupling polymer(s) used in the system are also elastomers. Elastomers are preferred for use as the central polymer in the star-shaped or stellate design of the gastric residence systems. Silicone elastomers or silicone rubbers, which can be prepared by injection molding from liquid silicone rubbers, are preferred elastomers. Such silicone elastomers are polysiloxanes, typically polydimethylsiloxanes, and can optionally incorporate varying amounts of silica (silicon dioxide) to adjust physical and chemical properties. Such silicone elastomers can be prepared from, for example, the KE-2090, KE-2096, or KE-2097 series of liquid silicone rubbers sold by Shin-Etsu Silicones of America, Inc., Akron, Ohio, United States. Crosslinked polycaprolactone, such as the elastomer prepared in Example 1B, is another preferred elastomer.

In one preferred embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Additional examples of elastomers which can be used include urethane-cross-linked polycaprolactones (see Example 1, section B), poly(acryloyl 6-aminocaproic acid) (PA6ACA), poly(methacrylic acid-co-ethyl acrylate) (EUDRAGIT L 100-55), and mixtures of poly(acryloyl 6-aminocaproic acid) (PA6ACA) and poly(methacrylic acid-co-ethyl acrylate) (EUDRAGIT L 100-55) (see Example 1, Section C).

Elastomer Properties: Compression Set

Compression set describes the permanent deformation of a material that has been subjected to compressive forces, after the removal of the compressive forces. The elastomer of a gastric residence system should show low compression set (low permanent deformation) during storage, so that the system properly unfolds and deploys when released from the container (such as a capsule) in which it is stored. Common protocols for compression set testing are ASTM D-395 and ASTM D-1414.

Elastomers used in the gastric residence systems and other assemblies of the invention have as low a compression set as possible. Elastomers can be used which have a compression set less than about 30%, such as about 30% to about 20%, about 30% to about 15%, about 30% to about 10%, about 30% to about 5%, or about 30% to about 1%. Preferably, elastomers are used which have a compression set less than about 25%, such as about 25% to about 20%, about 25% to about 15%, about 25% to about 10%, about 25% to about 5%, or about 25% to about 1%. Still more preferably, elastomers are used which have a compression set less than about 20%, such as about 20% to about 15%, about 20% to about 10%, about 20% to about 5%, or about 20% to about 1%. Even more preferably, elastomers are used which have a compression set less than about 15%, such as about 15% to about 10%, about 15% to about 5%, or about 15% to about 1%. Yet more preferably, elastomers are used which have a compression set less than about 10%, such as about 10% to about 5%, or about 10% to about 1%.

Elastomer Properties: Durometer

Figure 21:
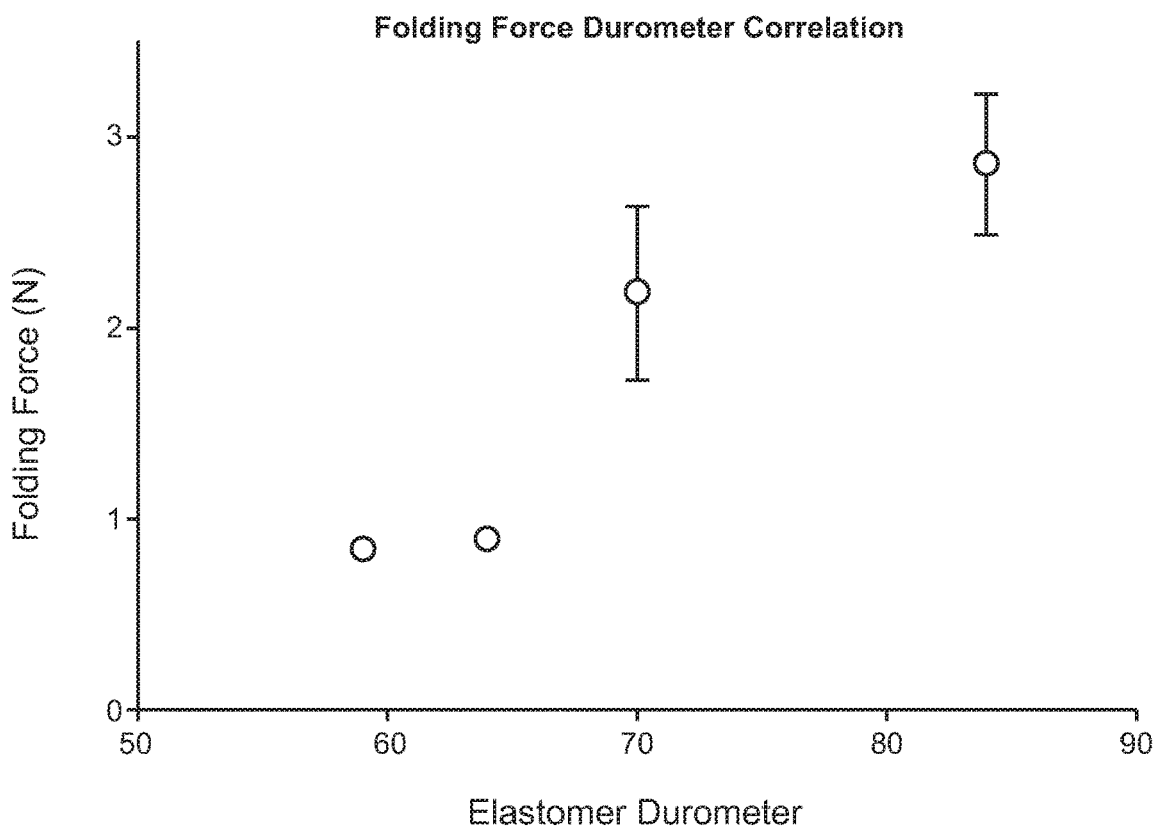
FIG. 21 shows the folding force/durometer correlation of a concave design.

The durometer of a material measures the elastic modulus or stiffness of a material. When tested using the funnel test, the durometer directly correlated with the folding force of the gastric residence system (see Example 8, Table 5, and FIG. 21). Elastomers used in the invention can have a durometer reading (on the Shore A scale) of about 5 A to about 90 A, about 5 A to about 75 A, about 10 A to about 70 A, or about 20 A to about 60 A.

Elastomer Properties: Tear Strength

The tear strength (or tear resistance) of a material measures the resistance of a material to undergo rupture. High tear strength prevents the elastomer from rupturing when placed under load in a capsule or when deployed and loaded in the gastric cavity. The material used for the elastomers used in the invention can have a tear strength of at least about 20 kN/m (kiloNewtons/meter), such as about 20 kN/m to about 40 kN/m, about 20 kN/m to about 50 kN/m, or about 20 kN/m to about 75 kN/m. The material used for the elastomers used in the invention can have a tear strength of at least about 25 kN/m, such as about 25 kN/m to about 40 kN/m, about 25 kN/m to about 50 kN/m, or about 25 kN/m to about 75 kN/m. The material used for the elastomers used in the invention can have a tear strength of at least about 30 kN/m, such as about 30 kN/m to about 40 kN/m, about 30 kN/m to about 50 kN/m, or about 30 kN/m to about 75 kN/m. The material used for the elastomers used in the invention can have a tear strength of at least about 35 kN/m, such as about 35 kN/m to about 40 kN/m, about 35 kN/m to about 50 kN/m, or about 35 kN/m to about 75 kN/m. Tear strength can be measured using the protocol described by ASTM D624, using a test piece geometry of Type A (geometry A).

Elastomer Properties: Biocompatibility

Because the gastric residence systems of the invention will be in contact with tissues in the digestive tract, biocompatible elastomers are used in the invention. USP Plastic Class VI (United States Pharmacopeia and National Formulary, USP-NF) is the most stringently tested measure of biocompatibility. Thus, elastomers used in the invention are preferably made from plastics meeting USP Class VI specifications.

Combined Elastomer Properties

As noted above, elastomers made from liquid silicone rubber (LSR) are preferred, especially for the star-shaped or stellate gastric residence systems. As noted in Example 8, Table 5, elastomers made from silicone rubber can be prepared which have good durometer, compression set, tear strength, and biocompatibility parameters.

Thus, in one embodiment, an elastomer is used in the gastric residence systems from a material which has a durometer value (Shore A scale) of between about 10-90 A, a compression set of less than about 30%, a tear strength of at least about 25 kN/m, and which meets USP Class VI specifications. In another embodiment, an elastomer is used in the gastric residence systems from a material which has a durometer value (Shore A scale) of between about 10-80 A, a compression set of less than about 20%, a tear strength of at least about 30 kN/m, and which meets USP Class VI specifications. In another embodiment, an elastomer is used in the gastric residence systems from a material which has a durometer value (Shore A scale) of between about 10-70 A, a compression set of less than about 10%, a tear strength of at least about 30 kN/m, and which meets USP Class VI specifications. In another embodiment, an elastomer is used in the gastric residence systems from a material which has a durometer value (Shore A scale) of between about 10-70 A, a compression set of less than about 10%, a tear strength of at least about 35 kN/m, and which meets USP Class VI specifications.

Other System Characteristics

Stabilization of Therapeutic Agents

Many therapeutic agents are prone to oxidative degradation when exposed to reactive oxygen species, which can be present in the stomach. A therapeutic agent contained in the system may thus oxidize due to the prolonged residence in the stomach of the system, and the extended release period of agent from the system. Accordingly, it is desirable to stabilize the agent to prevent oxidative and other degradation.

Anti-oxidant stabilizers that can be included in the systems to reduce or prevent oxidation of the therapeutic agent include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm).

Certain therapeutic agents can be pH-sensitive, especially at the low pH present in the gastric environment. Stabilizer compounds that can be included in the systems to reduce or prevent degradation of therapeutic agent at low pH include calcium carbonate, calcium lactate, calcium phosphate, sodium phosphate, and sodium bicarbonate. They are typically used in an amount of up to about 2% w/w.

The anti-oxidant stabilizers, pH stabilizers, and other stabilizer compounds are blended into the polymers containing the therapeutic agent by blending the stabilizer(s) into the molten carrier polymer-agent mixture. The s tabilizer(s) can be blended into molten carrier polymer prior to blending the therapeutic agent into the polymer-stabilizer mixture; or the stabilizer(s) can be blended with therapeutic agent prior to formulation of the blended therapeutic agent-stabilizer mixture in the carrier polymer; or stabilizer(s), therapeutic agent, and molten carrier polymer can be blended simultaneously. Therapeutic agent can also be blended with molten carrier polymer prior to blending the stabilizer(s) into the polymer-agent mixture.

In one embodiment, less than about 10% of the therapeutic agent remaining in the system is degraded or oxidized after a gastric residence period of about 24 hours. In one embodiment, less than about 10% of the therapeutic agent remaining in the system is degraded or oxidized after a gastric residence period of about 48 hours. In one embodiment, less than about 10% of the therapeutic agent remaining in the system is degraded or oxidized after a gastric residence period of about 72 hours. In one embodiment, less than about 10% of the therapeutic agent remaining in the system is degraded or oxidized after a gastric residence period of about 96 hours. In one embodiment, less than about 10% of the therapeutic agent remaining in the system is degraded or oxidized after a gastric residence period of about five days. In another embodiment, less than about 10% of the therapeutic agent remaining in the system is degraded or oxidized after a gastric residence period of about a week. In another embodiment, less than about 10% of the therapeutic agent remaining in the system is degraded or oxidized after a gastric residence period of about two weeks. In another embodiment, less than about 10% of the therapeutic agent remaining in the system is degraded or oxidized after a gastric residence period of about three weeks. In another embodiment, less than about 10% of the therapeutic agent remaining in the system is degraded or oxidized after a gastric residence period of about four weeks. In another embodiment, less than about 10% of the therapeutic agent remaining in the system is degraded or oxidized after a gastric residence period of about a month.

In one embodiment, less than about 5% of the therapeutic agent remaining in the system is degraded or oxidized after a gastric residence period of about 24 hours. In one embodiment, less than about 5% of the therapeutic agent remaining in the system is degraded or oxidized after a gastric residence period of about 48 hours. In one embodiment, less than about 5% of the therapeutic agent remaining in the system is degraded or oxidized after a gastric residence period of about 72 hours. In one embodiment, less than about 5% of the therapeutic agent remaining in the system is degraded or oxidized after a gastric residence period of about 96 hours. In one embodiment, less than about 5% of the therapeutic agent remaining in the system is degraded or oxidized after a gastric residence period of about five days. In another embodiment, less than about 5% of the therapeutic agent remaining in the system is degraded or oxidized after a gastric residence period of about a week. In another embodiment, less than about 5% of the therapeutic agent remaining in the system is degraded or oxidized after a gastric residence period of about two weeks. In another embodiment, less than about 5% of the therapeutic agent remaining in the system is degraded or oxidized after a gastric residence period of about three weeks. In another embodiment, less than about 5% of the therapeutic agent remaining in the system is degraded or oxidized after a gastric residence period of about four weeks. In another embodiment, less than about 5% of the therapeutic agent remaining in the system is degraded or oxidized after a gastric residence period of about a month.

Therapeutic Agents for Use in Gastric Residence Systems

Therapeutic agents which can be administered to or via the gastrointestinal tract can be used in the gastric residence systems of the invention. Therapeutic agents include, but are not limited to, drugs, pro-drugs, biologics, and any other substance which can be administered to produce a beneficial effect on an illness or injury. Therapeutic agents that can be used in the gastric residence systems of the invention include statins, such as rosuvastatin; nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; anti-dementia drugs, such as memantine; cardiac glycosides such as digoxin; alpha blockers such as tamsulosin; cholesterol absorption inhibitors such as ezetimibe; anti-gout treatments, such as colchicine; antihistamines, such as loratadine and cetirizine, opioids, such as loperamide; proton-pump inhibitors, such as omeprazole, antiviral agents, such as entecavir; antibiotics, such as doxycycline, ciprofloxacin, and azithromycin; anti-malarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as therapeutic agents in the gastric residence systems of the invention include proteins, polypeptides, polynucleotides, and hormones. Exemplary classes of therapeutic agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "therapeutic agent" includes salts, solvates, polymorphs, and co-crystals of the aforementioned substances. In certain embodiments, the therapeutic agent is selected from the group consisting of cetirizine, rosuvastatin, escitalopram, citalopram, risperidone, olanzapine, donezepil, and ivermectin. In another embodiment, the therapeutic agent is one that is used to treat a neuropsychiatric disorder, such as an anti-psychotic agent or an anti-dementia drug such as memantine.

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days, or up to about 7 days. In one embodiment, the gastric residence system has a residence time of about 10 days, or up to about 10 days. In one embodiment, the gastric residence system has a residence time of about 14 days, or up to about 14 days. In one embodiment, the gastric residence system has a residence time of about 3 weeks, or up to about 3 weeks. In one embodiment, the gastric residence system has a residence time of about 4 weeks, or up to about 4 weeks. In one embodiment, the gastric residence system has a residence time of about one month, or up to about one month.

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

In one embodiment, the gastric residence system has a residence time between about 24 hours and about three weeks. In one embodiment, the gastric residence system has a residence time between about 48 hours and about three weeks. In one embodiment, the gastric residence system has a residence time between about 72 hours and about three weeks. In one embodiment, the gastric residence system has a residence time between about 96 hours and about three weeks. In one embodiment, the gastric residence system has a residence time between about 5 days and about three weeks. In one embodiment, the gastric residence system has a residence time between about 6 days and about three weeks. In one embodiment, the gastric residence system has a residence time between about 7 days and about three weeks. In one embodiment, the gastric residence system has a residence time between about 10 days and about three weeks. In one embodiment, the gastric residence system has a residence time between about 14 days and about three weeks.

In one embodiment, the gastric residence system has a residence time between about 24 hours and about four weeks. In one embodiment, the gastric residence system has a residence time between about 48 hours and about four weeks. In one embodiment, the gastric residence system has a residence time between about 72 hours and about four weeks. In one embodiment, the gastric residence system has a residence time between about 96 hours and about four weeks. In one embodiment, the gastric residence system has a residence time between about 5 days and about four weeks. In one embodiment, the gastric residence system has a residence time between about 6 days and about four weeks. In one embodiment, the gastric residence system has a residence time between about 7 days and about four weeks. In one embodiment, the gastric residence system has a residence time between about 10 days and about four weeks. In one embodiment, the gastric residence system has a residence time between about 14 days and about four weeks. In one embodiment, the gastric residence system has a residence time between about three weeks and about four weeks.

In one embodiment, the gastric residence system has a residence time between about 24 hours and about one month. In one embodiment, the gastric residence system has a residence time between about 48 hours and about one month. In one embodiment, the gastric residence system has a residence time between about 72 hours and about one month. In one embodiment, the gastric residence system has a residence time between about 96 hours and about one month. In one embodiment, the gastric residence system has a residence time between about 5 days and about one month. In one embodiment, the gastric residence system has a residence time between about 6 days and about one month. In one embodiment, the gastric residence system has a residence time between about 7 days and about one month. In one embodiment, the gastric residence system has a residence time between about 10 days and about one month. In one embodiment, the gastric residence system has a residence time between about 14 days and about one month. In one embodiment, the gastric residence system has a residence time between about three weeks and about one month.

The gastric residence system releases a therapeutically effective amount of therapeutic agent during at least a portion of the residence time or residence period during which the system resides in the stomach. In one embodiment, the system releases a therapeutically effective amount of therapeutic agent during at least about 25% of the residence time. In one embodiment, the system releases a therapeutically effective amount of therapeutic agent during at least about 50% of the residence time. In one embodiment, the system releases a therapeutically effective amount of therapeutic agent during at least about 60% of the residence time. In one embodiment, the system releases a therapeutically effective amount of therapeutic agent during at least about 70% of the residence time. In one embodiment, the system releases a therapeutically effective amount of therapeutic agent during at least about 75% of the residence time. In one embodiment, the system releases a therapeutically effective amount of therapeutic agent during at least about 80% of the residence time. In one embodiment, the system releases a therapeutically effective amount of therapeutic agent during at least about 85% of the residence time. In one embodiment, the system releases a therapeutically effective amount of therapeutic agent during at least about 90% of the residence time. In one embodiment, the system releases a therapeutically effective amount of therapeutic agent during at least about 95% of the residence time. In one embodiment, the system releases a therapeutically effective amount of therapeutic agent during at least about 98% of the residence time. In one embodiment, the system releases a therapeutically effective amount of therapeutic agent during at least about 99% of the residence time.

Radiopacity; X-Ray Imaging; Magnetic Resonance Imaging

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or are added to a small portion of the system. Examples of suitable radiopaque substances are barium sulfate, bismuth subcarbonate, bismuth oxychloride, and bismuth trioxide. In one embodiment, these materials are not be blended into the polymers used to construct the gastric residence systems, so as not to alter therapeutic agent release from the carrier polymer, or desired properties of other system polymers. In another embodiment, these materials are blended into the polymers used in the gastric residence systems, where the altered release properties are taken into account when determining dosage, residence time, and other parameters. Metal striping or tips on a small portion of the system components can also be used, such as tungsten. Alternatively, a radiopaque fiducial can be incorporated into one or more components of the system.

Magnetic resonance imaging (MM) can also be used to visualize the gastric residence systems in vivo. The materials of the system may themselves be visualizable using Mill. Alternatively, small iron particles or superparamagnetic particles can be incorporated into the systems (similar to the approach used in Hansen et al., Invest. Radiol. 48(11):770 (2013)).

Manufacture/Assembly of System

The stellate or star-shaped design embodiment of the gastric residence system can be assembled by preparing carrier polymer-agent components as "arms" in the shape of elongate members. When the arms are prepared in the shape of a cylinder, they comprise a flat proximal end (one base of the cylinder, the first base), a distal end (the other base of the cylinder, a second base), and a curved outer surface therebetween enclosing the volume of the cylinder.

The central elastomer of the gastric residence system can be prepared in the shape of an "asterisk," such as element 320 in FIG. 3, Panel 3A. The elongate members (arms) comprised of carrier polymer-agent components can then be attached to the ends of each branch of the asterisk by heat welding, infrared welding, melt interfacing, adhesives, solvent welding, or other methods.

Example 1 describes preparation of carrier polymer-agent component "arms" (Section A) and central elastomer (Section B). Example 3 describes the effect of different solvents on the adhesive force of an enteric polymer used to join two polymer sheets.

Piecewise Assembly of Gastric Residence Systems

Manufacture of gastric residence systems of the invention can be performed by various methods. One such method comprises separate production of the various components of the gastric residence system, followed by assembly of the components, in a piecewise (that is, piece-by-piece) manner. Such a method comprises:

A. Forming an elastomer component. In some embodiments, the elastomer component is asterisk-shaped with a plurality of at least three branches.

B. Forming a plurality of at least three carrier polymer-agent components, which are elongate members comprising a proximal end and a distal end.

Note that forming step A and forming step B can be performed in any order, or simultaneously.

C. Attaching the elongate members to the elastomer component. When the elongate members are attached, and in the absence of any external constraining forces, the resulting assembly is the gastric residence system in its uncompacted form. The elongate members are attached to the elastomer component such that, in its uncompacted form, the gastric residence system has at least two perpendicular dimensions, each dimension of at least two centimeters, that is, the gastric residence system measures at least about 2 cm in length over at least two perpendicular directions; or the perimeter of the gastric residence system in its uncompacted state, when projected onto a plane, has two perpendicular dimensions, each of at least 2 cm in length. (Further possible values for the lengths of the perpendicular dimensions are provided in the section describing System Dimensions.)

In order to place the gastric residence system into a capsule or other container for administration to a patient, a further step can be performed, comprising:

D. Compacting the gastric residence system and inserting the system into a container, such as a capsule, suitable for oral administration or administration through a gastric tube or feeding tube.

Step A, the formation of an elastomer, can be performed by any method suitable for preparing a shaped polymer, such as by injection molding, gravity molding, compression molding, extrusion, or three-dimensional printing. The elastomer can be formed in the shape of a disk, a ring, a toroid, a torus, a sphere, an oblate ellipsoid (also called an oblate spheroid, an ellipsoid, or an oblate sphere; an oblate ellipsoid is a disk-shaped object), or any other shape which has at least one axis of rotational symmetry, such as a cube or a rectangular cuboid. "Toroid" and "torus" refer to a solid toroid and a solid torus, respectively; that is, a solid with an outer surface in the shape of a toroid or torus, and not simply the outer surface itself. Such a toroid or torus shape can be referred to as "toroidal." The shape can be concave on both sides, such as the bi-concave disk shown in FIG. 4A, FIG. 4B, FIG. 4C, FIG. 4D, or FIG. 18D, or can be concave on one side and convex on the other side, such as the concavo-convex disk shown in FIG. 5A, FIG. 5B, FIG. 5C, FIG. 5D, or FIG. 18B. The concavo-convex portion or bi-concave portion can be confined to a central part of the disk, as shown in FIG. 4A, FIG. 4B, FIG. 4C, FIG. 4D, FIG. 5A, FIG. 5B, FIG. 5C, FIG. 5D, FIG. 18B, and FIG. 18D. In some embodiments, the elastomer can be concave on one side and flat or substantially flat on the other side, a configuration described as mono-concave. Optionally, the shape of the elastomer can have branches, protrusions, or convexities where the carrier polymer-agent components which are elongate members can be attached. Optionally, the shape of the elastomer can have indentations, concavities, dimples, or recesses where the carrier polymer-agent components which are elongate members can be attached.

Step B, the formation of the plurality of at least three carrier polymer-agent components, in the shape of elongate members, can likewise be performed by any suitable method for making shaped polymers, such as injection molding, gravity molding, compression molding, extrusion, or three-dimensional printing using the carrier polymer-agent mixture. Prior to formation, the therapeutic agent is milled as described herein, and then mixed with the appropriate carrier polymer, dispersant, and other ingredients as described herein. The elongate members can be formed in the shape of solid rectangular prisms, solid triangular prisms, or solid cylinders; solid cylinders are preferred. Additionally, as noted herein, the elongate members can be formed from two, three, or more segments which are coupled by coupling polymers, preferably coupled by enteric polymers. Elongate members can be formed by joining together segments using butt joints (that is, the end of one segment can be joined to the end of another segment by adhesion, such as by a film of enteric polymer between and adhering to the ends of both of the segments, as in FIG. 6A or FIG. 6C), or by melting segments together (as in FIG. 6B), or can be formed by joining together segments using collar joints (that is, a film of an enteric polymer can be wrapped around the ends of two segments, as in FIG. 6D).

Step C, attaching the carrier polymer-agent component elongate members to the elastomer component, can be performed by various methods, such as heat welding, infrared welding, melt interfacing, adhesives, solvent welding, or any other method suitable for attachment of polymers. If the elastomer has branches, collar joints can be used for attaching the carrier polymer-agent component elongate members to the elastomer component. The attachments of the carrier polymer-agent component elongate members to the elastomer component can be formed using enteric polymers. Once the carrier polymer-agent components are attached to the elastomer component, the gastric residence system will be in its uncompacted form in the absence of any external constraining forces.

Step D, compacting the gastric residence system and inserting the system into a container, can be performed either manually or mechanically, by compacting, folding, or compressing the gastric residence system into its compacted configuration, and insertion of the system into a capsule or other container of appropriate size.

Overmolding Assembly

Figure 14A:
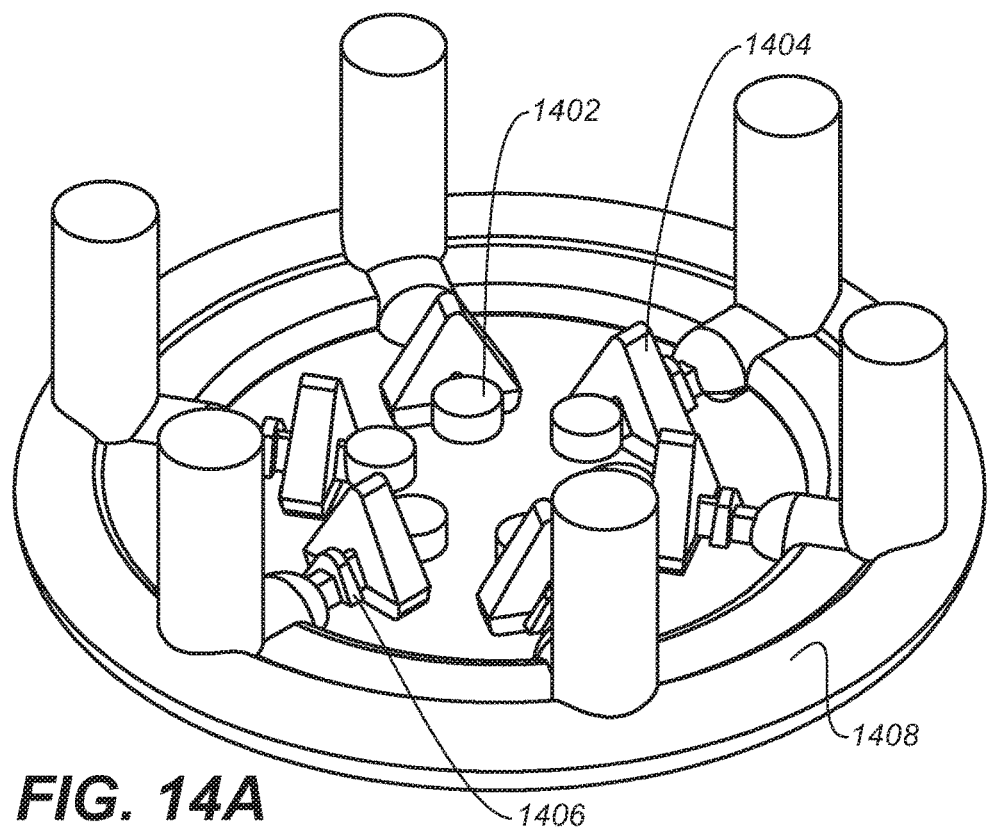
FIG. 14A shows injection molding of intercomponent anchors on a scaffold.
Figure 14B:
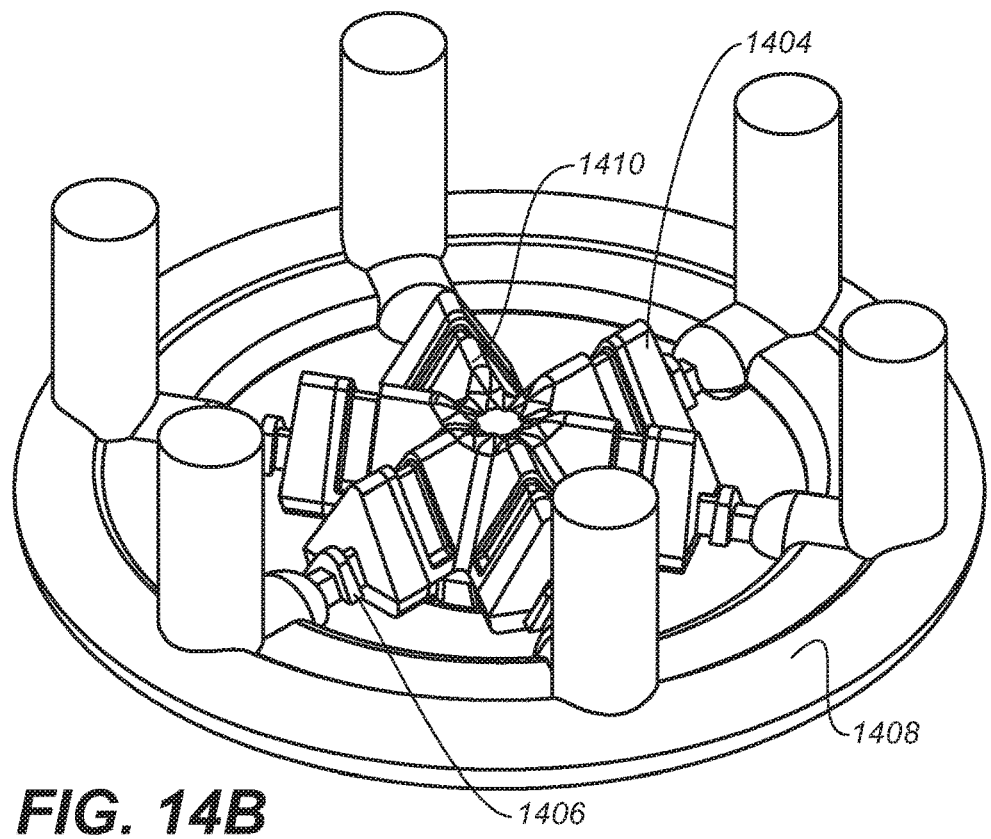
FIG. 14B shows injection molding of a silicone elastomer over a first portion of the intercomponent anchors.
Figure 15A:
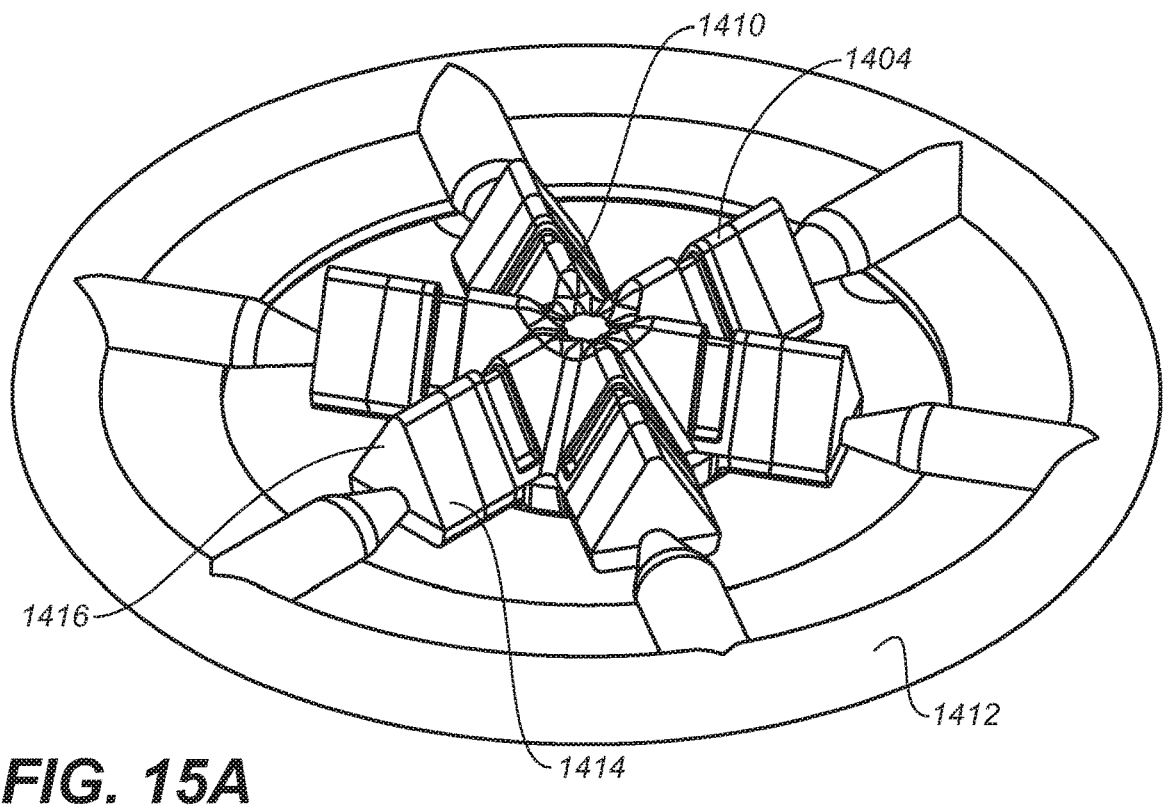
FIG. 15A shows injection molding of carrier polymer components over a second portion of the intercomponent anchors, along with a scaffold for the carrier polymer components.
Figure 15B:
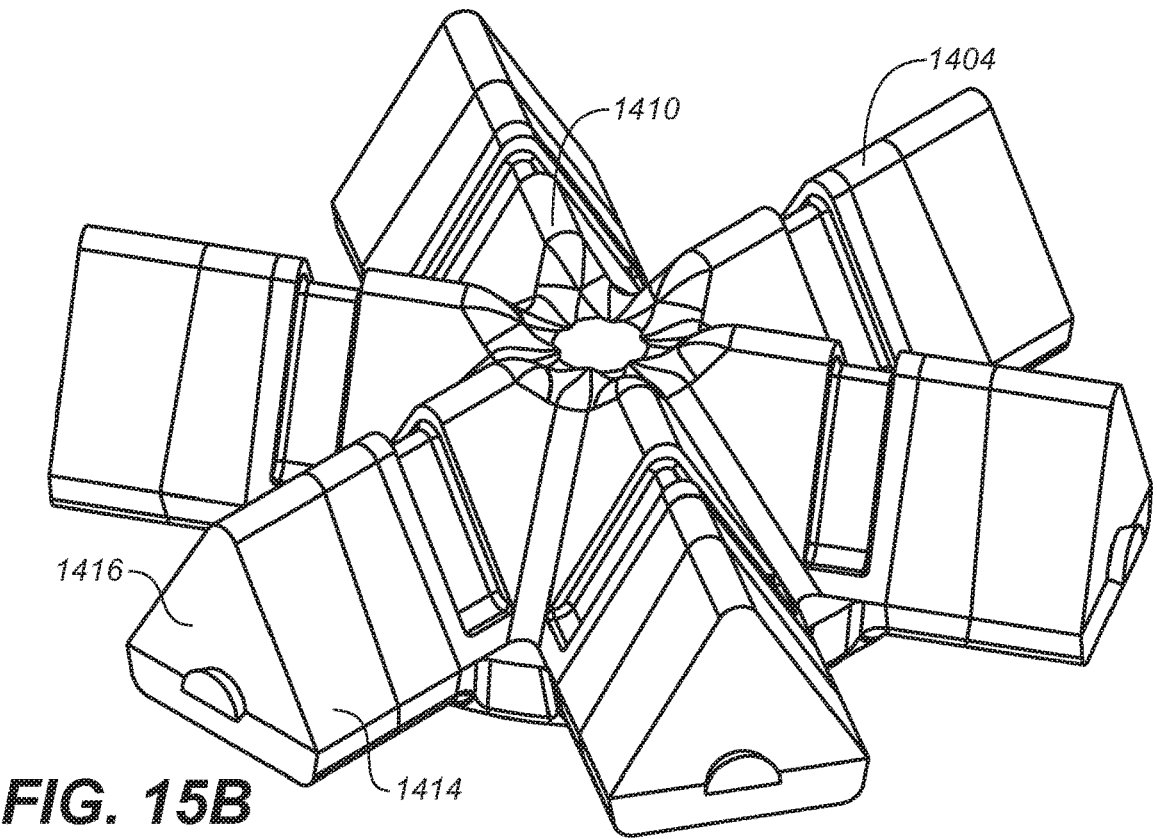
FIG. 15B shows an intermediate polymeric assembly/elastomer hub used to make gastric residence systems of the invention.

Another method of making the gastric residence systems proceeds by preparation of overmolding, using injection molding. Overmolding refers to the procedure of molding a second material onto an existing material by injection molding to form an integrated unit. FIG. 14B, FIG. 15A, and FIG. 15B show one embodiment of a method of making the gastric residence systems by overmolding, using a plurality of intercomponent anchors such as those illustrated in FIG. 14A. FIG. 14A shows a plurality of six intercomponent anchors connected by an optional scaffold. The anchors comprise a first portion 1402 and a second portion 1406 (for clarity, only one first portion 1402 is labeled on one intercomponent anchor, and only one second portion 1406 is labeled on an adjacent intercomponent anchor). The first and second portions are linked by a body 1404; the body is optional, and the first portion and second portion of the intercomponent anchors can be directly connected. In the embodiment shown in FIG. 14A, an optional scaffold 1408 holds the intercomponent anchors in position for the overmolding steps in the process. The scaffold for the intercomponent anchors is preferably made from the same material as the intercomponent anchors, to simplify the manufacture of the intercomponent anchors, but the scaffold can be made of a different material if desired.

While the intercomponent anchors, such as those shown in FIG. 14A, can be formed by injection molding, the anchors can alternatively be prepared by any suitable method and used in the overmolding method of preparing the gastric residence systems. The intercomponent anchors, as their name suggests, serve to link, or anchor, different components of the gastric residence system together. They can be made of any suitable polymer that adheres or joins well to the components to be linked. Polycarbonate bonds well to both silicone rubber and to polycaprolactone, and is a useful material for the intercomponent anchors. Other materials which can be used as intercomponent anchors include, but are not limited to, polyphenylsulfone (such as RADEL® polyphenylsulfone), a polyphenylene ether-polystyrene blend, polyphenylene ether, polystyrene, and polyether ether ketone (such as VICTREX® PEEK). The first portion of the intercomponent anchor, over which the elastomer will be overmolded, and the second portion of the intercomponent anchor, over which further material will be overmolded in order to attach the elongate members or arms of the gastric residence system, should be of a shape that permits a strong linkage after overmolding of the respective elastomer or further materials. Typically, the first portion and the second portion will independently have the shape of a protuberance with a distal knob, bulb, or other enlarged portion. The intercomponent anchors can be "dumbbell" shaped, where the thicker lobes at either end of the anchor are joined together by a thinner connection. Optionally, the intercomponent anchors can have a larger central body from which the first portion and second portion project in opposite directions from each other. The larger central body can have the dimensions of the elongate members of the gastric residence system, so as to form an intermediate region between the central elastomer and the remainder of the elongate members of the gastric residence system.

Figure 36A:
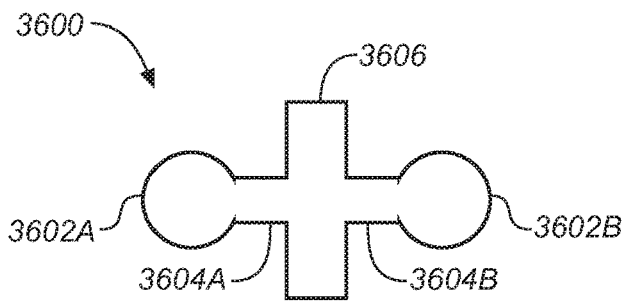
FIG. 36A shows an example of an intercomponent anchor.

Examples of intercomponent anchors are shown in FIG. 36A, FIG. 36B, FIG. 36C, FIG. 36D, and FIG. 36E. In FIG. 36A, intercomponent anchor 3600 has a body 3606 with two stalks 3604A and 3604B extending in opposite directions from the body. Enlarged knobs 3602A and 3602B attached to the corresponding stalks serve to secure the anchor in place when other components are attached to the anchor, for example, when elastomer, interfacing polymer, linker, or carrier polymer-therapeutic agent components are overmolded. Knob and stalk 3602A and 3604A form a first portion of the intercomponent anchor, to which a first component can be overmolded or otherwise attached, and knob and stalk 3602B and 3604B form a second portion of the intercomponent anchor, to which a second component can be overmolded or otherwise attached.

Figure 36B:
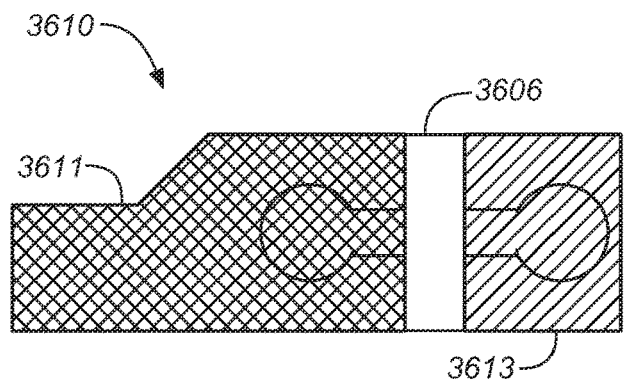
FIG. 36B shows the intercomponent anchor of FIG. 36B with elastomer and interfacing polymer (or linker) overlaid.

FIG. 36B shows assembly 3610, depicting the intercomponent anchor of FIG. 36A after elastomer component 3611 (diamond-hatched region) and a second component (such as an interfacing polymer component, a linker component, or a carrier polymer-therapeutic agent component) 3613 have been overmolded or otherwise attached to the intercomponent anchor. The body 3606 of the intercomponent anchor is still visible, while the stalks and knobs of the intercomponent anchor are buried within the components linked by the anchor.

Figure 36C:
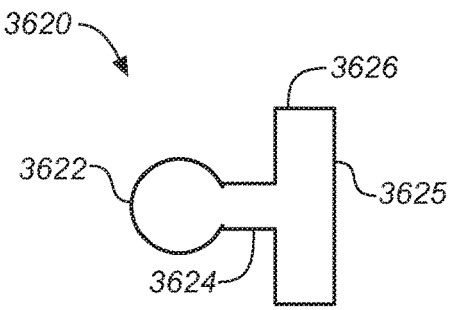
FIG. 36C shows another example of an intercomponent anchor.

FIG. 36C shows another possible configuration for an intercomponent anchor 3620. Stalk 3624 and knob 3622, protruding from body 3626, form a first portion of the intercomponent anchor, over which a first component (such as the elastomer component) can be overmolded or otherwise attached. Instead of overmolding a second component to the intercomponent anchor, a second component (such as an interfacing polymer component, a linker component, or a carrier polymer-therapeutic agent component) can be heat-welded, solvent-welded, or otherwise attached to face 3625 of the intercomponent anchor. This type of intercomponent anchor can be used when the welded or otherwise attached connection to the face 3625 of the intercomponent anchor is sufficiently strong.

Figure 36D:
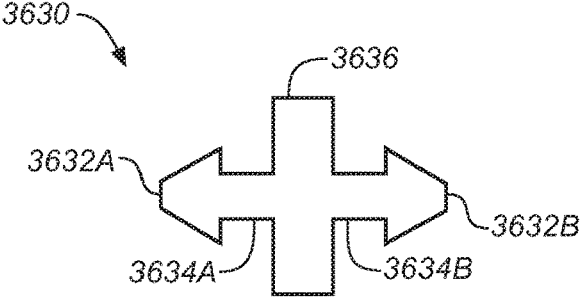
FIG. 36D shows another example of an intercomponent anchor.

FIG. 36D shows yet another possible configuration for an intercomponent anchor 3630, with body 3636 and two stalks 3634A and 3634B extending in opposite directions from the body. Enlarged regions 3632A and 3632B are attached to the corresponding stalks, showing a different possible shape for the enlarged region as compared to the knobs 3602A and 3604B of FIG. 36A. The edges and corners of the enlarged regions can be rounded or filleted if desired. Such rounding or filleting of any sharp edges or corners is preferable, as a safeguard in the unlikely event that one or both of the components of the intercomponent anchor detaches, exposing one of the regions 3632A or 3632B in the digestive tract. Such rounding or filleting should be used if a linker is overmolded or otherwise attached to the intercomponent anchor, as eventual disintegration of the linker will expose one of the regions 3632A or 3632B. As will be appreciated by one of skill in the art, exposure of sharp edges or corners in the digestive tract should be avoided.

Figure 36E:
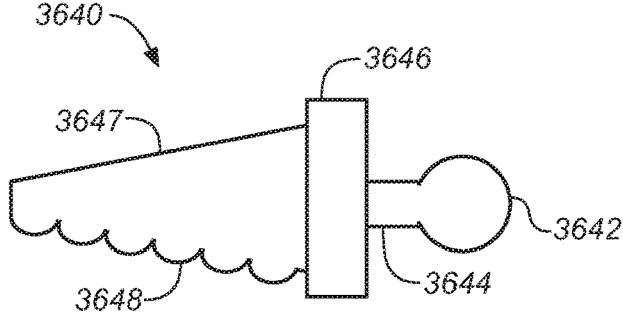
FIG. 36E shows another example of an intercomponent anchor.

FIG. 36E shows yet another possible configuration for an intercomponent anchor 3640. This configuration has body 3646, stalk 3644, and knob 3642 on one side, as in FIG. 36A. The other side of the intercomponent anchor has a tapered triangular prism 3647 with a corrugated bottom surface. The absence of a narrow stalk reduces the number of potential weak points in the anchor. The corrugations (only one corrugation, 3648, is labeled) increase the surface area available for bonding to the component which is overmolded or otherwise attached to the prism 3647. This is particularly useful for increasing adhesion between the intercomponent anchor and the elastomer component. Again, any sharp edges or corners can be rounded or filleted.

The initial step of the overmolding method begins by overmolding the elastomer component onto the intercomponent anchors. The elastomer component can be liquid silicone rubber, such as a polysiloxane, such as a polydimethylsiloxane, or a mixture of liquid silicone rubber and silica, a mixture of a polysiloxane and silica, or a mixture of polydimethylsiloxane and silica. The elastomer is overmolded over the intercomponent anchors by injection molding, to produce the elastomer-intercomponent anchor assembly shown in FIG. 14B. The first portion of the intercomponent anchors (1402 in FIG. 14A) is now completely covered by the central elastomer 1410. The second portion 1406 of the intercomponent anchors, the optional body of the intercomponent anchor 1404 connecting the first portion and second portion of the intercomponent anchors, and the optional scaffold 1408 remain visible, as they are not covered by the elastomer.

If an optional scaffold was used during the first overmolding step, it is preferably removed at this point in the process, in order to expose the maximum surface area of the second portion of the intercomponent anchors. The central elastomer can now serve to maintain the intercomponent anchors in the correct position. However, in an alternate embodiment of the method, the optional scaffold can remain in place for the subsequent step.

In the next step, an interfacing polymer component is overmolded over the second portion of the intercomponent anchors, to form an elastomer-intercomponent anchor-interfacing polymer assembly. One advantage of using the interfacing polymer is to provide for low-temperature heat welding or infrared welding. One embodiment of such an elastomer-intercomponent anchor-interfacing polymer assembly is shown in FIG. 15A. The central elastomer 1410 and optional body of the intercomponent anchor 1404 are still visible, while the second portion of the intercomponent anchors (1406 in FIG. 14A and FIG. 14B) is now covered by the interfacing polymer 1414. An optional scaffold 1412 is also depicted in FIG. 15A, which can provide for easier manipulation of the elastomer-intercomponent anchor-interfacing polymer assembly. The scaffold for the interfacing polymer components is preferably made from the same material as the interfacing polymer components, to simplify manufacture, but the scaffold can be made of a different material if desired. An outer face of each interfacing polymer component is available (one such outer face 1416 is labeled in FIG. 15A) for connecting further elements of the elongate arms of the stellate gastric residence system. The interfacing polymer can be made of any polymer which can be bonded to the remainder of the gastric residence system that will be attached to the outer faces of the interfacing polymer components. One suitable polymer for use as an interfacing polymer is polycaprolactone, such as polycaprolactone (PCL) of Mn approximately 80,000. Typically, when attaching two different elements, where each element comprises a common polymer, the common polymer is used as the interfacing polymer. For example, if a linker comprising 50% HPMCAS and 50% PCL is to be attached to a carrier polymer-therapeutic agent component comprising PCL and a drug, then PCL can be used as the interfacing polymer.

If the optional scaffold 1412 of FIG. 15A is used, it can be trimmed away during a subsequent step to produce the final elastomer-intercomponent anchor-interfacing polymer assembly, as shown in FIG. 15B. The central elastomer 1410, the optional body of the intercomponent anchor 1404, one of the interfacing polymer components 1414, and an outer face 1416 of one of the interfacing polymer components are depicted in FIG. 15B.

Linkers can be attached to the outer faces of the interfacing polymer components of the elastomer-intercomponent anchor-interfacing polymer assembly. Such linkers can be enteric linkers or time-dependent linkers. Alternatively, a single type of linker material can be used which has both time-dependent and enteric properties. Alternatively, a compound linker can be used which comprises both a material that is an enteric linker and a material that is a time-dependent linker; for example, a time-dependent linker can be affixed to the outer face of the interfacing polymer, and then an enteric linker can be affixed to the time-dependent linker. A preferred linker is a blend of hydroxypropyl methylcellulose acetate succinate (HPMCAS) and polycaprolactone (PCL).

When a hydroxypropyl methylcellulose acetate succinate (HPMCAS) polycaprolactone linker is used, the ratio of HPMCAS to polycaprolactone can be between about 80% HPMCAS:20% PCL to about 20% HPMCAS:80% PCL; between about 70% HPMCAS:30% PCL to about 30% HPMCAS:70% PCL; between about 60% HPMCAS:40% PCL to about 40% HPMCAS:60% PCL; between about 80% HPMCAS:20% PCL to about 50% HPMCAS:50% PCL; between about 80% HPMCAS:20% PCL to about 60% HPMCAS:40% PCL; between about 70% HPMCAS:30% PCL to about 50% HPMCAS:50% PCL; between about 70% HPMCAS:30% PCL to about 60% HPMCAS:40% PCL; between about 20% HPMCAS:80% PCL to about 40% HPMCAS:60% PCL; between about 20% HPMCAS:80% PCL to about 50% HPMCAS:50% PCL; between about 30% HPMCAS:70% PCL to about 40% HPMCAS:60% PCL; between about 30% HPMCAS:70% PCL to about 50% HPMCAS:50% PCL; or about 80% HPMCAS:20% PCL, about 70% HPMCAS:30% PCL, about 60% HPMCAS:40% PCL, about 50% HPMCAS:50% PCL, about 40% HPMCAS:60% PCL, about 30% HPMCAS:70% PCL, or about 20% HPMCAS:80% PCL.

Once the desired linkers are in place, carrier polymer-therapeutic agent components (also referred to as carrier polymer-agent components) can then be affixed to the linkers, to produce the completed gastric residence system. A preferred carrier polymer is polycaprolactone.

The above described methods can be summarized as a method of making an elastomer-intercomponent anchor assembly, where the elastomer-intercomponent anchor assembly is suitable for use in a gastric residence system, comprising attaching an elastomer component over a first portion of a plurality of at least three intercomponent anchors, such as by overmolding an elastomer component over a first portion of a plurality of at least three intercomponent anchors. The intercomponent anchors can comprise a polymer. The intercomponent anchors can comprise polycarbonate, polyphenylsulfone, a polyphenylene ether-polystyrene blend, polyphenylene ether, polystyrene, or polyether ether ketone. The intercomponent anchors can comprise polycarbonate. The intercomponent anchors can comprise polyphenylsulfone. The intercomponent anchors can comprise a polyphenylene ether-polystyrene blend. The intercomponent anchors can comprise polyphenylene ether. The intercomponent anchors can comprise polystyrene. The intercomponent anchors can comprise polyether ether ketone. The number of intercomponent anchors can be three. The number of intercomponent anchors can be four. The number of intercomponent anchors can be five. The number of intercomponent anchors can be six. The number of intercomponent anchors can be seven. The number of intercomponent anchors can be eight. Preferably, the number of intercomponent anchors is six. The intercomponent anchors have a first portion and a second portion, which can optionally be connected by a body (or third portion). Preferably, the elastomer component is attached to the intercomponent anchors, where the intercomponent anchors are spaced at approximately equal radial intervals in a plane around the elastomer, such as the arrangement shown in FIG. 14A and FIG. 14B. The elastomer component can be attached to the intercomponent anchors by overmolding. The first portions of the intercomponent anchors are arranged such that the elastomer is attached to (such as by overmolding) over all of the first portions (such as the arrangement shown in FIG. 14B); that is, when the intercomponent anchors are spaced at approximately equal radial intervals in a plane prior to attaching (such as by overmolding) the elastomer, the first portions of the intercomponent anchors face the inside of the circle described by the intercomponent anchors (such as the arrangement shown in FIG. 14A).

Once the elastomer-intercomponent anchor assembly has been prepared, an interfacing polymer can be attached to the second portion of each intercomponent anchor. This results in the preparation of an elastomer-intercomponent anchor-interfacing polymer assembly suitable for use in a gastric residence system. In one embodiment, interfacing polymer can be attached to the second portion of each intercomponent anchor by overmolding interfacing polymer over the second portion of each intercomponent anchor. A separate component of interfacing polymer is attached to (such as by overmolding on) each individual second portion of each intercomponent anchor, such that if there are six intercomponent anchors, six individual components of interfacing polymer will be used, where each one of the components of interfacing polymer is attached to one and only one of a corresponding intercomponent anchor. That is, each one of the plurality of interfacing polymer components is attached to a second portion of a corresponding one of the at least three intercomponent anchors of the elastomer-intercomponent anchor assembly. When attachment is performed by overmolding, each one of a plurality of interfacing polymer components is overmolded over a second portion of a corresponding one of the at least three intercomponent anchors of the elastomer-intercomponent anchor assembly.

The elastomer-intercomponent anchor-interfacing polymer assembly has truncated "arms" which can serve as attachment points for additional components of the gastric residence system. In further embodiments, an elastomer-intercomponent anchor-interfacing polymer-linker assembly is prepared, by attaching a linker to each interfacing polymer component. That is, each linker is attached to a corresponding one of each interfacing polymer component. If there are N interfacing polymer components, then N linkers will be attached, one linker to each interfacing polymer component. Heat welding or infrared welding can be used to attach the linkers to the elastomer-intercomponent anchor-interfacing polymer assembly to form the elastomer-intercomponent anchor-interfacing polymer-linker assembly. The heat weld or infrared weld can then optionally be annealed. The linkers can be enteric linkers. The linkers can be time-dependent linkers. The linkers can comprise both an enteric linker and a time-dependent linker (for example, by making a compound linker using both enteric material and time-dependent material).

A gastric residence system can then be formed by attaching carrier polymer-therapeutic agent components to the elastomer-intercomponent anchor-interfacing polymer-linker assembly. Each carrier polymer-therapeutic agent component can be attached to a corresponding one of the linkers of the elastomer-intercomponent anchor-interfacing polymer-linker assembly, resulting in a gastric residence system. Such assemblies are shown in Entry A, Entry B, and Entry C of FIG. 33. Heat welding or infrared welding can be used to attach the carrier polymer-therapeutic agent components to the elastomer-intercomponent anchor-interfacing polymer-linker assembly. The heat weld or infrared weld can then optionally be annealed.

In an alternate embodiment, a gastric residence system can then be formed by attaching interfacing polymer-(carrier polymer-therapeutic agent) components to the elastomer-intercomponent anchor-interfacing polymer-linker assembly. Such an assembly is shown in Entry D of FIG. 33. The interfacing polymer component and the (carrier polymer-therapeutic agent) component can be attached together with heat welding or infrared welding to form the interfacing polymer-(carrier polymer-therapeutic agent) component, followed optionally by annealing of the heat weld or infrared weld. The interfacing polymer portion of each interfacing polymer-(carrier polymer-therapeutic agent) components can be attached to a corresponding one of the linkers of the elastomer-intercomponent anchor-interfacing polymer-linker assembly, resulting in a gastric residence system. Heat welding or infrared welding can be used to attach the interfacing polymer-(carrier polymer-therapeutic agent) components to the elastomer-intercomponent anchor-interfacing polymer-linker assembly. The heat weld or infrared weld can then optionally be annealed.

Direct Attachment of Linker to Elastomer

Alternatively, an elastomer-intercomponent anchor-linker assembly can be produced. The elastomer-intercomponent anchor assembly is prepared as described above. Overmolding of the linker, such as an enteric linker or time-dependent linker, can then be performed, comprising overmolding linker material over a second portion of a corresponding one of the at least three intercomponent anchors of the elastomer-intercomponent anchor assembly. This produces an elastomer-intercomponent anchor-linker assembly. Preparation of the elastomer-intercomponent anchor-linker assembly can then be followed by attaching interfacing polymer-(carrier polymer-therapeutic agent) components to the elastomer-intercomponent anchor-linker assembly to form the gastric residence system, in the arrangement of elastomer-intercomponent anchor-linker-interfacing polymer-(carrier polymer-therapeutic agent). Heat welding or infrared welding can be used to attach the interfacing polymer-(carrier polymer-therapeutic agent) components to the elastomer-intercomponent anchor-linker assembly. The heat weld or infrared weld can then optionally be annealed.

In another embodiment, preparation of the elastomer-intercomponent anchor-linker assembly can then be followed by attaching (carrier polymer-therapeutic agent) components to the elastomer-intercomponent anchor-linker assembly to form the gastric residence system, in the arrangement of elastomer-intercomponent anchor-linker-(carrier polymer-therapeutic agent). Heat welding or infrared welding can be used to attach the (carrier polymer-therapeutic agent) components to the elastomer-intercomponent anchor-linker assembly. The heat weld or infrared weld can then optionally be annealed.

As can be appreciated, in some embodiments, various combinations of elements of the assemblies can be used, with some combination omitting a certain element or elements (with resulting omission of the element or elements in the final gastric residence system). Thus, the following arrangements can be used for the assemblies and systems:

Use of Interfacing Polymer-Linker-Interfacing Polymer to Attach Elastomer to Carrier Polymer-Therapeutic Agent Component:
Elastomer-intercomponent anchor assembly;
Elastomer-intercomponent anchor-interfacing polymer assembly;
Elastomer-intercomponent anchor-interfacing polymer-linker assembly;
Elastomer-intercomponent anchor-interfacing polymer-linker-interfacing polymer assembly;
Elastomer-intercomponent anchor-interfacing polymer-linker-interfacing polymer-(carrier polymer-therapeutic agent component): gastric residence system.

Use of Interfacing Polymer-Linker to Attach Elastomer to Carrier Polymer-Therapeutic Agent Component:
Elastomer-intercomponent anchor assembly;
Elastomer-intercomponent anchor-interfacing polymer assembly;
Elastomer-intercomponent anchor-interfacing polymer-linker assembly;
Elastomer-intercomponent anchor-interfacing polymer-linker-(carrier polymer-therapeutic agent component): gastric residence system.

Use of Linker-Interfacing Polymer to Attach Elastomer to Carrier Polymer-Therapeutic Agent Component:
Elastomer-intercomponent anchor assembly;
Elastomer-intercomponent anchor-linker assembly;
Elastomer-intercomponent anchor-linker-interfacing polymer assembly;
Elastomer-intercomponent anchor-linker-interfacing polymer-(carrier polymer-therapeutic agent component): gastric residence system.

Use of Linker to Attach Elastomer to Carrier Polymer-Therapeutic Agent Component:
Elastomer-intercomponent anchor assembly;
Elastomer-intercomponent anchor-linker assembly;
Elastomer-intercomponent anchor-linker-(carrier polymer-therapeutic agent component): gastric residence system.

As can be appreciated, making the polymeric assemblies and gastric residence systems can be performed using multiple joining or welding steps that can be performed in any order, and any welding step can be followed by an annealing step if desired. Possible assembly sequences are shown in FIG. 33.

Figure 33:
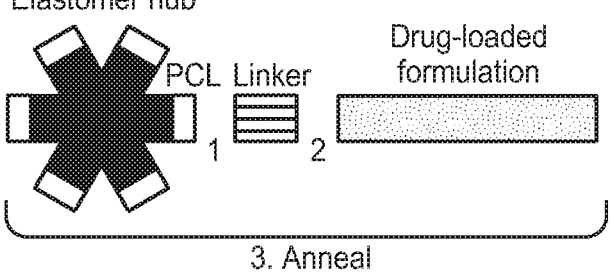
FIG. 33 shows some embodiments of methods for making the gastric residence systems and intermediate assemblies of the invention.

Entry A of FIG. 33 shows an assembly method that proceeds as follows:
1. Welding of the interfacing polymer of the elastomer hub to linker. The interfacing polymer shown in FIG. 33, entry A is polycaprolactone. The elastomer hub can be an elastomer-intercomponent anchor-interfacing polymer assembly or an elastomer-interfacing polymer assembly. Welding of the linker to the interfacing polymer produces an elastomer-intercomponent anchor-interfacing polymer-linker assembly or an elastomer-interfacing polymer-linker assembly.
2. Welding linker to drug-loaded formulation (carrier polymer-therapeutic agent component) to form the gastric residence system dosage form;
3. Annealing entire dosage form (gastric residence system).

This method A is suitable for use when all components, particularly the carrier polymer-therapeutic agent component, are stable to the conditions used in the annealing step. If a component, such as the carrier polymer-therapeutic agent component, is unstable under the annealing conditions, an alternate method is preferable.

Another assembly method is shown in Entry B of FIG. 33:
1. Welding of a segment of interfacing polymer (in the figure, a PCL segment is used) to the linker.
2. Welding of the interfacing polymer-linker to the drug-loaded formulation (carrier polymer-therapeutic agent component).
3. Annealing of the interfacing polymer-linker-(carrier polymer-therapeutic agent component) arm (i.e., the elongate member).
4. Welding of the arm to the hub to form the gastric residence system. The hub can be an elastomer-intercomponent anchor-interfacing polymer assembly or an elastomer-interfacing polymer assembly.

Because the final weld in step 4 welds two interfacing polymers (in one embodiment, both interfacing polymers can be PCL), annealing of the final weld is not needed for the weld to have sufficient strength. This avoids an annealing step for the central elastomer. However, if any component of the arm, such as the carrier polymer-therapeutic agent component, is unstable under the annealing conditions, an alternate method is preferable.

Entry C of FIG. 33 shows yet another assembly method:
1. Welding the hub (the hub can be an elastomer-intercomponent anchor-interfacing polymer assembly or an elastomer-interfacing polymer assembly) to the linker;
2. Annealing the hub-linker assembly; and
3. Welding the drug formulation (carrier polymer-therapeutic agent component) to the linker of the hub-linker assembly to form the gastric residence system.

This procedure has the advantage of not exposing the carrier polymer-therapeutic agent component to the annealing conditions, and is preferred when that component is unstable under annealing conditions. It can be used when the weld between the carrier polymer-therapeutic agent component and the remainder of the gastric residence system is sufficiently strong without being annealed.

Another assembly method is shown in entry D of FIG. 33:
1. Welding the hub (the hub can be an elastomer-intercomponent anchor-interfacing polymer assembly or an elastomer-interfacing polymer assembly) to a linker, to form an elastomer-intercomponent anchor-interfacing polymer-linker assembly or an elastomer-interfacing polymer-linker assembly;
2. Welding the elastomer-intercomponent anchor-interfacing polymer-linker assembly or the elastomer-interfacing polymer-linker assembly to a segment of interfacing polymer (such as PCL), to form an elastomer-intercomponent anchor-interfacing polymer-linker-interfacing polymer assembly or an elastomer-interfacing polymer-linker-interfacing polymer assembly;
3. Annealing the elastomer-intercomponent anchor-interfacing polymer-linker-interfacing polymer assembly or elastomer-interfacing polymer-linker-interfacing polymer assembly;
4. Welding the drug-loaded formulation (the carrier polymer-therapeutic agent component) to the elastomer-intercomponent anchor-interfacing polymer-linker-interfacing polymer assembly or elastomer-interfacing polymer-linker-interfacing polymer assembly to form the gastric residence system.

This procedure also has the advantage of not exposing the carrier polymer-therapeutic agent component to the annealing conditions, and is preferred when that component is unstable under annealing conditions. The welds to the linker are annealed, and their strength is enhanced. This method can be used when the weld between the carrier polymer-therapeutic agent component and the remainder of the gastric residence system is sufficiently strong without being annealed. Since an interfacing polymer is used at the weld point between the carrier polymer-therapeutic agent component and the rest of the system, the strength of the weld can be stronger compared to a weld between a linker and a carrier polymer-therapeutic agent component (where neither weld has been annealed). However, adding another interfacing polymer segment slightly reduces the volume available for the carrier polymer-therapeutic agent component, which must be slightly shorter to accommodate the extra interfacing polymer segment used.

The foregoing assemblies and gastric residence systems, methods for making the assemblies, and methods for making the gastric residence systems, have been described using intercomponent anchors between the elastomer and the interfacing polymer. However, the assemblies and gastric residence systems, and methods for making the assemblies and gastric residence systems, can be prepared without utilizing intercomponent anchors. In such systems, components can be attached by using heat welding, infrared welding, or overmolding of one component over another.

Use of Interfacing Polymer-Linker-Interfacing Polymer to Attach Elastomer to Carrier Polymer-Therapeutic Agent Component (No Intercomponent Anchors):
  Elastomer-interfacing polymer assembly;
  Elastomer-interfacing polymer-linker assembly;
  Elastomer-interfacing polymer-linker-interfacing polymer assembly;
  Elastomer-interfacing polymer-linker-interfacing polymer-(carrier polymer-therapeutic agent component): gastric residence system.

Use of Interfacing Polymer-Linker to Attach Elastomer to Carrier Polymer-Therapeutic Agent Component (No Intercomponent Anchors):
  Elastomer-interfacing polymer assembly;
  Elastomer-interfacing polymer-linker assembly;
  Elastomer-interfacing polymer-linker-(carrier polymer-therapeutic agent component): gastric residence system.

Use of Linker-Interfacing Polymer to Attach Elastomer to Carrier Polymer-Therapeutic Agent Component (No Intercomponent Anchors):
  Elastomer-linker assembly;
  Elastomer-linker-interfacing polymer assembly;
  Elastomer-linker-interfacing polymer-(carrier polymer-therapeutic agent component): gastric residence system.

Use of Linker to Attach Elastomer to Carrier Polymer-Therapeutic Agent Component (No Intercomponent Anchors):
  Elastomer-linker assembly;
  Elastomer-linker-(carrier polymer-therapeutic agent component): gastric residence system.

Welding of Components: Heat Welding, Infrared Welding

The various components of the gastric residence system or polymer assemblies can be attached to each other by various methods. One convenient method for attachment is heat welding, which involves heating a first surface on a first component at a first temperature to provide a first heated surface, heating a second surface on a second component at a second temperature to provide a second heated surface, and then contacting the first heated surface with the second heated surface (or equivalently, contacting the second heated surface with the first heated surface). The first temperature may be the same as the second temperature, or the first temperature and the second temperature may be different, depending on the properties of the first and second components to be welded together. Heating of the first surface or of the second surface can be performed by contacting the respective surface with a metal platen (a flat metal plate) at the respective temperature. For ease of manufacture, a dual-temperature platen can be used where a first end of the platen is at the first temperature and a second end of the platen is at the second temperature; the first surface can be pressed against the first end of the platen, the second surface can be pressed against the second end of the platen, and then the platen can be removed and the resulting first heated surface can be contacted with the resulting second heated surface. The contacting heated surfaces are pressed together with some degree of force or pressure to ensure adherence after cooling (the applied force or pressure is optionally maintained during the cooling process). Heat welding is also referred to as heat fusion. Example 12 and Table 7 show various conditions that can be used to attach components by heat welding.

Another method for attachment of the various components of the gastric residence systems, or polymer assemblies, is infrared welding. Infrared welding is performed by contacting a first surface on a first component with a second surface on a second component, and irradiating the region of the contacting surfaces with infrared radiation, while applying force or pressure to maintain the contact between the two surfaces, followed by cooling of the attached components (the applied force or pressure is optionally maintained during the cooling process).

Annealing of Components: Heat Annealing in an Oven, Infrared Annealing

After each welding step, an annealing step can optionally be used to increase the strength of the weld. The welded first and second components can be heat annealed by placing the welded components in an oven set to a third temperature (if the components were welded by heat welding, the third temperature can be the same as the first temperature, the same as the second temperature, or different from the first temperature and second temperature used in heat welding). The welded first and second components can be infrared annealed by irradiating the welded region with infrared radiation. Infrared annealing has the advantage that a localized area can be irradiated, unlike heat annealing in an oven where all of the first and second components will be heated.

Any combination of welding and annealing can be used. Heat welding of components can be followed by heat annealing in an oven of the heat weld; heat welding of components can be followed by infrared annealing of the heat weld; infrared welding of components can be followed by heat annealing in an oven of the infrared weld; or infrared welding of components can be followed by infrared annealing of the infrared weld.

Gastric Delivery Pharmacokinetics for Gastric Residence Systems

The gastric residence systems of the invention provide for high bioavailability of the therapeutic agent as measured by $AUC_{inf}$ after administration of the systems, relative to the bioavailability of a conventional oral formulation of the therapeutic agent. The systems also provide for maintenance of a substantially constant plasma level of the therapeutic agent.

Relative bioavailability, $F_{REL}$, of two different formulations, formulation A and formulation B, is defined as:

$$F_{REL}=100\times(AUC_A\times Dose_B)/(AUC_B\times Dose_A)$$

where $AUC_A$ is the area under the curve for formulation A, $AUC_B$ is the area under the curve for formulation B, $Dose_A$ is the dosage of formulation A used, and $Dose_B$ is the dosage of formulation B used. AUC, the area under the curve for the plot of therapeutic agent plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the therapeutic agent has dropped to a negligible amount.

In one embodiment, the substantially constant plasma level of therapeutic agent provided by the gastric residence systems of the invention can range from at or above the trough level of the plasma level of therapeutic agent when administered daily in a conventional oral formulation (that is, $C_{min}$ of therapeutic agent administered daily in immediate-release formulation) to at or below the peak plasma level of therapeutic agent when administered daily in a conventional oral formulation (that is, $C_{max}$ of therapeutic agent administered daily in immediate-release formulation). In another embodiment, the substantially constant plasma level of therapeutic agent provided by the gastric residence systems of the invention can be about 50% to about 90% of the peak plasma level of therapeutic agent when administered daily in a conventional oral formulation (that is, $C_{max}$ of therapeutic agent administered daily in immediate-release formulation). The substantially constant plasma level of therapeutic agent provided by the gastric residence systems of the invention can be about 75% to about 125% of the average plasma level of therapeutic agent when administered daily in a conventional oral formulation (that is, $C_{ave}$ of therapeutic agent administered daily in immediate-release formulation). The substantially constant plasma level of therapeutic agent provided by the gastric residence systems of the invention can be at or above the trough level of plasma level of therapeutic agent when administered daily in a conventional oral formulation (that is, $C_{min}$ of therapeutic agent administered daily in immediate-release formulation), such as about 100% to about 150% of $C_{min}$.

The gastric residence systems of the invention can provide bioavailability of therapeutic agent released from the system of at least about 50%, at least about 60%, at least about 70%, or at least about 80% of that provided by an immediate release form comprising the same amount of therapeutic agent. As indicated above, the bioavailability is measured by the area under the plasma concentration-time curve (AUCinf).

Methods of Treatment Using the Gastric Residence Systems

The gastric residence systems can be used to treat conditions requiring administration of a therapeutic agent over an extended period of time. For long-term administration of therapeutic agents which are taken for months, years, or indefinitely, administration of a gastric residence system once weekly, once every two weeks, or once a month can provide substantial advantages in patient compliance and convenience.

Once a gastric residence system has been administered to a patient, the system provides sustained release of therapeutic agent over the period of gastric retention. After the period of gastric retention, the system degrades and passes out of the stomach. Thus, for a system with a gastric retention period of one week, the patient will swallow (or have administered to the stomach via other means) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the therapeutic agent in the system, comprises introducing a new gastric residence system every D-days into the stomach of the patient, by oral administration or other means, over the total desired treatment period. The number of gastric residence systems administered to the patient will be (T-total) divided by (D-days). For example, if treatment of a patient for a year (T-total=365 days) is desired, and the gastric residence period of the system is 7 days (D-days=7 days), approximately 52 gastric residence systems will be administered to the patient over the 365 days, as a new system will be administered once every seven days.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days)) (rounded to an integral number), for administration every D-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the therapeutic agent contained in the gastric residence systems. For example, if the total treatment period prescribed for the patient is one year, and the gastric residence system has a residence time of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the therapeutic agent contained in the gastric residence systems, are also included in the invention. The articles of manufacture may be supplied in appropriate packaging, such as dispensers, trays, or other packaging that assists the patient in administration of the gastric residence systems at the prescribed interval.

EXEMPLARY EMBODIMENTS

The invention is further described by the following embodiments. The features of each of the embodiments are combinable with any of the other embodiments where appropriate and practical.

Embodiment 1. A gastric residence system for administration to the stomach of a patient, comprising: an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and a curved outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach.

Embodiment 2. The gastric residence system of embodiment 1, wherein a separation angle between one elongate member of the plurality of at least three carrier polymer-agent components to a nearest adjacent other elongate member is approximately equal for each elongate member.

Embodiment 3. The gastric residence system of embodiment 1, wherein each elongate member is comprised of at least two segments, each segment comprising a proximal end, a distal end, and an outer surface therebetween; where the segments are attached together by an enteric polymer.

Embodiment 4. The gastric residence system of embodiment 3, wherein the enteric polymer is adherent to: a distal end of a first segment and an adjacent proximal end of a second segment, thereby joining the first and second segments.

Embodiment 5. The gastric residence system of embodiment 3, wherein the enteric polymer is a film wrapped around a distal portion of the outer surface of a first segment and an adjacent proximal portion of the outer surface of a second segment, thereby forming a collar joint between the first and second segments.

Embodiment 6. The gastric residence system of any one of embodiments 3-5, wherein the distal end of the first segment is concave and the adjacent proximal end of the second segment is convex, or the distal end of the first segment is convex and the adjacent proximal end of the second segment is concave.

Embodiment 7. The gastric residence system of embodiment 4, wherein the enteric polymer adherent to the ends of the segments extends beyond the area between the ends of the segments.

Embodiment 8. The gastric residence system of any one of embodiments 1-7, wherein each elongate member is attached to the elastomer component by an enteric polymer.

Embodiment 9. The gastric residence system of embodiment 8, wherein the enteric polymer is adherent to the proximal end of each elongate member and the elastomer component.

Embodiment 10. The gastric residence system of any one of embodiments 1-9, wherein the elastomer component has an asterisk shape with a plurality of at least three branches, and each elongate member is attached to a different branch of the elastomer component.

Embodiment 11. The gastric residence system of embodiment 10, wherein the proximal end of each elongate member attached to a different branch of the elastomer component is attached by a film of an enteric polymer wrapped around at least a portion of the proximal end of the elongate member and at least a portion of the branch, thereby forming a collar joint between the elongate member and branch.

Embodiment 12. The gastric residence system of any one of embodiments 3-7, wherein the enteric polymer between segments is selected from the group consisting of poly(methacrylic acid-co-ethyl acrylate), cellulose acetate phthalate, cellulose acetate succinate, and hydroxypropyl methylcellulose phthalate.

Embodiment 13. The gastric residence system of any one of embodiments 8, 9 or 11, wherein the enteric polymer between segments and the enteric polymer attaching elongate members to the elastomer component is selected from the group consisting of poly(methacrylic acid-co-ethyl acrylate), cellulose acetate phthalate, cellulose acetate succinate, and hydroxypropyl methylcellulose phthalate.

Embodiment 14. The gastric residence system of any one of embodiments 1-13, wherein the carrier polymer comprises polycaprolactone.

Embodiment 15. The gastric residence system of any one of embodiments 1-14, wherein the elastomer component comprises cross-linked polycaprolactone.

Embodiment 16. The gastric residence system of any one of embodiments 1-15, wherein the gastric residence system measures at least about 2 cm in length over at least two perpendicular directions.

Embodiment 17. A gastric residence system according to any one of embodiments 1-16, wherein the carrier polymer-agent components are produced by hot melt extrusion.

Embodiment 18. A gastric residence system according to any one of embodiments 1-17, wherein the therapeutic agent or a salt thereof comprises particles, wherein at least about 80% of the mass of particles have sizes between about 2 microns and about 50 microns in diameter.

Embodiment 19. The gastric residence system of embodiment 18, wherein the particles are crystalline.

Embodiment 20. The gastric residence system of embodiment 18, wherein the particles are amorphous.

Embodiment 21. The gastric residence system of any one of embodiments 1-20, wherein: the carrier polymer-agent arms further comprise a dispersant.

Embodiment 22. The gastric residence system of embodiment 21, wherein the dispersant is selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 23. The gastric residence system of any one of embodiments 1-22, wherein the elastomer component is bi-concave.

Embodiment 24. The gastric residence system of any one of embodiments 1-22, wherein the elastomer component is concavo-convex.

Embodiment 25. The gastric residence system of any one of embodiments 1-24, wherein the gastric residence system is in its compacted form and is in a container or capsule.

Embodiment 26. A method of making a gastric residence system of any one of embodiments 1-24, comprising: forming an elastomer component; forming a plurality of at least three carrier polymer-agent components, which are elongate members comprising a proximal end and a distal end; and attaching the elongate members to the elastomer component.

Embodiment 27. The method of embodiment 26, further comprising compacting the gastric residence system and inserting the system into a container suitable for oral administration or administration through a gastric tube or feeding tube.

Embodiment 28. The method of embodiment 26 or embodiment 27, wherein forming a plurality of at least three carrier polymer-agent components which are elongate members comprises forming the elongate members from at least two segments.

Embodiment 29. The method of embodiment 28, wherein forming the elongate members from at least two segments comprises forming a collar joint between the segments.

Embodiment 30. The method of any one of embodiments 26-29, wherein attaching the elongate members to the elastomer component comprises adhering the elongate members to the elastomer component.

Embodiment 31. The method of any one of embodiments 26-29, wherein the elastomer component is asterisk-shaped with a plurality of at least three branches Embodiment 32. The method of embodiment 31, wherein attaching the elongate members to the asterisk-shaped elastomer component comprises forming a collar joint between the elongate members and the branches of the elastomer component.

Embodiment 33. A gastric residence system for administration to the stomach of a patient, comprising: an elastomer component, wherein the elastomer is bi-concave or concavo-convex; a plurality of at least three carrier polymer-agent components comprising a carrier polymer and a therapeutic agent or a salt thereof, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach.

Embodiment 34. The gastric residence system of embodiment 33, wherein a separation angle between one elongate member of the plurality of at least three carrier polymer-agent components to a nearest adjacent other elongate member is approximately equal for each elongate member.

Embodiment 35. The gastric residence system of embodiment 33 or embodiment 34, wherein each elongate member is comprised of at least two segments, each segment comprising a proximal end, a distal end, and an outer surface therebetween, where the segments are attached together by an enteric polymer.

Embodiment 36. The gastric residence system of embodiment 35, wherein the enteric polymer is adherent to a distal end of a first segment and an adjacent proximal end of a second segment, thereby joining the first and second segments.

Embodiment 37. The gastric residence system of embodiment 35, wherein the enteric polymer is a film wrapped around a distal portion of the outer surface of a first segment and an adjacent proximal portion of the outer surface of a second segment, thereby forming a collar joint between the first and second segments.

Embodiment 38. The gastric residence system of any one of embodiments 33-35, wherein the distal end of the first segment is concave and the adjacent proximal end of the second segment is convex, or the distal end of the first segment is convex and the adjacent proximal end of the second segment is concave.

Embodiment 39. The gastric residence system of embodiment 34, wherein the enteric polymer adherent to the ends of the segments extends beyond the area between the ends of the segments.

Embodiment 40. The gastric residence system of any one of embodiments 33-39, wherein:
the elastomer component has the approximate shape of an oblate ellipsoid or disk.

Embodiment 41. The gastric residence system of any one of embodiments 33-39, wherein:
the elastomer component has an approximately asterisk shape, wherein the asterisk shape has at least three branches, and the proximal end of each elongate member is attached to a different branch of the elastomer component.

Embodiment 42. The gastric residence system of any one of embodiments 33-41, wherein each elongate member is attached to the elastomer component by an enteric polymer.

Embodiment 43. The gastric residence system of embodiment 42, wherein the enteric polymer is adherent to the proximal end of each elongate member and the elastomer component.

Embodiment 44. The gastric residence system of embodiment 41, wherein the proximal end of each elongate member attached to a different branch of the elastomer component is attached by a film of an enteric polymer wrapped around at least a portion of the proximal end of the elongate member and at least a portion of the branch, thereby forming a collar joint between the elongate member and branch.

Embodiment 45. The gastric residence system of any one of embodiments 35-39, wherein the enteric polymer which attaches the segments is selected from the group consisting of poly(methacrylic acid-co-ethyl acrylate), cellulose acetate phthalate, cellulose acetate succinate, and hydroxypropyl methylcellulose phthalate.

Embodiment 46. The gastric residence system of any one of embodiments 42-45, wherein the enteric polymer between segments and the enteric polymer attaching elongate members to the elastomer component is selected from the group consisting of poly(methacrylic acid-co-ethyl acrylate), cellulose acetate phthalate, cellulose acetate succinate, and hydroxypropyl methylcellulose phthalate.

Embodiment 47. The gastric residence system of any one of embodiments 33-46, wherein the carrier polymer comprises polycaprolactone.

Embodiment 48. The gastric residence system of any one of embodiments 33-47, wherein the elastomer component comprises cross-linked polycaprolactone.

Embodiment 49. The gastric residence system of any one of embodiments 33-48, wherein the gastric residence system measures at least about 2 cm in length over at least two perpendicular directions.

Embodiment 50. A gastric residence system according to any one of embodiments 33-49, wherein the carrier polymer-agent components are produced by hot melt extrusion.

Embodiment 51. A gastric residence system according to any one of embodiments 33-50, wherein the therapeutic agent or a salt thereof comprises particles, wherein at least about 80% of the mass of particles have sizes between about 2 microns and about 50 microns in diameter.

Embodiment 52. The gastric residence system of embodiment 51, wherein the particles are crystalline.

Embodiment 53. The gastric residence system of embodiment 51, wherein the particles are amorphous.

Embodiment 54. The gastric residence system of any one of embodiments 33-53, wherein:
the carrier polymer-agent arms further comprise a dispersant.

Embodiment 55. The gastric residence system of embodiment 54, wherein the dispersant is selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 56. The gastric residence system of any one of embodiments 33-55, wherein the elastomer component is bi-concave.

Embodiment 57. The gastric residence system of any one of embodiments 33-55, wherein the elastomer component is concavo-convex.

Embodiment 58. The gastric residence system of any one of embodiments 33-57, wherein the gastric residence system is in its compacted form and is in a container or capsule.

Embodiment 59. A method of making a gastric residence system of any one of embodiments 33-57, comprising: forming an elastomer component; forming a plurality of at least three carrier polymer-agent components, which are elongate members comprising a proximal end and a distal end; and attaching the elongate members to the elastomer component.

Embodiment 60. The method of embodiment 59, further comprising compacting the gastric residence system and inserting the system into a container suitable for oral administration or administration through a gastric tube or feeding tube.

Embodiment 61. The method of embodiment 59 or embodiment 60, wherein forming a plurality of at least three carrier polymer-agent components which are elongate members comprises forming the elongate members from at least two segments.

Embodiment 62. The method of embodiment 60, wherein forming the elongate members from at least two segments comprises forming a collar joint between the segments.

Embodiment 63. The method of any one of embodiments 59-62, wherein the elastomer component is asterisk-shaped with a plurality of at least three branches.

Embodiment 64. The method of any one of embodiments 59-63, wherein attaching the elongate members to the elastomer component comprises adhering the elongate members to the elastomer component.

Embodiment 65. The method of embodiment 63, wherein attaching the elongate members to the asterisk-shaped elastomer component comprises forming a collar joint between the elongate members and the branches of the elastomer component.

Embodiment 66. A gastric residence system for administration to the stomach of a patient, comprising: an elastomer component, a plurality of at least three carrier polymer-agent components comprising a carrier polymer and a therapeutic agent or a salt thereof, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween, where the segments are attached together by an enteric polymer film wrapped around a distal portion of the outer surface of a first segment and an adjacent proximal portion of the outer surface of a second segment, thereby forming a collar joint between the first and second segments; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of therapeutic agent over at least a portion of the period in which the system is retained in the stomach.

Embodiment 67. The gastric residence system of embodiment 66, wherein a separation angle between one elongate member of the plurality of at least three carrier polymer-agent components to a nearest adjacent other elongate member is approximately equal for each elongate member.

Embodiment 68. The gastric residence system of embodiment 66 or embodiment 67, wherein the distal end of the first segment is concave and the adjacent proximal end of the second segment is convex, or the distal end of the first segment is convex and the adjacent proximal end of the second segment is concave.

Embodiment 69. The gastric residence system of any one of embodiments 66-68, wherein the elastomer component has the approximate shape of an oblate ellipsoid or disk.

Embodiment 70. The gastric residence system of any one of embodiments 66-68, wherein the elastomer component has an approximately asterisk shape, wherein the asterisk shape has at least three branches, and the proximal end of each elongate member is attached to a different branch of the elastomer component.

Embodiment 71. The gastric residence system of any one of embodiments 66-70, wherein each elongate member is attached to the elastomer component by an enteric polymer.

Embodiment 72. The gastric residence system of embodiment 71, wherein the enteric polymer is adherent to the proximal end of each elongate member and the elastomer component.

Embodiment 73. The gastric residence system of embodiment 71, wherein the proximal end of each elongate member attached to a different branch of the elastomer component is attached by a film of an enteric polymer wrapped around at least a portion of the proximal end of the elongate member and at least a portion of the branch, thereby forming a collar joint between the elongate member and branch.

Embodiment 74. The gastric residence system of any one of embodiments 66-73, wherein the enteric polymer between segments is selected from the group consisting of poly(methacrylic acid-co-ethyl acrylate), cellulose acetate phthalate, cellulose acetate succinate, and hydroxypropyl methylcellulose phthalate.

Embodiment 75. The gastric residence system of any one of embodiments 71-73, wherein the enteric polymer attaching elongate members to the elastomer component is selected from the group consisting of poly(methacrylic acid-co-ethyl acrylate), cellulose acetate phthalate, cellulose acetate succinate, and hydroxypropyl methylcellulose phthalate.

Embodiment 76. The gastric residence system of any one of embodiments 66-75, wherein the carrier polymer comprises polycaprolactone.

Embodiment 77. The gastric residence system of any one of embodiments 66-76, wherein the elastomer component comprises cross-linked polycaprolactone.

Embodiment 78. The gastric residence system of any one of embodiments 66-77, wherein the gastric residence system measures at least about 2 cm in length over at least two perpendicular directions.

Embodiment 79. A gastric residence system according to any one of embodiments 66-78, wherein the carrier polymer-agent components are produced by hot melt extrusion.

Embodiment 80. A gastric residence system according to any one of embodiments 66-79, wherein the therapeutic agent or a salt thereof comprises particles, wherein at least about 80% of the mass of particles have sizes between about 2 microns and about 50 microns in diameter.

Embodiment 81. The gastric residence system of embodiment 80, wherein the particles are crystalline.

Embodiment 82. The gastric residence system of embodiment 80, wherein the particles are amorphous.

Embodiment 83. The gastric residence system of any one of embodiments 66-82, wherein the carrier polymer-agent arms further comprise a dispersant.

Embodiment 84. The gastric residence system of embodiment 83, wherein the dispersant is selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 85. The gastric residence system of any one of embodiments 66-84, wherein the elastomer component is bi-concave.

Embodiment 86. The gastric residence system of any one of embodiments 66-84, wherein the elastomer component is concavo-convex.

Embodiment 87. The gastric residence system of any one of embodiments 66-86, wherein the gastric residence system is in its compacted form and is in a container or capsule.

Embodiment 88. A method of making a gastric residence system of any one of embodiments 66-86, comprising: forming an elastomer component; forming a plurality of at least three carrier polymer-agent components, which are elongate members comprising a proximal end and a distal end; and attaching the elongate members to the elastomer component.

Embodiment 89. The method of embodiment 88, further comprising compacting the gastric residence system and inserting the system into a container suitable for oral administration or administration through a gastric tube or feeding tube.

Embodiment 90. The method of embodiment 88 or embodiment 89, wherein forming the elongate members from at least two segments comprises forming a collar joint between the segments.

Embodiment 91. The method of any one of embodiments 88-90, wherein the elastomer component is asterisk-shaped with a plurality of at least three branches.

Embodiment 92. The method of any one of embodiments 88-91, wherein attaching the elongate members to the elastomer component comprises adhering the elongate members to the elastomer component.

Embodiment 93. The method of embodiment 91, wherein attaching the elongate members to the asterisk-shaped elastomer component comprises forming a collar joint between the elongate members and the branches of the elastomer component.

Embodiment 94. A method of administering a therapeutic agent to a patient, comprising administering a gastric residence system of any one of embodiment 1-25, 33-58, or 66-87 to the patient.

Embodiment 95. The method of embodiment 94, wherein the gastric residence system has a gastric retention period of D days, and a new gastric residence system is administered to the patient every D days over a total desired treatment period.

Embodiment 96. The method of embodiment 95, wherein the gastric retention period of D days is seven days.

Embodiment 97. The gastric residence system of any one of embodiment 1-25, 33-58, or 66-87, wherein the therapeutic agent or salt thereof is milled.

Embodiment 98. The gastric residence system of embodiment 97, wherein the therapeutic agent or salt thereof is milled with a compound selected from the group consisting of silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants.

Embodiment 99. The method of making a gastric residence system of any one of embodiments 26-32, 59-65, and 88-93, further comprising milling the therapeutic agent or salt thereof prior to blending the therapeutic agent or salt thereof with the carrier polymer to form the carrier polymer-agent component.

Embodiment 100. The method of embodiment 99, wherein the wherein the therapeutic agent or salt thereof is milled with a compound selected from the group consisting of silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants.

EXAMPLES

The invention is further illustrated by the following non-limiting examples.

Example 1

Preparation of Elastomer for Use in Systems

A. Preparation of 80 k PCL star arms for elastomer interfacing: Polycaprolactone (PCL) beads (Mn~80 k, Sigma Cat #440744) were loaded into a 00el-sized, star-shaped polydimethylsiloxane (PDMS) mold. The beads were melted in an oven 90-100° C. for 20-30 min or until fully melted. Additional polymer beads were added and melted as needed to completely fill the mold. Once filled and completely molten, the mold was removed from the oven and covered with a Teflon sheet. A weight was placed on top of the Teflon sheet to ensure a flat upper surface to the molded shape. Stars were allowed to cool at room temperature for at least 1 h.

After cooling, the PCL stars were removed from the mold and trimmed of any excess PCL using a scalpel or razor blade. Star arms were then cut away from the center portion of the star. Cuts were made along the arms at a position 1-5 mm from the point at which star arms meet. The six star arms were then replaced in the PDMS mold and the central portion was discarded, leaving a space in the center of the mold for formation of the elastic crosslinked PCL element.

B. Preparation of elastic crosslinked PCL: Polycaprolactone (PCL) diol (3.2 g, Mn~900: Sigma Cat #189405), PCL triol (1.2 g. Mn~530: Sigma Cat #200409), and linear PCL (Mn~14 k, Sigma Cat #440752; or Mn~45 k, Sigma Cat #704105; or Mn~55 k, Scientific Polymer Products Cat #1029; 1.2 g) were loaded into a 20-mL glass vial with a magnetic stir bar and heated to 70° C. The mixture was stirred gently at a rate of 100-150 rpm for at least two hours. Crosslinker (1.573 mL of hexamethylene diisocyanate, Sigma Cat #52649) was then added and the mixture was stirred at 70° C. for an additional 20-40 min. The prepolymer mixture was then degassed under vacuum for 2-5 minutes. The prepolymer was then transferred to the desired mold, a 00el-sized star shape in which the star arms were previously filled with 80 k PCL as described above. The prepolymer was then cured in the presence of the 80 k PCL arms to ensure strong interfacing of the elastomer to the PCL arms. The polymer was cured for 48 hours at 70° C., then removed from the oven and allowed to set for at least 2 days at room temperature. The 80 k PCL arms were then cut at a position 0.5-3 mm from the interface of the PCL with the crosslinked elastomer. This produced an elastic central asterisk shape, with arms capped with thin layers of PCL at their ends. The thin layers of PCL allow for later melt interfacing to therapeutic agent-loaded arms (carrier polymer-agent components), such as those prepared in Section A of this Example.

Mixing temperatures, curing temperatures, and curing times may be varied for other crosslinking agents, such as toluene diisocyanate (Sigma Cat #T3985) or cyclohexylene diisocyanate (Sigma Cat #269360).

C. PA6ACA-EUDRAGIT L 100-55 elastomer: A different enteric elastomer can be prepared from poly(acryloyl 6-aminocaproic acid) (PA6ACA) and poly(methacrylic acid-co-ethyl acrylate) (EUDRAGIT L 100-55), as described in Zhang et al., "A pH-responsive supramolecular polymer gel as an enteric elastomer for use in gastric devices," Nature Materials 14(10):1065-71 (epub Jul. 27, 2015). Briefly, the enteric elastomer is prepared by co-precipitation of a solution of PA6ACA sodium salt and L 100-55 sodium salt in polymer weight ratios of 1:0, 1:1 and 1:2 via addition of 6M HCl solution. The polymer is then compacted by ultracentrifugation, and cut into the desired shape for the system.

Example 2

Preparation of Enteric Polymer for Use in Systems

An enteric polymer suitable for use in the systems is prepared from methyl methacrylate and n-butyl methacrylate (EVONIK Plastoid B) and poly(methacrylic acid-co-ethyl acrylate) (EUDRAGIT L 100-55). Briefly, the enteric polymer is prepared by dissolving Plastoid B and EUDRAGIT L 100-55 in acetone in a 30:70 w/w ratio. The resulting mixture is poured into a mold and the solvent is evaporated over 24 h to form a thin film.

Example 3

Effect of Solvent on Adhesion Force of Enteric Materials

Figure 7A:
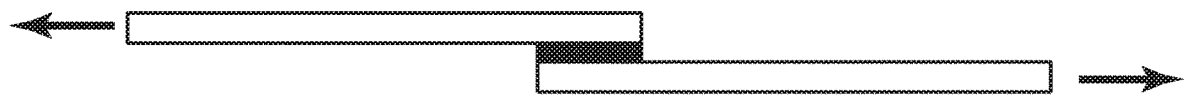
FIG. 7 shows enteric linker adhesion as a function of solvent used to wet the enteric linker for adhesion to polymer sheets.
Figure 7B:
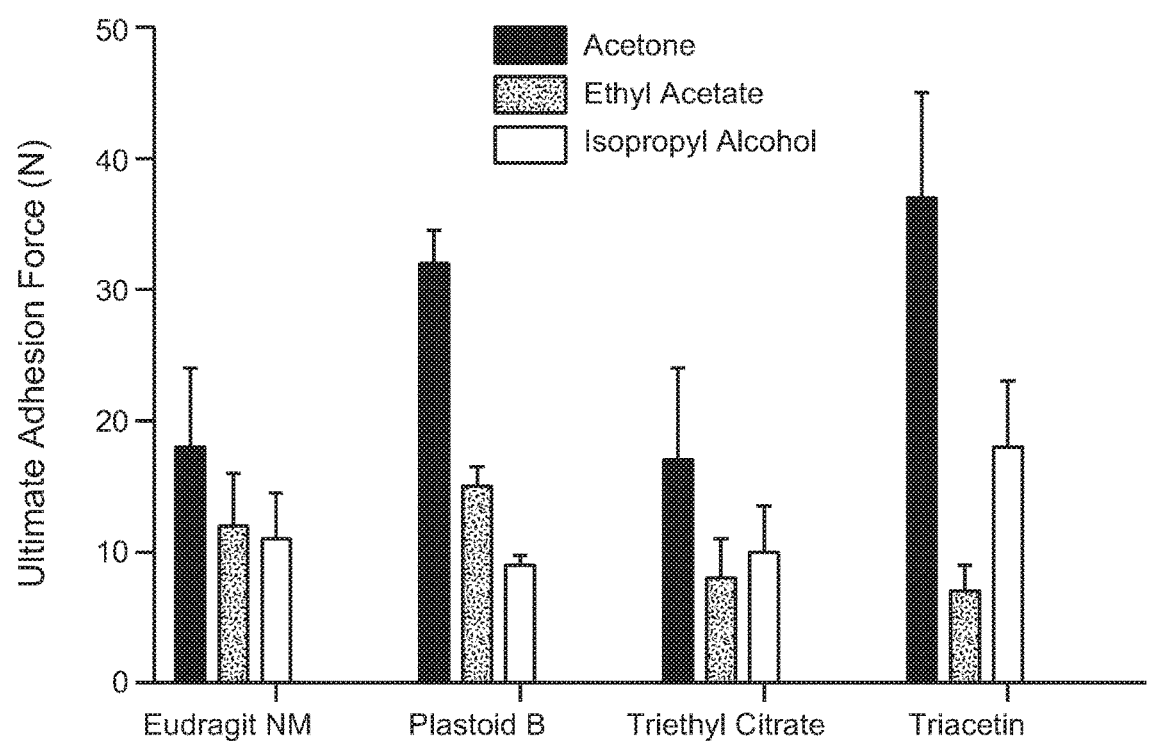

The influence of solvent (acetone, isopropyl alcohol, and ethyl acetate) and plasticizer (Eudragit NM, Plastoid B, Triethyl Citrate, and Triacetin) on the adhesion force of enteric materials were quantified using ASTM D3163, a standardized shear-lap joint mechanical test. The results are shown in FIG. 7. The top figure A illustrates a side view of the experimental setup. Two 2-mm thick PCL (Mn 55 k) polymer sheets are adhered to an enteric material, Eudragit L100-55 (methyl methacrylate) combined with a plasticizer (in a 70%/30% enteric material/plasticizer ratio), using a solvent and pressure. The polymer sheets are then loaded into a tensile testing machine and pulled apart. The force/stress that causes the linker-polymer bond to break is recorded. Results are shown in the bottom figure B, and indicate that using acetone as a solvent and Plastoid B or Triacetin as plasticizers leads to the greatest adhesion force.

Figure 9A:
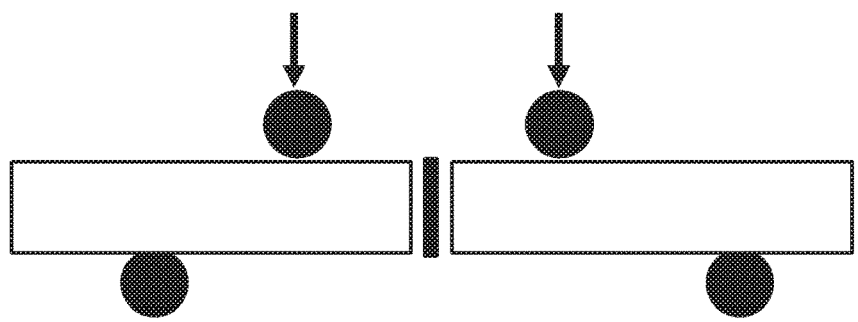
FIG. 9, panels A, B, and C, shows four-point bending flexural tests for single layer and collar Plastoid B and Triacetin enteric linkers. Panel A shows the flexural test arrangement for the single layer linker. Panel B shows the flexural test arrangement for the collar linker. Panel C shows the results of the flexural tests.
Figure 9B:
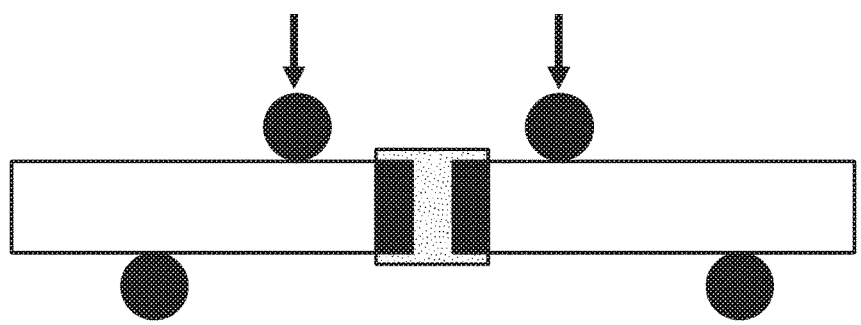
Figure 9C:
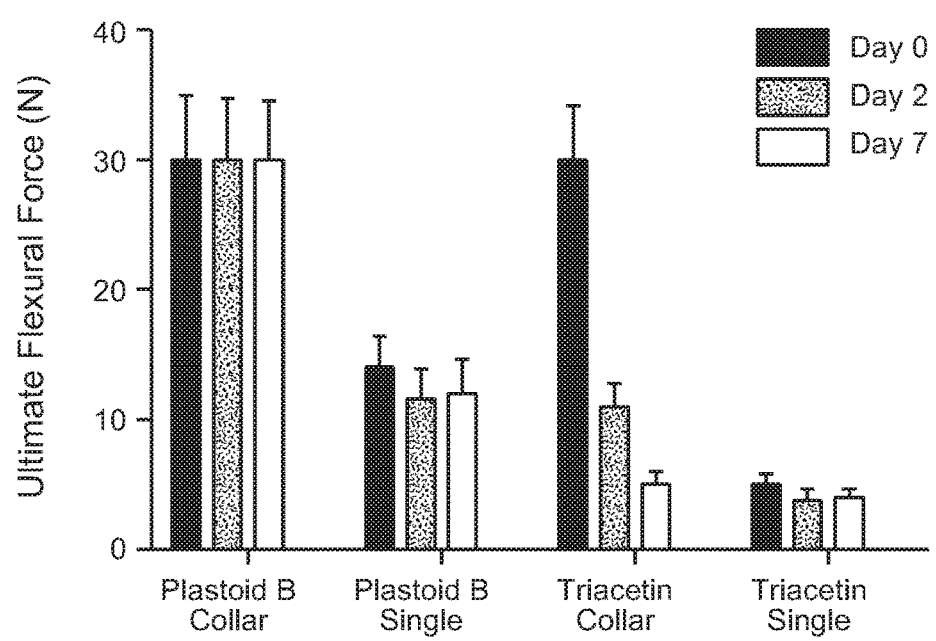
Figure 10A:
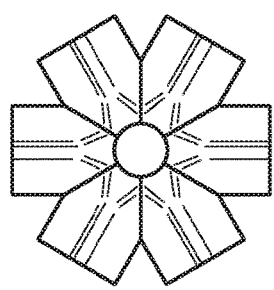
FIG. 10, panels A, AA, B, BB, C, and CC, shows the effect of varying the length of the asterisk branches of the central elastomer (panels A, B, C) when the elastomer is compacted (panels AA, BB, and CC, corresponding to panels A, B, and C, respectively).
Figure 10B:
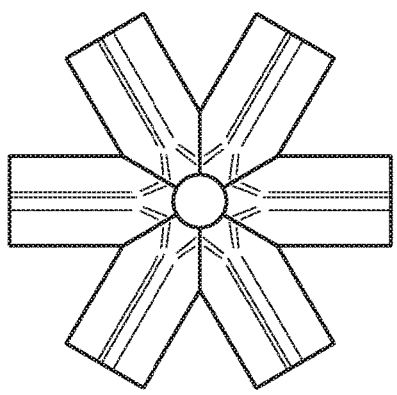
Figure 10C:
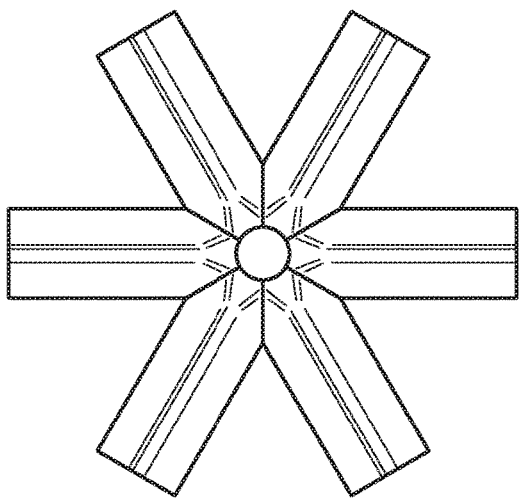
Figure 10A:
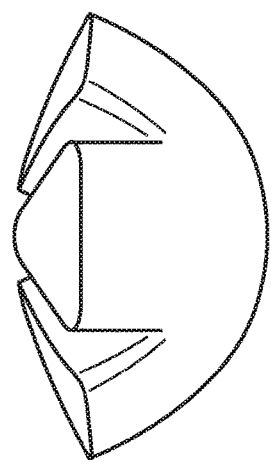
Figure 10B:
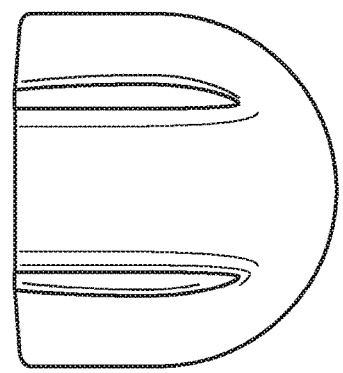
Figure 10C:
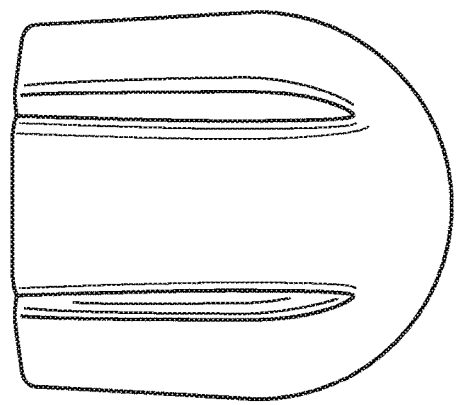

Enteric films as described in Example 2 are cut into triangles using a punch and 5 mm strips using a straight edge and scalpel. Triangles have the same cross-section as arms and are used for linking together arms through a butt-joint (single layer linker). Strips are used for wrapping adjacent arms through a collar joint. Arms made of 55 K PCL are cut at a 90 degree angle at the midpoint using a straight edge and scalpel. The arms are then joined together using a solvent bond. For the butt joint, acetone is brushed onto both surfaces of the film using a paint-brush and is then pressed between two PCL arms. Pressure is maintained for 60 seconds and then the joined arms and linker are left at room temperature for 24 hours before testing. For the collar joint, acetone is brushed onto one surface of the film using a paint-brush. The film is wrapped around the three edges of the triangle with equal overlap on both sides of the PCL interface. Pressure is applied to the three surfaces for 60 seconds and then the joined arms and linker are left at room temperature before testing. A four-point bending flexural test (ASTM D790) is used to evaluate the strength of the interface. Briefly, the joined specimen spans two rods with the interface directly at the midpoint. Two rods apply force adjacent to the linker causing the specimen to bend in flexion. The force and displacement are recorded and the maximum flexural force recorded. FIG. 9, Panel A shows the four-point bending flexural test for the butt joint (single layer enteric linker), while FIG. 9, Panel B shows the four-point bending flexural test for the collar linker.

Plastoid B—L100-55 and Triacetin—L100-55 enteric films were tested using this technique at Day 0, Day 2, and Day 7 of incubation in simulated gastric fluid (FASSGF). The results are shown in FIG. 9, Panel C. It was found that collar joints formed the strongest bond and Plastoid B films were the least susceptible to degradation in FASSG.

Example 4

Polymer Creep Testing

A standardized creep test (ASTM D2990) is used to evaluate the extension of the elastomeric material with time when exposed to a constant tensile load. The elastomer is cast into 2 mm sheets using a heated hydraulic press with 2 mm thick steel shanks. A dogbone die (ASTM D638 Type II) is used to cut out specimens for mechanical testing. The test duration is 1,000 hours at 23 degrees Celsius and 50 degrees Celsius under constant humidity. The minimum creep rate, creep strength, and rupture strength are reported from the test.

Gastric residence systems are assembled and then placed into the appropriate sized capsules. The capsules are stored at 23 degrees Celsius and 50 degrees Celsius under constant humidity for periods ranging up to 3 years. Following incubation, resident systems are removed from capsules and subjected to the "funnel" test of Example 5 to evaluate resistance to contraction, which simulates resistance to passage through the pyloric valve.

Example 5

Funnel Testing to Simulate Resistance to Pyloric Passage

The star-shaped gastric residence systems are placed in a plastic funnel with an outer diameter sufficiently large to accommodate the system in its uncompacted configuration. The outer diameter narrows down to a spout diameter of 2 cm. A plunger is used to push the system gradually through the funnel, and the force on the plunger throughout the test is recorded. This test simulates the amount of force required to push the gastric residence system through the pyloric valve.

Example 6

Using Injection Molding to Manufacture Elastomer

Injection molding was used to form elastomers in a concavo-convex and biconcave disk geometry. A three-shot mold process was developed to enable the elastomer to be thermally bonded to gastric residence system arms. The first shot material was polycarbonate (Lexan 940-701), an impact resistant thermoplastic that forms strong bonds with a range of self-adhesive thermoplastic and thermoset elastomers. This first shot material acted as a coupling between the elastomer and polycaprolactone required to form a thermal bond with drug loaded segments. The first shot design included a mechanical interlock to strengthen the bond between the elastomer and thermoplastic while acting as a platform for ejection out of the mold (FIG. 14A).

The second shot material was self-adhesive liquid silicone rubber (Shin-Etsu 2097), which has been shown to form a strong chemical bond with polycarbonate. The first shot polycarbonate part was placed into the mold and silicone was shot over top of the thermoplastic (FIG. 14B). When placing the polycarbonate part into the mold there was no contamination of the contact surfaces ensuring a strong chemical bond between the two materials. The mold incorporated a cold deck to prevent flashing of the silicone by precisely controlling the cure temperature.

A trimming fixture was developed to remove and expose the surfaces of the polycarbonate to polycaprolactone during the third shot overmold. Excess polycarbonate required for mechanical support of the part during the liquid silicone rubber overmold was trimmed with the fixture. The polycarbonate-silicone part was then placed into a third injection mold where polycaprolactone was shot over top of the polycarbonate surfaces (FIG. 15A). A mechanical interlock was included to strengthen the interface between the two materials. A trimming fixture was developed to remove the excess polycaprolactone required for achieving complete injection of the material (FIG. 15B), resulting in a gastric residence system hub intermediate assembly.

During the development of all three molds MoldFlow analysis (Autodesk Moldflow) was conducted to determine the ultimate shot size and parting lines. All molds were created out of steel and were machined using computer numeric control (CNC) tools.

Example 7

Designing Elastomer to Meet Functional Requirements

The finite element method was used to develop and evaluate elastomer designs that satisfied the gastric residence system mechanical requirements. The optimal elastomer would incorporate features that increased the folding force of the elastomer while minimizing local stress concentrations. Sufficient folding force is needed to achieve gastric residence as it enables the gastric residence system to resist gastric contractions. Minimizing stress concentrations is desirable to promote mechanical stability in the capsule by reducing compression set in the elastomer.

Figure 16A:
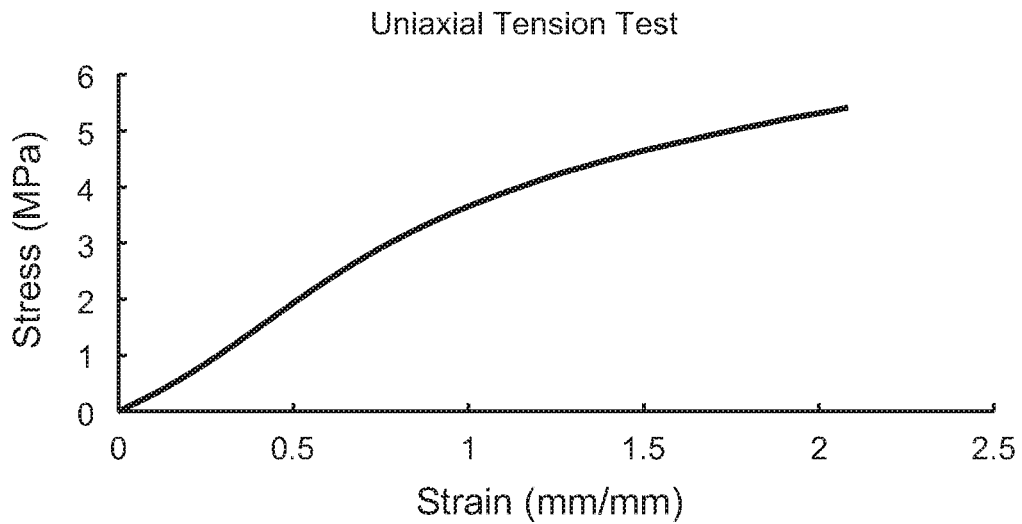
FIG. 16A shows a tension test of a silicone elastomer.
Figure 16B:
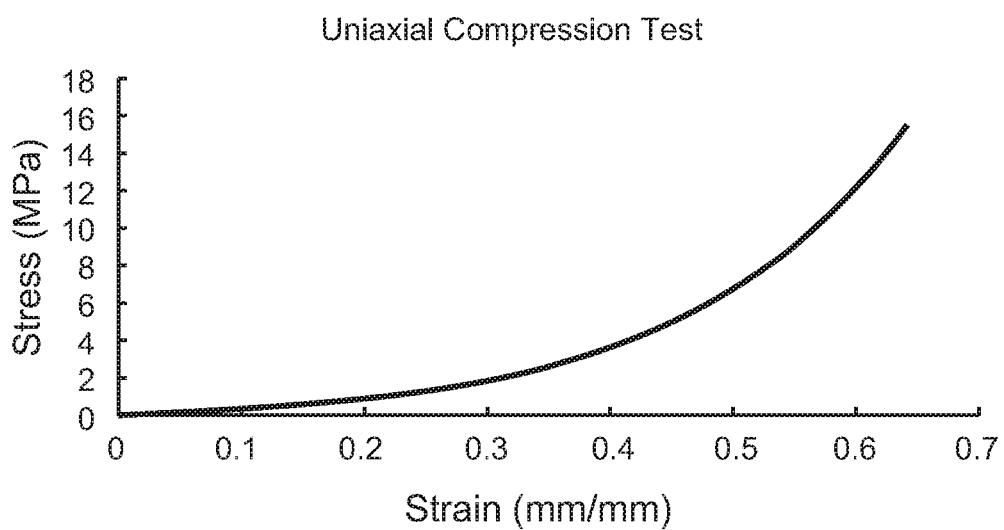
FIG. 16B shows a compression test of a silicone elastomer.

Elastomer designs were generated in 3D CAD software (Solidworks) that folded into OOEL capsules and interfaced with drug loaded arms. Liquid silicone rubber (Shin Etsu 2097) was mechanical characterized in tension (FIG. 16A) and compression (FIG. 16B) and the data was used to generate a nonlinear material model (Mooney-Rivlin) in finite element analysis simulation software (Solidwork Simulation) (FIG. 16A, FIG. 16B). The funnel test was modelled and used to simulate the folding force of the elastomer (FIG. 17A, FIG. 17B). The thermoplastic coupling (Polycarbonate) and polycaprolactone arms were modelled as linear elastic materials. All linear elastic properties were generated from supplier data sheets.

Gastric residence systems and the funnel test apparatus were meshed and the appropriate boundary conditions applied. A rod was used to press the gastric residence system through the funnel and the resultant force calculated on the tip of the rod. A range of designs were analyzed and three major families emerged that met the desired design requirements: a concavo-convex design (FIG. 18A, FIG. 18B), biconcave disk design (FIG. 18C, FIG. 18D), and torus design (FIG. 18E). The stress and strain distributions were analyzed and features were added to minimize stress concentrations (FIG. 19A, FIG. 19B, FIG. 19C, FIG. 19D). Designs were also modified to ensure they incorporated parting lines that would enable them to be formed with injection molding techniques.

The concavo-convex design had four major features that affected the folding force of the gastric residence system: 1) increasing the depth of the design increased the folding force; 2) decreasing the width of the gastric residence system increased the folding force; 3) decreasing the depth of the hinge increased the folding force; and 4) decreasing the width of the hinge increased the folding force. These four parameters were adjusted to modify the folding force of the gastric residence system.

The biconcave disk design had two major features that affected the folding force of the gastric residence system: 1) increasing the height of the design increased the folding force; and 2) decreasing the width of the gastric residence system increased the folding force.

By incorporating a concave recess in both the concavo-convex and biconcave disk designs led to an optimal force-displacement curve (FIG. 20). Optimally, the folding force of a gastric residence system would reach a maximum prior to passing through a 2 cm hole (approximate size of the human pylorus). A drop in the force following this displacement would decrease the stress applied to the elastomer while stored in a capsule increasing the mechanical stability. Both designs incorporated this feature.

Example 8

Elastomer Material Properties

The material properties of the elastomer are important in fulfilling the function of the gastric residence system. A range of materials were mechanically screened to establish if they were suitable for the elastomer (Table 5).

TABLE 5

| Elastomer | Durometer (shore A scale) | Compression Set | Tear Strength |
|---|---|---|---|
| Shin-Etsu KE 2090 Series Liquid Silicone Rubber (LSR) | 10-70 A | <10% | 35 kN/m |
| Momentive Silopren 2600 Series Liquid Silicone Rubber (LSR) | 10-80 A | <20% | 30 kN/m |
| Pebax 2533 Thermoplastic Elastomer (TPE) | 75 A | <60% | 38 kN/m |
| Polytek Polyurethane Thermoset | 70-90 A | <30% | 34 kN/m |

Parameters evaluated for the elastomer included: 1) Durometer—this is a measure of the elastic modulus or stiffness of a material. When tested using the funnel test, the durometer directly correlated with the folding force of the gastric residence system (FIG. 21) Compression set—this is a measure of the creep behavior or likelihood of a material to become permanently deformed when placed under a constant deformation. Low compression set materials prevent the gastric residence system from becoming permanently deformed when stored in capsules; and 3) Tear Strength—this is a measure of the resistance of a material to undergo rupture. High tear strength prevents the elastomer from rupturing when placed under load in a capsule or when deployed and loaded in the gastric cavity.

Figure 23:
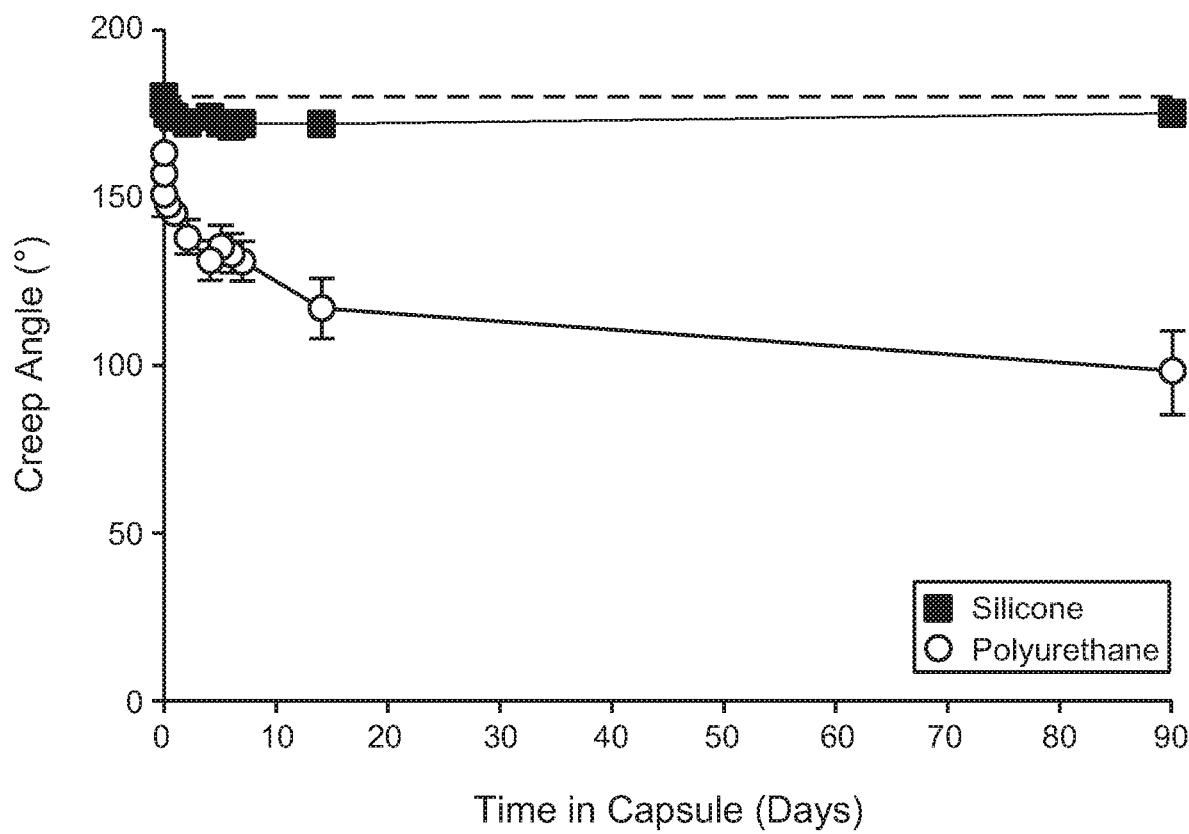
FIG. 23 shows the creep angle as a function of time in a capsule for a silicone elastomer assembly (squares) and a polyurethane elastomer assembly (circles).

All thermoplastic elastomers were found to have higher compression set to liquid silicone rubber thermosets. Specifically, the Shin-Etsu 2090 self-adhesive thermoset was found to have a very low compression set (<10%) compared to both thermoplastic and thermoset materials. Additionally, the Shin-Etsu 2090 had comparable tear strength to thermoplastics at the same durometer. A creep in capsule test was conducted to compare the permanent deformation incurred from storage in a capsule (FIG. 22, FIG. 23). The test involved placing gastric residence systems into capsules and measuring the permanent deformation angle. Liquid silicone rubber (FIG. 22, left panels) performed significantly better than a polyurethane elastomer (FIG. 22, right panels) over a three-month creep in capsule test.

Example 9

Production and Evaluation of Collar Linkers

An enteric polymer suitable for joining drug loaded arms was prepared from methyl methacrylate and n-butyl methacrylate (EVONIK Plastoid B) and poly(methacrylic acid-co-ethyl acrylate (EUDRAGIT L 100-55). Briefly, the enteric polymer was prepared by dissolving Plastoid B and EUDRAGIT L 100-55 in acetone in a 10:90 w/w ratio. The resulting mixture was poured into a mold and the solvent was evaporated over 24 h to form a thin film 250 um in thickness.

The film was then cut into 3.7 mm height×2 mm width rectangles using a scalpel and straight edge. Arms 20 mm in length were perpendicularly sectioned at the center point resulting in two 10 mm length arm sections. The arm segments were aligned and pressed together forming a butt joint. One side of the rectangular enteric films was sprayed with acetone to wet the surface. The film was pressed against the butt joint forming an adhesive bond and connecting the two arm segments. Two more rectangles were placed on the remaining edges forming a continuous collar around the drug loaded arm. Arms were left for 24 h for the adhesive bond to fully form.

Arms with linkers were incubated in fasted state simulated gastric fluid (FaSSGF) and fasted state intestinal fluid (FaSSIF). FaSSGF was prepared by dissolving 2 g of NaCl in 0.9 L of purified water. The pH was adjusted to 1.6 using HCl. The volume was then made up to 1.0 L with purified water at room temperature. Next, 0.06 g of FaSSGF Biorelevent powder was added to 0.5 L of the HCl/NaCl solution. The volume was then made up to 1 L with the HCl/NaCl solution at room temperature.

FaSSIF was prepared by first preparing a buffer solution consisting of 0.42 g of NaOH, 4.47 g of $NaH_2PO_4$, and 6.186 g of NaCl in 0.9 L of purified water. The pH was adjusted to 6.5 using 1 N NaOH. The volume was then made up to 1.0 L. Next, 2.24 g FaSSIF Biorelevent powder was added to 0.5 L of buffer and stirred until completely dissolved. The volume was made up to 1 L with buffer at room temperature and then left for 2 hour before use.

Arms were placed in 15 mL falcon tubes and 15 mL of FaSSGF or FaSSIF was added. The falcon tubes were incubated in an incubator shaker at 37 C and 100 RPM. Media was changed every 24 h to simulate sink conditions. Specimens were immediately mechanically characterized for adhesion and flexion following removal from incubation media.

Figure 24A:
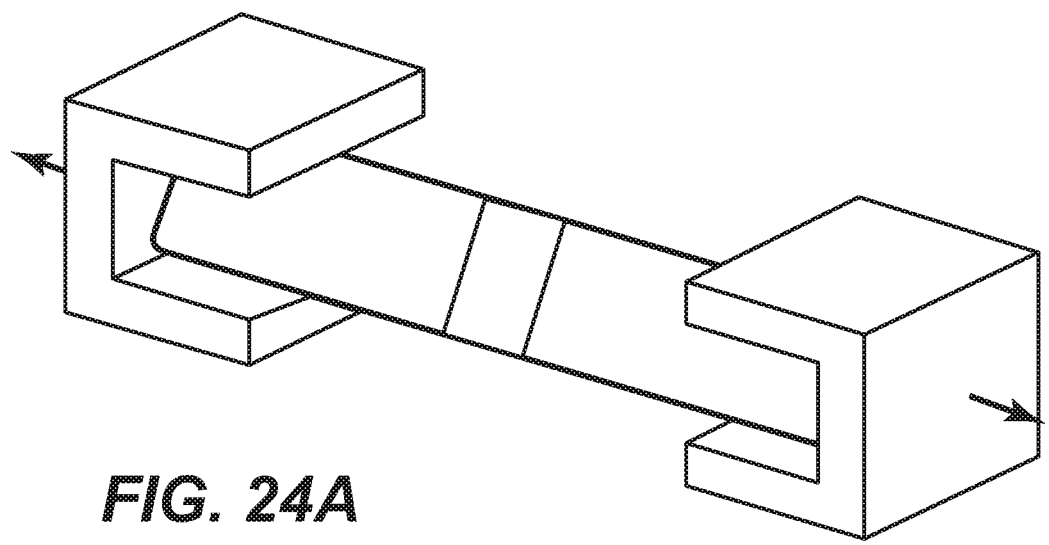
FIG. 24A shows a pull-apart test setup for testing adhesion strength of linkers.

Standard tensile grips were used to test the adhesion of the linker to arms (FIG. 24A). A gauge length of 10 mm was used for all specimens. Grips were tightened sufficiently to ensure that slippage did not occur at the grips while not causing significant damage to the arms. Load was applied to the specimen at a rate of 0.1 mm/s throughout the test. The pull-apart test was terminated when the specimen failed (sharp decrease in force).

Figure 24B:
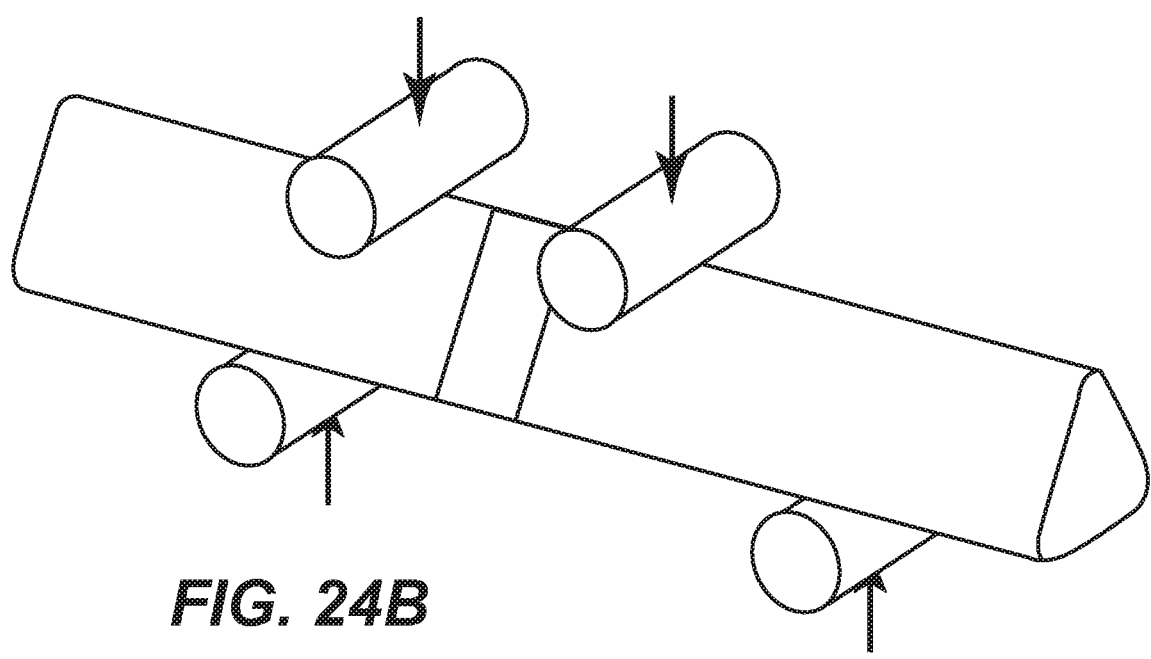
FIG. 24B shows a four-point bending test setup for testing flexural strength of linkers.

A four-point bending fixture was used to evaluate the flexural strength of specimens (FIG. 24B). The lower span was 18 mm and the upper span was 10 mm. Specimens were placed in the center of the fixture and did not slip throughout the test. The top fixture was placed in contact with the specimen prior to testing, but not loaded above 0.1 N. Load was applied to the specimen at a rate of 0.1 mm/s through the test. The flexural test was terminated when the specimen failed (sharp decrease in force) or when the defection at the center of the specimen reached a maximum deflection of 4 mm.

Both the adhesion and flexural force of linkers remained stable in FaSSGF, but quickly reduced in FaSSIF (FIG. 25A: adhesion, left, FaSSGF; right, adhesion, FaSSIF-B) (FIG. 25B: bending, left, FaSSGF; right, bending, FaSSIF-B).

Figure 26A:
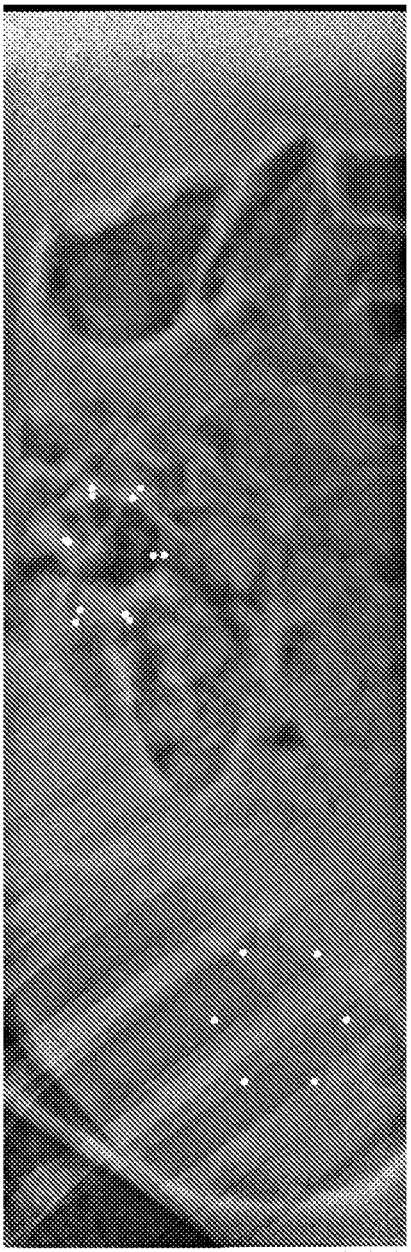
FIG. 26A shows gastric residence systems which were endoscopically placed in the stomach (single fiducials) and in the small intestine (double fiducials) on day 0.
Figure 26B:
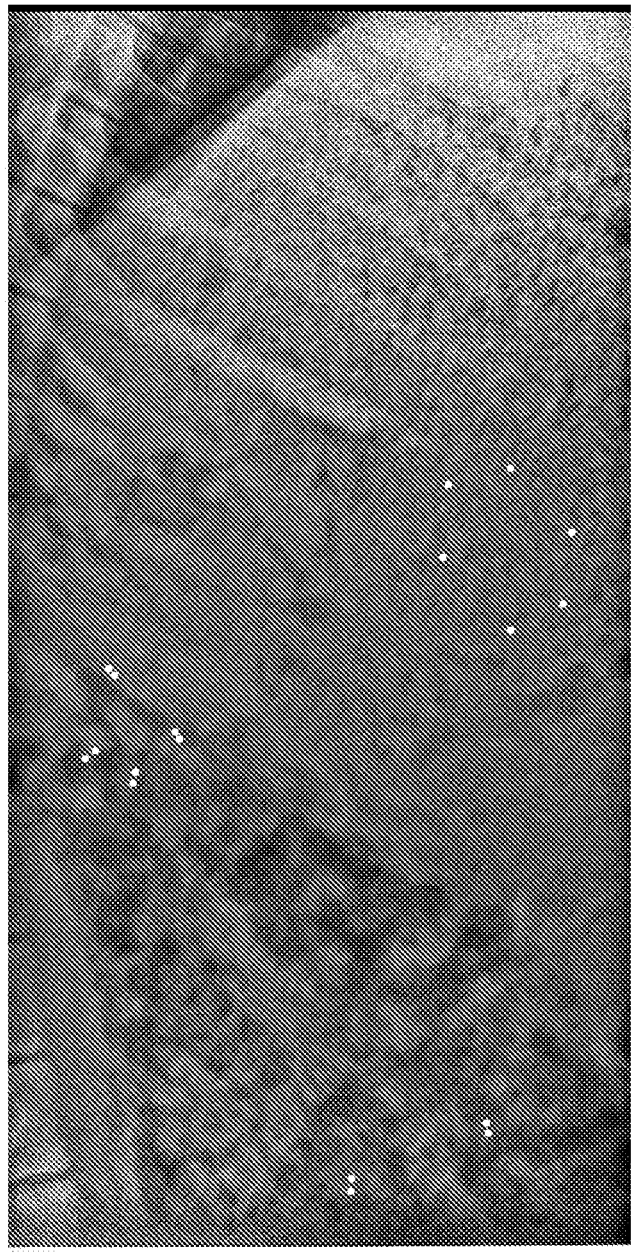
FIG. 26B shows the two gastric residence systems from FIG. 26A at day 1, showing arms breaking apart in the intestine but not the stomach.

Collar linkers were tested in vivo by endoscopically placing gastric residence systems with collar linkers into the stomach and small intestine. Gastric residence systems were identified by placing two sets of fiducial markers in gastric residence systems placed in the small intestine and a single set in gastric residence system placed in the stomach. X-rays were taken immediately after placement (FIG. 26A) and at 24 h (FIG. 26B). The number of intact arms was documented.

Example 10

Hot Melt Extrusion for Production of Drug Arms and Linkers

Figure 27A:
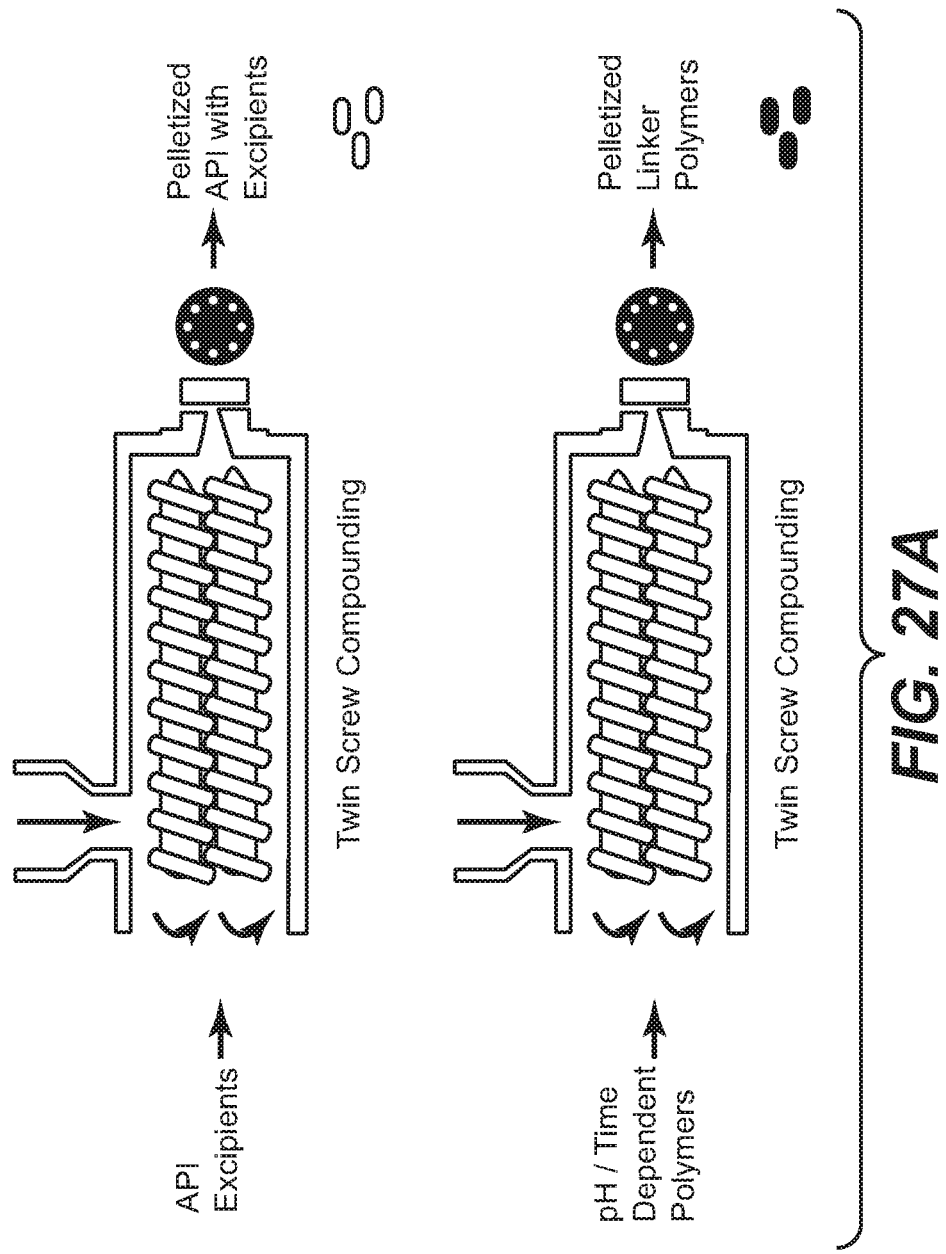
FIG. 27A shows schematics of extrusion devices for preparing therapeutic agent/active pharmaceutical ingredient blends (API) (top) and blends for pH-dependent linkers or time-dependent linkers (bottom) in pelletized form.

Hot melt extrusion was used to uniformly blend and extrude triangular rod stock. Twin screw extrusion was used to compound and pelletize drug loaded arms and linker blends (FIG. 27A). Polycaprolactone, drug, and excipients were blended prior to compounding using a bag mixer. The polymer blend was added to a gravimetric feeder and consistently fed into an 18 mm, 40 L/D twin screw extruder (Leistritz). The screw speed was set to 500 RPM and the temperature to 100 C for drug loaded arms. The compounded material was pulled through a die with two 2.5 mm diameter holes and pelletized into 1.5 mm lengths with a dual-drive pelletizer.

Figure 27B:
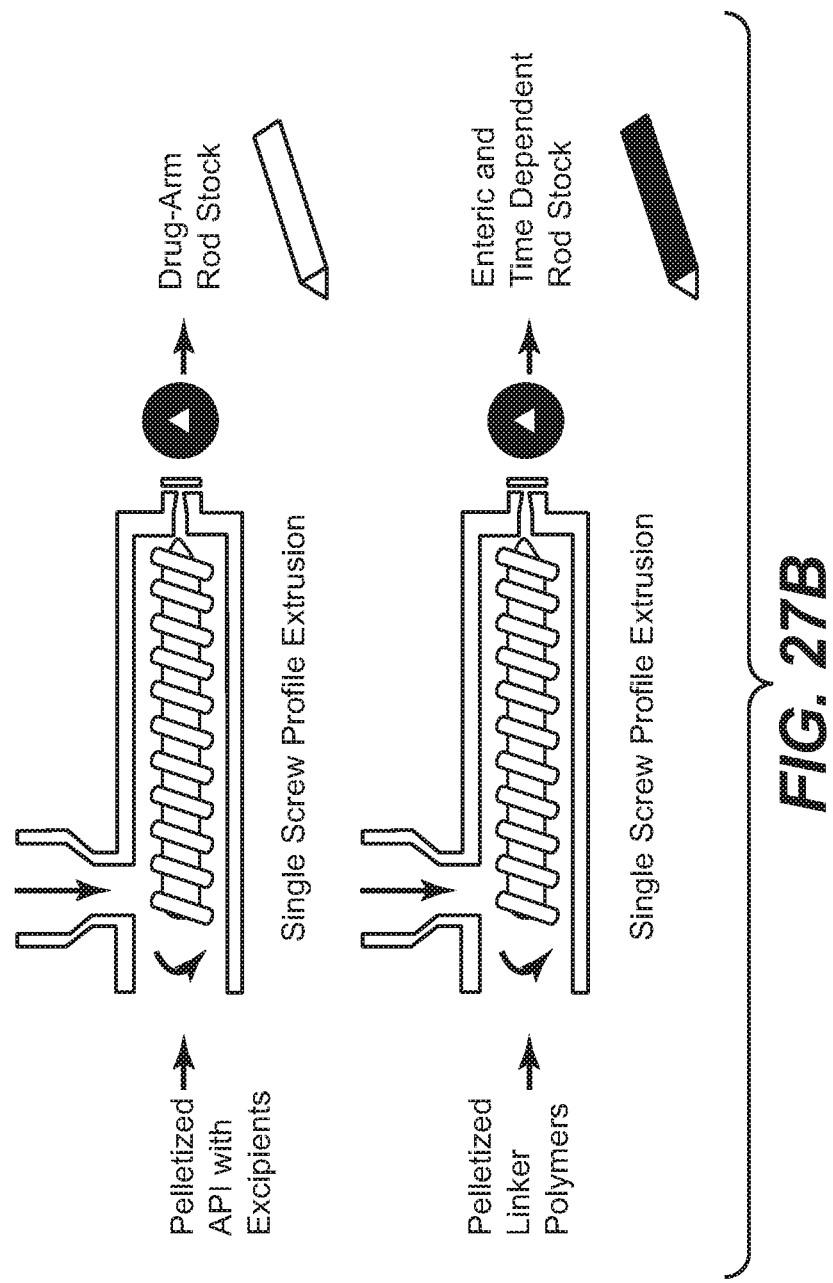
FIG. 27B shows schematics of extrusion devices for preparing therapeutic agent/active pharmaceutical ingredient blends (API) (top) and blends for pH-dependent linkers or time-dependent linkers (bottom) in the form of rod stock.

Drug and linker pellets were independently fed into a single screw extruder and fed at a constant rate to keep the extruder full (FIG. 27B). A custom triangular die was designed and machined to extrude triangular rod stock with the required geometry. As polymer blends were pulled from the die a 3-axis digital micrometer was used to measure each edge of the triangle rod stock. The micrometer was connected to the puller in a closed-feedback loop which allowed for precise geometric tolerances. The rod stock traveled through a vortex blower which helped solidify the polymer. An in-line cutter was used to section the material at 30 cm increments and triangular rods were collected.

Example 11

Compounding and Profile Extrusion of Linker Materials

Linker components were blended by twin screw extrusion using a Haake MiniCTW micro-compounder. Polymer powders or pellets were weighed and blended into a physical mixture before loading onto the extruder. Materials were loaded into the micro-compounder and batch mixed at a rate of 75 rpm for 10-20 minutes at a temperature of roughly 20° C. above the melting temperature of the highest melting component; see Table 6. After batch mixing, the polymer melt was extruded through a triangular die onto a conveyor belt and cooled at ambient temperature. Profile extrusion was performed at a screw speed of 10-30 rpm and conveyor speed was adjusted to achieve a consistent triangular profile.

TABLE 6

| Polymer | Melting temperature | Extrusion temperature |
|---|---|---|
| Polycaprolactone | 60-65° C. | 100° C. |
| HPMC-AS | 120° C. | 140-160° C. |
| Aquaprene 8020 | 100-110° C. | 120-130° C. |
| PEVA | 110-120° C. | 130-150° C. |

Example 12

Hot Plate Welding Optimization

Generation of triangular rod stock for weld optimization. Triangular rod stock of linker material was generated by profile extrusion as described in example 6. Triangular rods of PCL were generated either by profile extrusion or by gravity molding of PCL pellets into a PDMS mold in a 120° C. oven. Linker material and of PCL rod stocks were cut into 1-cm segments.

Hot plate welding of linker materials to PCL. One centimeter segments of linker materials were welded to one centimeter segments of PCL using a custom hot plate welding apparatus. The apparatus includes tools to align and interface the two sections of material and a dual temperature heat platen for melting the two materials. For each linker formulation, the side of the heat platen that contacted the PCL segment was set to a temperature of 90-120° C. and the side of the heat platen that contacted the linker material was set to a temperature of roughly 20° C. above the extrusion temperature. The two materials were placed in contact with the heat platen for 5-10 seconds, removed from heat, and the two molten components were brought into contact and allowed to solidify at ambient temperature. Samples were then allowed to cure at room temperature or at 8° C. overnight before analysis.

Weld strength evaluation by four-point bending. The welded samples were loaded into a custom built four-point bending apparatus (FIG. 24B). Force was recorded over a total displacement of up to 3 mm. For samples that did not break during the assay, the maximum applied force in the first 1200 microns of displacement was recorded for a comparison of weld strength. For samples that underwent brittle breakage before reaching a 1200 micron displacement, the maximum force at break was recorded. Six samples were tested at each condition. Results for the optimization of the hot plate welding conditions for HPMC-AS-based linker materials are shown in Table 7.

drug loaded formulations. The two materials were placed in contact with the heat platen for 5-10 seconds, removed from heat, and the two molten components were brought into contact and allowed to solidify at ambient temperature. After cooling, the welded linker material was cut to a length of 3 mm. The cut end of the linker material was then welded to another 1-cm segment of drug loaded formulation using the same procedure, creating a 23-mm-long drug-loaded rod containing a 3-mm linker.

Post weld oven annealing. The drug-loaded triangular rods containing linkers were placed into a PDMS mold to retain their geometry during annealing. Molds were placed into an oven at a temperature of 140° C. or 160° C. for 15 or 30 minutes and then allowed to cool at ambient temperature.

Figure 28:
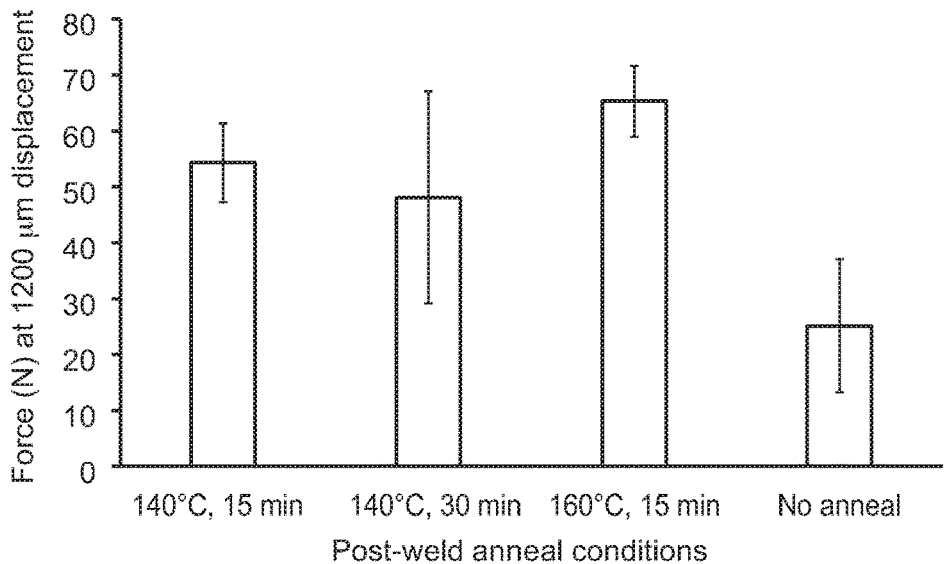
FIG. 28 shows weld strength enhancement via post-weld annealing in a four-point bending assay for (carrier polymer-agent)-linker-(carrier polymer-agent) samples.
Figure 29A:
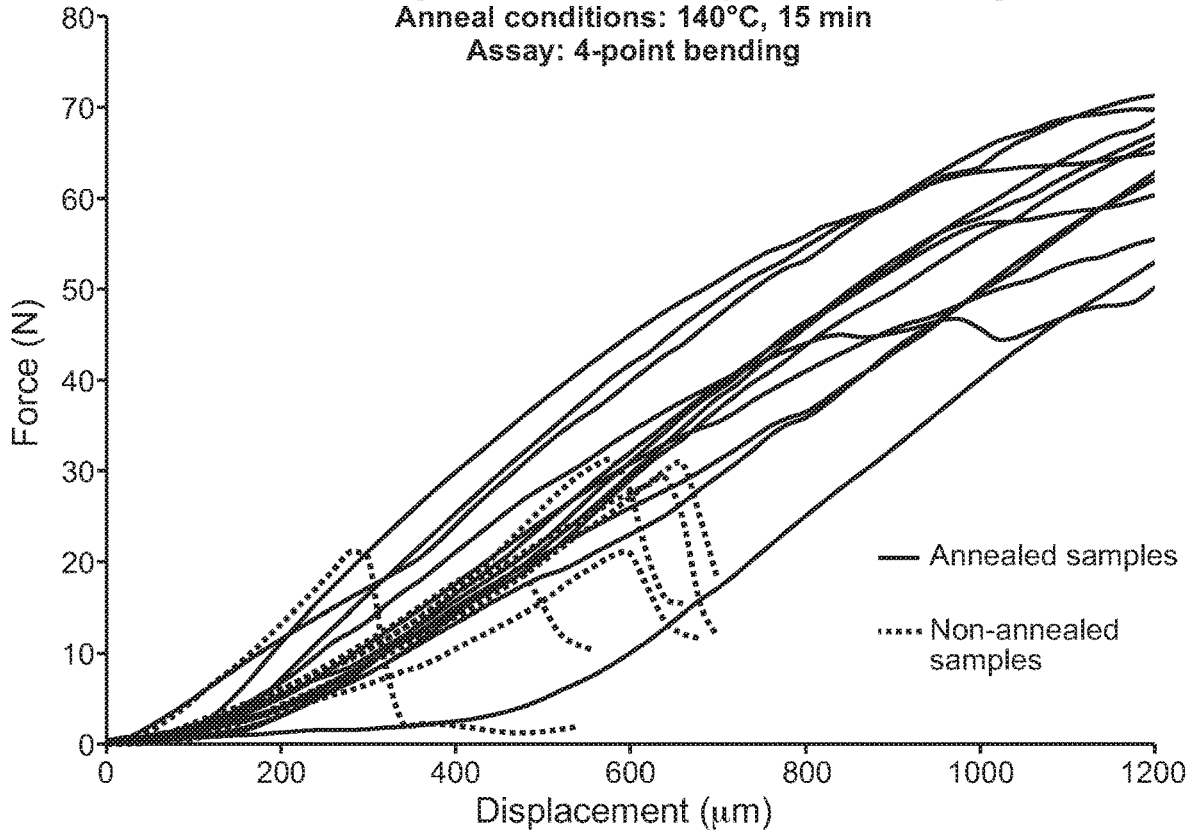
FIG. 29A shows force-displacement curves for annealed and non-annealed (carrier polymer-agent)-linker-(carrier polymer-agent) samples. Post weld-annealing consistently improves breakage force of welded linkers.

Weld strength evaluation by four-point bending. The welded and annealed samples were loaded into a custom built four-point bending apparatus (FIG. 24B). Force was recorded over a total displacement of up to 3 mm. For samples that did not break during the assay, the maximum applied force in the first 1200 microns of displacement was recorded for a comparison of weld strength. For samples that underwent brittle breakage before reaching a 1200 micron displacement, the maximum force at break was recorded. Results are shown in FIG. 28. Results were confirmed when the experiment was repeated with 12 samples and an anneal condition of 140° C. for 15 minutes. Force-displacement curves for each of these samples are shown in FIG. 29A. All non-annealed controls underwent brittle breakage before reaching a displacement of 800 microns. Though some annealed samples were observed to tear at higher displacements, none underwent brittle breakage during the assay.

TABLE 7

| Weld Conditions | Storage Conditions After Welding Before 4 pt Bend Test | Average Bending Force (N) | Comments |
| --- | --- | --- | --- |
| 160° C., 10 seconds on heat plate | RT for 24 hrs | 29.11 ± 3.43 N | (Control) All welds broke during testing |
| 160° C., 10 seconds on heat plate | 8° C. for 24 hrs | 43.49 ± 5.32 N | All welds broke during testing |
| 180° C., 10 seconds on heat plate | 8° C. for 24 hrs | 48.46 ± 8.38 N | All welds broke during testing, 2 of 4 welds broke within the linker |
| 180° C., 5 seconds on heat plate | 8° C. for 24 hrs | 51.97 ± 10.36 N | 2 of 4 welds broke within the linker, other 2 welds tore at the weld and did not fully break |

Example 13

Post-Weld Annealing for Improved Weld Strength

Hot plate welding of linker materials into drug-loaded rods. Triangular rod stock of drug formulation and of linker material were generated by extrusion as described in Example 11 and cut into 1-cm segments. The drug formulation used was 12% Eudragit RL (an ammoniomethacrylate copolymer), 5% P407 (a polyoxyethylene-polyoxylpropylene glycol copolymer), 20% memantine HCl, 0.5% silica, 0.5% alpha-tocopherol, with the balance Mn 80 k PCL. One centimeter segments of linker materials (70% HPMCAS/ 30% PCL) were welded to one centimeter segments of drug loaded formulation using the custom hot plate welding apparatus described in Example 12. The dual heat platen was set to 180° C. for the linker materials and 100° C. for the Example 14

Post-Weld Annealing with Localized Heat Via Infrared Welding

PCL rods containing linkers were generated by hot plate welding using the same procedure as described in Example 13. Samples were placed into a PDMS mold and covered with aluminum foil. 2-3 mm slits were cut in the aluminum foil at the position of the linkers to expose only the linker material while the PCL segments remained covered. Samples were placed under an IR lamp (Dinghua A01r) and heated to 140° C. for 1-2 minutes. The foil resist was then removed and samples were allowed to cool at ambient temperature. Visual inspection of the IR-annealed samples confirmed that PCL melted in the area 1-2 mm from the weld but that the remainder of the PCL rod remained solid. This method of localized heat application can enable post-weld annealing with minimal exposure of drug-containing components to heat.

Localized heating by IR can be integrated into the assembly process using standard IR welding equipment along with custom molds and masks. Masks are designed to allow IR to contact only areas near welds and to reflect IR away from heat-sensitive components of the gastric residence system, such as drug-loaded formulations. Molds can be designed with IR reflective surfaces arranged underneath welds to reflect IR toward the bottom of the sample, allowing IR heating to reach all three faces of the triangular rod from a single IR source. To further protect heat-sensitive components of the gastric residence system, molds can be designed with channels to allow air or liquid cooling to selected regions of the gastric residence system.

Example 15

Linker Flexural Strength Over One Week in Simulated Gastric Fluid

Hot plate welding of linker materials into PCL rods. Triangular rod stock of PCL and of linker material were generated by extrusion as described in Example 11 and cut into 1-cm segments. One centimeter segments of linker materials were welded to one centimeter segments of PCL using the custom hot plate welding apparatus described in Example 12. The dual heat platen was set to 180° C. for the linker materials and 100° C. for PCL. The two materials were placed in contact with the heat platen for 5-10 seconds, removed from heat, and the two molten components were brought into contact and allowed to solidify at ambient temperature. After cooling, the welded linker material was cut to a length of 3 mm. The cut end of the linker material was then welded to another 1-cm segment of drug loaded formulation using the same procedure, creating a 23-mm drug-loaded rod containing a 3-mm linker.

Figure 30A:
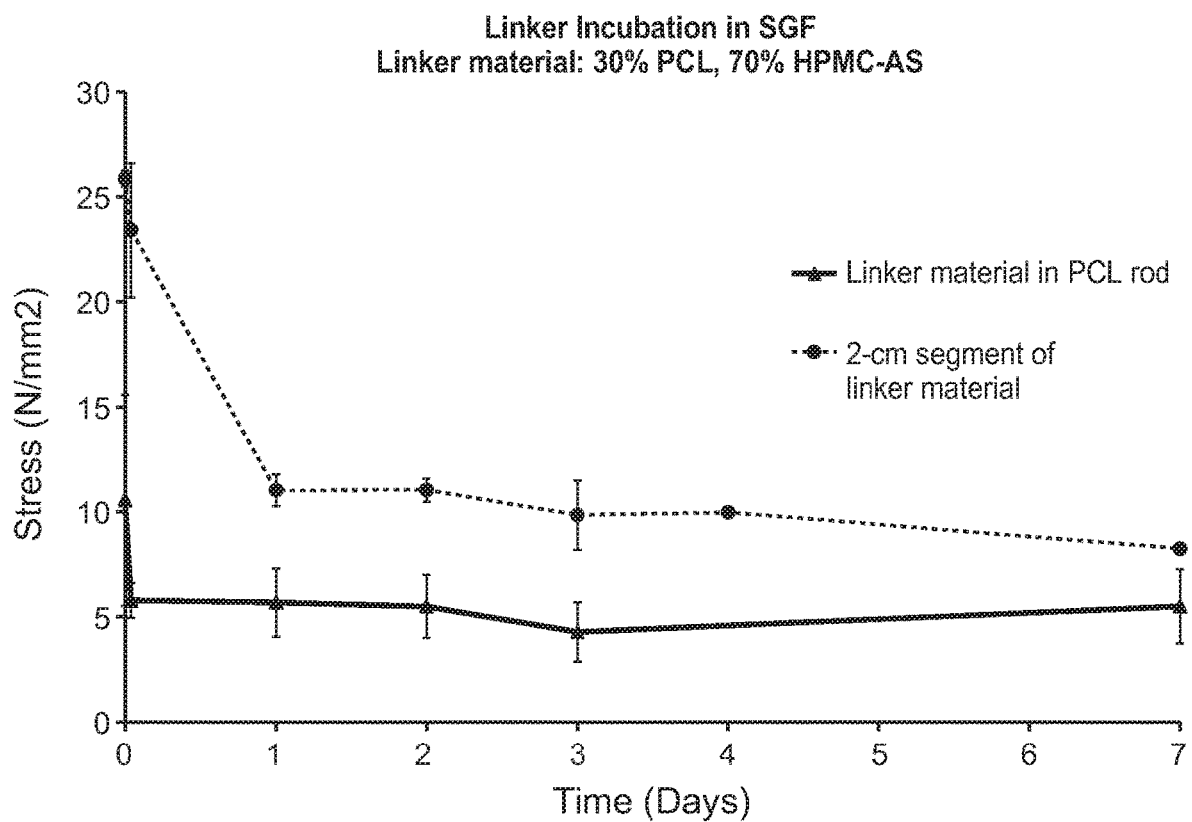
FIG. 30A shows an in vitro analysis of linker strength during one week in SGF. Stress at 1200 micron displacement in the four-point bending test is plotted against time in SGF.

Incubation in simulated gastric fluid and flexural strength analysis. Biorelevant fasted state simulated gastric fluid (FaSSGF) was prepared per the manufacturer's instructions (biorelevant.com). PCL arms containing linkers as well as 2-cm rod stock of linker materials were loaded into 15-mL centrifuge tubes with 10 mL FaSSGF and placed in a shaking incubator at 37° C. and 200 rpm. Samples were removed at each time point and analyzed by the four-point bending test as described in Example 13. Results are shown in FIG. 30A for a linker material composed of 70% HPMC-AS MF (Ashland), 30% PCL (MW 80 k, Sigma Aldrich). Three samples were tested at each time point.

Example 16

Linker Performance Evaluation In Vivo: Gastric Retention in Dogs

Preparation of component materials. Polycaprolactone rod stock was generated by gravity molding of 80 k PCL in a PDMS mold in an oven at 120° C. Triangular rod stock of linker material was generated by extrusion as described in Example 11 and cut into 1-cm segments. Linker formulations were composed of Ashland HPMCAS-MF and 80 k PCL, blended in ratios of 70/30, 50/50, and 30/70 wt/wt. Polytek 90 A durometer polyurethane central elastomers were generated by oven curing to PCL arms at 120° C.

Gastric residence system assembly. Rod stock of PCL and linker materials were hot plate welded together to generate PCL arms containing 2-3 mm linker segments, as described in Example 13. For the 70% HPMCAS/30% PCL linkers and the 50% HPMCAS/50% PCL linkers, the linker-containing PCL arms were then placed in a PDMS mold, annealed in a 160° C. oven for 30 min, then allowed to cool at room temperature. To enable X-ray imaging of gastric residence systems, a 1.5-mm stainless steel bead was added to the end of each arm of the gastric residence system by melting the PCL on the 100° C. heat platen and reshaping the molten polymer around the bead. PCL arms containing linker segments and steel fiducials were then hot plate welded to the central elastomer by hot plate welding as described in Example 13. The heat platen temperature was set to 100° C. and the PCL components were placed in contact with the platen for 5 seconds before the molten materials were interfaced. After assembly, gastric residence systems were stored at room temperature for 24 hours before folding force analysis as described in Example 5. Gastric residence systems were folded and loaded into 00el HPMC capsules (Capsugel) immediately before dosing in dogs.

Figure 31:
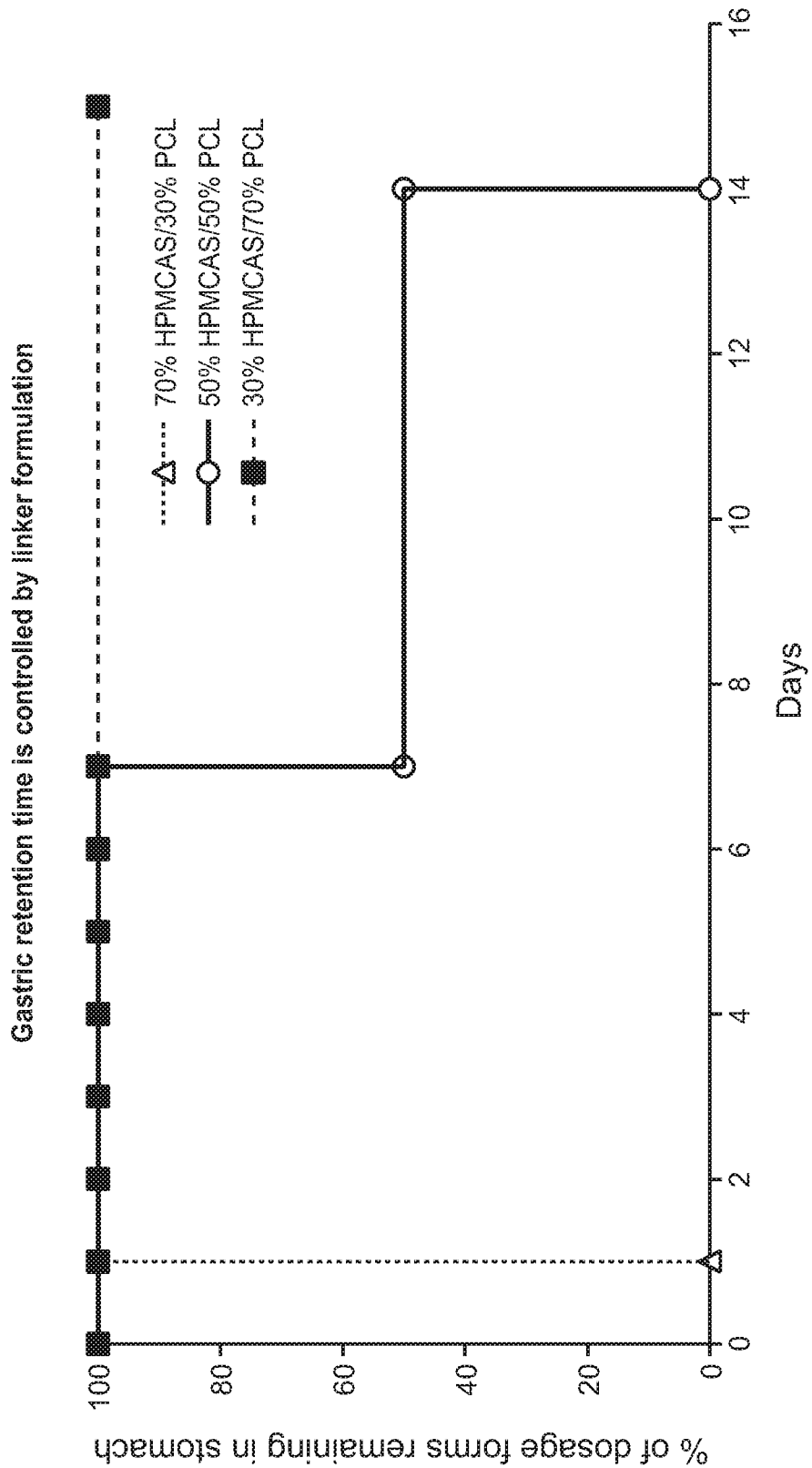
FIG. 31 shows gastric retention of gastric residence systems containing different linker formulations in a dog model.

Analysis of gastric retention in dogs. Capsules containing the gastric residence systems were administered to male, juvenile hound or beagle dogs after fasting for 12 hours. Gastric residence systems were placed in the back of the throat and followed with a food chase. Ventrodorsal X-rays were collected within an hour after dosing and daily for one week. If gastric residence systems were retained in the body longer than one week, X-rays were taken three times per week until the gastric residence systems passed. The six steel fiducials per gastric residence system enabled analysis of the location (stomach or lower GI tract) and intactness of each gastric residence system. Average retention times of gastric residence systems containing different linkers are shown in FIG. 31.

Example 17

Linker In Vitro Evaluation by Four-Point Bending with Fatigue Loading

Figure 32:
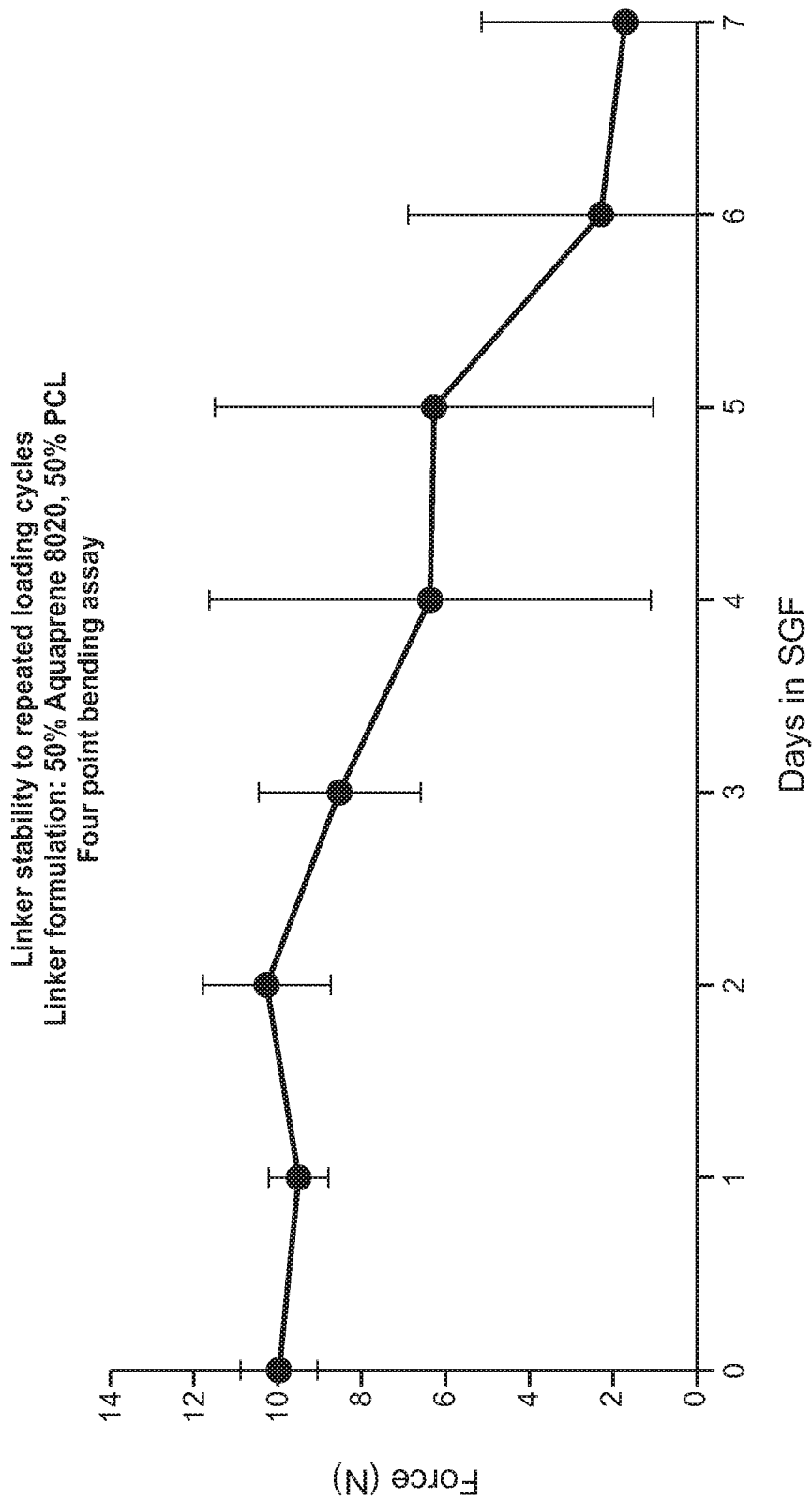
FIG. 32 shows an in vitro analysis of linker strength during one week in SGF: Cyclic fatigue loading is evaluated by the four-point bending assay.

PCL rods containing linkers were generated by hot plate welding following the same procedure described in Example 15. Biorelevant fasted state simulated gastric fluid (FaSSGF) was prepared per the manufacturer's instructions (biorelevant.com). PCL arms containing linkers were loaded into 15-mL centrifuge tubes with 10 mL FaSSGF and placed in a shaking incubator at 37° C. and 200 rpm. Samples were removed at each time point and analyzed by a fatigue loading four-point bending assay. Samples were subjected to a 10% deflection (300 microns) for 100 cycles and the maximum flexural force for each cycle was recorded and averaged. After analysis, each sample was replaced to the incubator in SGF and analyzed daily by the same non-destructive test. Results are shown in FIG. 32 for a linker material composed of 50% Aquaprene 8020, 50% PCL, MW 80 k. Five samples were tested at each time point.

Example 18

Additional Measures of Linker Performance for In Vitro-In Vivo Correlation

Assays for linker mechanical strength. Rods of PCL or drug-loaded formulation containing linkers can be assembled as described in Example 15. The mechanical properties of these rods can be assessed by several assays, including four-point bending (FIG. 24B) and tensile testing (FIG. 25A). Samples can be measured before and after incubation in a simulated gastric environment for varying periods of time.

A custom four-point bending fixture was designed and built to accommodate the unique geometry of the gastric residence system arms (lower span=18 mm, upper span=10 mm). Samples were centered on the lower span so that the linker segment of the arm sat in the center of the upper span. A load was applied downward to the top of the sample to a maximum deflection of 3 mm. Force was recorded and plotted as a function of displacement (FIG. 29A, Example 13).

Tensile testing is performed using a similar custom fixture, by modifying the linear actuator with tensile grips. The sample is placed vertically in the fixture and grips are attached at each end. Force is applied upward, pulling on the ends of the sample, and force is recorded and plotted as a function of displacement.

In either test, samples can be analyzed destructively or non-destructively, using a single deflection or cyclic fatigue loading. Multiple assays can be designed using either fixture by specifying deflection, force, number of fatigue loading cycles, and deflection rate.

Figure 29B:
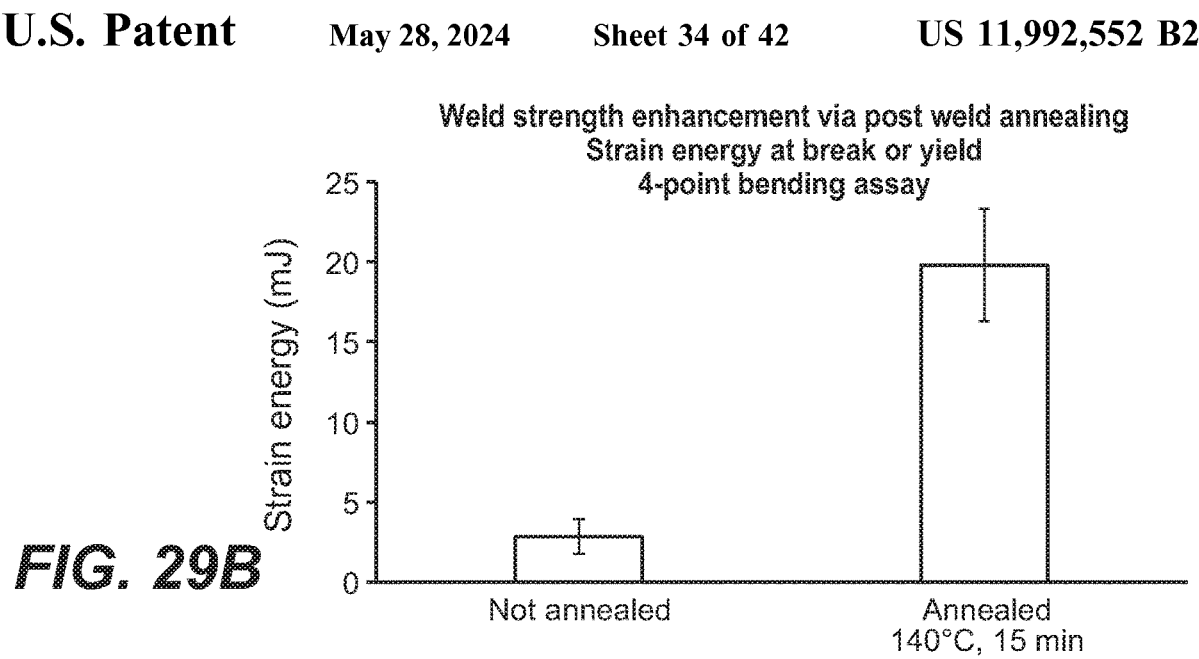
FIG. 29B shows strain energy (in mJ) at linker break or yield in the four-point bending assay for annealed and non-annealed (carrier polymer-agent)-linker-(carrier polymer-agent) samples, demonstrating the weld strength enhancement from annealing.
Figure 29C:
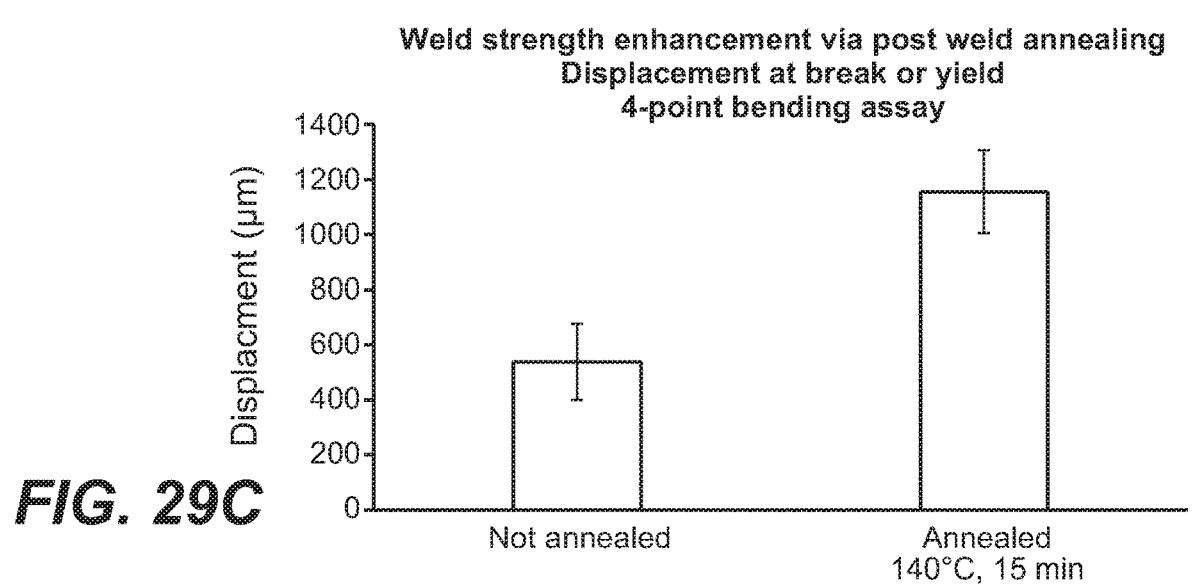
FIG. 29C shows displacement at breakage in the four-point bending assay for annealed and non-annealed (carrier polymer-agent)-linker-(carrier polymer-agent) samples.
Figure 29D:
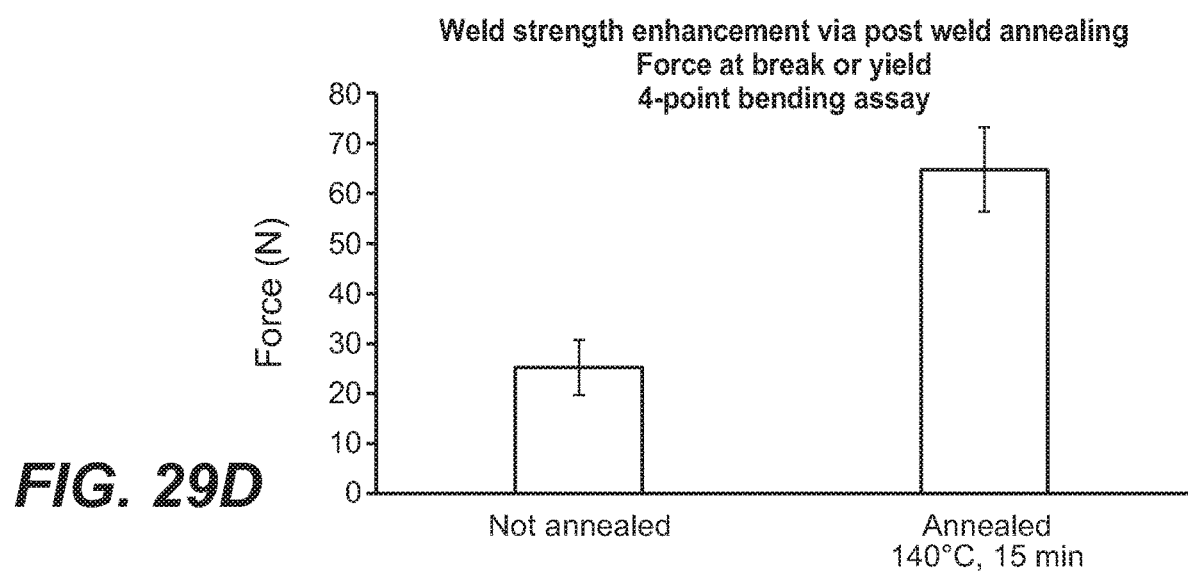
FIG. 29D shows force at breakage in the four-point bending assay for annealed and non-annealed (carrier polymer-agent)-linker-(carrier polymer-agent) samples.

Analysis of force-displacement data. Raw force-displacement data (FIG. 29A) can provide information on several mechanical properties that can be predictive of in vivo performance. These data can be used directly, or they can be normalized to the geometry of the sample to obtain stress-strain curves. In destructive assays, potentially useful readouts include force, displacement, stress and/or strain at break or at yield, as well as modulus, toughness, compliance, strain energy, and resilience. In non-destructive assays, number of fatigue loading cycles until sample failure (break or yield) can also be recorded. Alternative ways of analyzing the data from Example 13 are shown in FIG. 29B and FIG. 29C. FIG. 29B shows weld strength enhancement via post-weld annealing by measuring and comparing strain energy for non-annealed and annealed samples in mJ at the break or yield of the weld in the four-point bending assay. FIG. 29C shows weld strength enhancement via post-weld annealing by measuring the displacement at breakage or yielding of the non-annealed and annealed samples. FIG. 29D shows force at breakage or yielding of the non-annealed and annealed samples, again demonstrating weld strength enhancement via post-weld annealing.

Example 19

Gastric Residence System Assembly including Post-Weld Annealing

Gastric residence system performance relies on strong and consistent welding between the linker, drug formulation, and elastomer components. Hot plate welding protocols can be optimized to achieve strong bonds between two components made of pure PCL or between PCL and drug-loaded formulations, which are composed primarily of PCL (Example 12). For dissimilar plastics, especially plastics with different melting temperatures, achieving strong bonds by hot plate welding can be challenging. For welding of linker materials to PCL or to drug-loaded formulations, it was observed that a post-weld annealing step could significantly improve weld strength (Example 13). The post-weld annealing process involves placing welded samples into a mold and heating in an oven at 140-160° C. for 15-30 min. Post-weld oven annealing may be necessary to achieve consistent weld strength, but this exposure to heat may affect the stability and performance of drug-loaded formulations. Liquid silicone rubber (LSR) elastomer centers are expected to be stable to anneal conditions.

Various methods of making the polymeric assemblies and gastric residence systems are illustrated in FIG. 33. Entry A of FIG. 33 shows an assembly method that proceeds as follows:
1. Welding of the interfacing polymer of the elastomer hub to linker. The interfacing polymer shown in FIG. 33, entry A is polycaprolactone. The elastomer hub can be an elastomer-intercomponent anchor-interfacing polymer assembly or an elastomer-interfacing polymer assembly. Welding of the linker to the interfacing polymer produces an elastomer-intercomponent anchor-interfacing polymer-linker assembly or an elastomer-interfacing polymer-linker assembly.
2. Welding linker to drug-loaded formulation (carrier polymer-therapeutic agent component) to form the gastric residence system dosage form;
3. Annealing entire dosage form (gastric residence system).

Another assembly method is shown in Entry B of FIG. 33:
1. Welding of a segment of interfacing polymer (in the figure, a PCL segment is used) to the linker.
2. Welding of the interfacing polymer-linker to the drug-loaded formulation (carrier polymer-therapeutic agent component).
3. Annealing of the interfacing polymer-linker-(carrier polymer-therapeutic agent component) arm (i.e., the elongate member).
4. Welding of the arm to the hub to form the gastric residence system. The hub can be an elastomer-intercomponent anchor-interfacing polymer assembly or an elastomer-interfacing polymer assembly.

Entry C of FIG. 33 shows yet another assembly method:
1. Welding the hub (the hub can be an elastomer-intercomponent anchor-interfacing polymer assembly or an elastomer-interfacing polymer assembly) to the linker;
2. Annealing the hub-linker assembly; and
3. Welding the drug formulation (carrier polymer-therapeutic agent component) to the linker of the hub-linker assembly to form the gastric residence system.

Another assembly method is shown in entry D of FIG. 33:
1. Welding the hub (the hub can be an elastomer-intercomponent anchor-interfacing polymer assembly or an elastomer-interfacing polymer assembly) to a linker, to form an elastomer-intercomponent anchor-interfacing polymer-linker assembly or an elastomer-interfacing polymer-linker assembly;
2. Welding the elastomer-intercomponent anchor-interfacing polymer-linker assembly or the elastomer-interfacing polymer-linker assembly to a segment of interfacing polymer (such as PCL), to form an elastomer-intercomponent anchor-interfacing polymer-linker-interfacing polymer assembly or an elastomer-interfacing polymer-linker-interfacing polymer assembly;
3. Annealing the elastomer-intercomponent anchor-interfacing polymer-linker-interfacing polymer assembly or elastomer-interfacing polymer-linker-interfacing polymer assembly;
4. Welding the drug-loaded formulation (the carrier polymer-therapeutic agent component) to the elastomer-intercomponent anchor-interfacing polymer-linker-interfacing polymer assembly or elastomer-interfacing polymer-linker-interfacing polymer assembly to form the gastric residence system.

Example 20

Preparation of 2-Part Polyurethane Central Elastomers

Star arms were prepared from 80 k PCL and loaded into 00el-sized PDMS molds as described in Example 1A. Poly 75-90 Liquid Rubber (Polytek Development Corp) 2-part polyurethane was prepared by blending the A and B components 2:1 by volume in a glass vial. Blended liquid rubber was transferred to the PDMS mold in sufficient quantity to fill the remaining volume of the mold and to contact all six PCL arms (140-160 uL). Molds were transferred to a 120° C. oven for 15 minutes. The oven was shut off and ramped down overnight to room temperature. Then the arms were removed from the oven and cured at room temperature for 7 days. The folding force of the cured elastomers was measured using the folding force assay described in Example 5. For assembly into various gastric residence systems, PCL arms were cut at a distance 1-3 mm from the interface of PCL with the cured polyurethane.

Example 21

Testing Enteric Properties of Linkers

Figure 30B:
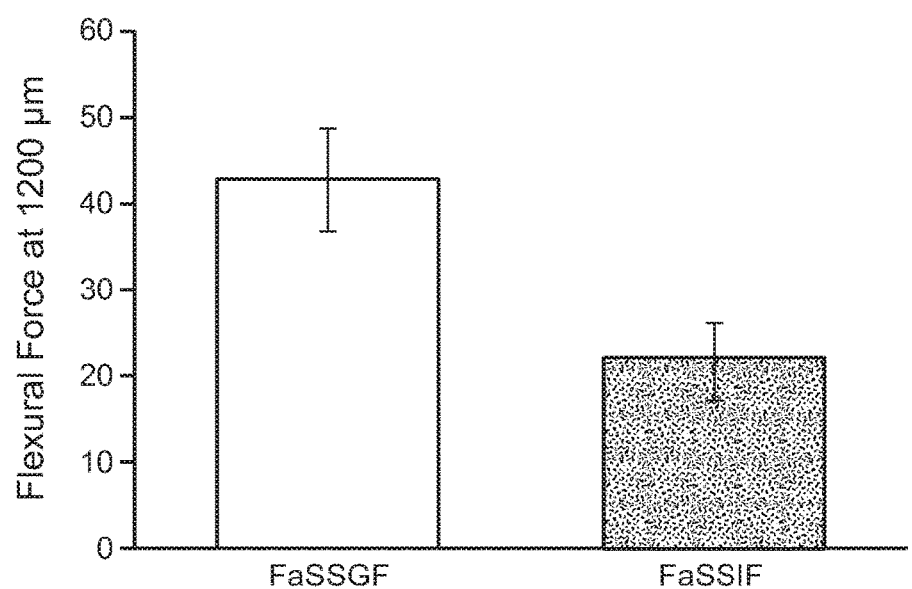
FIG. 30B shows an in vitro analysis of linker strength after one day incubation in FaSSGF versus after one day incubation in FaSSIF.

Triangular rods containing 2-mm linkers were prepared as described in Example 15 (linker formulation 30% Mn 80,000 PCL, 70% HPMCAS). Samples were incubated in FaSSGF and FaSSIF for 24 hours in a 37° C. incubator and agitated at a speed of 200 rpm. After incubation, flexural strength of the samples (n=4) was measured by the four-point bending as described in Example 13. Results are shown in FIG. 30B, showing that the linkers incubated in FaSSIF are weaker than the linkers incubated in FaSSGF.

Example 22

Measurement of Transverse (x-y Plane) Folding Forces

Figure 34A:
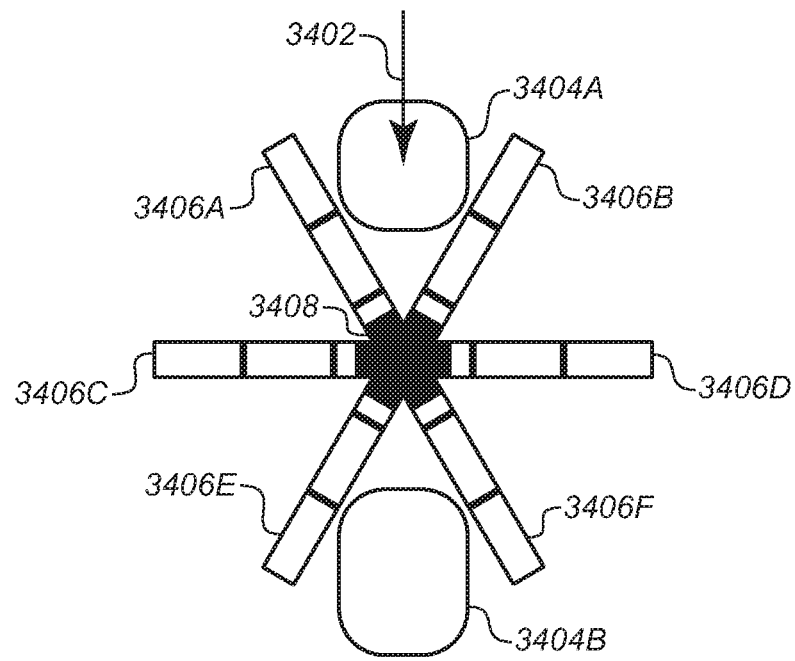
FIG. 34A shows a gastric residence system prior to being subjected to x-y bending (transverse) forces.
Figure 34B:
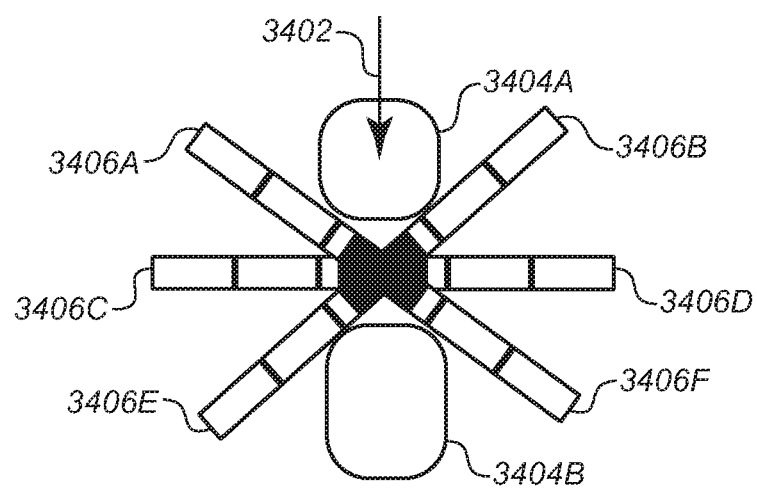
FIG. 34B shows a gastric residence system after being subjected to x-y bending (transverse) forces.

The x-y (transverse) bending force of gastric residence systems was measured using a custom loading rig, as illustrated in FIG. 34A. Gastric residence systems were mounted vertically by placing two arms 3406E and 3406F around a rectangular block 3404B with filleted edges. A second cylindrical block 3404A applied force 3402 downwards onto the gastric residence system, flexing elastomer 3408 and spreading arms 3406A, 3406B, 3406E, and 3406F in the x-y plane of the system (that is, the transverse direction). The load was measured throughout the test and the maximum load was documented as the x-y bending force. FIG. 34B shows the gastric residence system after it was subjected to x-y bending.

Resistance to x-y bending is dependent on the durometer of the material and amount of webbing between elastomer arms. As durometer is increased the x-y bending force increases. As webbing is increased, the x-y bending force increases.

The x-y bending force for the un-webbed concavo-convex design at 3 mm displacement was 0.17 (0.04) N, and was 0.43 (0.06) N for the fully webbed biconcave disk, both at 70 A durometer. Numbers in parentheses are standard deviations (n=3).

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A gastric residence system for administration to a stomach of a patient, comprising:
   a central elastomer component, wherein the central elastomer component is mono-concave, bi-concave, concavo-convex, or toroidal;
   a plurality of at least three carrier polymer-agent components comprising a carrier polymer and a therapeutic agent or a salt thereof,
   wherein each of the plurality of carrier polymer-agent components comprises an elongate member comprising a proximal end, a distal end, and an outer surface therebetween;
   wherein the proximal end of each elongate member is attached to the central elastomer component and projects radially from the central elastomer component, each elongate member having the distal end not attached to the elastomer component and located at a larger radial distance from the central elastomer component than the proximal end;
   wherein the central elastomer component is attached directly or indirectly to each elongate member by an intercomponent anchor, wherein the intercomponent anchor is a separate component from the central elastomer component and each of the elongate members;
   wherein a first portion of each intercomponent anchor is located within the central elastomer component, and a second portion of each intercomponent anchor is located within:
   a) a corresponding first segment of interfacing polymer, wherein each corresponding first segment of interfacing polymer is also attached directly or indirectly to a corresponding one of the elongate members;
   b) a corresponding segment of linker, wherein each corresponding segment of linker is also attached directly or indirectly to a corresponding one of the elongate members; or
   c) a corresponding one of the elongate members;
   wherein
   i) the central elastomer component is overmolded over the first portions of the intercomponent anchors, or
   ii) the first segment of each interfacing polymer, a first segment of the corresponding segment of each linker, or a first segment of each elongate member is overmolded over the corresponding second portion of the intercomponent anchors;
   wherein the gastric residence system has a compacted form when within a container that provides a constraining force, and is suitable for administration orally or through a feeding tube in the compacted form; and has an uncompacted form resulting from elastic recoil of the gastric residence system when released from the constraining force provided by the container in the stomach of the patient;
   wherein the gastric residence system is configured to be retained in the stomach for a period of at least about 24 hours; and wherein the gastric residence system is configured to release a therapeutically effective amount of the therapeutic agent or the salt thereof over at least a portion of the period in which the gastric residence system is retained in the stomach.

2. The gastric residence system of claim 1, wherein the linker comprises hydroxypropyl methyl cellulose acetate succinate (HPMCAS) and polycaprolactone (PCL); or wherein the linker comprises poly(lactic-co-glycolic acid) (PLGA).

3. The gastric residence system of claim 2, wherein the linker further comprises a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

4. The gastric residence system of claim 1, wherein the central elastomer component is overmolded over the first portions of the intercomponent anchors.

5. The gastric residence system of claim 1, wherein the first segment of each interfacing polymer, the first segment of the corresponding segment of each linker, or the first segment of each elongate member is overmolded over the corresponding second portion of the intercomponent anchors.

6. The gastric residence system of claim 1, wherein a maximum folding force of the gastric residence system occurs when the elongate members are at an angle between about 0 degrees and about 70 degrees from a fully unfolded plane of the gastric residence system.

7. The gastric residence system of claim 1, wherein the gastric residence system has an x-y bending force of at least about 0.2 newtons.

8. The gastric residence system of claim 1, wherein the central elastomer component comprises a plurality of branches equal in number to the plurality of at least three carrier polymer-agent components, and the central elastomer component further comprises webbing between the plurality of branches.

9. The gastric residence system of claim 1, wherein the second portion of each intercomponent anchor is located within the corresponding segment of linker, wherein each corresponding segment of linker is also attached directly or indirectly to a corresponding one of the elongate members.

10. The gastric residence system of claim 1, wherein at least one of the first portion or the second portion of each intercomponent anchor comprises a knob shape, and the first portion is located within the central elastomer component.

11. A gastric residence system for administration to a stomach of a patient, comprising:
a central elastomer component, wherein the central elastomer component is mono-concave, bi-concave, concavo-convex, or toroidal;
a plurality of at least three carrier polymer-agent components comprising a carrier polymer and a therapeutic agent or a salt thereof,
wherein each of the plurality of carrier polymer-agent components comprises an elongate member comprising a proximal end, a distal end, and an outer surface therebetween;
wherein the proximal end of each elongate member is attached to the central elastomer component and projects radially from the central elastomer component, each elongate member having the distal end not attached to the elastomer component and located at a larger radial distance from the central elastomer component than the proximal end;
wherein the central elastomer component is attached directly or indirectly to each elongate member by an intercomponent anchor, wherein the intercomponent anchor is a separate component from the central elastomer component and each of the elongate members;
wherein at least one of a first portion or a second portion of each intercomponent anchor comprises a knob shape, and the first portion is located within the central elastomer component;
wherein the gastric residence system has a compacted form when within a container that provides a constraining force, and is suitable for administration orally or through a feeding tube in the compacted form; and has an uncompacted form resulting from elastic recoil of the gastric residence system when released from the constraining force provided by the container in the stomach of the patient;
wherein the gastric residence system is configured to be retained in the stomach for a period of at least about 24 hours; and
wherein the gastric residence system is configured to release a therapeutically effective amount of the therapeutic agent or the salt thereof over at least a portion of the period in which the gastric residence system is retained in the stomach.

12. The gastric residence system of claim 11, wherein the second portion of each intercomponent anchor is located within:
a) a corresponding first segment of interfacing polymer, wherein each corresponding first segment of interfacing polymer is also attached directly or indirectly to a corresponding one of the elongate members;
b) a corresponding segment of linker, wherein each corresponding segment of linker is also attached directly or indirectly to a corresponding one of the elongate members; or
c) a corresponding one of the elongate members.

13. The gastric residence system of claim 12, wherein the linker comprises hydroxypropyl methyl cellulose acetate succinate (HPMCAS) and polycaprolactone (PCL); or wherein the linker comprises poly(lactic-co-glycolic acid) (PLGA).

14. The gastric residence system of claim 13, wherein the linker further comprises a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

15. The gastric residence system of claim 12, wherein the central elastomer component is overmolded over the first portions of the intercomponent anchors.

16. The gastric residence system of claim 12, wherein the first segment of each interfacing polymer, a first segment of the corresponding segment of each linker, or a first segment of each elongate member is overmolded over the corresponding second portion of the intercomponent anchors.

17. The gastric residence system of claim 11, wherein a maximum folding force of the gastric residence system occurs when the elongate members are at an angle between about 0 degrees and about 70 degrees from a fully unfolded plane of the gastric residence system.

18. The gastric residence system of claim 11, wherein the gastric residence system has an x-y bending force of at least about 0.2 newtons.

19. The gastric residence system of claim 11, wherein the central elastomer component comprises a plurality of branches equal in number to the plurality of at least three carrier polymer-agent components, and the central elastomer component further comprises webbing between the plurality of branches.

20. The gastric residence system of claim 12, wherein the second portion of each intercomponent anchor is located within a corresponding segment of linker, wherein each corresponding segment of linker is also attached directly or indirectly to a corresponding one of the elongate members.

* * * * *